(12) United States Patent
Percec

(10) Patent No.: US 9,777,034 B2
(45) Date of Patent: Oct. 3, 2017

(54) MODULAR SYNTHESIS OF AMPHIPHILIC JANUS GLYCODENDRIMERS AND THEIR SELF-ASSEMBLY INTO GLYCODENDRIMERSOMES

(71) Applicant: The Trustees of The University of Pennsylvania, Philadelphia, PA (US)

(72) Inventor: Virgil Percec, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/892,044

(22) PCT Filed: May 21, 2014

(86) PCT No.: PCT/US2014/038926
§ 371 (c)(1),
(2) Date: Nov. 18, 2015

(87) PCT Pub. No.: WO2014/190024
PCT Pub. Date: Nov. 27, 2014

(65) Prior Publication Data
US 2016/0108076 A1    Apr. 21, 2016

Related U.S. Application Data

(60) Provisional application No. 61/825,698, filed on May 21, 2013.

(51) Int. Cl.
C07H 15/26 (2006.01)
C07H 17/02 (2006.01)
C07H 1/00 (2006.01)

(52) U.S. Cl.
CPC ............... *C07H 17/02* (2013.01); *C07H 1/00* (2013.01); *C07H 15/26* (2013.01)

(58) Field of Classification Search
None
See application file for complete search history.

(56) References Cited

U.S. PATENT DOCUMENTS

| 7,498,372 | B2 | 3/2009 | Schaefer |
| 2009/0306310 | A1 | 12/2009 | Wu et al. |
| 2011/0021626 | A1 | 1/2011 | Astruc et al. |

OTHER PUBLICATIONS

Percec, et al., "Modular Synthesis of Amphiphilic Janus Glycodendrimers and Their Self-Assembly into Glycodendrimersomes and Other Complex Architectures with Bioactivity to Biomedically Relevant Lectins", J. Am. Chem. Soc., Jun. 19, 2013, 135(24), 9055-9077.
Percec, et al., "Self Assembly of Janus Dendrimers into Uniform Dendrimersomes and Other Complex Architectures", Science, May 21, 2010, 328(5981), 1009-1014.
Gimeno, Nelida, et al. "Janus-type dendromesogens: a tool to control the nanosegregation and polar organization of bent-core structures." Chemistry of Materials 25 (2013): 286-296 (published online Dec. 24, 2012).†
Liu, Yong, et al. "A supramolecular Janus hyperbranched polymer and its photoresponsive self-assembly of vesicles with narrow size distribution." Journal of the American Chemical Society 135 (2013): 4765-4770 (published online Mar. 6, 2013).†
Percec, Virgil, et al. "Self-assembly of Janus dendrimers into uniform dendrimersomes and other complex architectures." Science 328 (2010): 1009-1014.†

† cited by third party

*Primary Examiner* — Layla Berry
(74) *Attorney, Agent, or Firm* — Baker & Hostetler LLP

(57) ABSTRACT

The invention concerns compounds of the formula (I) wherein: $Y^1$ and $Y^2$ are independently a monosaccharide or disaccharide; $X^1$ and $X^2$ are independently —$(R^9$—O$)_m$—, —$(R^{10})_p$—, —O—$(R^{11}$—O$)_q$—, —$R^{16}$—O—$R^{17}$—O— or a covalent bond; $Q^1$ and $Q^2$ are independently a nitrogen-containing heterocycle moiety; $Z^1$ and $Z^2$ are independently —(O—$R^7$)—, —(O—C(=O)—$R^8$)a-, —O—C(=O)—$R^{12}$—C(=O)-$R^{13}$—, —O—C(=O)—$R^{14}$—C(=O)—$R^{15}$ or a covalent bond; $R^7$-$R^{17}$ are each independently $C_1$-$C_6$ alkyl; $R^1$-$R^6$ are each independently a linear or branched alkyl group; b, c, d, e, f, and g are 0 or 1, provided b+c+d equals at least 2 and e+f+g equals at least 2; and a, m, p, and q are each an integer from 1-6.

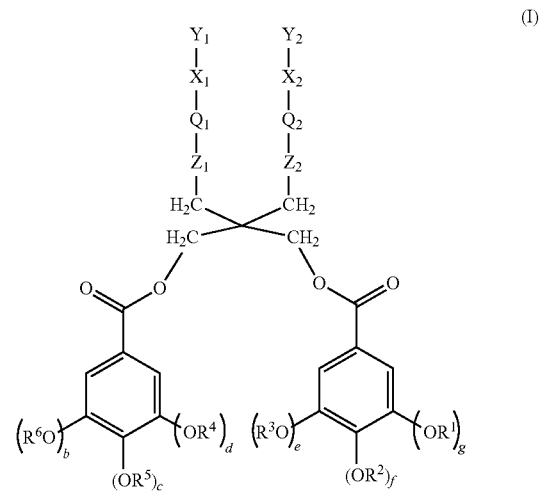

19 Claims, 21 Drawing Sheets

MODULAR SYNTHESIS OF AMPHIPHILIC JANUS GLYCODENDRIMERS AND THEIR SELF-ASSEMBLY INTO GLYCODENDRIMERSOMES

CROSS REFERENCE TO RELATED APPLICATIONS

This application is a National Stage Application filed under 35 U.S.C. 371 of International Application No. PCT/US2014/038926, filed May 21, 2014, which claims benefit of U.S. Provisional Patent Application No. 61/825,698 filed May 21, 2013, the disclosure of which is incorporated herein in its entirety.

GOVERNMENT RIGHTS

This invention was made with government support under Contract/Grant Nos. DMR-1066116 and DMR-1120901 awarded by the National Science Foundation. The government has certain rights in the invention.

TECHNICAL FIELD

The instant invention concerns amphiphilic Janus glycodendrimers and their self-assembly into glycodendrimersomes and other complex structures.

BACKGROUND

Glycans of glycoconjugates adorn cell surfaces with recognition elements for sugar-binding proteins (lectins) to mediate functions such as cell-cell recognition and adhesion, initiation of signaling, delivery and routing, also relevant for immune recognition. Multivalent glycan displays are essential to overcome the weak interactions between individual sugars and proteins in order to generate ligand selectivity to sugar-binding protein receptors. In addition to the structure of the glycans, the spatial mode of presentation, its dynamics, and adaptability play a salient role in turning glycan presence into ligand or counter-receptor functionality. The goal of understanding the route to specific recognition and control of cell physiology explains the chemical efforts toward tailoring diverse multivalent glycoconjugate displays accomplished via multivalent scaffolds. Mimics of natural glycoconjugates (glycoproteins and glycolipids) include glycopeptides, glycopolymers, glycodendrimers, glycoliposomes and synthetic glycolipids, cyclic clusters such as cyclophenes, and glycodynamers. Their availability facilitates experimental approaches to understand the functioning of complex assemblies such as microdomains in membranes and can also form the basis for potential medical applications such as blocking undesired lectin binding in inflammation/tumor progression or in infection, or stimulating the immune response by vaccination. Glycopolymers, glycodynamers and glycodendrimers provide some accessible mimics for the biodisplay of glycans but all require complex multistep synthesis to generate multivalency and are often build on toxic scaffolds. Vesicles presenting carbohydrates are more similar to biological cell membrane but lack precise structure since are prepared by co-assembly of several components by hydration followed by multiple fractionation via extrusion. This results in a random distribution of carbohydrates over the surface of vesicle. Therefore, a simple route to hard and soft vesicles that are fully programmable in regards to ligand density and type is in demand. Additions to the existing panel of glycoconjugates that mimic biological membranes will broaden their range of applications.

Recently, we reported a new class of amphiphiles called Janus dendrimers that self-assemble by simple injection of their ethanol solution in water into narrow size distribution and stable in time vesicles called dendrimersomes (Percec, V., et al., Science 2010, 328, 1009-1014). Moving toward applicability, we report here a simple strategy to an accelerated modular synthesis of the first examples of amphiphilic Janus glycodendrimers containing two identical carbohydrates in their hydrophilic part. They self-assemble by simple injection of their solution made in water miscible solvents such as THF and ethanol into water and buffer and by hydration, in unilamellar hard and soft spherical, polygonal and tubular vesicles, a,b, denoted glycodendrimersomes, aggregates of rod-like micelles9a, named glycodendrimermicelles, aggregates of Janus glycodendrimers named glycodendrimer aggregates or for short dendrimer aggregates, cubosomes, denoted glycodendrimercubosomes, as well as hard lamellae. By analogy with dendrimersomes and other complex architectures reported to self-assemble from simple amphiphilic Janus dendrimers, all supramolecular assemblies generated in water from Janus glycodendrimers are obtained with a predictable size that amplifies the multivalency of presentation of their sugars from 2 to n, display narrow molecular mass distribution that in the case of vesicles and liposomes is considered to be monodisperse, 12k and are stable over time. Structurally, they provide models for biological cell membranes with the typical glycan presence on their surface. These assemblies are of general interest as platforms for glycan ligand presentation since they offer a simple supramolecular approach to simulate the naturally multivalent display of carbohydrates. They also may be engineered into devices used in the lectin-mediated delivery of drugs, genes, imaging agents, of pharmaproteins used as therapeutics to block lectins and to act as vaccines targeting lectins on dendritic cells. The spherical nature of the supramolecular assemblies produced from self-assembling amphiphilic Janus glycodendrimers provides an additional advantage to covalent glycodendrimers4 as mimics, since their synthesis is simple and their water cavity can be exploited. Glycodendrimersomes offer an additional advantage to glycodendrimers, by providing mimics of the biological membranes rather than only modeling their surface. Therefore, they are expected, of being not only delivery devices but, to serve the same functions as covalent glycodendrimers. To prove bioactivity in binding to lectins and thereby in principle access the potential applications mentioned above, we demonstrate selective agglutination of glycodendrimersomes of different size with the plant lectin concanavalin A (Con A), the toxic mistletoe lectin Viscum album agglutinin (VAA), a potential biohazard akin to ricin, the bacterial lectin PA-IL from *Pseudomonas aeruginosa*, and two human lectins members of the galectin family galectin-3, Gal-3, and galectine-4, Gal-4, potently acting in adhesion, growth regulation and glycan routing.

SUMMARY

In some aspects, the invention concerns compounds of the formula:

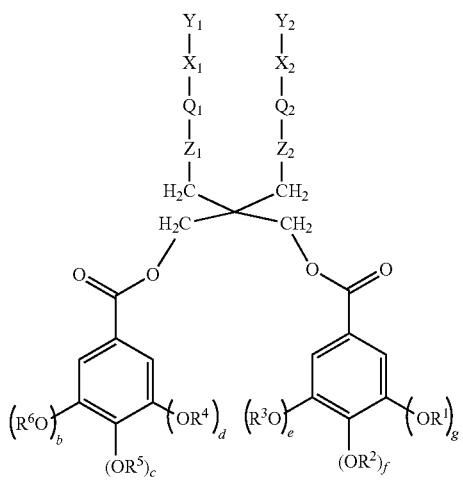

I wherein:

Y$^1$ and Y$^2$ are independently a monosaccharide or disaccharide;

X$^1$ and X$^2$ are independently —(R$^9$—O)$_m$—, —(R$^{10}$)—, —O—(R$^{11}$—O)$_q$—, —R$^{16}$—O—R$^{17}$—O— or a covalent bond;

Q$^1$ and Q$^2$ are independently a nitrogen-containing heterocycle moiety;

Z$^1$ and Z$^2$ are independently —(O—R$^7$)—, —(O—C(=O)—R$^8$)$_a$—, —O—C(=O)—R$^{12}$—C(=O)—R$^{13}$—, —O—C(=O)—R$^{14}$—C(=O)—R$^{15}$ or a covalent bond;

R$^7$-R$^{17}$ are each independently C$_1$-C$_6$ alkyl;

R$^1$-R$^6$ are each independently a linear or branched alkyl group;

b, c, d, e, f, and g are 0 or 1, provided b+c+d equals at least 2 and e+f+g equals at least 2; and a, m, p, and q are each an integer from 1-6.

In some embodiments, R$^1$-R$^6$ are each independently C$_4$-C$_{20}$ linear or branched alkyl group. In some embodiments, R$^1$-R$^6$ are the same. In certain embodiments, Y$^1$ and Y$^2$ are independently D-Mannose, D-Galactose or D-Lactose. In some compounds, Y$^1$ and Y$^2$ are the same.

In some preferred embodiments, Q$^1$ and Q$^2$ are

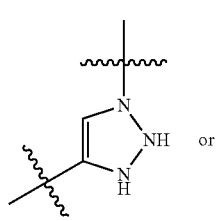 or

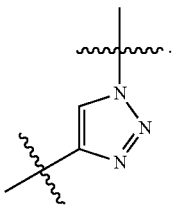

II

III where ~~~ through the line indicates that the line represents a bond position.

Certain compounds of the invention are such that a, m, p, and q are each independently an integer from 1-4. For some compounds, X$^1$, X$^2$, Z$^1$ and Z$^2$ are covalent bonds. In other compounds, X$^1$ and X$^2$ are covalent bonds. In yet other compounds, Z$^1$ and Z$^2$ are covalent bonds.

Another aspect of the invention concerns methods for producing compounds of formula I. Some methods comprise contacting compounds of formula Y$^1$—X$^1$-E and Y$^2$—X$^2$-E with a compounds of formula IV

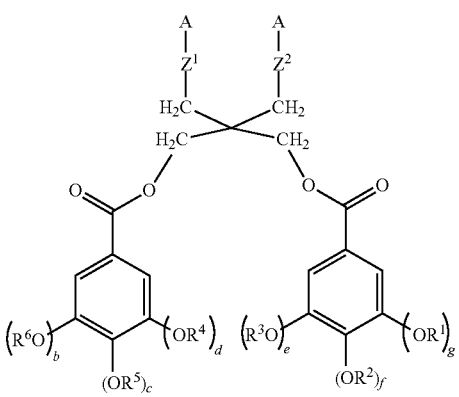

IV wherein A and E are selected from —C≡CH or —N$_3$ provided that A and E are not the same.

In further aspects, the invention concerns methods of producing self-assembled amphiphilic Janus glycodendrimers comprising introducing a compound of formula I into an aqueous media.

12G1-PE-spacer-TRZ-Man$_2$ 50ab and (b) (3,4)12G1-PE-spacer-TRZ-Gal$_2$ 50aa; tubular glycodendrimersome bundles assembled from (c) (3,4,5)12G1-PE-spacer-TRZ-Man$_2$ 50cb; mixture of tubular and spherical glycodendrimersomes assembled from (d) (3,4,5)12G1-PE-spacer-TRZ-Gal$^2$ 50ca.

Figure 5:
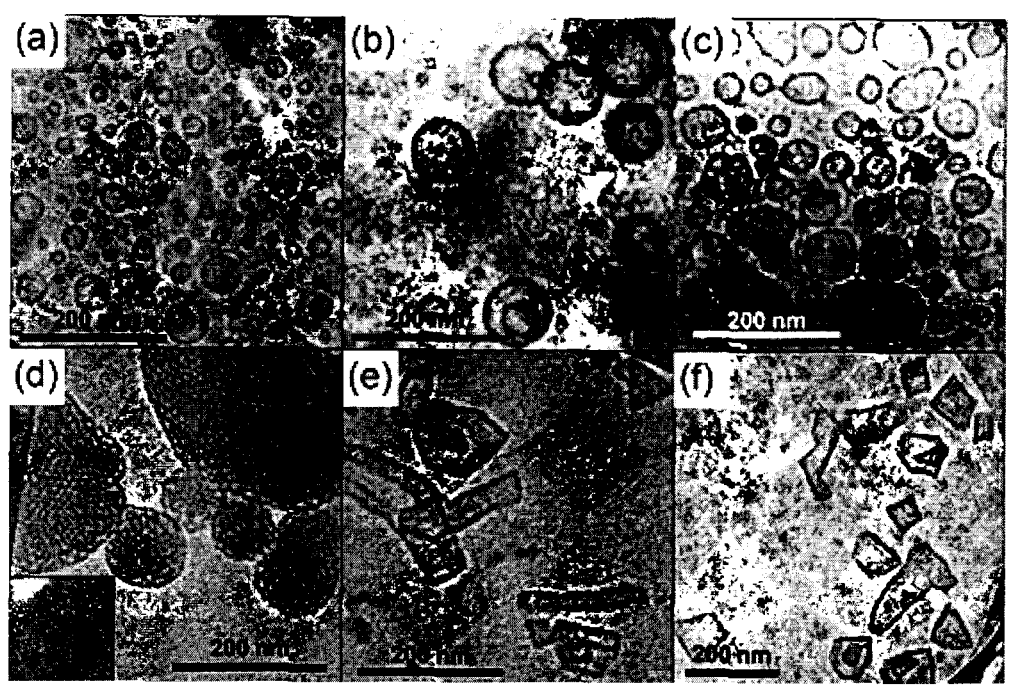

FIG. 5 presents selected cryo-TEM images of glycodendrimersomes assembled from (a) (3,5)12G1-PE-TRZ$_t$-3EO-Gal$_2$ 51ba, (b) (3,5)12G1-PE-TRZ$_t$-3EOMan$_2$ 51bb, and (c) (3,5)12G1-PE-TRZ$_t$-2EOMan$_2$ 51bc; glycodendrimercubosomes assembled from (d) (3,5)12G1-PE-TRZ$_t$-1EOMan$_2$ 51bd; solid lamellae assembled from (e) (3,4,5)12G1-PE-TRZ$_t$-3EOGal$_2$ 51ca and (f) (3,4,5)12G1-PE-TRZ$_t$-3EOMan$_2$ 51cb.

Figure 6:
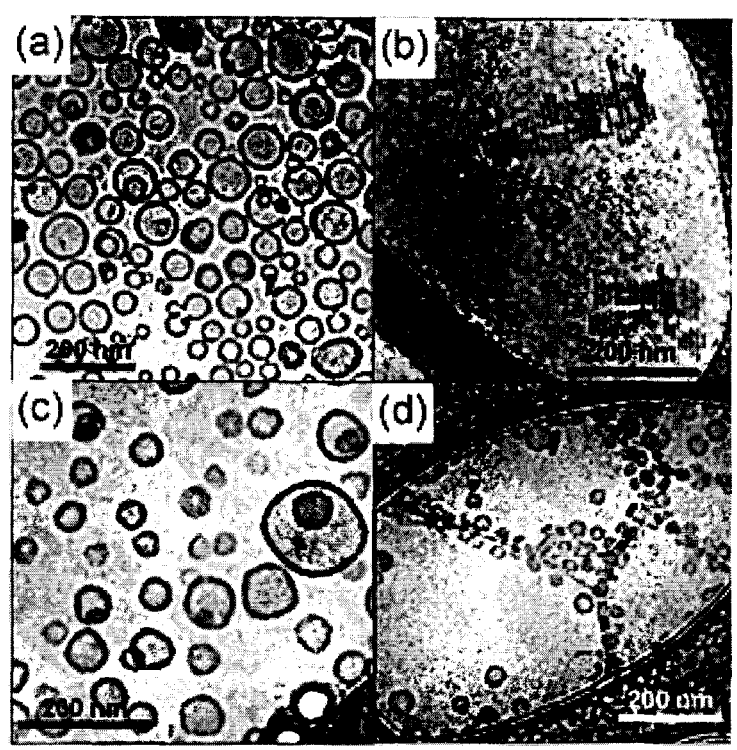

FIG. 6 presents selected cryo-TEM images of (a) glycodendrimersomes assembled from (3,5)12G1-PE-TRZ-4EOLac$_2$ 52bd; (b) rod-like glycodendrimermicelle bundles assembled from (3,4)12G1-PE-TRZ-4EOLac$_2$ 52ad; (c) glycodendrimersomes assembled from (3,4,5)12G1-PE-spacer-TRZ-4EOLac$_2$ 52dd and (d) glycodendrimersomes assembled from 3,4,5)12G1-PE-spacer-TRZ-1 EOLac$_2$ 52dc.

Figure 7:
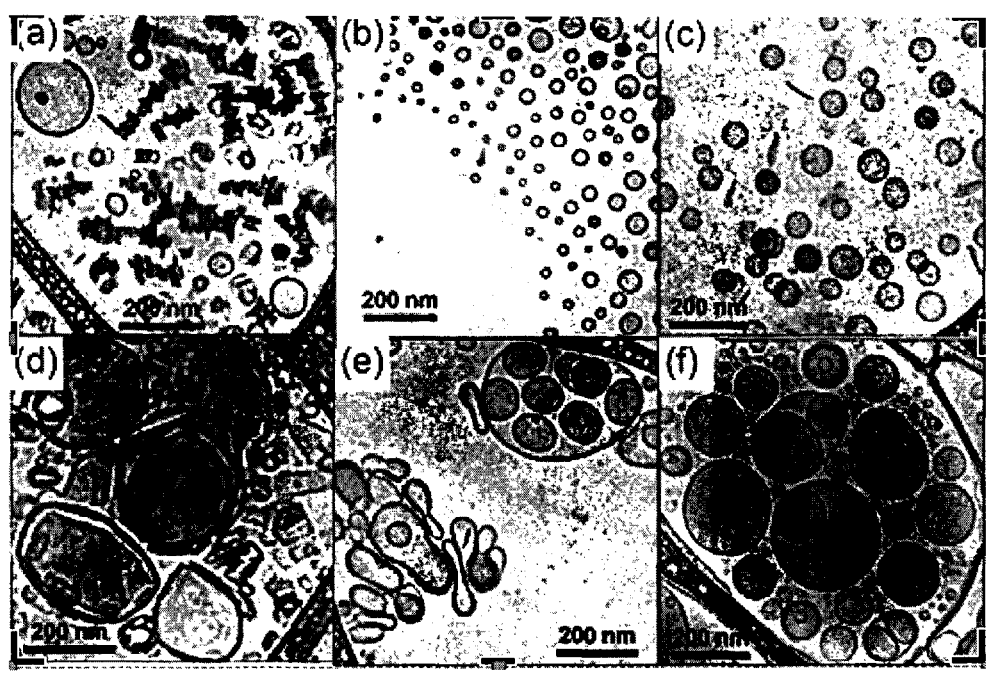

FIG. 7 presents selected cryo-TEM images of glycodendrimersomes and rod-like glycodendrimermicelles assembled from (a) (3,4)12G1-PE-TRZ$_t$-3EOLac$_2$ 53aa; (b) glycodendrimersomes assembled from (3,5)12G1-PE-TRZ$_t$-3EOLac$_2$ 53ba; (c) glycodendrimersomes and solid lamellae assembled from (3,4)2Et8G1-PE-TRZ$_t$-3EOLac$_2$ 53da; (d) solid and polygonal glycodendrimersomes assembled from (3,4,5)12G1-PE-TRZ$_t$-3EOLac$_2$ 53ca; (e) glycodendrimersomes assembled from (3,5)2Et8G1-PE-TRZ$_t$-3EOLac$_2$ 53ea and (f) glycodendrimersomes assembled from (3,4,5) 2Et8G1-PE-TRZ$_t$-3EOLac$_2$ 53fa.

Figure 8:
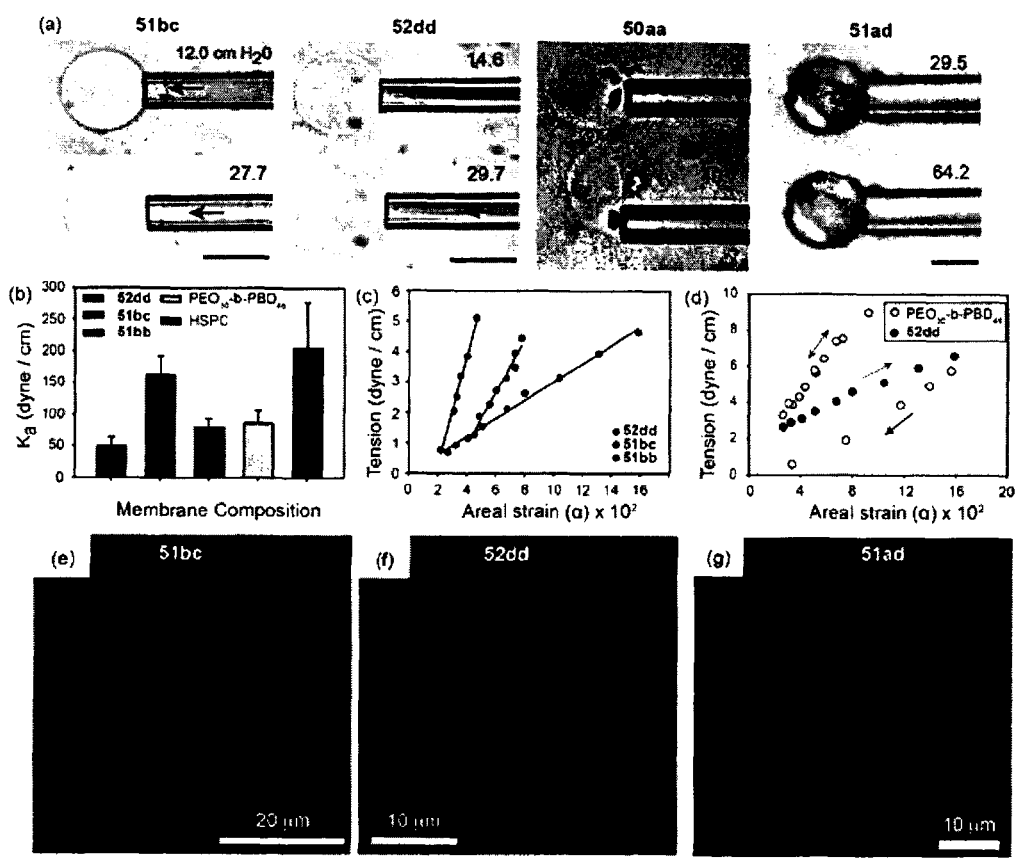

FIG. 8 shows (a) Micropipette aspiration of glycodendrimersomes assembled from (3,5)12G1-PE-TRZ$_t$-2EO-Man$_2$ 51be and (3,4,5)12G1-PE-spacer-TRZ-4EOLac$_2$ 52dd, and solid glycodendrimersome assembled from (3,4) 12G1-PE-spacer-TRZ-Gal$_2$ 50as and (3,4)12G1-PE-TRZ$_t$-1EOMan$_2$ 51ad, scale bar is 25 µm; (b) Comparison of elastic moduli of glycodendrimersomes assembled from 52dd, 51bc and 51bb with polymersomes of diblock copolymer PEO$_{30}$-b-PBD$_{46}$ and liposomes made from the lipid HSPC; (c) Plot of tension vs areal strain for glycodendrimersomes assembled from 52dd, 51bc and 51bb; (d) Comparison of tension vs areal strain plot for polymersome, PEO$_{30}$-b-PBD$_{46}$ and glycodendrimersome, 52dd. In (d), filled circles indicate measurements during initial vesicle stressing, and open circles indicate measurement taken during vesicle relaxation. Confocal microscopy images of (e,f) giant soft glycodendrimersomes and (g) giant hard glycodendrimersomes containing the hydrophobic Nile red dye.

Figure 9:
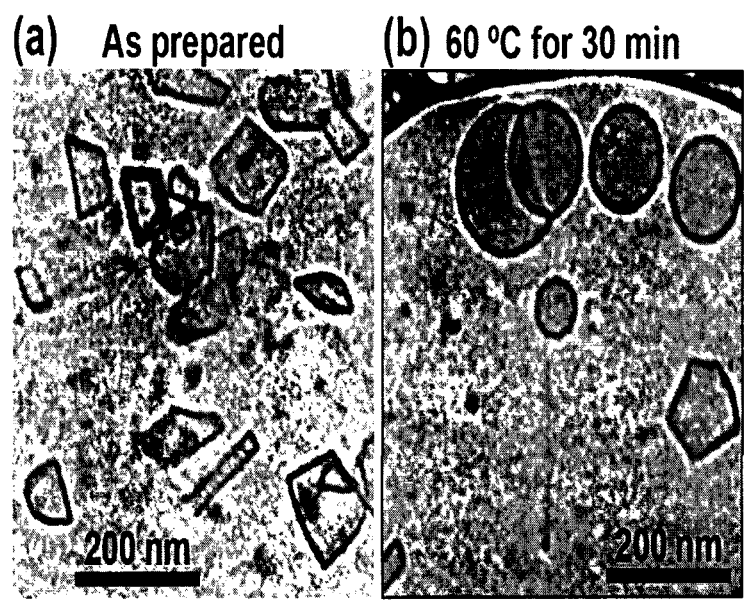

FIG. 9 presents (a) Cryo-TEM image of (3,4,5)12G1-PE-TRZ$_t$-3EOMan$_2$ 51cb obtained from an as prepared solution at concentration of 0.5 mg/mL. (b) Cryo-TEM image of the same solution after annealing at 60° C. for 30 min. The transition from solid lamellae to solid vesicles is clearly observed.

Figure 10:
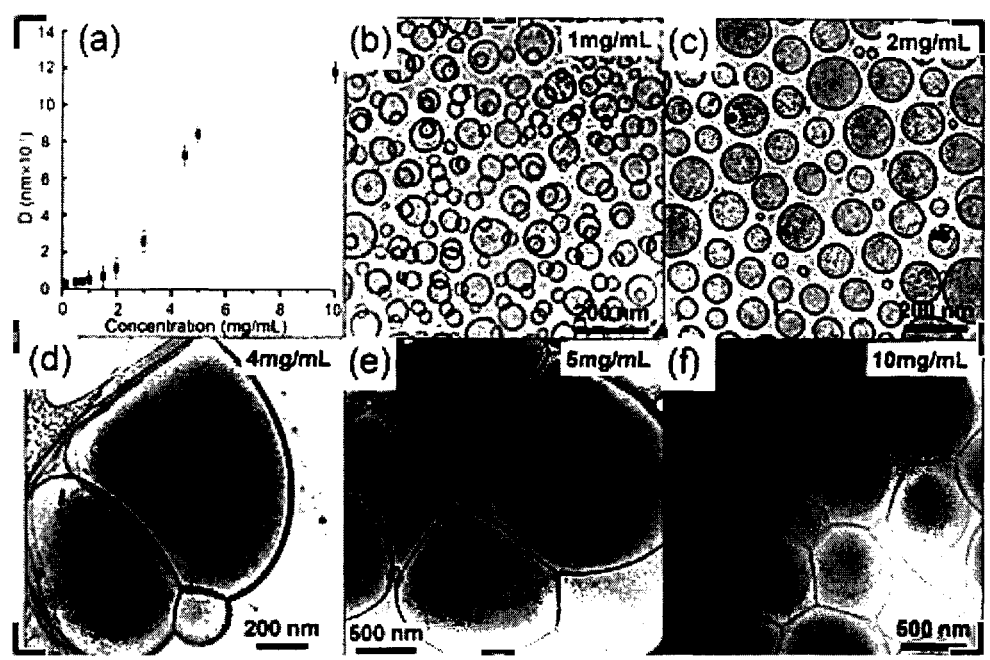

FIG. 10. (a) Plot of glycodendrimersome diameter vs concentration. The average vesicle size was obtained from DLS measurements. Cryo-TEM images of glycodendrimersomes assembled from (3,5)2Et8G1-PE-TRZ$_t$-3EOGal$_2$ 49bb at concentration of (b) 1 mg/mL, (c) 2 mg/mL, (d) 4 mg/mL, (e) 5 mg/mL, and (f) 10 mg/mL.

Figure 11:
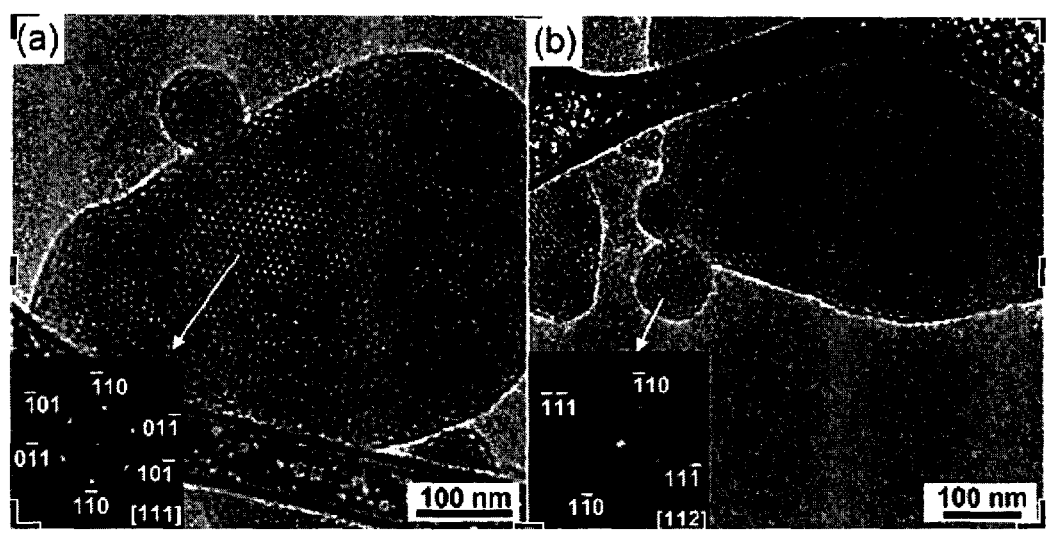

FIG. 11. Cryo-TEM images of (3,5)12G1-PE-TRZ$_t$-1EO-Man$_2$ 51bd showing the glycodendrimercubosome structure with Pn3̄m symmetry obtained at a concentration of 1.0 mg/mL. In (a), the inset documents the Fourier transform of the particle internal structure with a hexagonal arrangement of reflections corresponding to {110} crystallographic planes, indicating that the particle is orientated along the [111] direction. In (b), the Fourier transform shows the {111} reflections, indicating that the corresponding particle is oriented along the [112] direction, which is an about 20° tilt with respect to (a).

Figure 12:
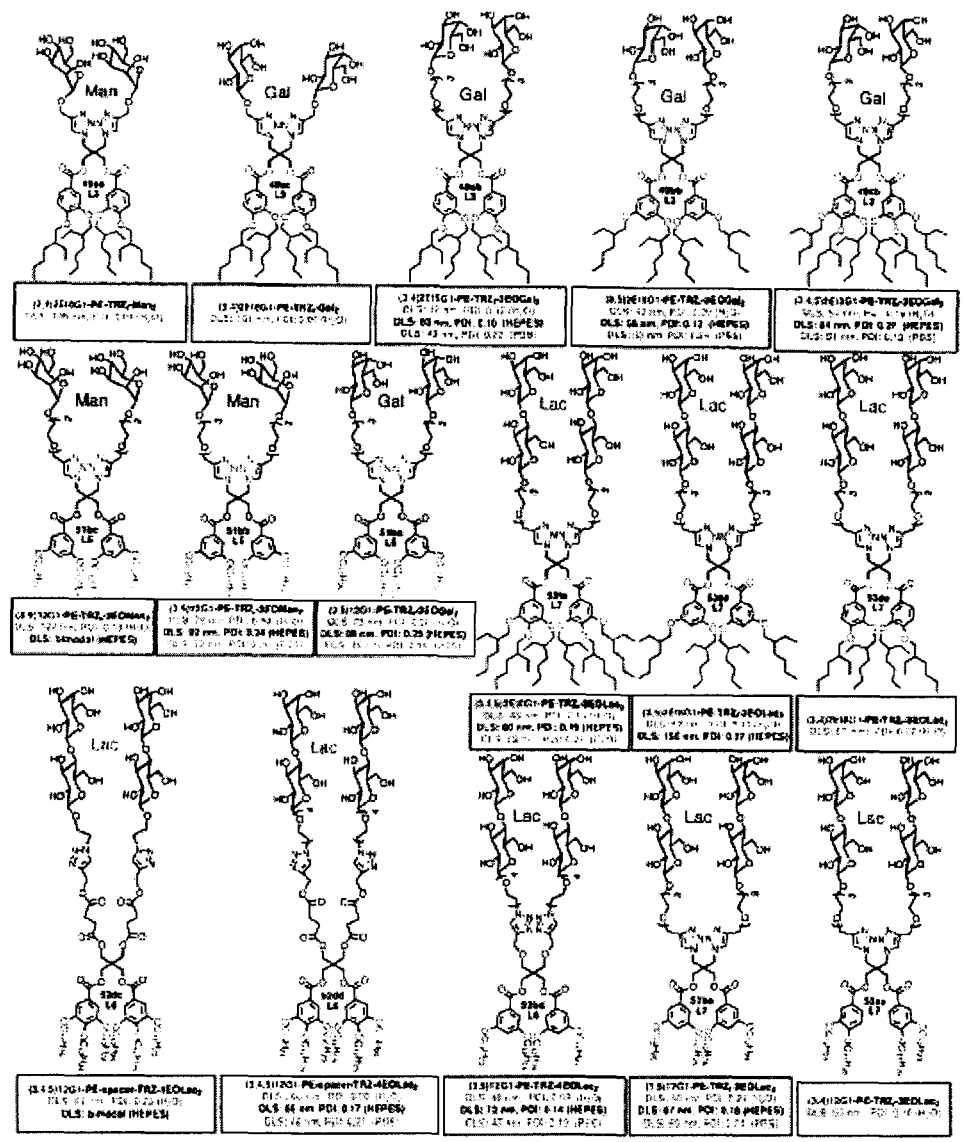

FIG. 12 shows structures of amphiphilic Janus glycodendrimers self-assembled by injection in water and buffer into single-type soft glycodendrimersomes with narrow polydispersity, good stability in buffer (marked in yellow) and in water (marked in blue and in yellow). The library number is indicated under the molecule code.

Figure 13:
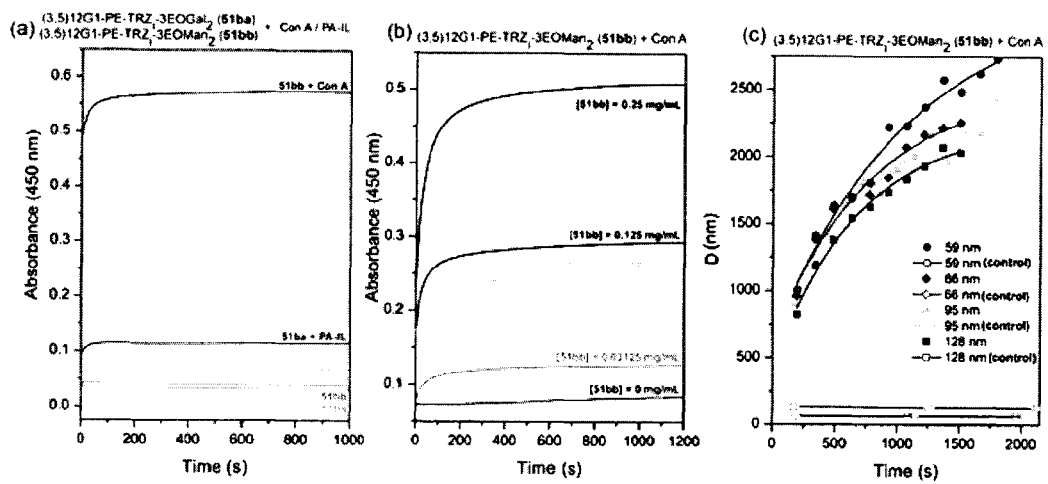

FIG. 13 presents (a) Agglutination of dendrimersomes prepared from (3,5)12G1-PE-TRZ$_t$-3EOGal$_2$ (51ba) and (3,5)12G1-PE-TRZ$_t$-3EOMan$_2$ (51bb) in the presence of Con A and PA-IL. [(51ba]=0.5 mg/mL (900 µL), [51bb]=0.5 mg/mL (600 µL), [Con A]=0.3 mg/mL (100 µL), [PA-IL]= 0.0625 mg/mL (100 µL) in HEPES buffer (1.0 mM MnCl$_2$ and 1.0 mM CaCl$_2$). (b) Agglutination of dendrimersomes prepared from (3,5)12G1-PE-TRZ$_t$-3EOMan$_2$ (51bb) at different concentration (0 to 0.25 mg/mL, 900 µL) in the presence of Con A (0.125 mg/mL, 100 µL) in 10 mM HEPES (1.0 mM MnCl$_2$ and 1.0 CaCl$_2$). (c) Agglutination of dendrimersomes prepared from 51bb with different size in the presence of Con A recorded by DLS. [51bb]=0.0625 mg/mL (400 µL), [Con A]=0.5 mg/mL (100 &L) in HEPES buffer (1.0 mM MnCl$_2$ and 1.0 mM CaCl$_2$).

Figure 14:
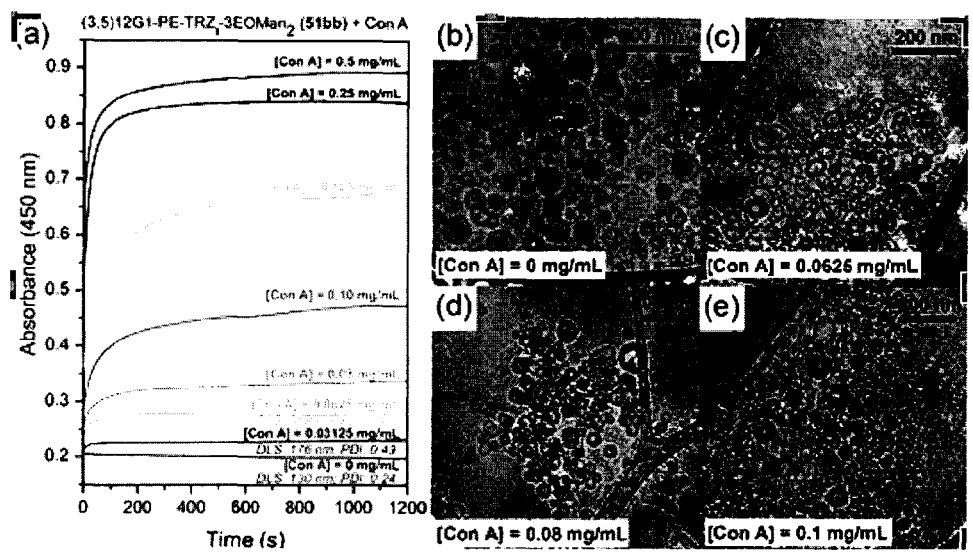

FIG. 14 presents (a) Agglutination of dendrimersomes prepared from (3,5)12G1-PE-TRZ$_t$-3EOMan$_2$ (51bb) in the presence of different concentrations of Con A. [51bb]=0.5 mg/mL (900 µL), [Con A]=0-0.5 mg/mL (100 µL) in 10 mM HEPES buffer (1.0 mM MnCl$_2$ and 1.0 mM CaCl$_2$) (a). Corresponding Cryo-TEM images at indicated Con A concentration. The agglutination effect can be clearly visualized (b,c,d,e).

Figure 15:
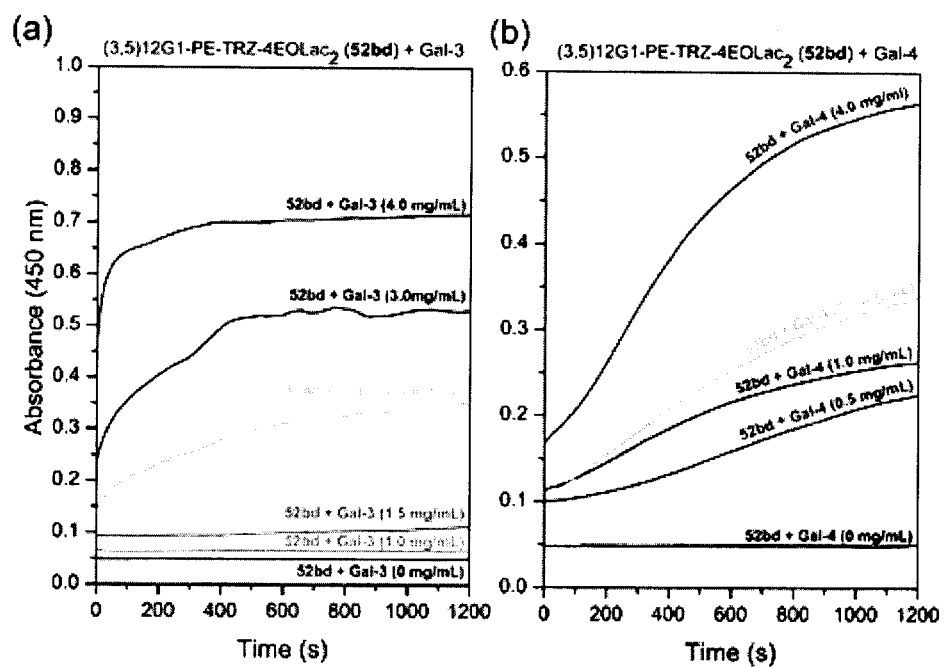

FIG. 15 presents agglutination of dendrimersomes prepared from (3,5)12G1-PE-TRZ-4EOLac$_2$ (52bd) in the presence of different concentration of Gal-3 (a) and Gal-4 (b). [52bd]=1.0 mg/mL (900 µL), [Gal-3]=0-4.0 mg/mL (100 µL), [Gal-4]=0-4.0 mg/mL (100 µL) in 10 mM HEPES buffer (1.0 mM MnCl$_2$ and 1.0 mM CaCl$_2$).

Figure 16:
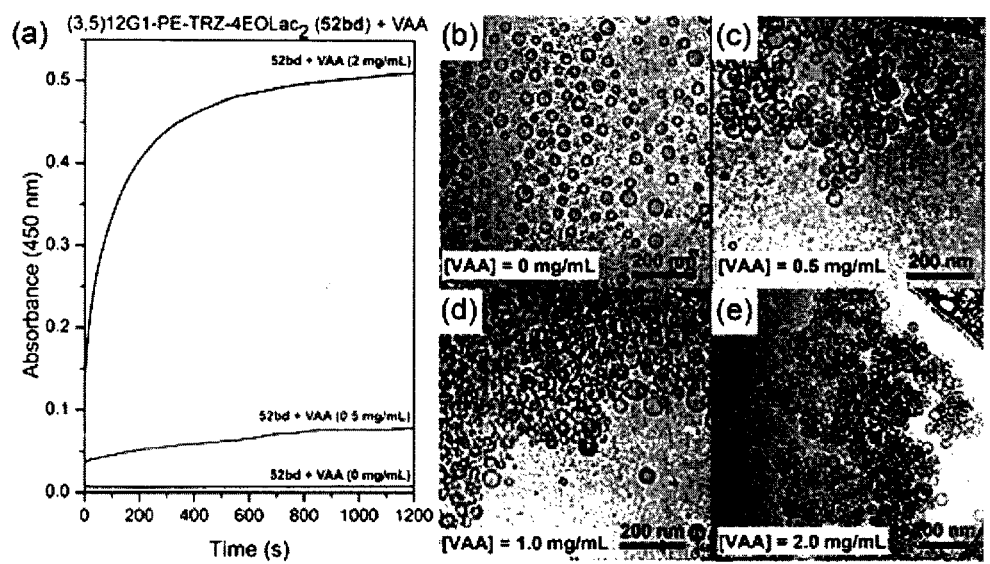

FIG. 16 shows agglutination of dendrimersomes prepared from (3,5)12G1-PE-TRZ-4EOLac$_2$ (52bd) in the presence of different concentration of VAA. [52bd]=1.0 mg/mL (900 µL), [VAA]=0-2.0 mg/mL (100 µL) in 10 mM HEPES buffer (1.0 mM MnCl$_2$ and 1.0 mM CaCl$_2$) (a). Corresponding cryo-TEM images at indicated VAA concentration. The agglutination effect can be clearly visualized (b,c,d,e).

Figure 17:
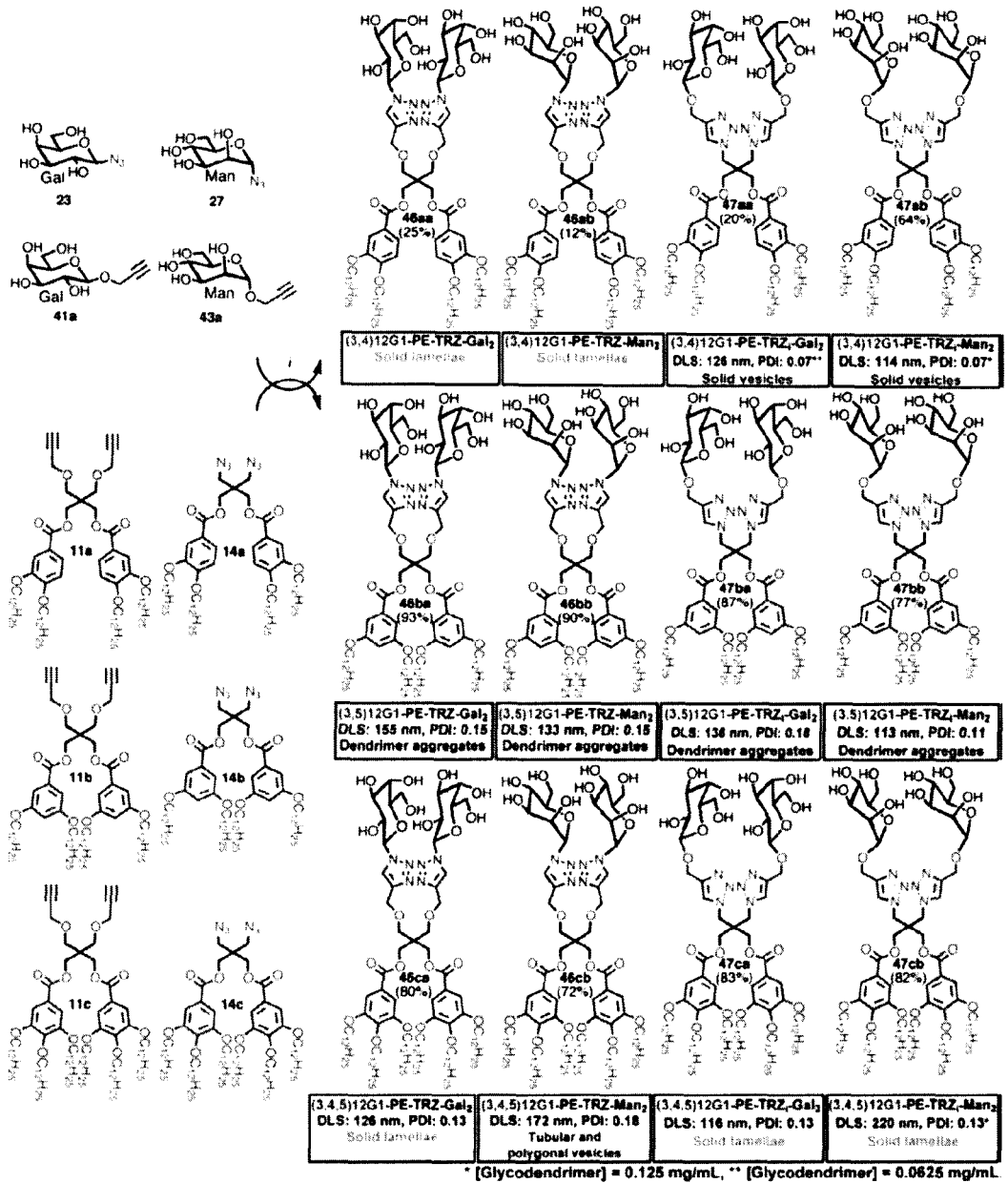

FIG. 17 shows modular synthesis of constitutional Isomeric Libraries 1 (46aa to 46cb) and 2 (47aa to 47cb) Containing twelve Amphiphilic janus glycodendrimers with D-mannose and D-galactose and the summary of their self-assembly by injection of their THF solution into water. Reagents and conditions: (i) CuSO$_4$.5H$_2$O, sodium ascorbate, THF/water (25° C.).

Figure 18:
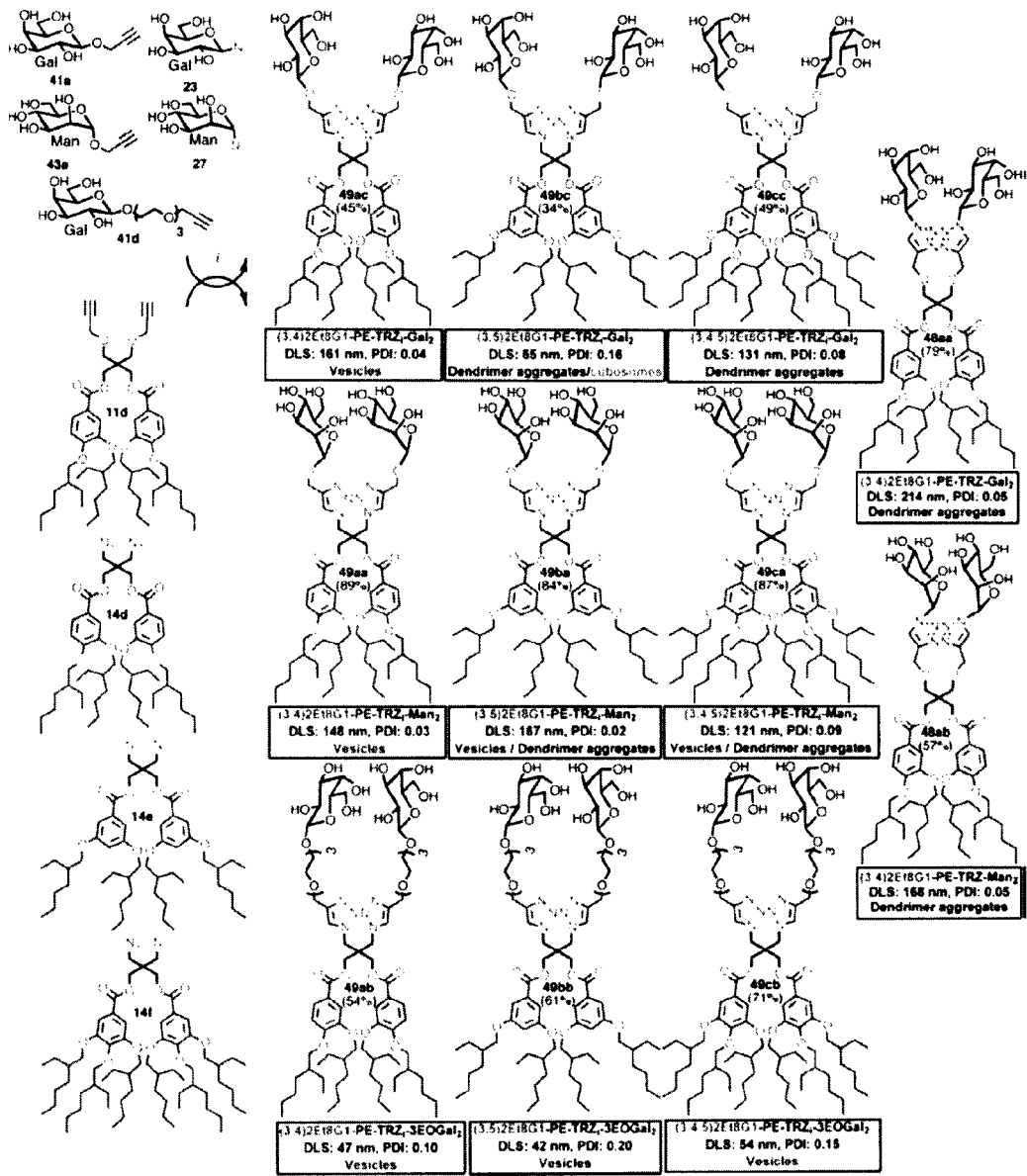

FIG. 18 shows modular synthesis of Library 1 (48aa to 49bb) containing eleven amphiphilic Janus glycodendrimers with branched hydrophobic alkyl groups and D-mannose and D-galactose in their hydrophilic part and the summary of their self-assembly by injection of their THF solution into water. Reagents and conditions: (i) CuSO$_4$.5H$_2$O, sodium ascorbate, THF/water (25° C.). Reagents and conditions: (i) CuSO$_4$.5H$_2$O, sodium ascorbate, THF/water (25° C.).

Figure 19:
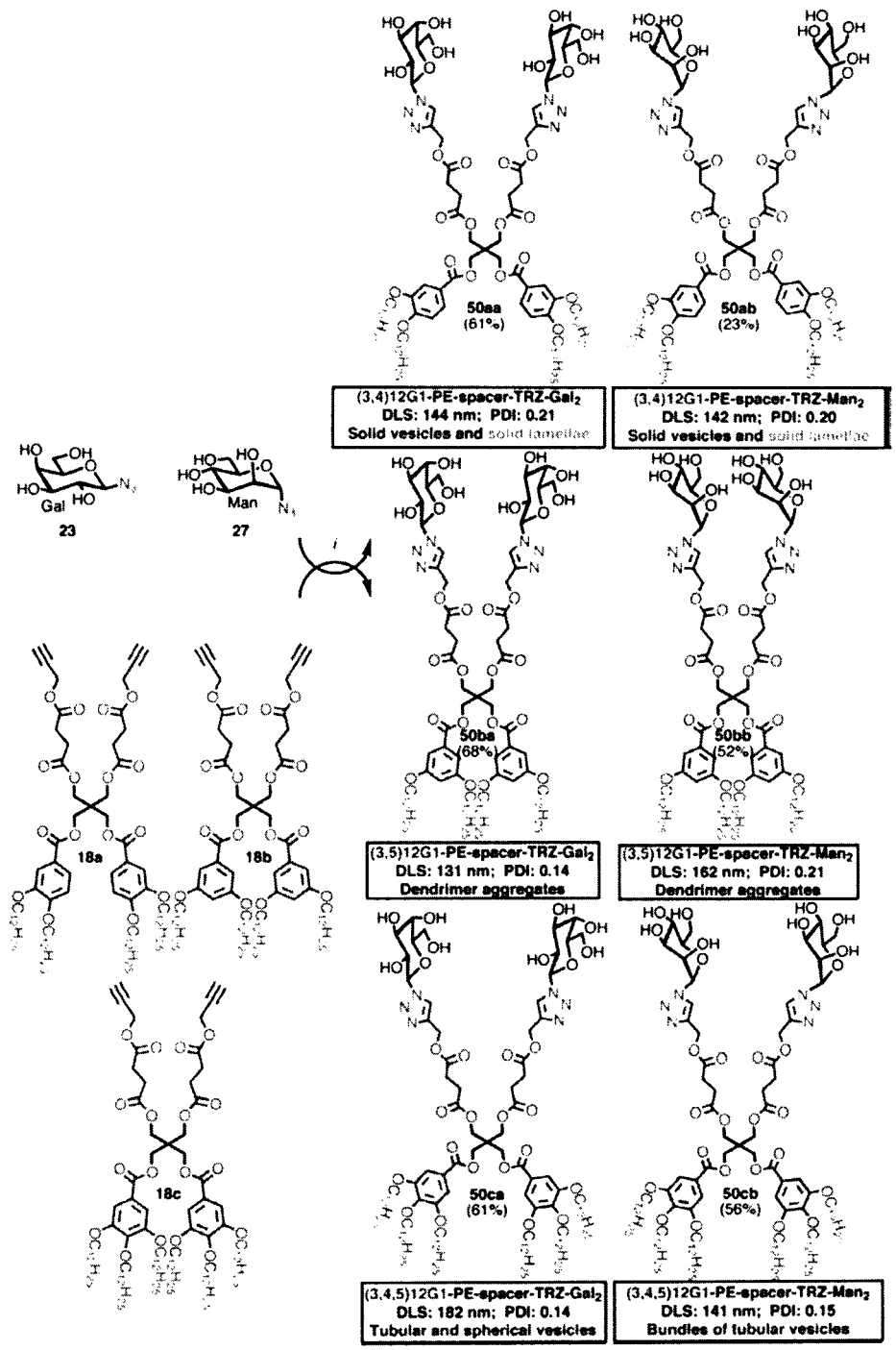

FIG. 19 shows modular synthesis of Library 4 (50aa to 50cb) containing six amphiphilic Janus glycodendrimers with hydrophobic linear n-alkyl groups, a succinic ester spacer, D-mannose, D-galactose or D-lactose in their hydrophilic part and the summary of their self-assembly by the injection of their THF solution into water. Reagents and conditions: (i) $CuSO_4 \cdot 5H_2O$, sodium ascorbate, THF/water (25° C.).

Figure 20:
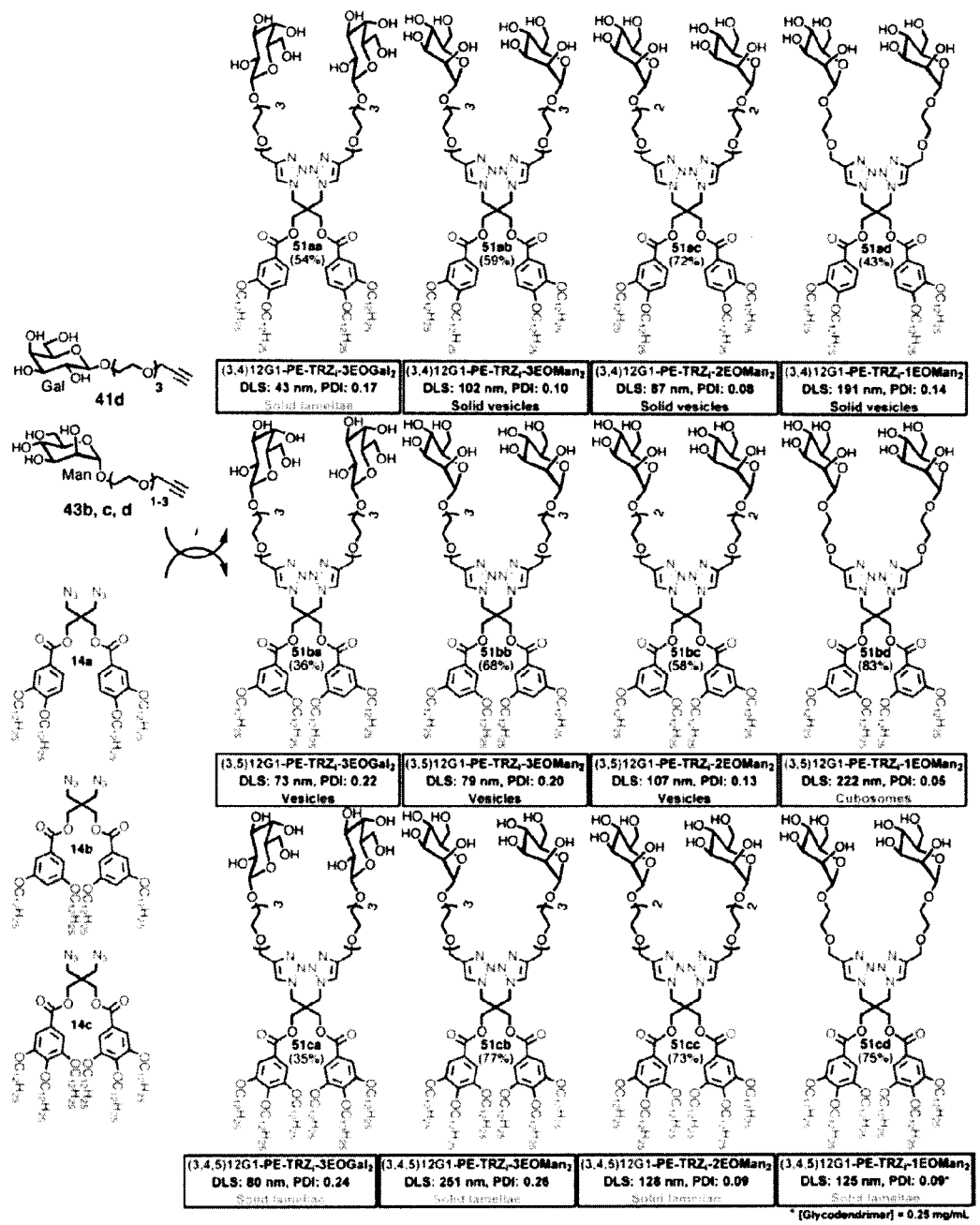

FIG. 20 shows modular synthesis of Library 5 (51aa to 51cd) containing twelve amphiphilic Janus glycodendrimers with linear n-alkyl groups, D-mannose or D-galactose connected via mono-, di- and tri(ethylene)glycol spacers and summary of self-assembly by injection of THF or EtOH solution into water. Reagents and conditions: (i) $CuSO_4 \cdot 5H_2O$, sodium ascorbate, THF/water (25° C.).

Figure 21:
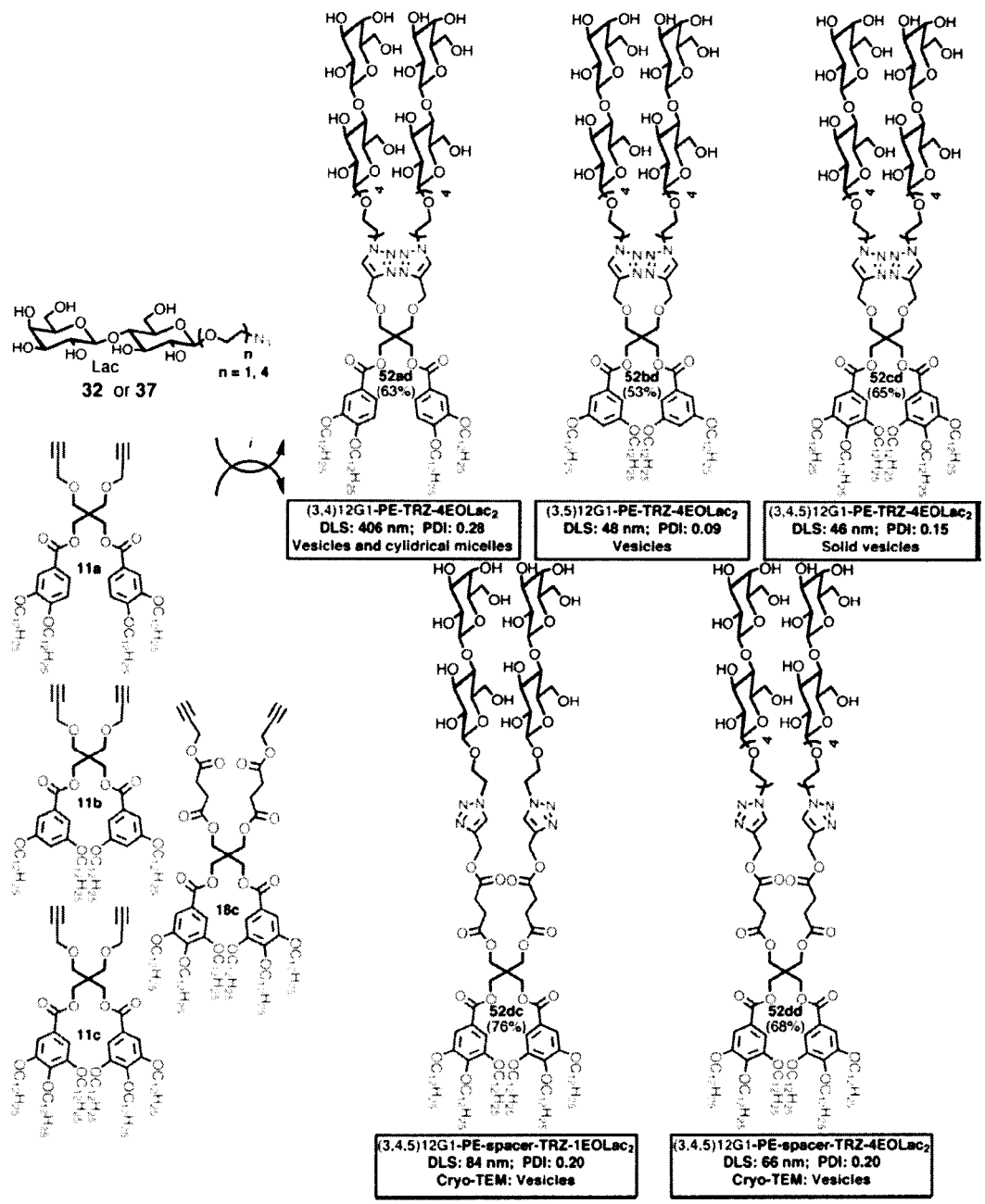

FIG. 21 shows modular synthesis of Library 6 (52ad to 52dd) containing five amphiphilic Janus glycodendrimers with linear n-alkyl groups and D-lactose and summary of self-assembly by injection of THF solution into water. Reagents and conditions: (i) $CuSO_4 \cdot 5H_2O$, sodium ascorbate, THF/water (25° C.).

Figure 22:
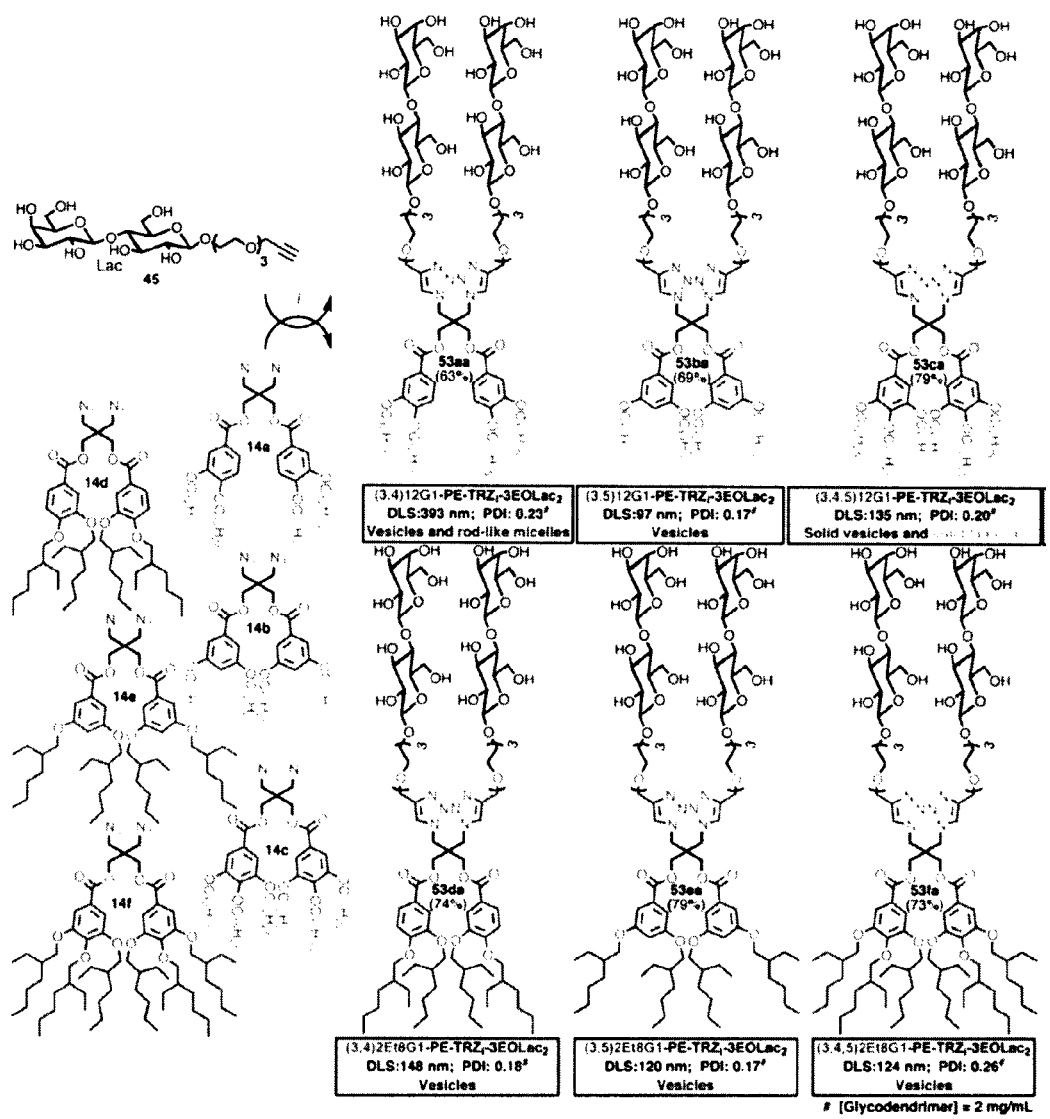

FIG. 22 shows modular synthesis of Library 7 (53aa to 53fa) containing six amphiphilic Janus glycodendrimers with linear and branched alkyl groups and D-lactose and their self-assembly by injection of their THF solution into water. Reagents and conditions: (i) $CuSO_4 \cdot 5H_2O$, sodium ascorbate, THF/water (25° C.).

DETAILED DESCRIPTION OF ILLUSTRATIVE EMBODIMENTS

The modular synthesis of seven libraries containing 51 self-assembling amphiphilic Janus dendrimers with the monosaccharides D-mannose, D-galactose and the disaccharide D-lactose in their hydrophilic part is reported. These unprecedented sugar-containing dendrimers are named amphiphilic Janus glycodendrimers.

The present disclosure may be understood more readily by reference to the following description taken in connection with the accompanying Figures and Examples, all of which form a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of any claimed disclosure. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to methods of operating a device and systems and to the devices and systems providing said methods. That is, where the disclosure describes and/or claims a method or methods for operating a flow battery, it is appreciated that these descriptions and/or claims also describe and/or claim the devices, equipment, or systems for accomplishing these methods.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

The invention is illustrated by the following examples, which are not intended to be limiting in nature.
Selection of Modular Synthetic Strategies and Structures for *Amphiphilic Janus Glycodendrimers*.

Figure 1:
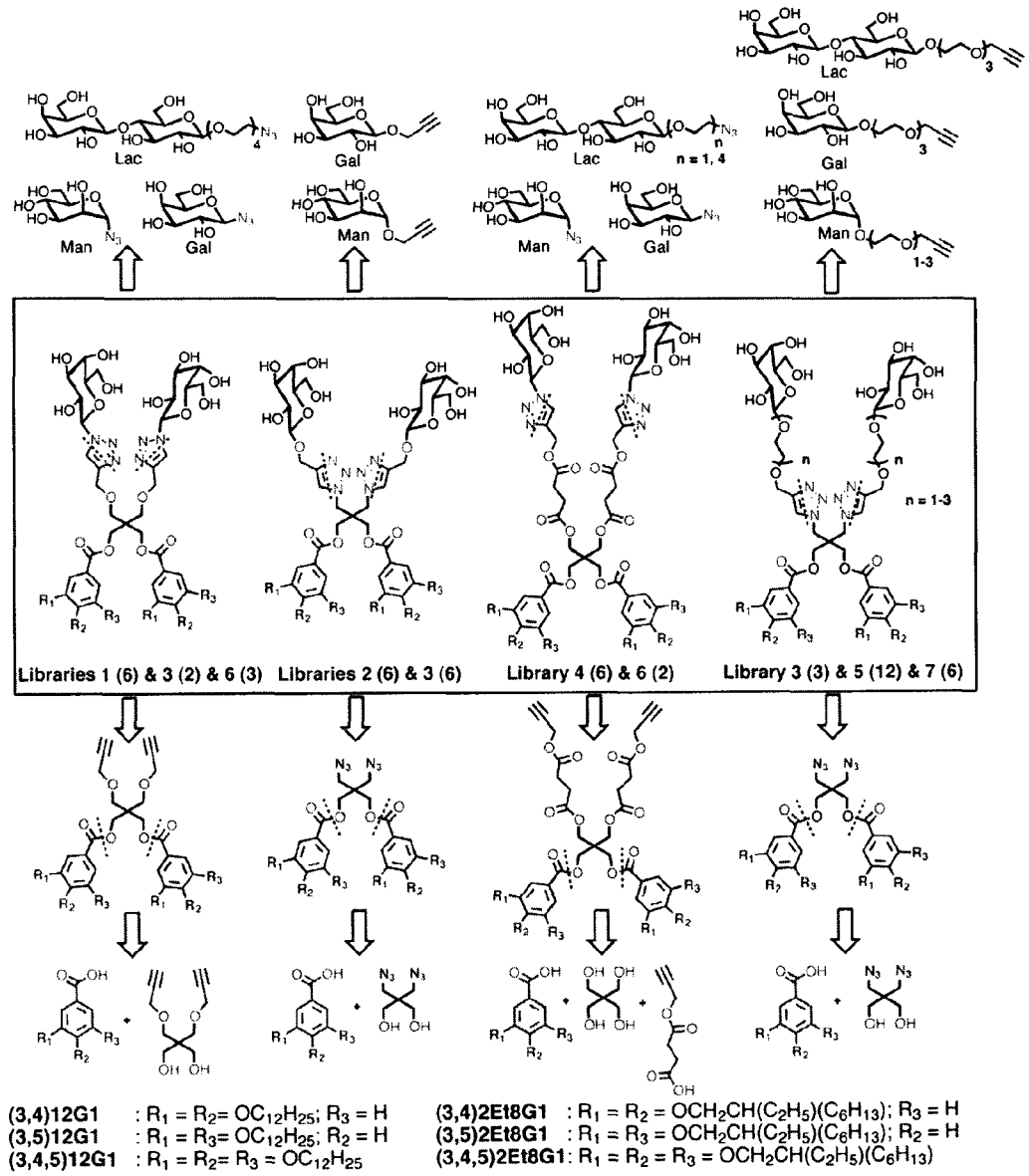
FIG. 1 presents modular approaches to the synthesis of seven libraries of amphiphilic Janus glycodendrimers. The numbers in between parenthesis represent the number of Janus dendrimers in the corresponding library.

Four accelerated modular strategies are elaborated for the synthesis of seven libraries of amphiphilic Janus glycodendrimers in FIG. 1.

Libraries 1 and 2 shown in the first two left side columns from FIG. 1 are constitutional isomers and were expected to provide the shortest synthetic routes to self-assembling amphiphilic Janus glycodendrimers. The modular synthetic methodologies for these two libraries involve the synthesis of twin-hydrophobic dendrons containing n-alkyl groups and functionalized with alkyne or azide attached directly to the focal point of the Janus dendrimer precursor. In the second step of this modular methodology, the unprotected monosaccharides D-mannose and D-galactose containing alkyne and azide aglyconic groups as models for any other carbohydrate headgroups, were rapidly combined with the complementary twin-hydrophobic dendrons via copper-catalyzed click chemistry. Discrimination between alkyne vs azide at each of the two dendrimer fragments as the preferred mode of synthesis together with assembly was the driving force behind these experiments. The modular strategy employed in the synthesis of library 3 consisting of a mixture of constitutional isomers is similar to that used for libraries 1 and 2 except that, in order to increase solubility, the n-alkyl groups of the twin-hydrophobic dendrons were replaced with branched alkyls. A third modular approach was used to construct libraries 4 and 6 (third column from the left side of FIG. 1). Library 4 contains a succinic ester spacer between the twin-hydrophobic dendrons and their alkynes used in the click chemistry. This spacer was incorporated to enhance solubility and flexibility, and as shown later, an important factor in recognition studies. This library contains D-mannose, D-galactose and D-lactose in the hydrophilic part of the Janus dendrimers. The fourth modular approach (libraries 3, 5 and 7) incorporates hydrophilic oligooxyethylene spacers between the carbohydrate and the twin-hydrophobic dendrimers. These spacers were expected to increase hydrophilicity, flexibility and solubility.

These modular strategies evolved during the analysis of the structure and properties of the supramolecular assemblies generated from each individual library of amphiphilic Janus glycodendrimers and were directed towards the construction of soft single-type glycodendrimersomes containing D-mannose, D-galactose and D-lactose in the hydrophilic part, which are glycan ligands for the five lectin receptors selected for binding experiments. Details of these design strategies and their selection will be discussed in each subsection dedicated to the synthesis and analysis of individual libraries. This study required the investigation of no less than seven libraries containing 51 compounds demonstrating the challenges encountered when taking the concept of simple amphiphilic Janus dendrimers that self-assemble into dendrimersomes to the more complex amphiphilic Janus glycodendrimers that self-assemble into glycodendrimersomes.

Synthesis of Twin-Hydrophobic Dendrons Functionalized with Alkyne and Azide Groups.

The first generation hydrophobic dendritic acids 4a,b,c,d were synthesized from natural phenolic acids' as reported previously (Scheme 1). Compounds 4e,f are new derivatives synthesized by the same procedures as those used for the previously reported compounds. Esterification of protocatechuic acid (1a), α-resorcylic acid (1b), and gallic acid (1c) in refluxing MeOH with $H_2SO_4$ as catalyst yielded methyl 3,4-dihydroxybenzoate (2a), methyl 3,5-dihydroxybenzoate (2b) and methyl 3,4,5-trihydroxybenzoate (2c) in 73-83% yield. Etherification of 2a,b,c with 1-bromododecane or 2-ethylhexyl bromide gave first-generation hydrophobic esters 3a,b,c,d,e,f containing linear and branched alkyl groups on periphery in 46 to 99% yield. The hydrophobic first generation dendritic acids 4a,b,c,d,e,f were obtained by the hydrolysis of the corresponding esters 3a,b,c,d,e,f with KOH in refluxing ethanol (94-100% yield).

Scheme 1. Synthesis of the First Generation Hydrophobic Dendritic Acids 4a,b,c,d,e,f and of the Alkyne Anhydride 6

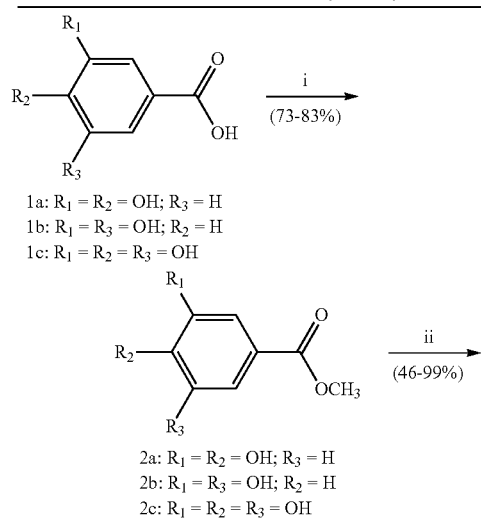
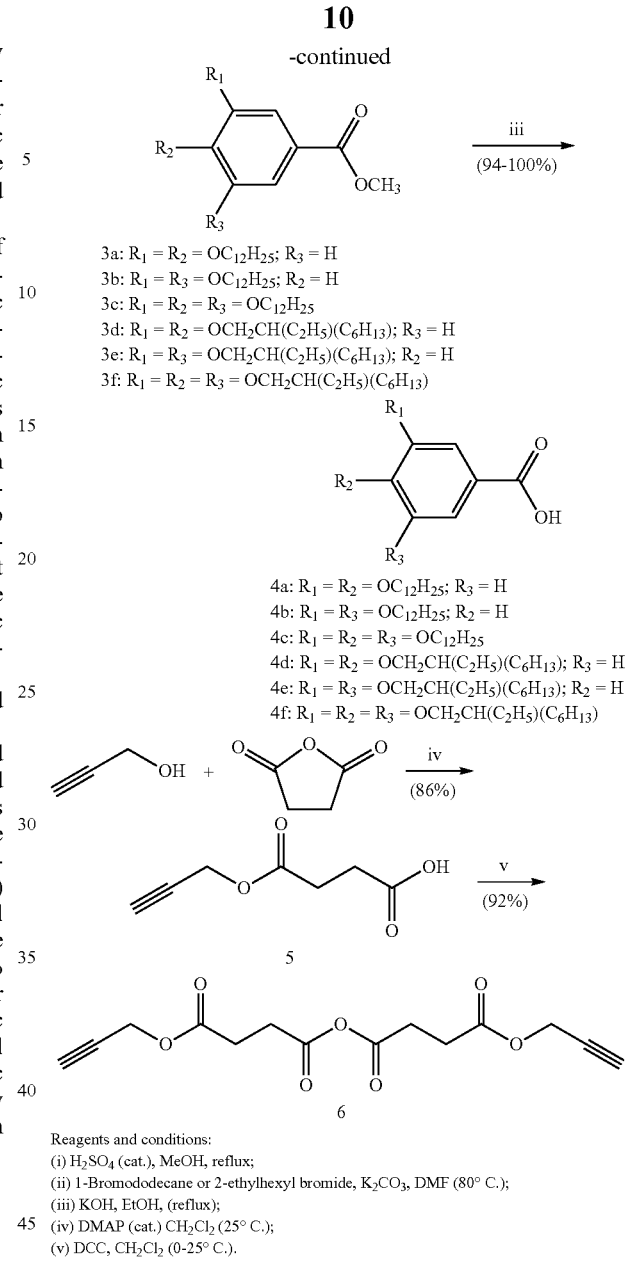

Reagents and conditions:
(i) $H_2SO_4$ (cat.), MeOH, reflux;
(ii) 1-Bromododecane or 2-ethylhexyl bromide, $K_2CO_3$, DMF (80° C.);
(iii) KOH, EtOH, (reflux);
(iv) DMAP (cat.) $CH_2Cl_2$ (25° C.);
(v) DCC, $CH_2Cl_2$ (0-25° C.).

The modular methodology elaborated for the preparation of libraries of amphiphilic Janus glycodendrimers involves three independent steps. The first one consists of the synthesis of three libraries of twin-hydrophobic dendrons functionalized with alkyne directly attached to their apex, via a succinic ester at their apex, or with azide directly attached to the apex (Scheme 2). In the first step of this synthesis, pentaerythritol 7 was monoprotected with p-anisaldehyde under acidic conditions to generate the methoxybenzylidene acetal 8 in 80% yield.[ii] Compound 8 was etherified with propargyl bromide to produce 9 in 91% yield after column chromatography.[iii] Deprotection of 9 with HOAc in water yielded 10 (90% yield). Esterification of 10 with 4a,b,c,d in the presence of DCC/DPTS in $CH_2Cl_2$ produced 11a,b,c,d in 33-95% yield after column chromatography. Bromination of 7 with HBr, $H_2SO_4$—AcOH at reflux generated 12 in 34% yield which upon reaction with $NaN_3$ in DMSO at 110° C. for 16 h produced 13 in 92% yield. Esterification of 13 with 4a,b,c,d,e,f with DCC/DPTS in $CH_2Cl_2$ at 25° C. generated 14a,b,c,d,e,f in 87 to 99% yield. The second library of hydrophobic twin-dendrons functionalized with alkynes on their periphery contains a succinic ester spacer that connects the alkyne to the pentaerythritol branching point (Scheme 2, bottom). In this case, pentaerythritol 7 was monoprotected as benzylidene acetal 15[iv] (61% yield), which after esterification with 4a,b,c produced 16a,b,c in 93 to 98% yield. Deprotection of the benzylidene acetal by hydrogenolysis using Pd/C and $H_2$ generated 17a,b,c in 99 to 100% yield. The esterification of 17a,b,c with the acetylene anhydride 6,[v] that was prepared by the esterification of propargyl alcohol with succinic anhydride followed by dehydration with DCC (bottom of Scheme 1), produced 18a,b,c in 60 to 88% yield.

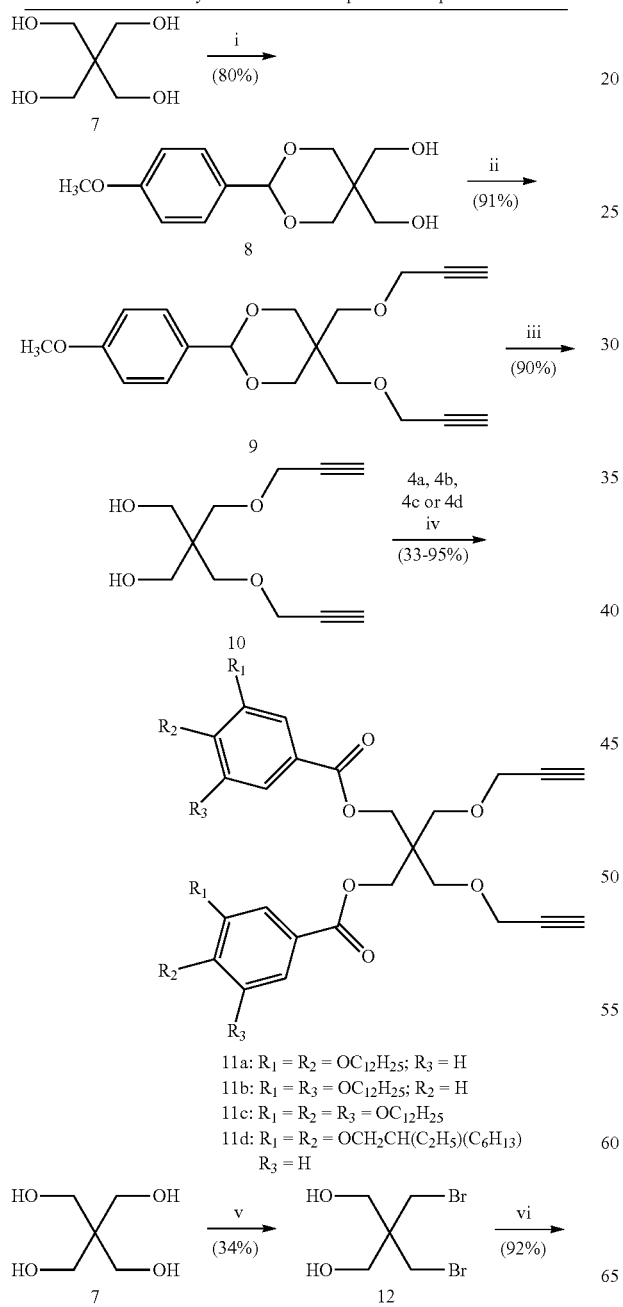

Scheme 2. Synthesis of the Twin-Hydrophobic Dendrons Functionalized with Alkyne and Azide Groups at their Apex -continued

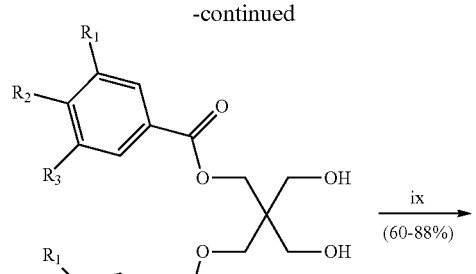

17a: $R_1 = R_2 = OC_{12}H_{25}$; $R_3 = H$
17b: $R_1 = R_3 = OC_{12}H_{25}$; $R_2 = H$
17c: $R_1 = R_2 = R_3 = OC_{12}H_{25}$

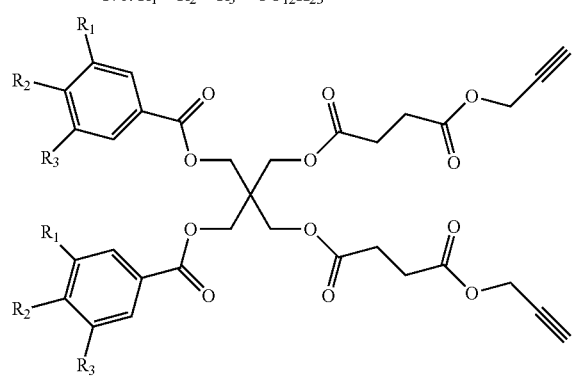

18a: $R_1 = R_2 = OC_{12}H_{25}$; $R_3 = H$
18b: $R_1 = R_3 = OC_{12}H_{25}$; $R_2 = H$
18c: $R_1 = R_2 = R_3 = OC_{12}H_{25}$

Reagents and conditions:
(i) p-Anisaldehyde, HCl, water (25° C.);
(ii) Propargyl bromide, NaH, DMF (0-25° C.);
(iii) $CH_3CO_2H$-water (50° C.);
(iv) DCC, DPTS, $CH_2Cl_2$ (25° C.);
(v) HBr, $H_2SO_4$ — AcOH (reflux);
(vi) $NaN_3$, DMSO (110° C.);
(vii) Benzaldehyde, HCl, water,
(vii) $H_2$, Pd/C, MeOH — $CH_2Cl_2$ (25° C.);
(ix) 6, DMAP, pyridine, $CH_2Cl_2$ (25° C.).

Synthesis of the Glycosyl Azides of D-Galactose, D-Mannose and D-Lactose.

The stereoselective synthesis of the glycosyl azides of D-galactose,[vi,vii] D-mannose and D-lactose is outlined in Scheme 3. Acetylation of 19 with $Ac_2O$ at reflux in the presence of AcONa gave the β-anomer 20 (47% yield) that was transformed into the α-anomer 21 with HBr/AcOH. Compound 21 was treated without isolation with $NaN_3$ in DMSO to produce the β-D-glycosyl azide 22 in 98% yield after column chromatography. Standard Zemplén de-O-acetylation of 22 with MeONa in MeOH generated 23 (99%).[vi] Acetylation of 24 with $Ac_2O$ catalyzed by $I_2$ produced the mixture of α- and β-anomers 25 in 99% yield. The α-azide 26 was obtained by reacting 25 with $TMSN_3$ in the presence of $SnCl_4$ in $CH_2Cl_2$ in 96% yield after column chromatography.[vii] Reaction of 26 with MeONa in MeOH at 25° C. produced 27 (99% yield).[vii] Compound 28 was acetylated under the same conditions as for 19 to give the β-anomer 29 (95% yield) which was reacted with 2-bromoethanol in the presence of $BF_3.OEt_2$ in $CH_2C_2$ at 25° C. to give 30. Compound 30 was treated without purification with $NaN_3$ to give 31 (60% for two steps). Standard Zemplén de-O-acetylation of 31 with MeONa in MeOH at 25° C. produced 32 (98%).[viii] Intermediate 29 was also reacted with tetra(ethylene)glycol monotosylate 34. Compound 34 was prepared from tetra(ethylene)glycol, 33, and TsCl in the presence of pyridine as base.[ix]

Scheme 3. Stereoselective Synthesis of the Glycosyl Azides 23, 27, 32 and 37

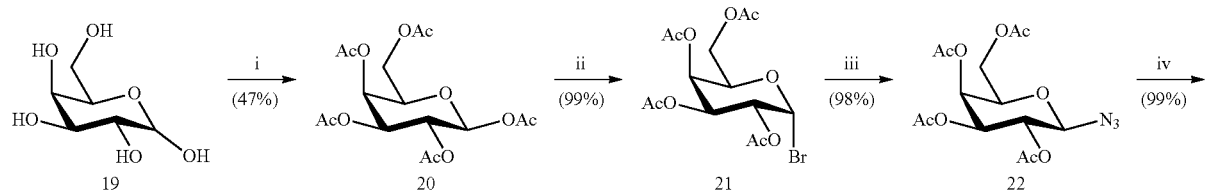

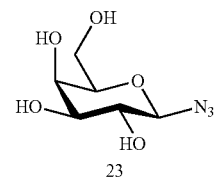

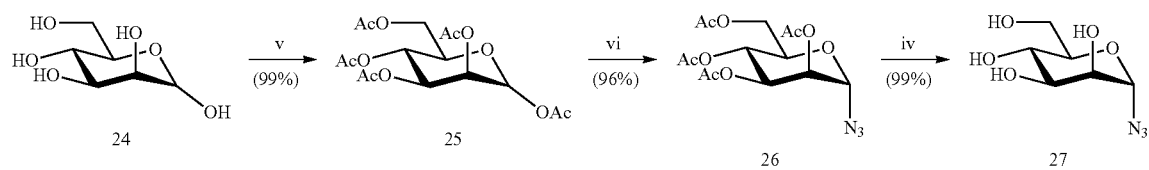

-continued
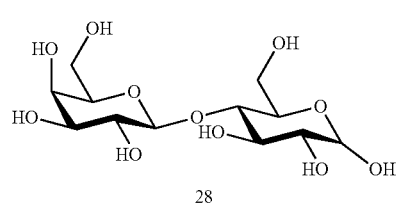
28
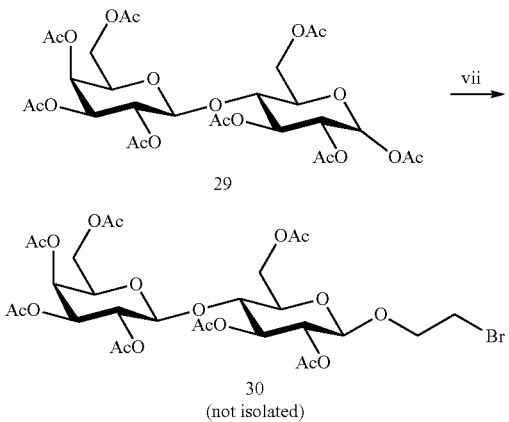
29
30 (not isolated)
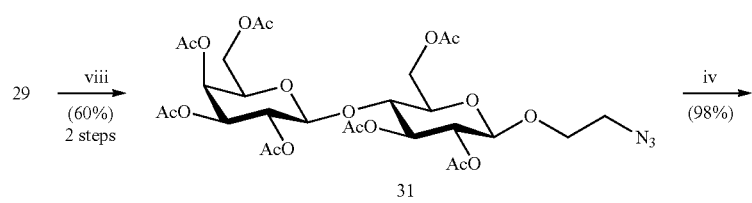
31
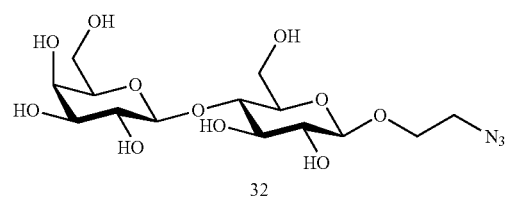
32
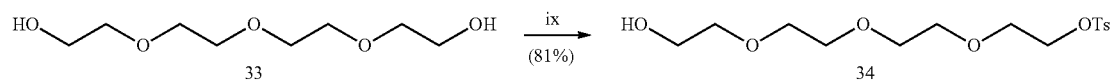
33 → 34
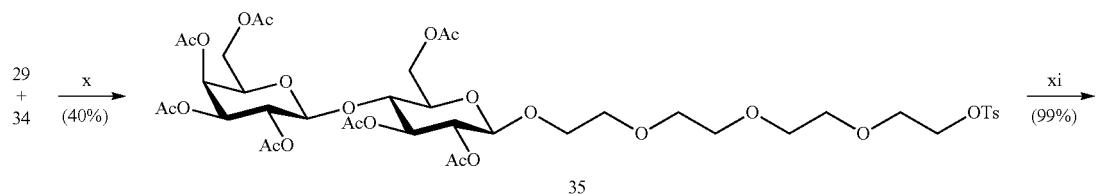
35
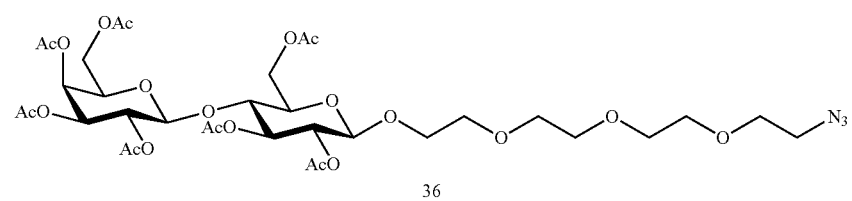
36
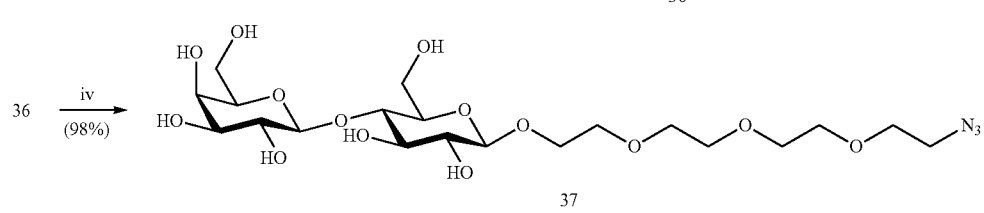
37

Reagents and conditions:
(i) AcONa, Ac$_2$O, (reflux);
(ii) 33% HBr/AcOH (25° C.);
(iii) NaN$_3$, DMSO (25° C.);
(iv) 1M MeONa in MeOH, MeOH (25° C.);
(v) I$_2$, Ac$_2$O, (0-25° C.);
(vi) TMSiN$_3$, SnCl$_4$, CH$_2$Cl$_2$ (25° C.);
(vii) 2-Bromoethanol, BF$_3$·Et$_2$O, CH$_2$Cl$_2$ (0 to 25° C.);
(viii) NaN$_3$, DMF (80° C.);
(ix) TsCl, pyridine, CH$_2$Cl$_2$ (25° C.);
(x) BF$_3$·Et$_2$O, CH$_2$Cl$_2$ (0 to 25° C.);
(xi) NaN$_3$, NaI, DMF (70° C.).

Lactosyl acetate 29 was reacted with 34 in the presence of BF$_3$·OEt$_2$ in CH$_2$Cl$_2$ at 0 to 25° C. and subsequently with NaN$_3$ in the presence of NaI in DMF at 70° C. to generate 36 in 99% yield. Final lactosyl azide 37 was obtained in 98% yield by the reaction of 36 with MeONa in MeOH.

Synthesis of the Propargylated Glycosides of D-Galactose, D-Mannose and D-Lactose.

Compound selective Synthesis 39b,c,d were synthesized in 28%, 90% and 93% yield (after purification by column chromatography) by the monoetherification of ethylene glycol, 38b, di(ethylene)glycol, 38c, and tri(ethylene)glycol, 38d, with propargyl bromide following literature procedures (Scheme 4).[x,xi] Glycosylation of 20, 25 and 29 with propargylated alcohols, 39b,c,d was performed in either CH$_2$Cl$_2$ or CH$_3$CN and was catalyzed with BF$_3$Et$_2$O at 0° C. to yield 40a, d (36 to 59% yield), 42a,b,c,d and 44 in 26 to 79% yield after purification by column chromatography.[xii] Standard Zemplén de-O-acetylation of 40a,d, 42a,b,c,d and 44 with MeONa in MeOH at 25° C. produced 41a,d, 43a,b,c,d and 45 in 82 to 100% yield.[xi,xii]

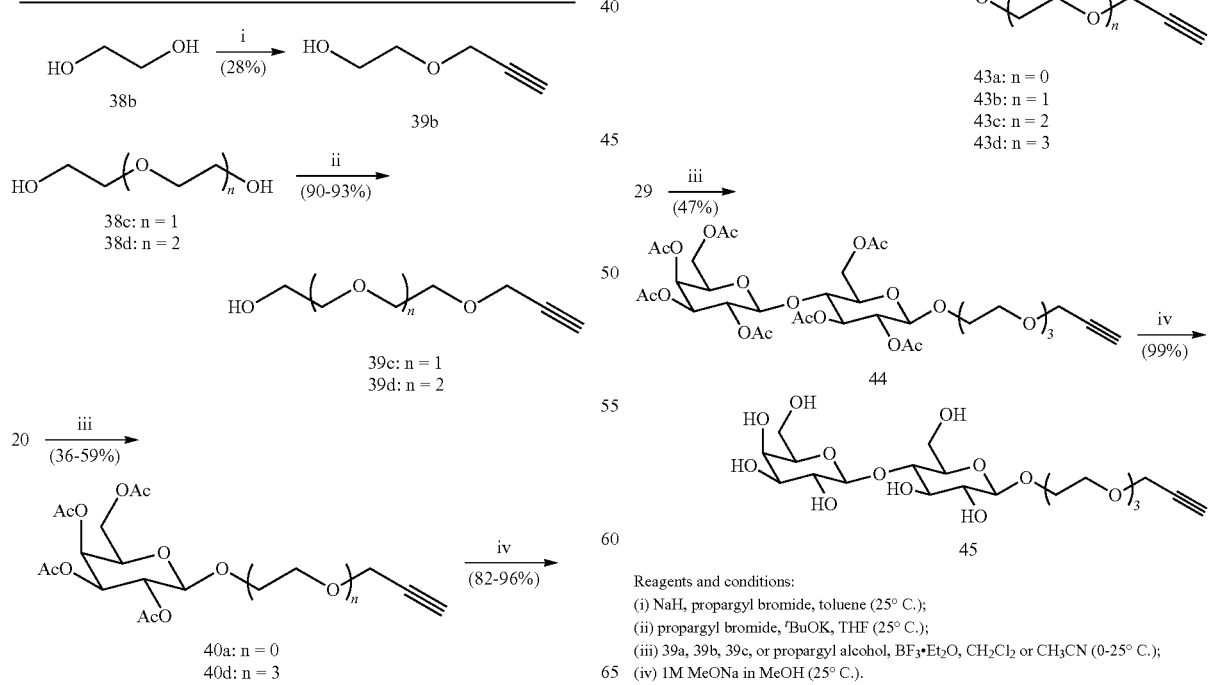

Scheme 4. Synthesis of the propargylated Glycosides 41a, 41d, 43a, 43b, 43c, 43d and 45

Reagents and conditions:
(i) NaH, propargyl bromide, toluene (25° C.);
(ii) propargyl bromide, $^t$BuOK, THF (25° C.);
(iii) 39a, 39b, 39c, or propargyl alcohol, BF$_3$·Et$_2$O, CH$_2$Cl$_2$ or CH$_3$CN (0-25° C.);
(iv) 1M MeONa in MeOH (25° C.).

Accelerated Modular Synthesis of Two Constitutional Isomeric Libraries Containing Twelve *Amphiphilic Janus Glycodendrimers Presenting* D-Mannose and D-Galactose.

The first of the two constitutional isomeric libraries of amphiphilic Janus glycodendrimers was synthesized by an accelerated modular synthesis via click chemistry-mediated assembly[xiii] of the twin-hydrophobic dendrons containing alkynes directly attached to their apex, 11a,b,c from Schemes 2, with the glycosyl azides 23, 27 of D-galactose and D-mannose from Scheme 3. This processing generates the six amphiphilic Janus glycodendrimers 46aa,ab,ba,bb,ca,cb given in the left two columns of Scheme 5. The second constitutional isomeric library was produced by click chemistry of the twin-hydrophobic dendrons containing the azide groups at their apex, 14a,b,c from Scheme 2, with the glycosyl alkynes 41a, 43a from Scheme 4 to generate the six amphiphilic Janus glycodendrimers 47aa,ab,ba,bb,ca,cb from the right side two columns of Scheme 5. These constitutional isomeric libraries were expected to select the most suitable synthesis and products.

FIG. 17 shows modular synthesis of constitutional Isomeric Libraries 1 (46aa to 46cb) and 2 (47aa to 47cb) Containing twelve Amphiphilic janus glycodendrimers with D-mannose and D-galactose and the summary of their self-assembly by injection of their THF solution into water. Reagents and conditions: (i) $CuSO_4 \cdot 5H_2O$, sodium ascorbate, THF/water (25° C.).

Self-Assembly of Janus Glycodendrimers by Injection of their THF or Ethanol Solution into Water and Analysis by DLS, Cryo-TEM, and Micropipette-Aspiration Experiments. Hard and Soft Assemblies.

The simplest method for the self-assembly of amphiphilic molecules into vesicles and liposomes involves the injection of their solution in a water-miscible solvent such as ethanol or THF into water or buffer. This methodology has been shown to be efficient for the self-assembly of amphiphilic Janus dendrimers into monodisperse vesicles called dendrimersomes. The resulting assemblies were first analyzed by dynamic light scattering (DLS) for size, polydispersity (PDI), and stability in time. Assemblies stable in time were subsequently analyzed by cryogenic-transmission electron microscopy (cryo-TEM) to determine their structure. Sharp edges in various supramolecular assemblies indicate structures generated from crystalline unilamellar membranes that will be called hard assemblies while continuous surfaces indicate fluid or soft assemblies. Micropipette aspiration experiments carried out on giant vesicles obtained by hydration are complementary to cryo-TEM experiments in the discrimination between hard and soft glycodendrimersomes. This combination of methods will be used to discuss the results summarized in Scheme 5 for the constitutional isomeric libraries 1 and 2. Compounds 46aa,ab display limited solubility in THF. All other Janus glycodendrimers from Scheme 5 are soluble in THF but not in ethanol. Assemblies of compounds 46aa,ab produced by the injection of 100 μL of their solution containing 1.25 mg/mL in THF, into 2 mL of millipore water generated a final concentration of 0.0625 mg/mL that is stable for less than one hour. To overcome the limited solubility of 46aa,ab in THF, various modifications of their primary structure were investigated. They include the replacement of n-alkanes from their hydrophobic twin-dendrons with branched alkanes and incorporation of various hydrophilic and hydrophobic spacers in different parts of the Janus glycodendrimer. The rest of these modifications will be discussed in the next sections. Injection of aliquot of THF solutions (100 μL of 10 mg/mL) of all Janus glycodendrimers from Scheme 5 except 47aa (100 μL of 1.25 mg/mL), 47ab, 47cb (100 μL both of 2.5 mg/mL), into millipore water (2 mL) followed by five seconds of vortex mixing induces self-assembly into structures stable over time. The size distribution values of all assemblies from Scheme 5 are narrow and within the values that are considered monodisperse for vesicles. Traditionally, monodisperse vesicles are prepared by hydration followed by complex and multiple extrusion procedures.[k,xiv] The dimensions of all assemblies from Scheme 5 range from 114 nm to 126 nm and are suitable for drug delivery and other applications. These Janus dendrimers self-assemble into solid lamellae (FIG. 2a,c), solid vesicles named solid glycodendrimersomes (FIG. 2b), glycodendrimer aggregates, and tubular and polygonal dendrimersomes (FIG. 2c,d).

Figure 2:
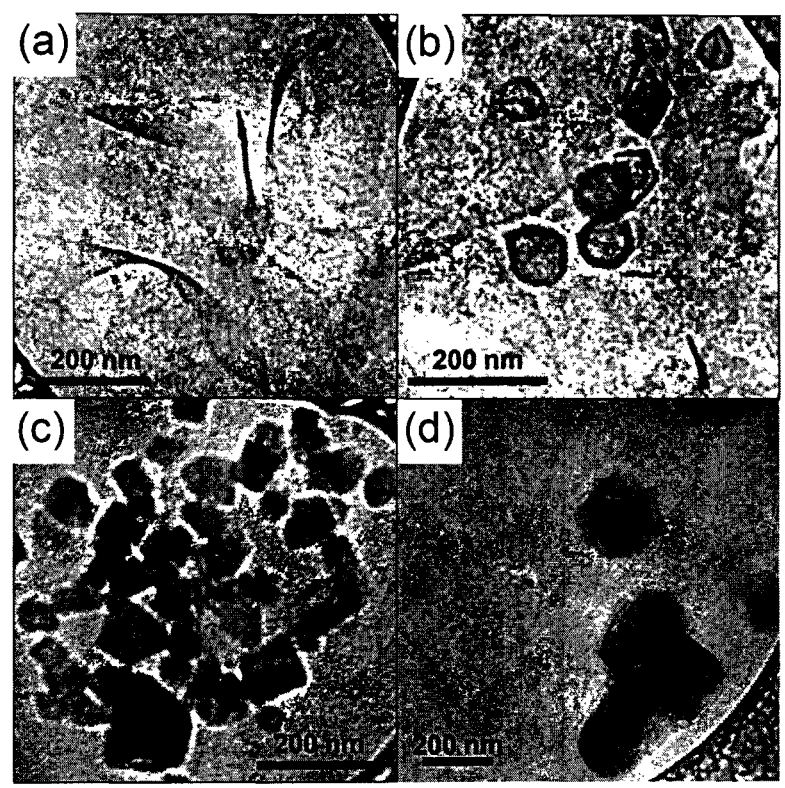
FIG. 2 shows elected cryo-TEM images of solid lamellae assembled from (a) (3,4)12G1-PE-TRZ-Gal$_2$ 46aa; (b) solid glycodendrimersomes assembled from (3,4)12G1-PE-TRZ$_i$-Man$_2$ 47ab; (c) solid lamellae assembled from (3,4,5)12G1-PE-TRZ-Gal$_2$ 46ca; (d) polygonal glycodendrimersomes assembled from (3,4,5)12G1-PE-TRZ-Gal$_2$ 46cb.

Compounds 46aa,ab self-assemble into sheet-like solid lamellae (FIG. 2a,c). This 2D sheet-like as well as other solid morphologies imply that their membrane is either crystalline and stiff or amorphous and below its glass transition temperature. This prevents the closing process required to form a 3D vesicle. A hard or solid vesicle is a 3D particle constructed from a unilamellar bilayered membrane in a similar way as the regular fluid and soft vesicles (FIG. 2b). However, the sharp edges/corners of the structure indicate that its membrane is rigid. The glycodendrimer aggregates are not traditional micelles since a conventional micelle should have a dimension of about two molecular length of the Janus dendrimer, which is much smaller than the size observed here. The glycodendrimer aggregates are hard droplets consisting of a Janus glycodendrimer-rich phase suspended in water which are similar to a hard oil droplet. The phase separation of hydrophilic and hydrophobic segments happens only on the particle surface but not inside where is disordered due to its slow kinetics. Compound 46cb generated a mixture of morphologies indicating that the rates of formation of each morphology are similar (FIG. 2d) and/or that they have similar stabilities. It should be noted that at concentrations smaller than 0.5 mg/mL, the nano-tubular morphology is dominant, while at concentrations higher than 0.5 mg/mL, the polygonal glycodendrimersome that has a shape similar to an icosahedron is dominant (FIG. 2d). A quantitative and comparative analysis of solid and soft assemblies by a combination of cryo-TEM and micropipette-aspiration experiments will be presented in a different section.

Modular Synthesis and Analysis of Library 3 Containing Eleven *Amphiphilic Janus Glycodendrimers with Branched Alkyl Groups in their Hydrophobic Part and* D-Mannose or D-Galactose.

The low solubility of Janus glycodendrimers from the constitutional isomeric libraries 1 and 2 (Scheme 5) prompted us to explore pathways to prevent membrane crystallization, enhance solubility and ability of amphiphilic Janus dendrimers to generate soft assemblies.

Figure 3:
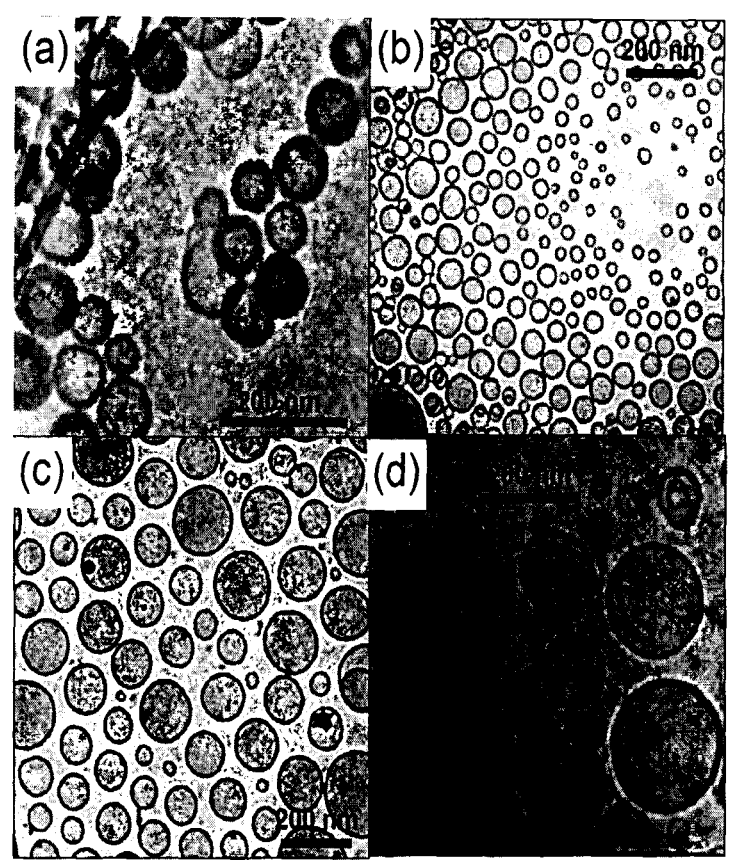
FIG. 3 shows selected cryo-TEM images of glycodendrimersomes assembled from (a) (3,4)2Et8G1-PE-TRZi-Man$_2$ 49aa; (b) (3,4)2Et8G1-PE-TRZ$_i$-3EOGal$_2$ 49ab; (c) (3,5)2Et8G1-PE-TRZi-3EOGal$_2$ 49bb; and (d) (3,4,5) 2Et8G1-PE-TRZi-3EOGal$_2$ 49cb.

Three twin-hydrophobic dendrons containing branched alkyl groups in their hydrophobic part and alkyne (11d) or azide (14d,e,f) groups were combined with the carbohydrates 23 and 27 containing azide groups, with the carbohydrates 41a and 43a containing the alkyne directly attached, and with 41d that has the alkyne attached to the carbohydrate via a tri(ethylene)glycol spacer. This provided eleven Janus glycodendrimers (Scheme 6). All these Janus glycodendrimers are soluble in THF (10 mg/mL to 40 mg/mL) and after injection produced concentrations in water from 0.5 mg/mL up to 2 mg/mL. The injection in water of their THF solutions generated assemblies with polydispersity ranging from 0.03 to 0.20. Five of these Janus glycodendrimers, 49ac,aa,ab,bb,cb, produced only soft glycodendrimersomes with size ranging from 42 nm to 167 nm. Compounds 49ba,ca assemble into mixtures of soft glycodendrimersomes and dendrimer aggregates, 48aa,ab,cc into dendrimer aggregates, while 49bc into mixtures of dendrimer aggregates and cubosomes. The analysis of the structure of cubosomes will be presented in a later section. These experiments demonstrated a remarkable improvement in solubility, polydispersity and ability to generate single-component glycodendrimersomes. Selected examples of cryo-TEM experiments are shown in FIG. 3. Compounds with branched alkyl chains in the hydrophobic side and a long tri(ethylene)glycol spacer in the hydrophilic side (FIG. 3b, c, d) induce the formation of high-quality glycodendrimersomes. Interestingly, for the branched compound without hydrophilic spacer (FIG. 3a), the resulting glycodendrimersomes possess walls with two distinct membrane thicknesses. The extension of the thick wall is about three times larger than that of the regular thin wall which is about the thickness of two Janus dendrimer length (~7 nm). The inner wall of the thick vesicles has darker color than the rest of the wall, indicating a more ordered and denser packing of molecules forming the vesicle wall, while the lighter color signifies a disordered aggregate of compound-rich phase surrounding the vesicle.

This appearance suggests that the absence of the hydrophilic spacer does not favor the assembly of unilamellar membranes but instead induces the formation of kinetically trapped intermediates such as thick-wall vesicles that cannot be stabilized into unilamellar vesicles.

FIG. 18 shows modular synthesis of Library 1 (48aa to 49bb) containing eleven amphiphilic Janus glycodendrimers with branched hydrophobic alkyl groups and D-mannose and D-galactose in their hydrophilic part and the summary of their self-assembly by injection of their THF solution into water. Reagents and conditions: (i) $CuSO_4.5H_2O$, sodium ascorbate, THF/water (25° C.). Reagents and conditions: (i) $CuSO_4.5H_2O$, sodium ascorbate, THF/water (25° C.).

The efficiency of vesicle formation is also dependent on the number and position of the alkyl chains from the hydrophobic side. The 3,4-disubstitution pattern shown in FIG. 3a produces mostly vesicles. For the compound with 3,5-disubstitution pattern (49ba), the coexistence of thick-wall glycodendrimersomes and large dendrimer aggregates is observed, while for compound with 3,4,5-trisubstitution (49ca), the formation of dendrimer aggregates is dominant with only few glycodendrimersomes being observed.

Modular Synthesis and Analysis of Library 4 Containing Six Janus Glycodendrimersomes with a Succinic Ester Spacer in the Hydrophobic Part and D-Mannose, D-Galactose or D-Lactose.

A second approach to enhance solubility and flexibility involved the incorporation of a succinic ester spacer in between the twin-hydrophobic dendron and its alkyne groups, while maintaining linear n-alkyl groups on the periphery of the dendron (Scheme 7). The twin-hydrophobic dendrons 18a,b, c were coupled with carbohydrates containing the azide group attached directly (23, 27), to generate the six Janus glycodendrimers from Scheme 7. These molecules show acceptable solubility in THF to result after injection in a concentration of 0.25 to 0.5 mg/mL in water. The polydispersity of their assemblies is narrow (0.14 to 0.21).

FIG. 19 shows modular synthesis of Library 4 (50aa to 50cb) containing six amphiphilic Janus glycodendrimers with hydrophobic linear n-alkyl groups, a succinic ester spacer, D-mannose, D-galactose or D-lactose in their hydrophilic part and the summary of their self-assembly by the injection of their THF solution into water. Reagents and conditions: (i) $CuSO_4.5H_2O$, sodium ascorbate, THF/water (25° C.).

Figure 4:
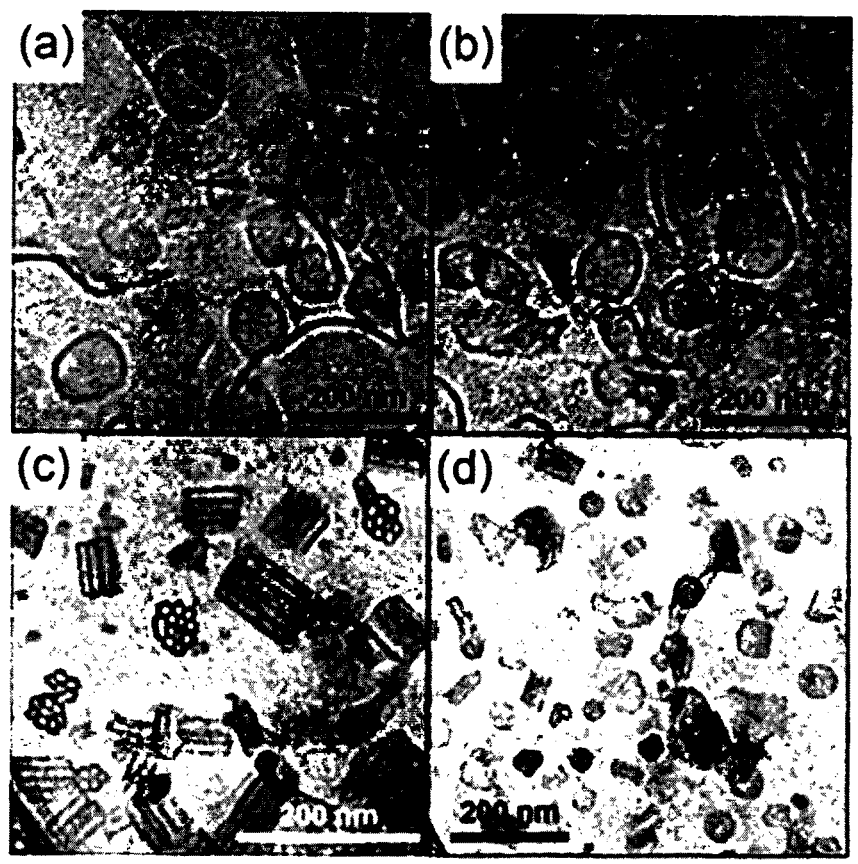
FIG. 4 shows selected cryo-TEM images of solid lamellae and solid glycodendrimersomes assembled from (a) (3,4)

The dimensions of the supramolecular assemblies resulted from these Janus dendrimers range from 131 to 182 nm. However, their 3,4-disubstituted dendrons (50aa,ab) generate solid lamellae and solid vesicles, while the 3,5-disubstituted compounds (50ba,bb) produce dendrimer aggregates. Only the 3,4,5-trisubstituted molecules (50ca, cb) lead to interesting assemblies consisting of mixtures of tubular and soft spherical glycodendrimersomes and also bundles of tubular dendrimersomes. FIG. 4 illustrates examples of these assemblies. Solid vesicles displaying an asymmetric shape with sharp edges are shown in FIG. 4a,b. The curved feature in the TEM images is the projection of curved solid lamellae with an edge-on orientation. They are membranes that are too stiff to form a 3D solid vesicle by closing a broken solid vesicle.

The nano-tubular structures shown in FIG. 4c tend to aggregate and produce bundles at relatively high concentration. At concentrations lower than 0.25 mg/mL, single tubes are observed. The hexagonal arrangement of rings observed in FIG. 4c is the projection of tubular bundles with their long axis perpendicular to the film. This image indicates that the nano-tubes possess uniform diameter and length. In addition, their diameter to length aspect ratio appears to be constant.

Modular Synthesis and Analysis of Library 5 Containing Twelve Janus Glycodendrimers with Linear Hydrophobic n-Alkyl Groups and D-Mannose or D-Galactose Connected by Mono-, Di- and Tri(Ethylene)Glycol Spacers.

Libraries 1, 2 (Scheme 1) and 4 (Scheme 7) contained linear n-alkyl groups in their hydrophobic part. In order to increase solubility and flexibility, a succinic ester spacer was incorporated between the hydrophobic and hydrophilic fragments of the Janus dendrimers in the case of library 4. Libraries 1,2,4 generated mostly hard assemblies and tubular vesicles. However, the replacement of the linear n-alkyl groups with a branched hydrophobic segment together with a tri(ethylene)glycol spacer produced only vesicles (see 49ab,bb,cb from library 3 of Scheme 6). Therefore, we decided to investigate the role of ethylene glycol spacers in the case of Janus dendrimers containing linear n-alkyl groups in their hydrophobic part. Subsequently, we combined 14a,b,c with 43b,c, 41d and 43d containing ethylene glycol, di(ethylene)glycol and tri(ethylene)glycol spacers between D-mannose or D-galactose and the alkyne group to generate the library 5 from Scheme 8 containing twelve Janus glycodendrimers. All Janus glycodendrimers from Scheme 8 are soluble both in THF (5 to 10 mg/mL) and in ethanol. After injection the concentration in water ranges from 0.25 to 0.5 mg/mL. The polydispersity of these assemblies ranges from 0.05 to 0.26 while their size varies from 43 to 222 nm. The 3,4-disubstituted hydrophobic segments of the Janus dendrimer (top row in Scheme 8) lead to solid lamellae for 51aa and solid vesicles for 51ab,ac,ad. The replacement of the 3,4-disubstituted hydrophobic part with a 3,5-disubstituted (middle row in Scheme 8) produced soft vesicles for 51ba,bb,bc and cubosomes for 51bd. The assembly of cubosomes as a result of shortening the ethylene glycol spacer was also observed for simple dendrimersomes. The transition from 3,5-disubstitution to 3,4,5-trisubstitution (bottom row in Scheme 8) changed the assemblies in water from soft to hard generating solid lamellae for 51ca,cb,cc,cd. Selected examples of soft and hard assemblies from library 5 are shown in FIG. 5. The dependence of the structure assembled in water on the 3,4-, 3,5- and 3,4,5-substitution patterns is in line with the molecular mechanism of unilamellar structure formation reported in a previous publication for simple dendrimersomes.

FIG. 20 shows modular synthesis of Library 5 (51aa to 51cd) containing twelve amphiphilic Janus glycodendrimers with linear n-alkyl groups, D-mannose or D-galactose connected via mono-, di- and tri(ethylene)glycol spacers and summary of self-assembly by injection of THF or EtOH solution into water. Reagents and conditions: (i) $CuSO_4.5H_2O$, sodium ascorbate, THF/water (25° C.).

Modular Synthesis of the Library 6 Containing Five Janus Glycodendrimers with and without Succinic Ester Spacer and D-Lactose Connected Via Mono- and Tetra(Ethylene) Glycol Spacers.

The main goal of these investigations is to delineate the molecular principles that produce single-type soft glycodendrimersomes and other complex glycoarchitectures with D-mannose, D-galactose and D-lactose on their periphery. The experiments reported in Schemes 6 and 8 provided molecular instructions for the design of soft glycodendrimersomes presenting D-mannose and D-galactose. Scheme 9 demonstrates the development of the molecular principles that yield glycodendrimersomes with D-lactose as sugar headgroup. Based on the experience accumulated with the other libraries, 3,4-, 3,5- and 3,4,5-di- and trisubstituted hydrophobic patterns with and without succinic acid ester and alkyne, 11a,b,c, and 18c, were selected and combined with D-lactose-containing ethylene glycol and tetra(ethylene)glycol spacers connected to the azide group, 32 and 37, to generate the five Janus glycodendrimers reported in Scheme 9. All these Janus glycodendrimers are soluble in THF (5 to 40 mg/mL) and their assemblies are stable over time in water in the range of concentrations from 0.25 to 2.0 mg/mL. The polydispersity of these assemblies ranges from 0.15 to 0.29, while their size varies from 46 to 406 nm. With the exception of 52ad, the only 3,4-disubstituted compound which forms a mixture of soft vesicles and bundles of rod-like micelles, all other Janus glycodendrimers generate soft glycodendrimersomes. It is interesting that 52ad forms rod-like micelles aligned side by side with each other. This complex arrangement leads to a long ribbon-like structure (FIG. 6b).

FIG. 21 shows modular synthesis of Library 6 (52ad to 52dd) containing five amphiphilic Janus glycodendrimers with linear n-alkyl groups and D-lactose and summary of self-assembly by injection of THF solution into water. Reagents and conditions: (i) $CuSO_4.5H_2O$, sodium ascorbate, THF/water (25° C.).

Modular Synthesis of Library 7 Containing Six Janus Glycodendrimersomes with Branched and Linear Hydrophobic Alkyl Groups and D-Lactose Connected Via a Tri(ethylene) Glycol Spacer.

The diversity of glycodendrimersomes with D-lactose was increased by combining linear and branched alkyl groups in the hydrophobic part of the twin-dendrons containing azides (14a,b,c,d,e,f) with D-lactose containing the alkyne group attached via a tri(ethylene)glycol spacer (45) (Scheme 10). This strategy provided six new Janus glycodendrimers. Library 7 generated a remarkable series of results. All Janus glycodendrimersomes from Scheme 9 are soluble in THF and their assemblies are stable over time in water in concentrations higher than 0.5 and up to 2.0 mg/mL. Even at these high concentrations in water these assemblies display size distributions ranging from 0.17 to 0.23 and sizes ranging from 97 to 393 nm. The Janus glycodendrimer 53aa assembles in a combination of soft glycodendrimersomes and rod-like micelles, while 53ca produces solid vesicles and solid lamellae. Compounds 53ba,da,ea,fa self-assemble into soft glycodendrimersomes. Representative cryo-TEM experiments are summarized in FIG. 7.

The morphology of rod-like micelles assembled from 53aa (FIG. 7a) is similar to that obtained from 52ad (FIG. 6b). At the same time, it was observed that the self-assembly tendency shifted toward a higher concentration of soft vesicles for the case of 53aa compared with 52ad, which indicates that vesicle formation is favored by a shorter hydrophilic spacer (tri-53aa, vs tetra(ethylene)glycol, 52ad).

FIG. 22 shows modular synthesis of Library 7 (53aa to 53fa) containing six amphiphilic Janus glycodendrimers with linear and branched alkyl groups and D-lactose and their self-assembly by injection of their THF solution into water. Reagents and conditions: (i) $CuSO_4.5H_2O$, sodium ascorbate, THF/water (25° C.).

The small sheet-like features seen in FIG. 7c are a suspension of solid lamellae coexisting with a high concentration of soft glycodendrimersomes. Libraries 6 and 7 consist of glycodendrimersomes with D-lactose as head group that will allow the investigation of their physical properties, as well as molecular recognition and agglutination experiments with D-lactose-binding proteins.

Discrimination Between Hard and Soft Glycodendrimersomes and Determination of their Structure and Physical Properties.

A combination of techniques including confocal microscopy on giant glycodendrimersomes containing hydrophobic dyes in their membrane, micropipette-aspiration experiments on giant glycodendrimersomes, and cryo-TEM before and after annealing above the melting temperature of the assembly was used to discriminate between soft or fluid and hard or crystalline glycodendrimersomes. FIG. 8 shows examples of micropipette-aspiration experiments performed on soft (left two images in FIG. 8a) and hard (right two images in FIG. 8a) giant glycodendrimersomes prepared by hydration experiments. The solid membranes made from 50aa,ad cannot be aspirated, and, therefore, the vesicle from 50aa buckles in response to the applied suction pressure. On the other hand, the mechanical properties of fluid dendrimersomes can be determined through the micropipette-aspiration in which a controlled pressure applied to the vesicle results in a uniform tension along the membrane. Two such examples generated from 51bc,dd are shown in FIG. 8a. FIG. 8b illustrates the comparison of the elastic moduli of glycodendrimersomes obtained from 52dd, 51bc,bb with that of polymersomes made from the diblock copolymer $PEO_{30}$-b-$PBD_{46}$ and of liposomes made from the lipid HSPC.[xv] In response to the increase in membrane tension, the fluid vesicle stretches and exhibits a lateral expansion, resulting in an increase in area. The slope of the area change in response to the membrane tension is the elastic modulus of the membrane. The linear change in membrane area in response to the applied membrane tension indicates that the glycodendrimersomes obtained from 52dd, 51bc,bb are generated from a fluid unilamellar membrane (FIG. 8c). Vesicles of 52dd were able to stretch to critical area strains greater than 20%, while vesicles of 51bc were only able to extend to 5-10% critical area strains. These results show that the membrane of 52dd has an elastic modulus of 49.6±15 dyne/cm (average result obtained with 11 vesicles) and is more elastic than that of 51bc, with an elastic modulus of 163±30 dyne/cm (average result obtained with 13 vesicles). FIG. 8d indicates that unlike polymersomes of $PEO_{30}$-b-$PBD_{46}$, vesicles of 52dd display hysteresis. The filled circles are based on measurements during initial vesicle stretching. Open circles are measurements taken during vesicle relaxation. FIG. 8e,f presents confocal microscopy images of giant soft glycodendrimersomes formed by 51bc and 52dd, respectively. A microphotograph of giant solid glycodendrimersome is shown in FIG. 8g. The giant glycodendrimersomes (size larger than 10 μm) were prepared by the film hydration method.[a] Soft vesicles (FIG. 8e, f) exhibit a uniform spherical shape, while hard vesicles (FIG. 8g) display a less regular structure, thus confirming the results of the cryo-TEM and micropipette-aspiration experiments.

The thickness of the membrane forming the vesicle wall was measured from the cryo-TEM images by using a published method.[xvi] The membrane thickness is approximately equal to the length of two Janus glycodendrimers (6.8±0.5 to 7.5±0.5 nm) that construct the unilamellar bilayer structure except for the thick vesicles obtained from 49aa,ba. The annealing effect of the solid lamellae was also studied. FIG. 9 shows the cryo-TEM images of the nanostructure formed by 51cb before and after annealing. The sample was prepared by injection at room temperature with a concentration of 0.5 mg/mL in water.

As shown in FIG. 9a, a solid lamellae constructed from a stiff membrane formed. Interestingly, after annealing this solution at 60° C. for 30 min, a morphological change from solid lamellae to spherical vesicles is observed.

This result indicates that the solid lamellae with sharp edges in the as prepared solution represents a kinetically trapped morphology constrained by the stiff membrane. Upon annealing at higher temperature, the membrane become flexible and closes up to form a soft spherical vesicle. The wall may become solid again or change back to a solid lamellae when the temperature is brought back to room temperature. So far, the vesicles investigated remain smooth and spherical in shape as in the case shown in FIG. 9b. These experiments reveal that glycodendrimersomes are the thermodynamic product of the self-assembly in water. To our knowledge, the transition from tubular to solid lamellae and to spherical vesicles upon annealing was observed only once before in the case of a stereo-complex of amphiphilic peptides.[b] The experiments reported here indicate that this morphological change seems to be general for solid aggregates generated from hard amphiphilic assemblies in water. A detailed study on hard assemblies produces from Janus glycodendrimers will be reported in due time.

Assembly of Glycodendrimersomes with Different Dimensions by the Injection Method.

Vesicles with different diameter and narrow polydispersity are desirable to relate structure to activity aspects in bio-assays important for use as delivery nano-containers, vaccines, lectin blockers, targeted delivery devices and for molecular recognition experiments with programmable glycan ligand presentations of biological membranes. They are also required for the determination of their structure and physical properties. Therefore, the preparation of glycodendrimersomes with different dimensions by the injection method was investigated. FIG. 10 shows the concentration-size relation experiments on the assembly of glycodendrimersomes from 49bb by injection in water with a final concentration in water ranging from 0.125 mg/mL to 10 mg/mL.

The DLS results (FIG. 10a) demonstrated the increase of vesicle size with increasing the final concentration in water. At 10 mg/mL, the solution is opaque due to the large particle size and high particle density but does not exhibit any sign of precipitation. At a concentration above 10 mg/mL, vesicles with an average size of the order of a micrometer were obtained. These results demonstrated that is possible to generate giant glycodendrimersomes by simple injection. These vesicles are stable in water and buffer even at concentrations higher than 10 mg/mL. FIGS. 10b to 10f show the corresponding cryo-TEM images at the indicated concentration. The relationship between size and concentration observed in DLS is further supported by cryo-TEM. Moreover, the cryo-TEM images collected at a concentration higher than 4 mg/mL reveal multiple large vesicles squeezing themselves in the copper grids because of large size and high particle density. These vesicles freely deform when touching each other, indicating a high level of flexibility of the soft vesicle wall. Other glycodendrimersomes in this study exhibit a similar relationship between size and concentration.

Structure of Glycodendrimercubosomes by the Analysis of the Fourier Transform of their Cryo-TEM.

Cubosomes are 3D bicontinuous liquid crystalline particles with cubic lattice symmetry assembled from amphiphilic molecules displaying a large specific surface area. FIG. 11 details the cryo-TEM images of cubosomes formed by 51bd at a concentration of 1.0 mg/mL. In the cubosome particle, the molecules form bicontinuous hydrophilic and hydrophobic channels, where bicontinuous describes the presence of two non-intersecting hydrophilic regions separated by the bilayer. The unique structure of cubosomes with a tortuous diffusion pathway and their ability to simultaneously incorporate water- and oil-soluble compounds are the basis of an active area of research for controlled-release applications. The structure of cubosomes can be elucidated by the analysis of the Fourier transform of their cryo-TEM images. FIG. 11a, b shows cubosome particles observed by cryo-TEM at different orientations. The texture of the particle results from the projection of the bicontinuous inner structure of the cubosome. The inset in FIG. 11a shows the Fourier transform of the indicated area. The hexagonal arranged bright spots are the {110} crystallographic plane reflections that suggest that the cubosome particle is oriented along the [111] direction. In the inset of FIG. 12b, the square pattern resulted from particles oriented along the [112] direction that shows the reflections of {111} plane.

Based on these observations, the cubosome of 51bd exhibits a Pn3m cubic symmetry. The particle in FIG. 11b is tilted about 20° with respect to that in FIG. 11a. This analysis was used to assign all glycodendrimercubosomes reported in Schemes 1 to 10.

Molecular Design Principles for Janus Glycodendrimers Assembling into Glycodendrimersomes with Narrow Size Distribution and Stable Over Time in Buffer.

FIG. 12 outlines the structures of the sixteen Janus glycodendrimers that self-assemble by injection in water and/or in buffer only in single-type soft glycodendrimersomes.

The resulting soft glycodendrimersomes exhibit narrow molar mass distribution and are stable over time. Their dimensions, polydispersity and stability in water (blue and yellow marked), PBS and HEPES buffers (yellow marked), are indicated in FIG. 12. The dimensions of glycodendrimersomes assembled in water and PBS are similar but smaller than those assembled in HEPES. Ten of these Janus glycodendrimersomes highlighted in yellow, assemble in glycodendrimersomes that are also stable in buffer. Six of them contain a tri(ethylene)glycol or tetra(ethylene)glycol spacer in the hydrophilic part and a branched or linear 3,5-disubstituted pattern in the hydrophobic part. Three of them contain the same oligooxyethylenic spacer length as previous six molecules but have a 3,4,5-branched or linear hydrophobic pattern in the hydrophobic part. Only one among the ten has a 3,4-disubstituted branched hydrophobic pattern with the same hydrophilic spacer length. Based on these observations, the following molecular design principles are established for the structure of Janus glycodendrimers that are expected to produce soft spherical glycodendrimersomes stable in buffer. Any mono- or disaccharide attached via a tri(ethylene)glycol or tetra(ethylene)glycol spacer with a 3,5-disubstituted linear or branched hydrophobic pattern will most probably self-assemble into uniform single-type soft glycodendrimersomes with favorable mechanical properties, narrow molar mass distribution and stability over time in buffer. This conclusion supports previous predictions concerning the dimensions, stability and mechanical properties, elaborated for simple amphiphilic Janus dendrimers and dendrimersomes.

Agglutination of Glycodendrimersomes with Plant, Bacterial and Human Lectins.

Glycodendrimersomes are of interest to enable specific surface contacts of their glycan display with receptors in lectin-targeted delivery of a cargo or as pharmaceuticals when for example they block the lectin-dependent docking of viruses onto cells. An essential prerequisite for considering bioapplications is to ascertain the ligand bioactivity of the sugar head groups in molecular recognition experiments with lectin receptors. Agglutination of glycodendrimersomes by lectins demonstrates an assumed amplification of the multivalency of the carbohydrates at the transition from the Janus glycodendrimer to glycodendrimersome from 2 to n. To reveal general reactivity, we present initial experiments on agglutination of glycodendrimersomes by various types of plant (the plant lectin concanavalin A, Con A, that binds to D-mannose, and the European mistletoe lectin Viscum album L. agglutin, VAA, that reacts with β-galactosides), bacterial (the β-galactoside-binding lectin PA-IL from Pseudomonas aeruginosa, a bacterium affecting cystic fibrosis patients and immunocompromized individuals, that binds to D-galactose) and human galectine-3, Gal-3, and galectine-4, Gal-4, sharing binding to D-lactose. Qualitative agglutination experiments were monitored in 10 mM HEPES buffer by a combination of DLS, UV-vis and cryo-TEM experiments. DLS experiments sense the agglutination process by a size increase in time that is observed upon mixing the appropriate glycodendrimersomes with the corresponding lectin. This correlation of mutually fitting specificities excludes carbohydrate-independent mechanisms.

A change in absorbance was invariably detected, revealing bioactivity of the sugar head groups. Representative UV-vis experiments over a time course of up to 33 min are shown in FIG. 13a for the agglutination of 51ba with PA-IL and of 51bb with Con A. Control experiments for 51ba and 51bb in the absence of the lectin are shown in the bottom of FIG. 13a. A control experiment for sugar specificity, for 51bb with PA-IL, is shown in the bottom of FIG. 13a. The increase in absorbance with time reflects the agglutination process. A concentration dependence of the agglutination of Con A with 51bb together with a control experiment are shown in FIG. 13b. A constant concentration of Con A was used in combination with different concentrations of 51bb.

Finally, FIG. 13c shows the agglutination of glycodendrimersomes of different diameters assembled from 51bb with Con A and the control experiments for each diameter are also presented. In the range of diameters investigated, the smallest glycodendrimersome provides the fastest agglutination, probably due to the highest surface/volume ratio.

These results demonstrate the importance of the injection method for the simple and rapid preparation of soft glycodendrimersomes with different dimensions, mechanical properties, dynamics, adaptability and degree of multivalency. In the next experiment, the concentration of Con A was varied while the concentration of 51bb was maintained constant. The course of agglutination monitored by UV-vis is shown in FIG. 14 a. FIGS. 14b to e describe the agglutination of 51bb with Con A monitored by cryo-TEM.

Having ascertained bioactivity with the plant leguminous and bacterial lectins, we next proceeded to test two human lectins. While sharing specificity to lactose, Gal-3 and Gal-4 have a different molecular design. Gal-3 has a collagenase-sensitive N-terminal tail relevant for aggregation when interacting with multivalent ligands, while Gal-4 presents two carbohydrate recognition domains connected by a 42-amino-acid linker peptide. It was thus of interest to ascertain bioactivity to human lectins as well as characterize the resulting profiles of a monomeric galectin capable to form aggregates with a bivalent protein of this family.

FIG. 15a shows the agglutination of 52bd with Gal-3, while FIG. 15b displays the course of agglutination of 52bd with Gal-4. In both cases, the concentration of 52bd was maintained constant, while the concentrations of Gal-3 and Gal-4 were varied.

Control experiments supporting lectin dependence of the agglutination experiments are also shown in FIG. 15a, b. Evidently, the obtained courses are different, yet reaching similar plateau values. The nature of the lectin thus influences the way agglutination proceeds. In this context, it should be noted that the mode of counter receptor cross-linking on the cell surface will determine the strength of the adhesive contacts (in trans, between "cells") and the response by initiating signaling (in cis, on a "cell" surface), directing attention to further work along this line. Interestingly, the plant toxin followed a saturation kinetics for Gal-3. The agglutination profiles of 52bd with different concentrations of VAA investigated by UV-vis are shown in FIG. 16a, while the similar experiment monitored by cryo-TEM is in FIG. 16b-e. Compound 51ba that contains D-galactose was also agglutinated by VAA and PA-IL, as expected based on the specificity of lectins. These results on courses of agglutination reveal that the glycodendrimersomes react differently to lectins, topology and adaptability of the soft vesicles with favorable mechanical properties playing a role, thus making them valuable models for further studies to relate lectin structure and glycan display on the course of agglutination. To our knowledge this study is one of the most comprehensive when considering the diversity of lectins used.

Seven libraries containing 51 self-assembling amphiphilic Janus glycodendrimers with three types of biogenic carbohydrates in their hydrophilic part have been synthesized by a simple and efficient accelerated modular strategy. These Janus glycodendrimers self-assemble by simple injection of their solution in a water-miscible solvent into water and buffer. The resulting supramolecular structures were analyzed by a combination of methods to determine their structure and to delineate the molecular principles leading to narrow size distribution and stability over time in water and in buffer for single-type soft and hard assemblies, including unilamellar spherical, polygonal and tubular glycodendrimersomes, Janus glycodendrimer aggregates, glycodendrimercubosomes as well as solid lamellae. Sixteen of these amphiphilic Janus glycodendrimers result in glycodendrimersome dimensions that are programmable via the concentration of the solution they are injected from. Ten of them, 49ab, 49bb, 49cb (library 3), 51ba, 51bb (library 5), 52dd, 52bd (library 6), 53ba, 53ea, 53fa (library 7) containing the same carbohydrates form glycodendrimersomes that are also stable in buffer. Simulating considerations for potential applications, binding studies of these glycodendrimersomes performed by agglutination experiments with plant, bacterial and human lectin receptors of biomedical interest demonstrated bioactivity of the multivalent ligand display of their sugar headgroups. Of note, the apparent differences in the courses of agglutination by human Gal-3 and Gal-4 revealed a topological dimension, beyond the cross-linking of surface-presented D-lactose in both cases. These assemblies can thus become pertinent as models of biological membranes to delineate structure-activity correlations at the level of multivalent, soft, dynamic and adaptable surface recognition, also enabling exploration of utility for targeting and lectin blocking. Mapping agglutination courses with native and structurally engineered proteins, also in the inhibitory setting mimicking physiologically relevant systems of functional competition,[xvii] will be crucial to test this concept. In principle the reported experiments demonstrated that glycodendrimersomes provide a new, simple and efficient mimic of cell membranes broadening the toolbox of glycopolymers, glycodynamers, glycopeptides, liposomes/nanoparticles and glycodendrimers. This new type of programmable surface ligand display with interactions in cis and in trans extends the application of surface-based carbohydrate microarrays that are used in high-throughput detection and specificity analysis of proteins[xviii] to dynamic measurements in solution, at the same level of specificities but with more complex functions. Mixing compounds with different headgroups even enables to take the route toward cell-membrane-like complexity, offering flexibility and accessibility changes for detailed bio-exploration in solution, not amendable by planar arrays on surface, with read-out for cis- and trans-interractions and versatile physicochemical analysis possible on structural properties, as documented by cryo-TEM, even after exposure to lectins. The library approach used to discover and predict the primary structures that are the platform for glycodendrimersomes is thus taken from principles of complex supramolecular systems, to the realm of Glycobiology, encouraging both studies on fundamental structure-activity correlations and applications. As the initial discovery of different agglutination courses attests, work toward selective sugar receptors blocking/targeting, for example in bacterial/viral attachment, lectin blocking in inflammation/tumor progression or delivery to antigen-processing dendritic cells in vaccination, will be based on these new tools for multivalent display even possibly beyond carbohydrates as ligands.

Materials 4-(Dimethylamino)pyridinium 4-toluenesulfonate (DPTS)[xix] was prepared according to a literature procedure. All other reagents were obtained from commercial sources and used without prior purification unless otherwise stated. $CH_2Cl_2$ was dried over $CaH_2$ and freshly distilled before used. DMF was dried from $CaH_2$ or ninhydrin, distilled, and kept over molecular sieves prior to use. Pyridine was distilled over $CaH_2$ and kept over molecular sieves. THF was distilled over Na/benzophenone immediately before use. Solvents and reagents were deoxygenated when necessary by purging with nitrogen. Water used for Zemplén treatment was nanopure grade, purified through Barnstead NANOPure II Filter with Barnstead MegOhm Sybron meter. Milli-Q water obtained by Milli-Q UV plus with the resistivity 18.2 MΩcm was used for vesicle preparation. The plant lectin concanavalin A (Con A, that binds to D-mannose) from *Canavalia ensiformis* (Jack bean) and the bacterial lectin *Pseudomonas aeruginosalectins* (PA-IL, that binds to D-galactose) were purchased from Sigma-Aldrich. The plant lectin from mistletoe (Viscum album L. agglutinin, VAA, that binds to D-galactose and D-lactose) was purified from extracts of dried leaves by affinity chromatography on lactose-bearing Sepharose 4B, obtained by divinyl sulfone activation of the resins. The elution was performed with 0.3 M lactose. The leaves extract was prepared by incubation of dried leaves overnight in 20 mM phosphate-buffered saline (pH=7.2), followed by homogenization, centrifugation and dialysis. Human galectins galectin-3 (Gal-3, binding to D-lactose) and galectin-4 (Gal-4, binding to D-lactose) were obtained by recombinant production and purified by affinity chromatography on lactosylated Sepharose 4B resin. Purity of preparations of lectins was ascertained by one- and two-dimensional gel electrophoresis using the IPGphor™ isoelectric focusing system and the Hoefer SE600 standard vertical unit (16×18 cm) with Immobiline™ dry strips (pH 3-10, linear) from Amersham Biosciences (Freiburg, Germany), by nano ESI-MS and by gel filtration on a Superose 12 HR10/30 column (GE Healthcare, Munich, Germany).[xx] The activity was verified by haemagglutination of trypsinized, glutaraldehyde-fixed rabbit erythrocytes and antibody-detected solid-phase assays using asialofetuin as matrix glycoprotein. All purified lectins were lyophilized and stored at −20° C.

Techniques $^1H$ NMR and $^{13}C$ NMR spectra were recorded at 300 or 600 MHz and 75 or 151 MHz, respectively, on a Varian Gemini 2000 spectrometer (300 MHz), on a Varian Inova (600 MHz), and on a Bruker DRX (500 MHz). All NMR spectra were measured at 25° C. in the indicated deuterated solvents. Proton and carbon chemical shifts (δ) are reported in ppm and coupling constants (J) are reported in Hertz (Hz). The resonance multiplicity in the $^1H$ NMR spectra are described as "s" (singlet), "d" (doublet), "t" (triplet), "quint" (quintuplet) and "m" (multiplet) and broad resonances are indicated by "br". Residual protic solvent of $CDCl_3$ ($^1H$, δ 7.27 ppm; $^{13}C$, δ 77.0 ppm (central resonance of the triplet)), and $D_2O$ ($^1H$, δ 4.67 ppm and 29.8 ppm for $CH_3$ of acetone for $^{13}C$ spectra of de-O-acetylated compounds) and tetramethylsilane (TMS) were used as the internal reference in the $^1H$- and $^{13}C$-NMR spectra. 2D homonuclear correlation $^1H$-$^1H$ COSY and 2D heteronuclear correlation $^1H$-$^{13}C$ HETCOR experiments were used to confirm NMR peak assignments. Fourier transform infrared (FTIR) spectra were obtained with a Bomem (Hartmann-Braun) MB series Michelson FTIR spectrometer and all spectra were measured on neat NaCl. The absorptions are given in wavenumbers ($cm^{-1}$). Evolution of the reaction was monitored by analytical thin-layer chromatography using silica gel 60 $F_{254}$ precoated plates (E. Merck) and compounds were visualized by 254 nm light, and with a molybdenum-cerium solution (100 ml $H_2SO_4$, 900 ml $H_2O$, 25 g $(NH_4)_6Mo_7O_{24}H_2O$, 10 g $Ce(SO_4)_2$) and subsequent development by gentle warming with a heat-gun. Purifications by flash column chromatography were performed using flash silica gel from Silicycle (60 Å, 40-63 μm) with the indicated eluent. The purity of the products was determined by a combination of thin-layer chromatography (TLC) on silica gel coated aluminium plates (with F253 indicator; layer thickness, 200 μm; particle size, 2-25 μm; pore size 60 Å) and high pressure liquid chromatography (HPLC) using Perkin-Elmer Series 10 high pressure liquid chromatograph equipped with a LC-100 column oven, Nelson Analytical 900 Series integrator data station and two Perkin-Elmer PL gel columns of 5×10-2 and 1×104 Å, THF was used as solvent at the oven temperature of 40° C. Detection was done by UV absorbance at 254 nm.

Accurate mass measurements (HRMS) were performed on a LC-MSD-TOF instrument from Agilent Technologies in positive electrospray mode (Mass Spectrometry Laboratory (Université de Montréal), or Plateforme analytique pour molécules organiques (Université du Quebec à Montréal), Québec, Canada), or a high-resolution double focusing chemical ionization mass spectrometer (Mass Spectrometry Facility, University of Pennsylvania). Either protonated molecular ions [M+nH]$^{n+}$ or sodium adducts [M+Na]$^{+}$ were used for empirical formula confirmation.

Matrix-assisted laser desorption/ionization time of flight (MALDI-TOF) mass spectrometry was performed on a PerSeptive Biosystem-Voyager-DE (Framingham, Mass.) mass spectrometer equipped with nitrogen laser (337 μm) and operating in linear mode. Internal calibration was performed using Angiotensin II and Bombesin as standards. The analytical sample was obtained by mixing the THF solution of sample (5-10 mg/mL) and THF solution of the matrix (2,5-dihydroxybenzoic acid, 10 mg/mL) in a 1/5 v/v ratio. The prepared solution of the sample and the matrix (0.5 μm) was loaded on the MALDI plate and allowed to dry at 23° C. before the plate was inserted into the vacuum chamber of the MALDI instrument. The laser steps and voltages applied were adjusted depending on both the molecular weight and the nature of each analyzed compound.

Dynamic light scattering (DLS) was performed with a Malvern Instruments particle sizer (Zetasizer® Nano S, Malvern Instruments, UK) equipped with 4 mW He—Ne laser 633 nm and avalanche photodiode positioned at 175° to the beam and temperature controlled cuvette holder. Instrument parameters were determined automatically along with measurement times. Experiments were performed in triplicate. The Janus-dendrimer (1 mg) dissolved in 100 μL of THF was injected into 2 mL of ultrapure water or buffer followed by 5 seconds of vortex mixing. DLS experiments were measured at 25° C. Different final concentration of dendrimersomes in water was prepared from varying the starting concentration of THF solution with the same injection volume (100 μL) into constant 2.0 mL of ultrapure water or buffer.

Cryo-TEM.

Cryogenic transmission electron microscopy was performed on a FEI Technai G2 12 microscope (Hillsboro, Oreg.) at voltage of 120 kV. Briefly, a droplet of 1.2 μL dendrimersome solution was pipetted onto a lacey carbon film coated on a copper grid loaded into an FEI Vitrobot apparatus. For some samples the droplet placement and blotting process was repeated in order to obtain suitable specimens for imaging. The sample was allowed to relax for approximately 10 seconds to remove any residual stresses imparted by blotting, then quickly plunged into liquefied ethane (~90 K) cooled by a reservoir of liquid nitrogen to ensure the vitrification of water. The vitrified samples were transferred to a Gatan 626 cryoholder in a cryo-transfer stage immersed in liquid nitrogen. During the imaging, the cryo-holder was kept below −170° C. to prevent sublimation of vitreous solvent. The digital images were recorded by a Gatan low-dose CCD camera. Image processing and analysis were completed with ImageJ 1.41 software. 3D surface plots of the intensity were created with ImageJ 1.41 for cryo-TEM.

Confocal Microscopy. Laser scanning confocal microscopy (LSCM) was used to expose giant vesicles to light at 515 nm. An Olympus Fluoview FV1000 confocal microscope with a UPLFLN 40× objective lens was used to image the vesicles with a scan speed of 4.0 μs pixel-1 (4.426 s frame-1). Nile Red signal was collected between 600-(50 nm.

Agglutination of glycodendrimersomes and lectins was monitored in 1.50 mL semi-micro disposable cuvettes at 25° C. at λ=450 nm by using a Shimadzu UV-visible spectrophotometer UV-1601 with Shimadzu/UV Probe software. The solution of lectin 100 μL was added into 900 μL of glycodendrimersome solution. The mixture was shaken for 2 s before recording the absorbance change in time. All experiments were carried out in 10 mM HEPES containing 1.0 mM CaCl$_2$ and MnCl$_2$. The concentration lectins and glycodendrimers solution can be found on the caption of each figure. The glycodendrimersome solutions were freshly prepared from injection method from THF or EtOH solution into HEPES buffer containing 1.0 mM CaCl$_2$ and MnCl$_2$. The same buffer was used to bring the lectins into solution and use immediately.

The micropipette aspiration experiment was performed as described previously. Briefly, micropipettes made of borosilicate glass tubing (Friedrich and Dimmock, Milville, N.J.) were prepared using a needle/pipette puller (model 720, David Kopf Instruments, Tujunga, Calif.) and microforged using a glass bead to give the tip a smooth and flat edge. Pipettes were filled with 290 mOsm PBS and mounted on a micromanipulator, and the pipette was connected via tubing to a manometer. A negative pressure, produced through the manometer using a syringe, was created in the pipette to pick up a giant vesicle. The pressure applied to the vesicle was increased in stepwise increments, and from this suction pressure (AP), the membrane tension (T) for a fluid membrane can be calculated from LaPlace's Law. The length of the vesicle extension into the pipette in response to suction pressure was used to calculate the resulting vesicle area strain, $\alpha$ t $\Delta A/\Delta_0$. The area elastic modulus was then measured by plotting $\alpha$ vs T in the high-tension regime (T>0.5 dyn/cm) and calculating the slope of this tension-strain curve. Experiments were imaged using DIC optics with a 40× objective and a Cohu black-and-white CCD camera (Cohu, Inc., San Diego, Calif.). ImageJ software was used to measure membrane extensions and vesicle diameters.

Synthesis

The Synthesis of Hydrophobic Twin Dendrons 3,4-Bis(dodecyloxy)benzoic acid (4a), 3,5-bis(dodecyloxy)benzoic acid (4b), methyl 3,4,5-tris(dodecyloxy)benzoate (4c) were prepared according to literature procedures.

Supporting Scheme 1. Synthesis of Hydrophobic First Generation Acids (4a-4f)

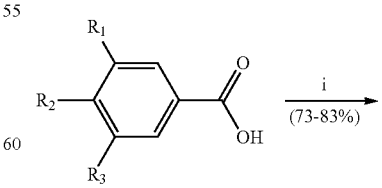

1a: R$_1$ = R$_2$ = OH; R$_3$ = H
1b: R$_1$ = R$_3$ = OH; R$_2$ = H
1c: R$_1$ = R$_2$ = R$_3$ = OH

-continued

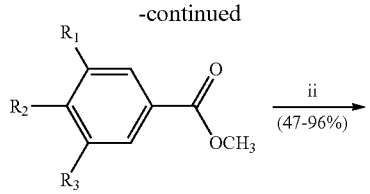

2a: $R_1 = R_2 = OH$; $R_3 = H$
2b: $R_1 = R_3 = OH$; $R_2 = H$
2c: $R_1 = R_2 = R_3 = OH$

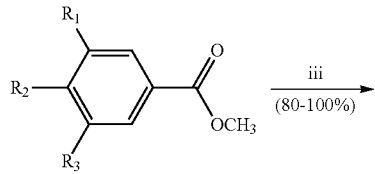

3a: $R_1 = R_2 = OC_{12}H_{25}$; $R_3 = H$
3b: $R_1 = R_3 = OC_{12}H_{25}$; $R_2 = H$
3c: $R_1 = R_2 = R_3 = OC_{12}H_{25}$
3d: $R_1 = R_2 = OCH_2CH(C_2H_5)(C_6H_{13})$; $R_3 = H$
3e: $R_1 = R_3 = OCH_2CH(C_2H_5)(C_6H_{13})$; $R_2 = H$
3f: $R_1 = R_2 = R_3 = OCH_2CH(C_2H_5)(C_6H_{13})$

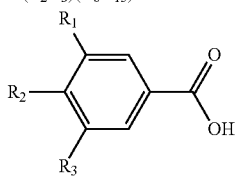

4a: $R_1 = R_2 = OC_{12}H_{25}$; $R_3 = H$
4b: $R_1 = R_3 = OC_{12}H_{25}$; $R_2 = H$
4c: $R_1 = R_2 = R_3 = OC_{12}H_{25}$
4d: $R_1 = R_2 = OCH_2CH(C_2H_5)(C_6H_{13})$; $R_3 = H$
4e: $R_1 = R_3 = OCH_2CH(C_2H_5)(C_6H_{13})$; $R_2 = H$
4f: $R_1 = R_2 = R_3 = OCH_2CH(C_2H_5)(C_6H_{13})$

Reagents and conditions:
(i) $H_2SO_4$ (cat.), MeOH, reflux;
(ii) 1-Bromododecane or 2-ethylhexyl bromide, $K_2CO_3$, DMF (80° C.);
(iii) KOH, EtOH, (reflux).

Methyl 3,4-bis((2-ethylhexyl)oxy)benzoate (3d).

Methyl 3,4-dihydroxybenzoate (1.34 g, 7.97 mmol, 1 equiv), 2-ethylhexyl bromide (3.39 g, 17.5 mmol, 2.2 equiv), $K_2CO_3$ (7.71 g, 55.8 mmol, 7 equiv) was heated at 120° C. for 22 h. The reaction mixture was cooled to room temperature and water was added. Product was successfully extracted with ethyl acetate; the organic phase was separated and dried. The rest was purified by column chromatography ($SiO_2$; hexane/EtAc 9/1) to give a yellowish oil as product. Yield 46%. $^1H$ NMR (500 MHz, $CDCl_3$) δ 7.64 (dd, J=8.4 Hz, J=2.0 Hz, 1H, ArH-6), 7.54 (d, J=2.0 Hz, 1H, ArH-2), 6.86 (d, J=8.5 Hz, 1H, ArH-5), 3.91 (dt, J=8.0 Hz, J=3.0 Hz, 4H, 2ArOCH$_2$), 3.87 (s, 3H, OCH3), 1.77 (dt, J=12.2 Hz, J=6.1 Hz, 2H, 2ArOCH$_2$CH), 1.61-1.26 (m, 16H, 2(CH$_2$)$_3$, 2(CH$_2$CH$_3$)), 0.94-0.88 (m, 12H, 4CH$_3$). $^{13}C$ NMR (126 MHz, $CDCl_3$) δ 166.9 (C=O), 153.4 (ArC-4), 148.8 (ArC-3), 123.3 (ArC-1), 122.1 (ArC-6), 113.7 (ArC-2), 111.5 (ArC-5), 71.3 (ArOCH$_2$), 71.1 (ArOCH$_2$), 51.7 (OCH$_3$), 39.4 (ArOCH$_2$CH), 39.3 (ArOCH$_2$CH), 30.5 (CH$_2$CH$_2$CH$_3$), 29.0 (CH$_2$CH$_2$CH$_3$), 23.8 (CHCH$_2$CH$_3$), 22.9 (CHCH$_2$CH$_3$), 13.95 (CH$_2$CH$_3$), 13.94 (CH$_2$CH$_3$), 11.08 (CH$_3$), 11.05 (CH$_3$). The spectroscopic data of 3d are in agreement with those previously reported.

Methyl 3,5-bis((2-ethylhexyl)oxy)benzoate (3e).

Into a suspension of methyl 3,5-dihydroxybenzoate (9.90 g, 58.9 mmol) and $K_2CO_3$ (32.55 g, 235.5 mmol) in degassed DMF (45 mL) was added 2-ethylhexyl bromide (25.01 g, 129.5 mmol) dropwise at room temperature under nitrogen atmosphere. The resulting mixture was heated to 70° C. and stirred for 12 h. The reaction mixture was cooled to room temperature and water was added. The product was extracted with ethyl acetate, washed with water, brine and dried over $MgSO_4$. The crude mixture was concentrated and purified by column chromatography ($SiO_2$; 0-5% EtOAc:hexane) to give a yellowish oil as product (14.04 g, 61%). $^1H$ NMR (500 MHz, $CDCl_3$) δ 7.14 (d, J=2.3, 2H, ArH-2,6), 6.62 (t, J=2.3, 1H, ArH-4), 3.88 (s, 3H, OCH$_3$), 3.87-3.81 (m, 4H, 2ArOCH$_2$), 1.70 (m, 2H, 2ArOCH$_2$CH), 1.52-1.34 (m, 8H, 4CH$_2$CH$_3$), 1.34-1.27 (m, 8H, 2(CH$_2$)$_2$CH$_2$CH$_3$), 0.90 (m, 12H, 4CH$_3$). $^{13}C$ NMR (126 MHz, $CDCl_3$) δ 167.2 (C=O), 160.6 (ArC-3,5), 131.9 (ArC-1), 107.7 (ArC-2,6), 106.7 (ArC-4), 70.9 (ArOCH$_2$), 52.3 (OCH$_3$), 39.5 (ArOCH$_2$CH), 30.7 (CH$_2$CH$_2$CH$_2$CH$_3$), 29.2 (CH$_2$CH$_2$CH$_3$), 24.0 (CH$_2$CH$_3$), 23.2 (CH$_2$CH$_3$), 14.2 (CH$_3$), 11.3 (CH$_3$). MALDI-TOF (m/z): [M]$^+$ calcd for $C_{24}H_{40}O_4$, 392.29; found 392.79.

Methyl 3,4,5-tris((2-ethylhexyl)oxy)benzoate (30).

Into a suspension of methyl 3,4,5-trihydroxybenzoate (10.00 g, 54.3 mmol) and $K_2CO_3$ (45.03 g, 325.8 mmol) in degassed DMF (45 mL) was added 2-ethylhexyl bromide (34.61 g, 180.1 mmol) dropwise at room temperature under nitrogen atmosphere. The resulting mixture was heated to 70° C. and stirred for 12 h. The reaction mixture was cooled to room temperature and water was added. The product was extracted with ethyl acetate washed with water, brine and dried over $MgSO_4$. The crude mixture was concentrated and purified by column chromatography ($SiO_2$; 0-5% EtOAc:hexane) to give a yellowish oil as product (21.54 g, 76%). $^1H$ NMR (500 MHz, $CDCl_3$) δ 7.23 (s, 2H, ArH-2,6), 3.92-3.83 (m, 9H, 3ArOCH$_2$, OCH$_3$), 1.73 (m, 2H, 2ArOCH$_2$CH), 1.67 (m, 1H, ArOCH$_2$CH), 1.60-1.36 (m, 12H, 6CH$_2$CH$_3$), 1.34-1.25 (m, 12H, 3(CH$_2$)$_2$CH$_2$CH$_3$), 1.01-0.79 (m, 18H, 6CH$_3$). $^{13}C$ NMR (126 MHz, $CDCl_3$) δ 167.2 (C=O), 153.2 (ArC-3,5), 142.5 (ArC-4), 124.7 (ArC-1), 107.6 (ArC-2,6), 76.1 (ArOCH$_2$), 71.4 (ArOCH$_2$), 52.2 (OCH$_3$), 40.8 (ArOCH$_2$CH), 39.7 (ArOCH$_2$CH), 30.7 (CH$_2$CH$_2$CH$_3$), 30.6 (CH$_2$CH$_2$CH$_3$), 29.4 (CH$_2$CH$_2$CH$_3$), 29.3 (CH$_2$CH$_2$CH$_3$), 24.0 (CH$_2$CH$_3$), 23.8 (CH$_2$CH$_3$), 23.3 (CH$_2$CH$_3$), 23.2 (CH$_2$CH$_3$), 14.3 (CH$_3$), 14.2 (CH$_3$), 11.3 (CH$_3$), 11.2 (CH$_3$). MALDI-TOF (m/z): [M]$^+$ calcd for $C_{32}H_{56}O_5$, 520.41; found 520.99.

3,4-Bis((2-ethylhexyl)oxy)benzoic Acid (4d).

Methyl 3,4-bis((2-ethylhexyl)oxy)benzoate (3d) (1.26 g, 3.21 mmol, 1 equiv), KOH (0.72 g, 12.8 mmol, 4 equiv), water (5 mL) and ethanol (30 mL) were refluxed for 2 h. Then reaction mixture was cooled to room temperature and concentrated hydrochloric acid was added carefully until pH=1. $CH_2Cl_2$ (60 mL) was added and combined organic solvents were separated, dried over $MgSO_4$ and evaporated to yield a yellow viscous oil. Yield: 99% $^1H$ NMR (500 MHz, $CDCl_3$) δ 7.74 (dd, J=8.4 Hz, J=1.8 Hz, 2H, ArH-6), 7.59 (d, J=1.8 Hz, 1H, ArH-2), 6.89 (d, J=8.5 Hz, 1H, ArH-5), 4.04-3.84 (m, 4H, 2ArOCH$_2$), 1.79 (dq, J=11.9 Hz, J=5.9 Hz, 2H, 2ArOCH$_2$CH), 1.66-1.17 (m, 16H, 2(CH$_2$)$_3$, 2(CH$_2$CH$_3$)), 1.05-0.82 (m, 12H, 4CH$_3$). $^{13}C$ NMR (126 MHz, $CDCl_3$) δ 172.3 (C=O), 154.3 (ArC-4), 148.9 (ArC-3), 124.4 (ArC-1), 121.2 (ArC-6), 114.1 (ArC-2), 111.6 (ArC-5), 71.5 (ArOCH$_2$), 71.3 (ArOCH$_2$), 39.5

(ArOCH$_2$CH), 39.4 (ArOCH$_2$CH), 30.5 (CH$_2$CH$_2$CH$_3$), 29.1 (CH$_2$CH$_2$CH$_2$CH$_3$), 23.0 (CH$_2$CH$_3$), 14.1 (CH$_2$CH$_3$), 14.0 (CH$_2$CH$_3$), 11.18 (CH$_3$), 11.15 (CH$_3$). The spectroscopic data of 4d are in agreement with those previously reported.

3,5-Bis((2-ethylhexyl)oxy)benzoic acid (4e).

Methyl 3,5-bis((2-ethylhexyl)oxy)benzoate (3e) (10.00 g, 25.47 mmol) was dissolved in EtOH (50 mL). KOH (7.69 g, 137 mmol) in water (10 mL) was added into the reaction mixture which then was refluxed for 12 h. The resulting solution was cooled to room temperature, acidified by 6M hydrochloric acid, diluted with water and then extracted with EtOAc to give a light brown liquid (9.80 g, 100%). $^1$H NMR (500 MHz, CDCl$_3$) δ 11.24 (br. s, 1H, CO$_2$H), 7.24 (d, J=2.2, 2H, ArH-2,6), 6.70 (t, J=2.2, 1H, ArH-4), 4.35-3.61 (m, 4H, 2ArOCH$_2$), 1.92-1.68 (m, 2H, 2ArOCH$_2$CH), 1.65-1.27 (m, 16H, 4CH$_2$CH$_3$, 2(CH$_2$)$_2$CH$_2$CH$_3$), 1.16-0.80 (m, 12H, 4CH$_3$). $^{13}$C NMR (126 MHz, CDCl$_3$) δ 172.5 (C=O), 160.6 (ArC-3,5), 131.1 (ArC-1), 108.3 (ArC-2,6), 107.6 (ArC-4), 70.9 (ArOCH$_2$), 39.5 (ArOCH$_2$CH), 30.7 (CH$_2$CH$_2$CH$_2$CH$_3$), 29.2 CH$_2$CH$_2$CH$_3$), 24.0 (CH$_2$CH$_3$), 23.2 (CH$_2$CH$_3$), 14.2 (CH$_3$), 11.3 (CH$_3$). MALDI-TOF (m/z): [M]$^+$ calcd for C$_{23}$H$_{38}$O$_4$, 378.28; found 379.05.

3,4,5-Tris((2-ethylhexyl)oxy)benzoic Acid (4).

Methyl 3,4,5-tris((2-ethylhexyl)oxy)benzoate (3f) (16.20 g, 31.11 mmol) was dissolved in EtOH (50 mL). KOH (9.19 g, 164 mmol) in water (10 mL) was added into the reaction mixture which then was refluxed for 12 h. The resulting solution was cooled to room temperature, acidified by 6M hydrochloric acid, diluted with water and then extracted with EtOAc to give a light brown liquid (17.83 g, 94%) $^1$H NMR (500 MHz, CDCl$_3$) δ 11.54 (br. s, 1H, CO$_2$H), 7.35 (s, 2H, ArH-2,6), 4.07-3.87 (m, 6H, 3ArOCH$_2$), 1.84-1.67 (m, 3H, 3ArOCH$_2$CH), 1.66-1.26 (m, 24H, 6CH$_2$CH$_3$, 3(CH$_2$)$_2$CH$_2$CH$_3$), 1.07-0.87 (m, 18H, 6CH$_3$). $^{13}$C NMR (126 MHz, CDCl$_3$) δ 172.5 (C=O), 153.2 (ArC-3,5), 143.3 (ArC-4), 123.7 (ArC-1), 108.2 (ArC-2,6), 76.1 (ArOCH$_2$), 71.5 (ArOCH$_2$), 40.8 (ArOCH$_2$CH), 39.7 (ArOCH$_2$CH), 30.7 (CH$_2$CH$_2$CH$_2$CH$_3$), 30.6 (CH$_2$CH$_2$CH$_2$CH$_3$), 29.5, 29.44, 29.43, 29.3, 24.0, 23.8, 23.3, 23.2, 14.3, 14.2, 11.34, 11.32, 11.31, 11.26. MALDI-TOF (m/z): [M+Na]$^+$ calcd for C$_{31}$H$_{54}$NaO$_5$, 529.39; found 529.99.

4-Oxo-4-(prop-2-yn-1-yloxy)butanoic Acid (5).

This compound was synthesized according to the literature procedure. DMAP (2.18 g, 17.8 mmol) and succinic anhydride (10.26 g, 102.6 mmol) were dissolved in 12.5 mL dry CH$_2$Cl$_2$. Propargyl alcohol (5.00 g, 89.5 mmol) was slowly added to the suspension and the reaction mixture was left to react 36 h at room temperature. The reaction mixture was diluted with 50 mL of CH$_2$Cl$_2$, then 50 mL of water was then added, followed by washing 3 times with NaHSO$_4$ 10%. The organic phase was dried over MgSO$_4$, filtered and concentrated. A white solid was obtained (10 g, 64.0 mmol) in 72% yield. $^1$H NMR (500 MHz, CDCl$_3$) δ 4.70 (d, 2H). 4.70 (d, 2H), 2.67-2.70 (m, 4H), 2.47 (t, 1H, —CH). $^{13}$C NMR (126 MHz, CDCl$_3$) δ 178.2, 171.3, 77.3, 75.1, 52.2, 28.7, 28.5.

4-Oxo-4-(prop-2-yn-1-yloxy)butanoic Anhydride (6).

This compound was synthesized according to a literature procedure. Error! Bookmark not defined. Compound 5 (10.0 g, 64.0 mmol) was dissolved in 25 mL dry CH$_2$Cl$_2$ and the solution was cooled to 0° C., followed by dropwise addition of a solution of freshly distilled DCC (6.6 g, 32.0 mmol) in 15 mL dry CH$_2$Cl$_2$. After 1 h at 0° C., the reaction was left to reach room temperature and stirred for 24 h. The reaction mixture was then filtered to remove all solids. After evaporation of the solvent, the final product was obtained as a white solid (8.68 g, 29.5 mmol) in 92% yield. $^1$H NMR (500 MHz, CDCl$_3$) δ 4.70 (d, 4H), 2.83-2.70 (m, 8H), 2.49 (t, 2H, —CH). $^{13}$C NMR (126 MHz, CDCl$_3$) δ 170.8, 167.6, 77.23, 75.16, 52.4, 30.0, 28.2.

Supporting Scheme 3. Synthesis of Twin-Hydrophobic Dendrons Functionalized with Alkynes

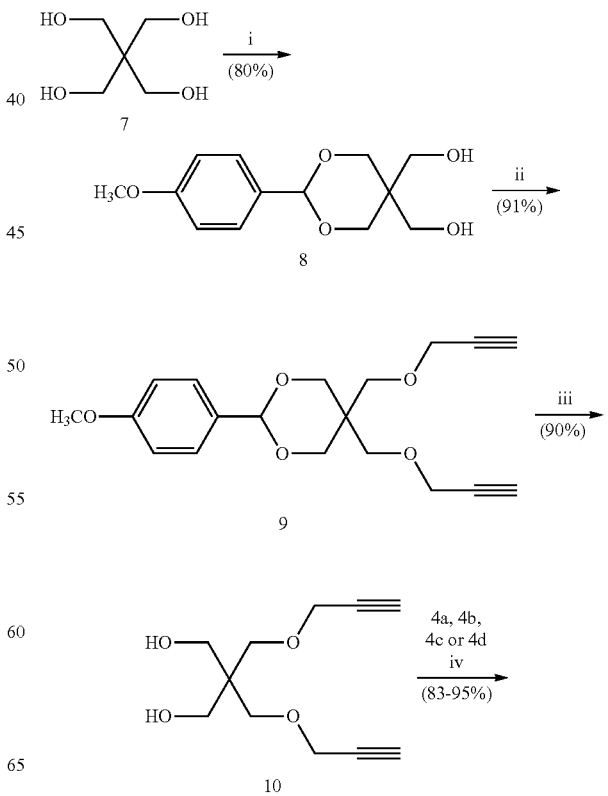

Supporting Scheme 2. Synthesis of Acetylene Anhydride (6)

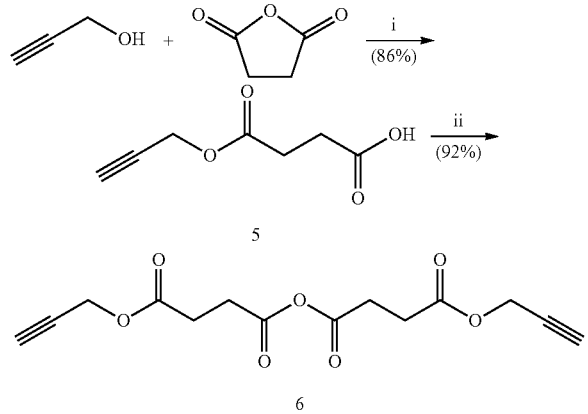

Reagents and conditions:
(i) DMAP (cat.) CH$_2$Cl$_2$ (25° C.);
(ii) DCC, CH$_2$Cl$_2$ (0-25° C.).

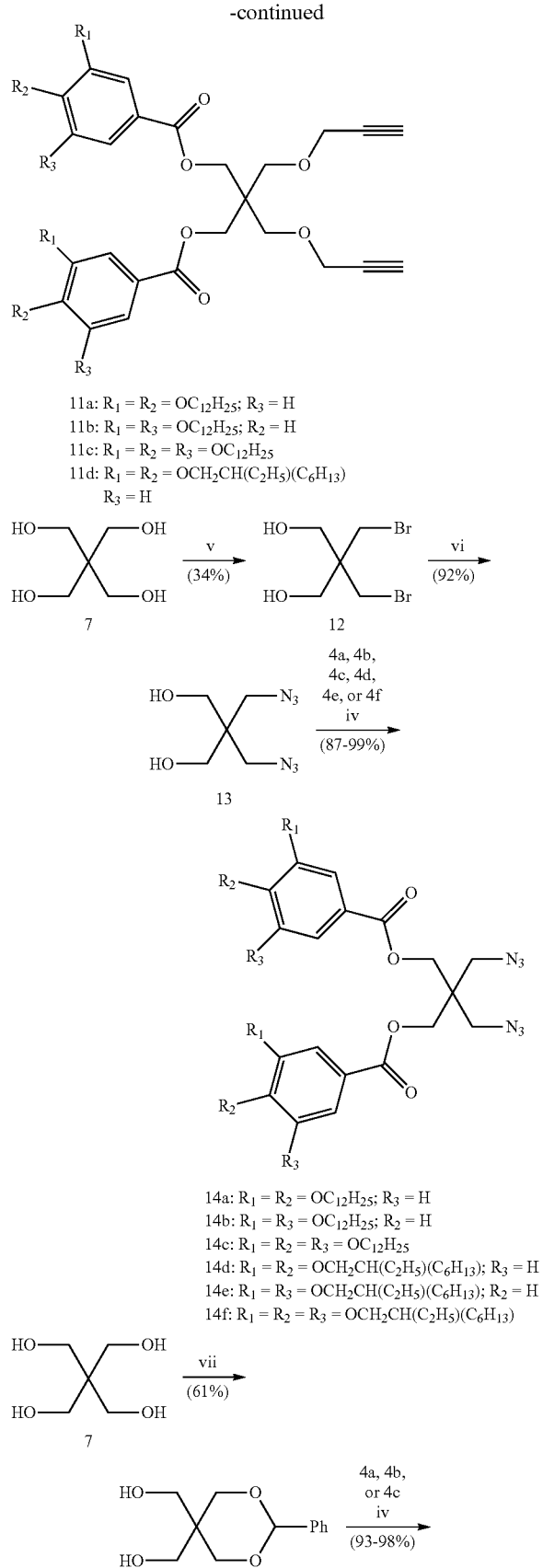
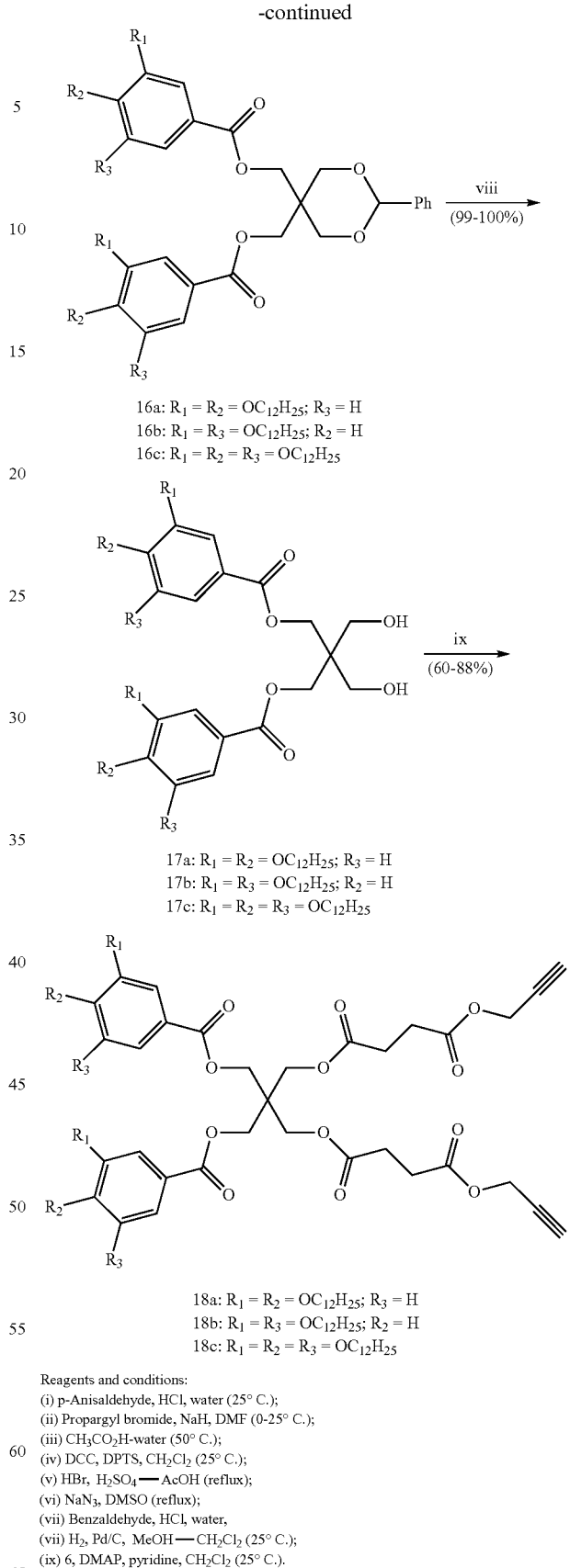

11a: $R_1 = R_2 = OC_{12}H_{25}$; $R_3 = H$
11b: $R_1 = R_3 = OC_{12}H_{25}$; $R_2 = H$
11c: $R_1 = R_2 = R_3 = OC_{12}H_{25}$
11d: $R_1 = R_2 = OCH_2CH(C_2H_5)(C_6H_{13})$; $R_3 = H$

14a: $R_1 = R_2 = OC_{12}H_{25}$; $R_3 = H$
14b: $R_1 = R_3 = OC_{12}H_{25}$; $R_2 = H$
14c: $R_1 = R_2 = R_3 = OC_{12}H_{25}$
14d: $R_1 = R_2 = OCH_2CH(C_2H_5)(C_6H_{13})$; $R_3 = H$
14e: $R_1 = R_3 = OCH_2CH(C_2H_5)(C_6H_{13})$; $R_2 = H$
14f: $R_1 = R_2 = R_3 = OCH_2CH(C_2H_5)(C_6H_{13})$

16a: $R_1 = R_2 = OC_{12}H_{25}$; $R_3 = H$
16b: $R_1 = R_3 = OC_{12}H_{25}$; $R_2 = H$
16c: $R_1 = R_2 = R_3 = OC_{12}H_{25}$

17a: $R_1 = R_2 = OC_{12}H_{25}$; $R_3 = H$
17b: $R_1 = R_3 = OC_{12}H_{25}$; $R_2 = H$
17c: $R_1 = R_2 = R_3 = OC_{12}H_{25}$

18a: $R_1 = R_2 = OC_{12}H_{25}$; $R_3 = H$
18b: $R_1 = R_3 = OC_{12}H_{25}$; $R_2 = H$
18c: $R_1 = R_2 = R_3 = OC_{12}H_{25}$

Reagents and conditions:
(i) p-Anisaldehyde, HCl, water (25° C.);
(ii) Propargyl bromide, NaH, DMF (0-25° C.);
(iii) $CH_3CO_2H$-water (50° C.);
(iv) DCC, DPTS, $CH_2Cl_2$ (25° C.);
(v) HBr, $H_2SO_4$—AcOH (reflux);
(vi) $NaN_3$, DMSO (reflux);
(vii) Benzaldehyde, HCl, water,
(viii) $H_2$, Pd/C, MeOH—$CH_2Cl_2$ (25° C.);
(ix) 6, DMAP, pyridine, $CH_2Cl_2$ (25° C.).

p-Methoxybenzylidene-pentaerythritol (8).

This product was prepared according to a previous literature procedure. Pentaerythritol, 7 (25.0 g, 184 mmol) was dissolved in water (180 mL) at 60° C. The solution was cooled to room temperature undisturbed. Into the stirring solution, concentrated HCl (1.0 mL) was added followed by p-anisaldehyde (1.0 mL, 8.2 mmol). After the precipitation formed, more p-anisaldehyde (22.5 mL, 185 mmol) was added dropwise and the reaction mixture was allowed to stir at room temperature for 3 h. The precipitate was filtered, washed with ice-cold slightly alkaline water ($Na_2CO_3$ solution), and $Et_2O$. The solid was dried under vacuum to give the product as a white solid (37.42 g, 80%). $^1$H NMR (500 MHz, DMSO-$d_6$) δ7.32 (d, J=8.7 Hz, 2H, ArH-2, 6), 6.90 (d, J=8.7 Hz, 2H, ArH-3, 5), 5.33 (s, 1H, CH-acetal), 4.64 (br s, 1H, OH), 4.56 (br s, 1H, OH), 3.88 (d, J=11.5 Hz, 2H, 2OCH$_a$H$_b$-ring), 3.79-3.71 (m, 5H, 2OCH$_a$H$_b$-ring, OCH$_3$), 3.66 (s, 2H, CH$_2$OH), 3.23 (s, 2H, CH$_2$OH). $^{13}$C NMR (126 MHz, DMSO-$d_6$) δ 159.4 (ArC-4), 131.3 (ArC-1), 127.5 (ArC-2, 6), 113.3 (ArC-3, 5), 100.7 (CH-acetal) 69.1 (OCH$_2$-ring), 61.1 (CH$_2$OH), 59.6 (OCH$_3$), 55.1 (C(CH$_2$O)$_4$).

2-(4-Methoxyphenyl)-5,5-bis((prop-2-yn-1-yloxy) methyl)-1,3-dioxane (9).

This product was prepared according to a previous literature procedure. To a solution of p-methoxybenzylidene-pentaerythritol (8) (7.62 g, 30.0 mmol) in dry DMF (150 mL) was added NaH (2.38 g, 99.0 mmol) in one portion at 0° C. and stirred for 30 min. Propargyl bromide (80% in toluene) was added dropwise and the reaction was allowed to stir at room temperature for 12 h. The water was added and the reaction mixture was extracted with $Et_2O$, washed with water and dried over MgSO4. The crude product was concentrated and purified by column chromatography (SiO$_2$, EtOAc:hexane=1:4) to give the product as a pale yellow oil (9.03 g, 91%). $^1$H NMR (500 MHz, CDCl$_3$) δ 7.45-7.38 (m, 2H, ArH-2, 6), 6.92-6.86 (m, 2H, ArH-3, 5), 5.38 (s, 1H, CH-acetal), 4.20 (d, J=2.3 Hz, 2H, CH$_2$C≡CH), 4.12 (d, J=2.3 Hz, 2H, CH$_2$C≡CH), 4.09 (d, J=11.8 Hz, 2H, OCH$_a$H$_b$-ring), 3.90-3.85 (m, 4H, OCH$_a$H$_b$-ring, CH$_2$OCH$_2$C≡), 3.80 (s, 3H, OCH$_3$), 3.36 (s, 2H, CH$_2$OCH$_2$C—), 2.43 (overlapping triplet, J=2.5 Hz, 2H, C≡CH). $^{13}$C NMR (126 MHz, CDCl$_3$) δ 160.2 (ArC-4), 131.0 (ArC-1), 127.5 (ArC-2, 6), 113.8 (ArC-3, 5), 101.9 (CH-acetal), 80.1 (C≡CH), 79.7 (C≡CH), 74.7 (C≡CH), 74.4 (C≡CH), 70.00 (CH$_2$OCH$_2$C—), 69.94 (CH$_2$OCH$_2$C—), 68.9 (OCH$_2$-ring), 58.92 (CH$_2$OCH$_2$C≡), 58.90 (CH$_2$Och$_2$C≡), 55.5 (OCH$_3$), 38.6 (C(CH$_2$O)$_4$).

2,2-Bis((prop-2-yn-1-yloxy)methyl)propane-1,3-diol (10).

This product was prepared according to a previous literature procedure. The solution of 9 in AcOH—H$_2$O (7:3) 80 mL was stirred at 50° C. for 2 h. The reaction mixture was cooled to room temperature, concentrated under reduced pressure, and purified by column chromatography (SiO$_2$, 10-20% EtOAc:hexane) to give the product as pale yellow oil (2.66 g, 90%). $^1$H NMR (500 MHz, CDCl$_3$) δ 4.16 (d, J=2.3 Hz, 4H, 2CH$_2$C≡CH), 3.69 (s, 4H, 2CH$_2$OCH$_2$C≡), 3.59 (s, 4H, 2CH$_2$OH), 2.50 (s, 2H, OH), 2.46 (t, J=2.4 Hz, 2H, C≡CH). $^{13}$C NMR (126 MHz, CDCl$_3$) δ 79.5 (C≡CH), 74.9 (C≡CH), 71.0 (CH$_2$OCH$_2$C≡), 64.4 (CH$_2$OH), 58.9 (CH$_2$OCH$_2$C≡), 45.0 (C(CH$_2$O)$_4$).

General Procedure for the Preparation of 11a, 11b, and 11c

Into a solution of 2,2-bis((prop-2-yn-1-yloxy)methyl)propane-1,3-diol (10) (0.40 g, 1.88 mmol, 1.0 equiv), substituted benzoic acid (4a, 4b, or 4c) (3.96 mmol, 2.1 equiv), and DPTS (0.55 g, 1.88 mmol, 1.0 equiv) in anhydrous CH$_2$Cl$_2$ (8.0 mL) was added DCC (1.01 g, 4.90 mmol, 2.6 equiv) in anhydrous CH$_2$Cl$_2$ (2.0 mL) in one portion at room temperature under nitrogen atmosphere. The reaction mixture was allowed to stir at room temperature for 12 h. The reaction mixture was diluted with Et$_2$O, filtered off the urea, and washed with Et$_2$O. Then the filtrate was concentrated and purified by column chromatography (SiO$_2$, 0-5% EtOAc:hexane) to give a white solid as a product.

2,2-Bis((prop-2-yn-1-yloxy)methyl)propane-1,3-diyl bis (3,4-bis(dodecyloxy)benzoate) (11a).

Following the general procedure. Yield: 1.81 g (83%). White solid. mp=50-51° C. Purity (HPLC): 99%+. $^1$H NMR (500 MHz, CDCl$_3$) δ 7.61 (dd, J=8.4 Hz, J=1.9 Hz, 2H, 2ArH-6), 7.53 (d, J=1.9 Hz, 2H, 2ArH-2), 6.82 (d, J=8.5 Hz, 2H, 2ArH-5), 4.44 (s, 4H, 2ArCO$_2$CH$_2$), 4.15 (d, J=2.3 Hz, 4H, 2OCH$_2$C≡C), 4.02 (m, 8H, 4ArOCH$_2$), 3.71 (s, 4H, 2CH$_2$OCH$_2$C—), 2.32 (t, J=2.3 Hz, 2H, 2C≡CH), 1.82 (m, 8H, 4ArOCH$_2$CH$_2$), 1.50-1.43 (m, 8H, 4ArOCH$_2$CH$_2$CH$_2$), 1.41-1.19 (m, 64H, 4(CH$_2$)$_8$CH$_3$), 0.88 (t, J=6.9 Hz, 12H, 4CH$_3$). $^{13}$C NMR (126 MHz, CDCl$_3$) δ 166.2 (C=O), 153.4 (ArC-4), 148.7 (ArC-3), 123.7 (ArC-1), 122.5 (ArC-6), 114.6 (ArC-2), 112.0 (ArC-5), 79.7 (C≡CH), 74.7 (C≡CH), 69.5 (ArOCH$_2$), 69.2 (ArOCH$_2$), 68.8 (CH$_2$OCH$_2$C—), 63.7 (ArCO$_2$CH$_2$), 58.9 (OCH$_2$C≡C), 44.1 (C(CH$_2$O)$_4$), 32.1 (CH$_2$CH$_2$CH$_3$), 29.9, 29.84, 29.79, 29.76, 29.60, 29.55, 29.52, 29.4, 29.2, 26.2 (ArOCH$_2$CH$_2$CH$_2$), 26.1 (ArOCH$_2$CH$_2$CH$_2$), 22.9 (CH$_2$CH$_3$), 14.3 (CH$_3$). MALDI-TOF (m/z): [M+Na]$^+$ calcd for $C_{73}H_{120}NaO_{10}$, 1180.72; found 1179.83.

2,2-Bis((prop-2-yn-1-yloxy)methyl)propane-1,3-diyl bis (3,5-bis(dodecyloxy)benzoate) (11b).

Following the general procedure. Yield: 2.07 g (95%). White soft solid. Purity (HPLC): 99%. $^1$H NMR (500 MHz, CDCl$_3$) δ 7.13 (d, J=2.2 Hz, 4H, 2ArH-2, 6), 6.62 (t, J=2.2 Hz, 2H, 2ArH-4), 4.45 (s, 4H, 2ArCO$_2$CH$_2$), 4.15 (d, J=2.3 Hz, 4H, 2OCH$_2$C≡C), 3.94 (t, J=6.5 Hz, 8H, 4ArOCH$_2$), 3.72 (s, 4H, 2CH$_2$OCH$_2$C≡), 2.36 (t, J=2.3 Hz, 2H, 2C≡CH), 1.80-1.73 (m, 8H, 4ArOCH$_2$CH$_2$), 1.47-1.40 (m, 8H, 4ArOCH$_2$CH$_2$CH$_2$), 1.38-1.19 (m, 64H, 4(CH$_2$)$_8$CH$_3$), 0.88 (t, J=6.9 Hz, 12H, 4CH$_3$). $^{13}$C NMR (126 MHz, CDCl$_3$) δ 166.2 (C=O), 160.3 (ArC-3, 5), 131.9 (ArC-1), 107.9 (ArC-2, 6), 106.3 (ArC-4), 79.6 (C≡CH), 74.9 (C≡CH), 68.50 (CH$_2$OCH$_2$C≡), 68.45 (ArOCH$_2$), 63.9 (ArCO$_2$CH$_2$), 58.9 (OCH$_2$C≡C), 44.0 (C(CH$_2$O)$_4$), 32.1 (CH$_2$CH$_2$CH$_3$), 29.82, 29.79, 29.77, 29.74, 29.6, 29.5, 29.3, 26.2 (ArOCH$_2$CH$_2$CH$_2$), 22.8 (CH$_2$CH$_3$), 14.3 (CH$_3$). MALDI-TOF (m/z): [M+Na]$^+$ calcd for $C_{73}H_{120}NaO_{10}$, 1180.72; found 1179.97.

2,2-Bis((prop-2-yn-1-yloxy)methyl)propane-1,3-diyl bis (3,4,5-tris(dodecyloxy)benzoate) (11c).

Following the general procedure. Yield: 2.55 g (89%). White solid. mp=39-40° C. Purity (HPLC): 99%+. $^1$H NMR (500 MHz, CDCl$_3$) δ 7.23 (s, 4H, 2ArH-2, 6), 4.44 (s, 4H, 2ArCO$_2$CH$_2$), 4.15 (d, J=2.3 Hz, 4H, 2OCH$_2$C≡C), 4.03-3.95 (m, 12H, 6ArOCH$_2$), 3.70 (s, 4H, 2CH$_2$OCH$_2$C≡), 2.32 (t, J=2.3 Hz, 2H, 2C≡CH), 1.83-1.71 (m, 12H, 6ArOCH$_2$CH$_2$), 1.50-1.43 (m, 12H, 6ArOCH$_2$CH$_2$CH$_2$), 1.38-1.20 (m, 96H, 6(CH$_2$)$_8$CH$_3$), 0.88 (t, J=6.9 Hz, 18H, 6CH$_3$). $^{13}$C NMR (126 MHz, CDCl$_3$) δ 166.1 (C=O), 153.0 (ArC-4), 142.7 (ArC-3, 5), 124.7 (ArC-1), 108.3 (ArC-2, 6), 79.6 (C≡CH), 74.7 (C≡CH), 73.7 (ArOCH$_2$), 69.4 (ArOCH$_2$), 68.8 (CH$_2$OCH$_2$C—), 63.8 (ArCO$_2$CH$_2$), 58.9 (OCH$_2$C≡C), 44.1 (C(CH$_2$O)$_4$), 32.1 (CH$_2$CH$_2$CH$_3$), 30.5 (CH$_2$CH$_2$CH$_3$), 29.90, 29.89, 29.87, 29.85, 29.82, 29.7, 29.6, 29.55, 29.53, 29.51, 26.3, 26.2, 22.8 (CH$_2$CH$_3$), 14.3 (CH$_3$). MALDI-TOF (m/z): [M+Na]$^+$ calcd for $C_{97}H_{168}NaO_{12}$, 1549.35; found 1548.74.

3-((3,4-bis((2-ethylhexyl)oxy)benzoyl)oxy)-2,2-bis((prop-2-yn-1-yloxy)methyl)propyl 3,4-bis(octan-3-yloxy)benzoate (11d).

Into a solution of 2,2-bis((prop-2-yn-1-yloxy)methyl)propane-1,3-diol (0.30 g, 1.41 mmol, 1.0 equiv), 3,4-bis((2-ethylhexyl)oxy) benzoic acid (1.12 g, 2.96 mmol, 2.1 equiv), and DPTS (0.42 g, 1.41 mmol, 1 equiv) in anhydrous $CH_2Cl_2$ (7 mL) was added DCC (0.75 g, 3.67 mmol, 2.6 equiv) in anhydrous $CH_2Cl_2$ (2 mL) in one portion at room temperature under nitrogen atmosphere. The reaction mixture was allowed to stir at room temperature for 12 h. The reaction mixture was diluted with $Et_2O$, filtered off the urea and washed with $Et_2O$. The filtrate was concentrated and purified by column chromatography ($SiO_2$, $CH_2Cl_2$) to give colorless oil as a product. $^1H$ NMR (500 MHz, $CDCl_3$) δ 7.62 (dd, J=8.4 Hz, J=1.9 Hz, 2H, 2ArH-6), 7.53 (d, J=1.8 Hz, 2H, 2ArH-2), 6.84 (d, J=8.5 Hz, 2H, 2ArH-5), 4.45 (s, 4H, $2ArCO_2CH_2$), 4.16 (d, J=2.2 Hz, 4H, $2OCH_2C\equiv C$), 3.97-3.86 (m, 8H, $4ArOCH_2$), 3.72 (s, 4H, $2CH_2OCH_2C\equiv$), 2.33 (t, J=2.2 Hz, 2H, $2C\equiv CH$), 1.77 (m, 4H, $4ArOCH_2CH$), 1.66-1.21 (m, 32H, $4(CH_2)_3CH_3$, $4CH_2CH_3$), 0.92 (m, 24H, $8CH_3$). $^{13}C$ NMR (126 Mhz, $CDCl_3$) δ 166.1 (C=O), 153.6 (ArC-4), 148.9 (ArC-3), 123.4 (ArC-1), 122.2 (ArC-6), 114.1 (ArC-2), 111.6 (ArC-5), 79.5 (C≡CH), 74.5 (C≡CH), 71.6 ($ArOCH_2$), 71.3 ($ArOCH_2$), 68.6 ($CH_2OCH_2C\equiv$), 63.4 ($ArCO_2CH_2$), 58.7 ($OCH_2C\equiv C$), 43.9 ($C(CH_2O)_4$), 39.5 ($ArOCH_2CH$), 39.4 ($ArOCH_2CH$), 30.6, 30.5, 29.08, 29.06, 23.90, 23.89, 23.86, 23.85, 23.02 ($CH_2CH_3$), 23.00 ($CH_2CH_3$), 14.0 ($CH_3$-hexyl branch), 11.2 ($CH_3$-ethyl branch), 11.1 ($CH_3$-ethyl branch). MALDI-TOF (m/z): $[M+Na^+]$ calcd for $C_{57}H_{88}O_{10}$, 956.29; found 957.20.

2,2-Bis(bromomethyl)propane-1,3-diol (12).

This compound was prepared according to a literature procedure.

2,2-Bis(azidomethyl)propane-1,3-diol (13).

This compound was prepared according to a literature procedure. Into a solution of 12 (2.00 g, 8.64 mmol) in anhydrous DMSO (6.0 mL) was added $NaN_3$ (1.24 g, 19.1 mmol) in one portion. The suspension was allowed to stir at 110° C. under $N_2$ atmosphere for 16 h. The reaction mixture was cooled to room temperature and water was then added. The mixture was extracted with EtOAc, washed three times with brine, and dried over $MgSO_4$. The crude mixture was filtered, concentrated and dried under vacuum to give the product as a light brown liquid (1.29 g, 92%). $^1H$ NMR (500 MHz, $CDCl_3$) δ 3.63, 3.43 (s, 4H), 2.09 (s, 2H). $^{13}C$ NMR (126 MHz, $CDCl_3$) δ 63.9, 52.0, 45.0. The spectroscopic data of 13 are in agreement with those previously reported.

2,2-Bis(azidomethyl)propane-1,3-diyl bis(3,4-bis(dodecyloxy)benzoate) (14a).

Into a solution of 13 (0.86 g, 4.62 mmol), 4a (5.00 g, 10.2 mmol), and DPTS (1.36 g, 4.63 mmol) in anhydrous $CH_2Cl_2$ (13 mL) was added the solution of DCC (2.49 g, 12.1 mmol) in $CH_2Cl_2$ (2 mL) in one portion at room temperature under nitrogen atmosphere. The reaction mixture was allowed to stir at room temperature for 12 h. The reaction mixture was diluted with $Et_2O$, filtered off the urea, and washed with $Et_2O$. The filtrate was concentrated and purified by column chromatography ($SiO_2$, 0-10% $Et_2O$:hexane) to give the product as a white solid (2.84 g, 54%). $^1H$ NMR (500 MHz, $CDCl_3$) δ 7.58 (dd, J=8.4, 2.0, 2H, 2ArH-6), 7.51 (d, J=2.0, 2H, 2ArH-2), 6.84 (d, J=8.5, 2H, 2ArH-5), 4.36 (s, 4H, $2ArCO_2CH_2$), 4.10-3.97 (m, 8H, $4ArOCH_2$), 3.59 (s, 4H, $2CH_2N_3$), 1.82 (m, 8H, $4ArOCH_2CH_2$), 1.46 (m, 8H, $4ArOCH_2CH_2CH_2$), 1.40-1.21 (d, J=47.4, 64H, $4(CH_2)_8CH_3$), 0.88 (t, J=6.9, 12H, $4CH_3$). $^{13}C$ NMR (126 MHz, $CDCl_3$) δ 165.9 (C=O), 153.8 (ArC-4), 148.9 (ArC-3), 123.7 (ArC-1), 121.7 (ArC-6), 114.5 (ArC-2), 112.1 (ArC-5), 69.5 ($ArOCH_2$), 69.2 ($ArOCH_2$), 63.4 ($ArCO_2CH_2$), 52.0 ($CH_2N_3$), 43.8 ($C(CH_2N_3)_2$), 32.1 ($CH_2CH_2CH_3$), 29.86, 29.84, 29.81, 29.79, 29.76, 29.58, 29.54, 29.52, 29.4, 29.2, 26.17, 26.13, 22.8 ($CH_2CH_3$), 14.3 ($CH_3$). MALDI-TOF (m/z): $[M+Na]^+$ calcd for $C_{67}H_{114}N_6NaO_8$, 1153.86; found 1154.17.

2,2-Bis(azidomethyl)propane-1,3-diyl bis(3,5-bis(dodecyloxy)benzoate) (14b).

Into a solution of 13 (0.70 g, 3.76 mmol), 4b (3.88 g, 7.90 mmol), and DPTS (1.11 g, 3.76 mmol) in anhydrous $CH_2Cl_2$ (13 mL) was added the solution of DCC (2.02 g, 9.78 mmol) in $CH_2Cl_2$ (2 mL) in one portion at room temperature under nitrogen atmosphere. The reaction mixture was allowed to stir at room temperature for 12 h. The reaction mixture was diluted with $Et_2O$, filtered off the urea, and washed with $Et_2O$. The filtrate was concentrated and purified by column chromatography ($SiO_2$, 0-5% EtOAc:hexane) to give the product as a colorless oil (4.24 g, 99.5%). $^1H$ NMR (500 MHz, $CDCl_3$) δ 7.10 (d, J=2.3, 4H, 2ArH-2,6), 6.64 (t, J=2.3, 2H, 2ArH-4), 4.36 (s, 4H, $2ArCO_2CH_2$), 3.95 (t, J=6.6, 8H, $4ArOCH_2$), 3.60 (s, 4H, $2CH_2N_3$), 1.87-1.72 (m, 8H, $4ArOCH_2CH_2$), 1.52-1.42 (m, 8H, $4ArOCH_2CH_2CH_2$), 1.42-1.20 (m, 64H, $4(CH_2)_8CH_3$), 0.88 (t, J=7.0, 12H, $4CH_3$). $^{13}C$ NMR (126 MHz, $CDCl_3$) δ 166.0 (C=O), 160.4 (ArC-3,5), 131.2 (ArC-1), 107.9 (ArC-2,6), 106.8 (ArC-4), 68.5 ($ArOCH_2$), 63.6 ($ArCO_2CH_2$), 51.8 ($CH_2N_3$), 43.7 ($C(CH_2N_3)_2$), 32.1 ($CH_2CH_2CH_3$), 29.81, 29.78, 29.76, 29.73, 29.54, 29.50, 29.3, 26.2, 22.8 ($CH_2CH_3$), 14.3 ($CH_3$). MALDI-TOF (m/z): $[M+Na]^+$ calcd for $C_{67}H_{114}N_6NaO_8$, 1153.86; found 1154.12.

2,2-Bis(azidomethyl)propane-1,3-diyl bis(3,4,5-tris(dodecyloxy)benzoate) (14c).

Into a solution of 13 (0.70 g, 3.76 mmol), 4c (5.33 g, 7.90 mmol), and DPTS (1.11 g, 3.76 mmol) in anhydrous $CH_2Cl_2$ (13 mL) was added the solution of DCC (2.02 g, 9.78 mmol) in $CH_2Cl_2$ (2 mL) in one portion at room temperature under nitrogen atmosphere. The reaction mixture was allowed to stir at room temperature for 12 h. The reaction mixture was diluted with $Et_2O$, filtered off the urea, and washed with $Et_2O$. The filtrate was concentrated and purified by column chromatography ($SiO_2$, 0-5% EtOAc:hexane) to give a product as a white solid (5.27 g, 93%). $^1H$ NMR (500 MHz, $CDCl_3$) δ 7.22 (s, 4H, 2ArH-2,6), 4.36 (s, 4H, $2ArCO_2CH_2$), 4.00 (m, 12H, $6ArOCH_2$), 3.57 (s, 4H, $2CH_2N_3$), 1.79 (m, 12H, $6ArOCH_2CH_2$), 1.47 (m, 12H, $6ArOCH_2CH_2CH_2$), 1.26 (m, 96H, $6(CH_2)_8CH_3$), 0.88 (t, J=6.8, 18H, $6CH_3$). $^{13}C$ NMR (126 MHz, $CDCl_3$) δ 165.9 (C=O), 153.1 (ArC-3,5), 143.2 (ArC-1), 123.9 (ArC-2,6), 108.4 (ArC-4), 73.7 ($ArOCH_2$), 69.5 ($ArOCH_2$), 63.5 ($ArCO_2CH_2$), 52.1 ($CH_2N_3$), 44.0 ($C(CH_2N_3)_2$), 32.1 ($CH_2CH_2CH_3$), 30.1, 29.86, 29.82, 29.80, 29.7, 29.59, 29.52, 29.50, 26.3, 26.2, 22.8 ($CH_2CH_3$), 14.3 ($CH_3$). MALDI-TOF (m/z): $[M+Na]^+$ calcd for $C_{91}H_{162}N_6NaO_{10}$, 1522.23; found 1522.29.

2,2-Bis(azidomethyl)propane-1,3-diyl bis(3,4-bis((2-ethyloctyl)oxy)benzoate) (14d).

Into a solution of 13 (1.20 g, 6.45 mmol), 4d (5.12 g, 13.5 mmol), and DPTS (1.90 g, 6.45 mmol) in anhydrous $CH_2Cl_2$ (13 mL) was added the solution of DCC (3.46 g, 9.78 mmol) in $CH_2Cl_2$ (2 mL) in one portion at room temperature under nitrogen atmosphere. The reaction mixture was allowed to stir at room temperature for 24 h. The reaction mixture was diluted with $Et_2O$, filtered off the urea, and washed with $Et_2O$. The filtrate was concentrated and purified by column chromatography ($SiO_2$, 0-10% $Et_2O$:hexane) to give a product as a colorless oil (5.25 g, 90%). $^1H$ NMR (500 MHz, CDCl$_3$) δ 7.59 (dd, J=8.4, 1.5, 2H, 2ArH-6), 7.52 (d, J=1.6, 2H, 2ArH-2), 6.85 (d, J=8.4, 2H, 2ArH-5), 4.37 (s, 4H, 2ArCO$_2$CH$_2$), 3.96-3.85 (m, 8H, 4ArOCH$_2$), 3.60 (s, 4H, 2CH$_2$N$_3$), 1.83-1.72 (m, 4H, 4ArOCH$_2$CH), 1.58-1.25 (m, 32H, 8CH$_2$CH$_3$, 4(CH$_2$)$_2$CH$_2$CH$_3$), 0.92 (m, 24H, 8CH$_3$). $^{13}$C NMR (126 MHz, CDCl$_3$) δ 166.0 (C=O), 154.1 (ArC-4), 149.2 (ArC-3), 123.5 (ArC-1), 121.5 (ArC-6), 114.1 (ArC-2), 111.8 (ArC-5), 71.7 (ArOCH$_2$), 71.5 (ArOCH$_2$), 63.3 (ArCO$_2$CH$_2$), 52.0 (CH$_2$N$_3$), 43.8 (C(CH$_2$N$_3$)$_2$), 39.7 (ArOCH$_2$CH), 39.5 (ArOCH$_2$CH), 30.72 (CH$_2$CH$_2$CH$_2$CH$_3$), 30.68 (CH$_2$CH$_2$CH$_2$CH$_3$), 29.23 (CH$_2$CH$_2$CH$_3$), 29.21 (CH$_2$CH$_2$CH$_3$), 24.06, 24.04, 24.02, 24.00, 23.17, 23.15, 14.2 (CH$_3$), 11.31 (CH$_3$), 11.28 (CH$_3$). MALDI-TOF (m/z): [M+Na]$^+$ calcd for C$_{51}$H$_{82}$N$_6$NaO$_8$, 929.61; found 929.81.

2,2-Bis(azidomethyl)propane-1,3-diyl bis(3,5-bis((2-ethyloctyl)oxy)benzoate) (14e).

Into a solution of 13 (0.60 g, 3.20 mmol), 4e (2.56 g, 6.76 mmol), and DPTS (0.95 g, 3.20 mmol) in anhydrous CH$_2$Cl$_2$ (13 mL) was added the solution of DCC (1.73 g, 8.38 mmol) in CH$_2$Cl$_2$ (2 mL) in one portion at room temperature under nitrogen atmosphere. The reaction mixture was allowed to stir at room temperature for 12 h. The reaction mixture was diluted with Et$_2$O, filtered off the urea, and washed with Et$_2$O. The filtrate was concentrated and purified by column chromatography (SiO$_2$, 0-5% Et$_2$O:hexane) to give the product as a colorless oil (2.59 g, 89%). $^1$H NMR (500 MHz, CDCl$_3$) δ 7.12 (d, J=2.3, 4H, 2ArH-2,6), 6.66 (t, J=2.2, 2H, 2ArH-4), 4.38 (s, 4H, 2ArCO$_2$CH$_2$), 4.08-3.81 (m, 8H, 4ArOCH$_2$), 3.61 (s, 4H, 2CH$_2$N$_3$), 1.72 (m, 4H, 4ArOCH$_2$CH), 1.57-1.28 (m, 32H, 8CH$_2$CH$_3$, 4(CH$_2$)$_2$CH$_2$CH$_3$), 1.03-0.86 (m, 24H, 8CH$_3$). $^{13}$C NMR (126 MHz, CDCl$_3$) δ 166.0 (C=O), 160.6 (ArC-3,5), 131.1 (ArC-1), 107.8 (ArC-2,6), 106.8 (ArC-4), 70.9 (ArOCH$_2$), 63.5 (ArCO$_2$CH$_2$), 51.8 (CH$_2$N$_3$), 43.7 (C(CH$_2$N$_3$)$_2$), 39.5 (ArOCH$_2$CH), 30.6 (CH$_2$CH$_2$CH$_2$CH$_3$), 29.2 (CH$_2$CH$_2$CH$_3$), 23.9 (CH$_2$CH$_3$), 23.1 (CH$_2$CH$_3$), 14.2 (CH$_3$), 11.2 (CH$_3$). MALDI-TOF (m/z): [M+Na]$^+$ calcd for C$_{51}$H$_{82}$N$_6$NaO$_8$, 929.61; found 930.04.

2,2-Bis(azidomethyl)propane-1,3-diyl bis(3,4,5-tris((2-ethyloctyl)oxy)benzoate) (14f).

Into a solution of 13 (0.57 g, 3.10 mmol), 4f (3.43 g, 6.77 mmol), and DPTS (0.95 g, 3.20 mmol) in anhydrous CH$_2$Cl$_2$ (13 mL) was added the solution of DCC (1.73 g, 8.38 mmol) in CH$_2$Cl$_2$ (2 mL) in one portion at room temperature under nitrogen atmosphere. The reaction mixture was allowed to stir at room temperature for 12 h. The reaction mixture was diluted with Et$_2$O, filtered off the urea, and washed with Et$_2$O. The filtrate was concentrated and purified by column chromatography (SiO$_2$, 0-5% Et$_2$O:hexane) to give a product as a pale yellow oil (3.23 g, 91%). $^1$H NMR (500 MHz, CDCl$_3$) δ 7.24 (s, 4H, 2ArH-2,6), 4.38 (s, 4H, 2ArCO$_2$CH$_2$), 3.95-3.83 (m, 12H, 6ArOCH$_2$), 3.58 (s, 4H, 2CH$_2$N$_3$), 1.72 (m, 6H, 6ArOCH$_2$CH), 1.62-1.27 (m, 48H, 12CH$_2$CH$_3$, 6(CH$_2$)$_2$CH$_2$CH$_3$), 0.96-0.87 (m, 36H, 12CH$_3$). $^{13}$C NMR (126 MHz, CDCl$_3$) δ 166.0 (C=O), 153.3 (ArC-3,5), 143.1 (ArC-1), 123.8 (ArC-2,6), 107.8 (ArC-4), 76.2 (ArOCH$_2$), 71.5 (ArOCH$_2$), 63.4 (ArCO$_2$CH$_2$), 52.2 (CH$_2$N$_3$), 44.0 (C(CH$_2$N$_3$)$_2$), 40.8 (ArOCH$_2$CH), 39.8 (ArOCH$_2$CH), 30.7 (CH$_2$CH$_2$CH$_2$CH$_3$), 30.6 (CH$_2$CH$_2$CH$_2$CH$_3$), 29.4 (CH$_2$CH$_2$CH$_3$), 29.3 (CH$_2$CH$_2$CH$_3$), 24.0 (CH$_2$CH$_3$), 23.8 (CH$_2$CH$_3$), 23.3 (CH$_2$CH$_3$), 23.2 (CH$_2$CH$_3$), 14.3 (CH$_3$), 14.2 (CH$_3$), 11.32 (CH$_3$), 11.28 (CH$_3$). MALDI-TOF (m/z): [M+Na]$^+$ calcd for C$_{67}$H$_{114}$N$_6$NaO$_{10}$, 1185.85; found 1185.83.

Monobenzalpentaerythritol (15).

This product was prepared according to previous literature procedure. Pentaerythritol, 7 (18.0 g, 132 mmole) was dissolved in water (130 mL) at 60° C. The solution was cooled to room temperature undisturbed. Into the stirring solution, concentrated HCl (0.7 mL) was added followed by benzaldehyde (3.0 mL, 30.0 mmol). After the precipitation formed, more benzaldehyde (11.0 mL, 108 mol) was added dropwise and the reaction mixture was allowed to stir at room temperature for 3 h. The precipitate was filtered and washed with ice-cold slightly alkaline water (Na$_2$CO$_3$ solution). The solid was heated with boiling slightly alkali water (Na$_2$CO$_3$ solution) for 10 min and filtered quickly through filter paper followed by washing with hot slightly alkali water. The filtrate was allowed to cool in ice bath and the crystal was collected by filtration and dried. The solid was purified by recrystallization from toluene to give the product as a white solid (18.0 g, 61%). $^1$H NMR (500 MHz, DMSO-d$_6$) δ 7.45-7.28 (m, 5H, ArH), 5.40 (s, 1H, CH-acetal), 4.64 (t, J=5.3 Hz, 1H, CH$_2$OH), 4.56 (t, J=5.2 Hz, 1H, CH$_2$OH), 3.90 (d, J=11.5 Hz, 2H, OCH$_a$H$_b$-ring), 3.79 (d, J=11.5 Hz, 2H, OCH$_a$H$_b$-ring), 3.66 (d, J=5.3 Hz, 2H, CH$_2$OH), 3.24 (d, J=5.2 Hz, 2H, CH$_2$OH). $^{13}$C NMR (126 MHz, DMSO-d$_6$) δ 138.8 (ArC-1), 128.7 (ArC-3, 5), 128.0 (ArC-4), 126.2 (ArC-2, 6), 100.7 (CH-acetal), 69.1 (OCH$_2$-ring), 61.1 (CH$_2$OH), 59.6 (C(CH$_2$O)$_4$).

(2-Phenyl-1,3-dioxane-5,5-diyl)bis(methylene) bis(3,4-bis(dodecyloxy)benzoate) (16a).

The monobenzalpentaerythritol, 12 (4.16 g, 18.5 mmol), (3,4)12G1-CO$_2$H (4a) (20.00 g, 40.75 mmol), and DPTS (5.45 g, 18.5 mmol) were dissolved in anhydrous CH$_2$Cl$_2$ (100 mL). DCC (9.94 g, 48.2 mmol) dissolved in anhydrous CH$_2$Cl$_2$ (10 mL) was added and the reaction was stirred for 12 h at room temperature under nitrogen atmosphere. After the reaction was complete, the mixture was diluted, filtered, and rinsed with Et$_2$O. The solvent was removed and the crude product was purified by column chromatography (SiO$_2$, 10% Et$_2$O:hexane) and followed by precipitation in MeOH to give a white solid as a product: 21.18 g (98%). $^1$H NMR (500 MHz, CDCl$_3$) δ 7.60 (m, 2H, 2ArH-6), 7.54-7.48 (m, 4H, 2ArH-2, PhH-3, 5), 7.38 (m, 3H, 3PhH-2, 4, 6), 6.83 (overlapped d, 2H, 2ArH-5), 5.51 (s, 1H, CH-acetal), 4.81 (s, 2H, ArCO$_2$CH$_2$), 4.32 (d, J=11.7 Hz, 2H, 2OCH$_a$H$_b$-ring), 4.25 (s, 2H, ArCO$_2$CH$_2$), 4.07-3.98 (m, 10H, 4ArOCH$_2$, 2OCH$_a$H$_b$-ring), 1.87-1.78 (m, 8H, 4ArOCH$_2$CH$_2$), 1.51-1.43 (m, 8H, 4ArOCH$_2$CH$_2$CH$_2$), 1.26 (m, 64H, 4(CH$_2$)$_8$CH$_3$), 0.88 (t, J=6.8 Hz, 12H, 4CH$_3$). $^{13}$C NMR (126 Mhz, CDCl$_3$) δ 166.0 (C=O), 165.9 (C=O'), 153.5 (ArC-4), 153.3 (ArC-4'), 148.6 (ArC-3), 148.51 (ArC-3'), 137.6 (PhC-1), 129.1 (PhC-3, 5), 128.3 (PhC-4), 126.1 (PhC-2, 6), 123.5 (ArC-1), 123.4 (ArC-1'), 122.0 (ArC-6), 121.5 (ArC-6'), 114.3 (ArC-2), 114.2 (ArC-2'), 111.84 (ArC-5), 111.80 (ArC-5'), 102.2 (CH-acetal), 69.7 (OCH$_2$-ring), 69.2 (ArOCH$_2$), 69.0 (ArOCH$_2$), 68.9 (ArOCH$_2$'), 63.7 (ArCO$_2$CH$_2$), 62.9 (ArCO$_2$CH$_2$'), 37.73 (C(CH$_2$O)$_4$), 31.8 (CH$_2$CH$_2$CH$_3$), 29.62, 29.60, 29.57, 29.55, 29.52, 29.35, 29.30, 29.28, 29.1, 28.98, 28.96, 25.94 (ArOCH$_2$CH$_2$CH$_2$), 25.88 (ArOCH$_2$CH$_2$CH$_2$), 22.6 (CH$_2$CH$_3$), 14.0 (CH$_3$). The spectroscopic data of 16a are in agreement with those previously reported.

(2-Phenyl-1,3-dioxane-5,5-diyl)bis(methylene) bis(3,5-bis(dodecyloxy)benzoate) (16b).

The monobenzalpentaerythritol (5.00 g, 22.3 mmol), (3,5) 12G1-CO$_2$H (4b) (24.07 g, 49.05 mmol), and DPTS (5.90 g, 22.3 mmol) were dissolved in anhydrous CH$_2$Cl$_2$ (120 mL). DCC (11.96 g, 57.97 mmol) dissolved in anhydrous CH$_2$Cl$_2$ (20 mL) was added and the reaction was stirred for 12 h at room temperature under nitrogen atmosphere. After the reaction was complete, the mixture was diluted, filtered, and rinsed with Et$_2$O. The solvent was removed and the crude product was purified by column chromatography (SiO$_2$, 5% Et$_2$O:hexane) and followed by precipitation in MeOH to give a white solid as a product: 25.29 g (97%). $^1$H NMR (500 MHz, CDCl$_3$) δ 7.55-7.46 (m, 2H, PhH-3, 5), 7.41-7.34 (m, 3H, PhH-2, 4, 6), 7.12 (d, J=2.3 Hz, 2H, ArH-2, 6), 7.11 (d, J=2.2 Hz, 2H, ArH-2', 6'), 6.64 (t, J=2.2 Hz, 1H, ArH-4), 6.62 (t, J=2.2 Hz, 1H, ArH-4'), 5.52 (s, 1H, CH-acetal), 4.82 (s, 2H, ArCO$_2$CH$_2$), 4.33 (d, J=11.8 Hz, 2H, 2OCH$_a$H$_b$-ring), 4.26 (s, 2H, ArCO$_2$CH$_2$), 4.03 (d, J=11.8 Hz, 2H, 2OCH$_a$H$_b$-ring), 3.98-3.90 (m, 8H, 4ArOCH$_2$), 1.81-1.73 (m, 8H, 4ArOCH$_2$CH$_2$), 1.48-1.40 (m, 8H, 4ArOCH$_2$CH$_2$CH$_2$), 1.26 (m, 64H, 4(CH$_2$).CH$_3$), 0.88 (t, J=6.9 Hz, 12H, 4CH$_3$). $^{13}$C NMR (126 MHz, CDCl$_3$) δ 166.3 (C=O), 166.2 (C=O'), 160.4 (ArC-3, 5), 160.3 (ArC-3', 5'), 137.8 (PhC-1), 131.7 (PhC-3, 5), 131.2 (PhC-4), 129.4 (PhC-2, 6), 128.5 (ArC-1), 126.3 (ArC-1'), 107.89 (ArC-2, 6), 107.85 (ArC-2', 6'), 106.81 (ArC-4), 106.5 (ArC-4'), 102.4 (CH-acetal), 69.9 (OCH$_2$-ring), 68.52 (ArOCH$_2$), 68.49 (ArOCH$_2$'), 64.2 (ArCO$_2$CH$_2$), 63.5 (ArCO$_2$CH$_2$'), 38.0 (C(CH$_2$O)$_4$), 32.1 (CH$_2$CH$_2$CH$_3$), 29.82, 29.79, 29.76, 29.73, 29.6, 29.5, 29.3, 26.2 (ArOCH$_2$CH$_2$CH$_2$), 22.8 (CH$_2$CH$_3$), 14.3 (CH$_3$). The spectroscopic data of 16b are in agreement with those previously reported.

(2-Phenyl-1,3-dioxane-5,5-diyl)bis(methylene) bis(3,4,5-tris(dodecyloxy)benzoate) (16c).

The monobenzalpentaerythritol (3.64 g, 16.3 mmol), (3,4,5)12G1-CO$_2$H (5c) (24.14 g, 35.8 mmol), and DPTS (4.78 g, 16.3 mmol) were dissolved in anhydrous CH$_2$Cl$_2$ (60 mL). DCC (8.72 g, 42.3 mmol) dissolved in anhydrous CH$_2$Cl$_2$ (10 mL) was added and the reaction was stirred for 12 h at room temperature under nitrogen atmosphere. After the reaction was complete, the mixture was diluted, filtered, and rinsed with Et$_2$O. The solvent was removed and the crude product was purified by column chromatography (SiO$_2$, 10% Et$_2$O:hexane), followed by precipitation in MeOH to give a white solid as a product: 23.35 g (90%). $^1$H NMR (500 MHz, CDCl$_3$) δ 7.53-7.48 (m, 2H, PhH-3, 5), 7.41-7.35 (m, 3H, PhH-2, 4, 6), 7.22 (s, 2H, ArH-2, 6), 7.22 (s, 2H, 2ArH-2', 6'), 5.51 (s, 1H, CH-acetal), 4.83 (s, 2H, ArCO$_2$CH$_2$), 4.32 (d, J=11.6 Hz, 2H, 2OCH$_a$H$_b$-ring), 4.24 (s, 2H, ArCO$_2$CH$_2$), 4.05-3.93 (m, 14H, 6ArOCH$_2$, 2OCH$_a$H$_b$-ring), 1.79 (m, 12H, 6ArOCH$_2$CH$_2$), 1.52-1.43 (m, 12H, 6ArOCH$_2$CH$_2$CH$_2$), 1.26 (m, 96H, 6(CH$_2$)$_8$CH$_3$), 0.88 (t, J=6.7 Hz, 18H, 6CH$_3$). $^{13}$C NMR (126 MHz, CDCl$_3$) δ 166.2 (C=O), 166.1 (C=O'), 153.1 (ArC-3, 5), 153.0 (ArC-3', 5'), 143.1 (ArC-4), 142.9 (ArC-4'), 137.8 (PhC-1), 129.4 (PhC-3, 5), 128.6 (PhC-4), 126.3 (PhC-2, 6), 124.5 (ArC-1), 124.0 (ArC-1'), 108.3 (ArC-2, 6), 108.2 (ArC-2', 6'), 102.5 (CH-acetal), 73.71 (ArOCH$_2$-4), 73.67 (ArOCH$_2$-4'), 70.1 (OCH$_2$-ring), 69.40 (ArOCH$_2$-3, 5), 69.38 (ArOCH$_2$-3', 5'), 64.0 (ArCO$_2$CH$_2$), 63.2 (ArCO$_2$CH$_2$,), 38.1 (C(CH$_2$O)$_4$), 32.1 (CH$_2$CH$_2$CH$_3$), 30.5 (CH$_2$CH$_2$CH$_3$), 29.90, 29.88, 29.86, 29.85, 29.80, 29.7, 29.6, 29.54, 29.52, 29.50, 26.28, 26.27, 26.22, 22.8 (CH$_2$CH$_3$), 14.3 (CH$_3$). The spectroscopic data of 16c are in agreement with those previously reported.

2,2-Bis(hydroxymethyl)propane-1,3-diyl bis(3,4-bis(dodecyloxy)benzoate) 17a).

(2-Phenyl-1,3-dioxane-5,5-diyl)bis(methylene) bis(3,4-bis(dodecyloxy)benzoate) (16a) (20.00 g, 17.1 mmol) was dissolved in 1:2 MeOH:CH$_2$Cl$_2$ (150 mL). Pd/C (0.60 g) was added and the flask was evacuated and filled with hydrogen three times. The reaction mixture was allowed to stir for 12 h under hydrogen atmosphere. The reaction mixture was filter through Celite® and was concentrated, and precipitated in MeOH to give the product as a white solid: 18.34 (99%). $^1$H NMR (500 MHz, CDCl$_3$) δ 7.62 (dd, J=8.5 Hz, J=1.9 Hz, 2H, 2ArH-6), 7.52 (d, J=1.8 Hz, 2H, 2ArH-2), 6.85 (d, J=8.5 Hz, 2H, 2ArH-5), 4.46 (s, 4H, 2ArCO$_2$CH$_2$), 4.07-3.97 (m, 8H, 4ArOCH$_2$), 3.71 (d, J=6.6 Hz, 4H, 2CH$_2$OH), 3.12 (t, J=6.1 Hz, 2H, 2CH$_2$OH), 1.87-1.78 (m, 8H, 4ArOCH$_2$CH$_2$), 1.52-1.43 (m, 8H, 4ArOCH$_2$CH$_2$CH$_2$), 1.40-1.15 (m, 64H, 4(CH$_2$)$_8$CH$_3$), 0.88 (t, J=6.9 Hz, 12H, 4CH$_3$). $^{13}$C NMR (126 MHz, CDCl$_3$) δ 167.3 (C=O), 153.9 (ArC-4), 148.8 (ArC-3), 124.0 (ArC-1), 121.6 (ArC-6), 114.5 (ArC-2), 112.1 (ArC-5), 69.5 (ArOCH$_2$-4), 69.19 (ArOCH$_2$-3), 63.0 (CH$_2$OH), 62.9 (ArCO$_2$CH$_2$), 46.1 (C(CH$_2$O)$_4$), 32.1 (CH$_2$CH$_2$CH$_3$), 29.85, 29.83, 29.81, 29.80, 29.78, 29.75, 29.6, 29.53, 29.51, 29.3, 29.2, 26.2 (ArOCH$_2$CH$_2$CH$_2$), 26.1 (ArOCH$_2$CH$_2$CH$_2$), 22.8 (CH$_2$CH$_3$), 14.3 (CH$_3$). The spectroscopic data of 17a are in agreement with those previously reported.

2,2-Bis(hydroxymethyl)propane-1,3-diyl bis(3,5-bis(dodecyloxy)benzoate) 17b).

(2-Phenyl-1,3-dioxane-5,5-diyl)bis(methylene) bis(3,5-bis(dodecyloxy)benzoate) (16b) (24.00 g, 20.52 mmol) was dissolved in 1:2 MeOH:CH$_2$Cl$_2$ (150 mL). Pd/C (0.72 g) was added and the flask was evacuated and filled with hydrogen three times. The reaction mixture was allowed to stir for 12 h under hydrogen atmosphere. The reaction mixture was filtered through Celite® and the solvent was evaporated to give the product as a white solid: 22.19 (100%). $^1$H NMR (500 MHz, CDCl$_3$) δ 7.13 (d, J=2.1 Hz, 4H, 2ArH-2, 6), 6.64 (s, 2H, 2ArH-4), 4.47 (s, 4H, 2ArCO$_2$CH$_2$), 3.94 (t, J=6.5 Hz, 8H, 4ArOCH$_2$), 3.74 (d, J=6.5 Hz, 4H, 2CH$_2$OH), 2.97 (br s, 2H, 2CH$_2$OH), 1.81-1.71 (m, 8H, 4ArOCH$_2$CH$_2$), 1.44 (m, 8H, 4ArOCH$_2$CH$_2$CH$_2$), 1.26 (m, 64H, 4(CH$_2$)$_8$CH$_3$), 0.88 (t, J=6.8 Hz, 12H, 4CH$_3$). $^{13}$C NMR (126 MHz, CDCl$_3$) δ 167.2 (C=O), 160.4 (ArC-3, 5), 131.1 (ArC-1), 108.0 (ArC-2, 6), 106.9 (ArC-4), 68.5 (ArOCH$_2$), 63.4 (CH$_2$OH), 62.9 (ArCO$_2$CH$_2$), 45.9 (C(CH$_2$O)$_4$), 32.1 (CH$_2$CH$_2$CH$_3$), 29.81, 29.78, 29.76, 29.72, 29.54, 29.50, 29.3, 26.2 (ArOCH$_2$CH$_2$CH$_2$), 22.8 (CH$_2$CH$_3$), 14.3 (CH$_3$). The spectroscopic data of 17b are in agreement with those previously reported.

2,2-Bis(hydroxymethyl)propane-1,3-diyl bis(3,4,5-tris (dodecyloxy)benzoate) (17c).

(2-Phenyl-1,3-dioxane-5,5-diyl)bis(methylene) bis(3,4,5-tris(dodecyloxy)benzoate) (16c) (22.48 g, 14.61 mmol) was dissolved in 1:2 MeOH:CH$_2$Cl$_2$ (150 mL). Pd/C (0.65 g) was added and the flask was evacuated and filled with hydrogen three times. The reaction mixture was allowed to stir for 12 h under hydrogen atmosphere. The reaction mixture was filter through Celite®, was concentrated, and precipitated in MeOH to give the product as a white solid: 20.94 (99%). $^1$H NMR (500 MHz, CDCl$_3$) δ 7.24 (s, 4H, 2ArH-2, 6), 4.47 (s, 4H, 2ArCO$_2$CH$_2$), 4.00 (m, 12H, 6ArOCH$_2$), 3.71 (s, 4H, 2CH$_2$OH), 3.08 (br s, 2H, 2CH$_2$OH), 1.89-1.64 (m, 12H, 6ArOCH$_2$CH$_2$), 1.52-1.43 (m, 12H, 6ArOCH$_2$CH$_2$CH$_2$), 1.26 (m, 96H 6(CH$_2$)$_8$CH$_3$), 0.88 (t, J=6.8 Hz, 18H, 6CH$_3$). $^{13}$C NMR (126 MHz, CDCl$_3$) δ 167.3 (C=), 153.1 (ArC-3, 5), 143.2 (ArC-4), 123.8 (ArC-1), 108.4 (ArC-2, 6), 73.7 (ArOCH$_2$-4), 69.4 (ArOCH$_2$-3, 5), 63.2 (CH$_2$OH), 62.9 (ArCO$_2$CH$_2$), 46.2 (C(CH$_2$O)$_4$), 32.1 (CH$_2$CH$_2$CH$_3$), 30.5 (CH$_2$CH$_2$CH$_3$), 29.88, 29.86, 29.84, 29.81, 29.79, 29.72, 29.58, 29.54, 29.52, 29.48, 26.3 (ArOCH$_2$CH$_2$CH$_2$), 26.2

(ArOCH$_2$CH$_2$CH$_2$), 22.8 (CH$_2$CH$_3$), 14.3 (CH$_2$CH$_3$). The spectroscopic data of 17c are in agreement with those previously reported.

O,O'-(2,2-Bis(((3,4-bis(dodecyloxy)benzoyl)oxy)methyl) propane-1,3-diyl) di(prop-2-yn-1-yl) disuccinate (18a).

2,2-Bis(hydroxymethyl)propane-1,3-diyl bis(3,4-bis(dodecyloxy)benzoate) (17a) (1.47 g, 1.36 mmol), 4-oxo-4-(prop-2-yn-1-yloxy)butanoic anhydride (9) (2.00 g, 6.79 mmol) and DMAP (103.4 mg, 0.922 mmol) were dissolved in anhydrous pyridine (2.4 mL) and anhydrous CH$_2$Cl$_2$ (6.2 mL). The reaction was stirred at room temperature in nitrogen atmosphere for 20 h. Water (half of total amount of reaction's mixture) was added and vigorous stirring was applied for 2 h to quench the excess anhydride. The mixture was then diluted with 30 ml CH$_2$Cl$_2$ and washed with 10% NaHSO$_4$, Na$_2$SO$_4$ 10% and brine. The organic phase was dried over MgSO$_4$ and the solvent was evaporated. The product was redissolved in the minimum amount of CH$_2$Cl$_2$ and precipitated in the cold MeOH to obtained the product as a white solid: 1.0 g (60%); mp=44-45° C. Purity (HPLC): 99%+. $^1$H NMR (500 MHz, CDCl$_3$) δ 7.57 (dd, J=8.4 Hz, J=2.0 Hz, 2H, 2ArH-6), 7.49 (d, J=2.0 Hz, 2H, 2ArH-2), 6.83 (d, J=8.5 Hz, 2H, 2ArH-5), 4.66 (d, J=2.5 Hz, 4H, 2OCH$_2$C≡C), 4.43 (s, 4H, 2ArCO$_2$CH$_2$), 4.33 (s, 4H, 2CH$_2$O$_2$CCH$_2$CH$_2$), 4.09-3.95 (m, 8H, 4ArOCH$_2$), 2.65 (s, 8H, 2CH$_2$O$_2$CCH$_2$CH$_2$), 2.45 (t, J=2.4 Hz, 2H, 2C≡CH), 1.88-1.77 (m, 8H, 4ArOCH$_2$CH$_2$), 1.50-1.43 (m, 8H, 4ArOCH$_2$CH$_2$CH$_2$), 1.39-1.20 (m, 64H, 4(CH$_2$)$_8$CH$_3$), 0.88 (t, J=6.9 Hz, 12H, 4CH$_3$). $^{13}$C NMR (126 MHz, CDCl$_3$) δ 171.5 (C═O)-succ., 171.2 (C═O)-succ., 165.8 (C═O), 153.5 (ArC-4), 148.6 (ArC-3), 123.6 (ArC-1), 121.5 (ArC-6), 114.2 (ArC-2), 111.8 (ArC-5), 77.4 (C≡CH), 75.0 (C≡CH), 69.2 (ArOCH$_2$-4), 69.0 (ArOCH$_2$-3), 62.9 CH$_2$O$_2$CCH$_2$CH$_2$, 62.7 (ArCO$_2$CH$_2$), 52.2 (OCH$_2$C≡C), 42.6 (C(CH$_2$O)$_4$), 31.9 (CH$_2$CH$_2$CH$_3$), 29.67, 29.65, 29.58, 29.41, 29.36, 29.33, 29.2, 29.0, 28.8, 28.7, 26.0 (ArOCH$_2$CH$_2$CH$_2$), 25.9 (ArOCH$_2$CH$_2$CH$_2$), 22.7 (CH$_2$CH$_3$), 14.1 (CH$_3$). MALDI-TOF (m/z): [M+Na]$^+$ calcd for C$_{81}$H$_{128}$NaO$_{16}$, 1379.91; found 1378.45.

O,O'-(2,2-Bis(((3,5-bis(dodecyloxy)benzoyl)oxy)methyl) propane-1,3-diyl) di(prop-2-yn-1-yl) disuccinate (18b).

2,2-Bis(hydroxymethyl)propane-1,3-diyl bis(3,5-bis(dodecyloxy)benzoate) (17b) (1.00 g, 0.924 mmol), 4-oxo-4-(prop-2-yn-1-yloxy)butanoic anhydride (9) (1.36 g, 4.62 mmol) and DMAP (70 mg, 0.63 mmol) were dissolved in anhydrous pyridine (1.6 mL) and anhydrous CH$_2$Cl$_2$ (6.2 mL). The reaction was stirred at room temperature in nitrogen atmosphere for 20 h. Water (half of total amount of reaction's mixture) was added and vigorous stirring was applied for 2 h to quench the excess anhydride. The mixture was then diluted with 30 ml CH$_2$Cl$_2$, washed with 10% NaHSO$_4$, Na$_2$SO$_4$ 10% and brine. The organic phase was dried over MgSO$_4$ and the solvent was evaporated. The product was purified by column chromatography (SiO$_2$, 10-20% EtOAc:hexane) to obtain the product as a viscous oil: 0.924 g (66%). Purity (HPLC): 99%+. $^1$H NMR (500 MHz, CDCl$_3$) δ 7.08 (d, J=2.3 Hz, 4H, 2ArH-2, 6), 6.63 (t, J=2.2 Hz, 2H, 2ArH-4), 4.66 (d, J=2.5 Hz, 4H, 2OCH$_2$C≡C), 4.45 (s, 4H, 2ArCO$_2$CH$_2$), 4.33 (s, 4H, 2CH$_2$O$_2$CCH$_2$CH$_2$), 3.94 (t, J=6.5 Hz, 8H, 4ArOCH$_2$), 2.66 (s, 8H, 2CH$_2$O$_2$CCH$_2$CH$_2$), 2.46 (t, J=2.5 Hz, 2H, 2C≡CH), 1.81-1.74 (m, 8H, 4ArOCH$_2$CH$_2$), 1.49-1.40 (m, 8H, 4ArOCH$_2$CH$_2$CH$_2$), 1.38-1.21 (m, 64H, 4(CH$_2$)$_8$CH$_3$), 0.88 (t, J=6.9 Hz, 12H, 4CH$_3$). $^{13}$C NMR (126 MHz, CDCl$_3$) δ 171.4 (C═O)-succ., 171.1 (C═O)-succ., 165.8 (C═O), 160.2 (ArC-3, 5), 131.0 (ArC-1), 107.6 (ArC-2, 6), 106.6 (ArC-4), 77.4 (C≡CH), 75.0 (C≡CH), 68.3 (ArOCH$_2$), 62.9 (CH$_2$O$_2$CCH$_2$CH$_2$), 62.7 (ArCO$_2$CH$_2$), 52.2 (OCH$_2$C≡C), 42.6 (C(CH$_2$O)$_4$), 31.9 (CH$_2$CH$_2$CH$_3$), 29.6, 29.56, 29.52, 29.4, 29.3, 29.1, 28.74, 28.71, 26.0 (ArOCH$_2$CH$_2$CH$_2$), 22.6 (CH$_2$CH$_3$), 14.0 (CH$_3$). MALDI-TOF (m/z): [M+Na]$^+$ calcd for C$_{81}$H$_{128}$NaO$_{16}$, 1379.91; found 1378.16.

O,O'-(2,2-Bis(((3,4,5-tris(dodecyloxy)benzoyl)oxy) methyl)propane-1,3-diyl) di(prop-2-yn-1-yl) disuccinate (18c). 2,2-Bis(hydroxymethyl)propane-1,3-diyl bis(3,4,5-tris(dodecyloxy)benzoate) (17c) (4.00 g, 2.76 mmol), 4-oxo-4-(prop-2-yn-1-yloxy)butanoic anhydride (9) (4.06 g, 13.8 mmol) and DMAP (0.20 g, 1.78 mmol) were dissolved in anhydrous pyridine (6 mL) and anhydrous CH$_2$Cl$_2$ (20 mL). The reaction was stirred at room temperature in nitrogen atmosphere for 20 h. Water (half of total amount of reaction's mixture) was added and vigorous stirring was applied for 2 h to quench the excess anhydride. The mixture was then diluted with 30 ml CH$_2$Cl$_2$ and washed with 10% NaHSO$_4$, Na$_2$SO$_4$ 10% and brine. The organic phase was dried over MgSO$_4$ and the solvent was evaporated. The product was redissolved in the minimum amount of DCM and precipitated in MeOH to obtained the product as a white soft solid: 4.20 g (88%). Purity (HPLC): 99%+. $^1$H NMR (500 MHz, CDCl$_3$) δ 7.19 (s, 4H, 2ArH-2, 6), 4.65 (d, J=2.5 Hz, 4H, 2OCH$_2$C≡C), 4.43 (s, 4H, 2ArCO$_2$CH$_2$), 4.31 (s, 4H, 2CH$_2$O$_2$CCH$_2$CH$_2$), 4.04-3.94 (m, 12H, 6ArOCH$_2$), 2.65 (s, 8H, 2CH$_2$O$_2$CCH$_2$CH$_2$), 2.44 (t, J=2.5 Hz, 2H, 2C≡CH), 1.84-1.70 (m, 12H, 6ArOCH$_2$CH$_2$), 1.51-1.43 (m, 12H, 6ArOCH$_2$CH$_2$CH$_2$), 1.39-1.19 (m, 96H, 6(CH$_2$), CH$_3$), 0.88 (t, J=6.9 Hz, 18H, 6CH$_3$). $^{13}$C NMR (126 MHz, CDCl$_3$) δ 171.5 (C═O)-succ., 171.2 (C═O)-succ., 165.8 (C═O), 152.9 (ArC-3, 5), 142.8 (ArC-4), 123.9 (ArC-1), 108.0 (ArC-2, 6), 75.0 (C≡CH), 73.5 (C≡CH), 69.2 (ArOCH$_2$), 62.63 (CH$_2$O$_2$CCH$_2$CH$_2$), 62.57 (ArCO$_2$CH$_2$), 52.2 (OCH$_2$C≡C), 42.8 (C(CH$_2$O)$_4$), 30.3 (ArOCH$_2$CH$_2$CH$_2$), 29.73, 29.70, 29.67, 29.64, 29.56, 29.44, 29.35, 29.33, 28.8, 28.7, 26.1 (ArOCH$_2$CH$_2$CH$_2$), 26.0 (ArOCH$_2$CH$_2$CH$_2$), 22.7 (CH$_2$CH$_3$), 14.1 (CH$_3$). MALDI-TOF (m/z): [M+Na]$^+$ calcd for C$_{105}$H$_{176}$NaO$_{18}$, 1748.28; found 1747.23.

3.2 The Synthesis of the Hydrophilic Part of the Janus Dendrimers

Supporting Scheme 4. Stereoselective Synthesis of the Glycosyl Azides

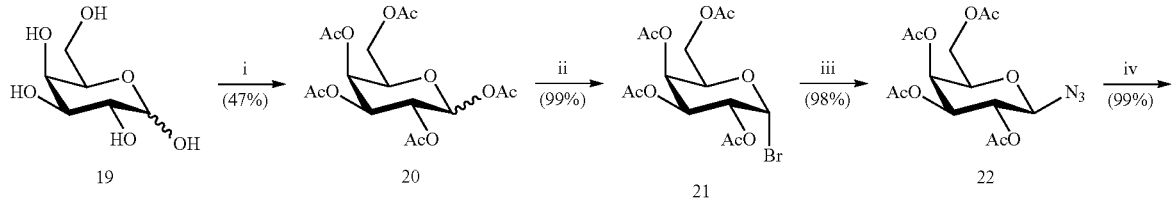

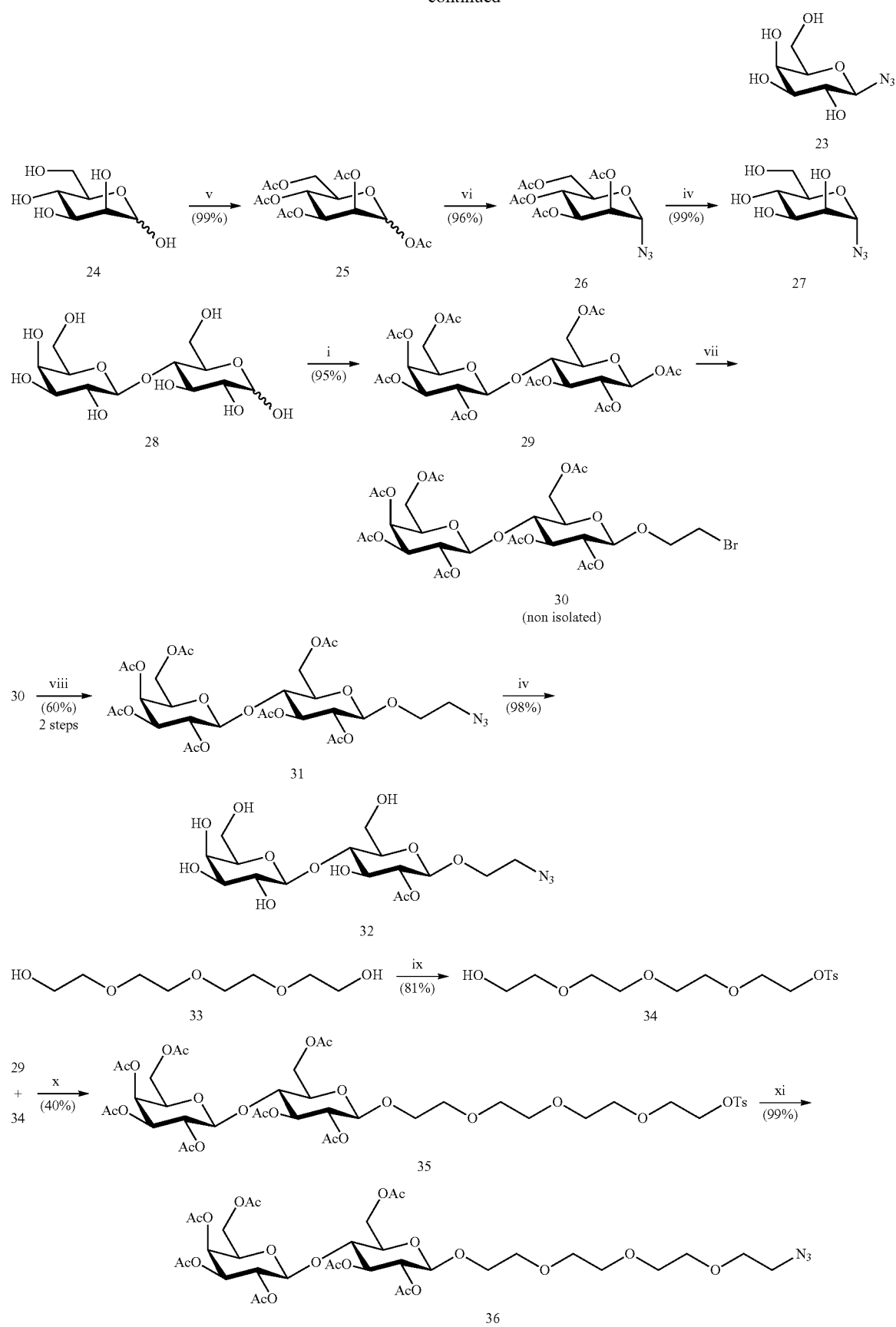

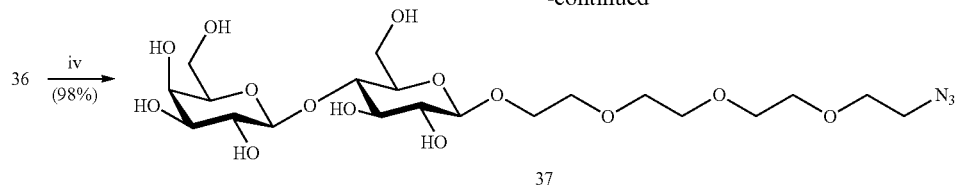

Reagents and conditions:
(i) AcONa, Ac$_2$O, (reflux);
(ii) 33% HBr/AcOH (25° C.);
(iii) NaN$_3$, DMSO (25° C.);
(iv) 1M MeONa in MeOH, MeOH (25° C.);
(v) I$_2$, Ac$_2$O, (0-25° C.);
(vi) TMSiN$_3$, SnCl$_4$, CH$_2$Cl$_2$ (25° C.);
(vii) 2-Bromoethanol, BF$_3$·Et$_2$O, CH$_2$Cl$_2$ (0 to 25° C.);
(viii) NaN$_3$, DMF (80° C.); (ix) TsCl, pyridine, CH$_2$Cl$_2$ (25° C.);
(x) BF$_3$·Et$_2$O, CH$_2$Cl$_2$ (0 to 25° C.); (xi) NaN$_3$, NaI, DMF (70° C.)

Penta-O-acetyl-β-D-galactopyranose (20).

The synthesis of this compound was adapted from a literature procedure. A suspension of sodium acetate (5.00 g, 61.1 mmol, 1.1 equiv.) in acetic anhydride (70 mL) was heated at reflux. D-Galactose 19 (10.0 g, 55.5 mmol, 1.0 equiv.) was then added into the mixture in small portions (1 to 2 g each time). The condenser should be closed immediately after each addition! After addition of D-galactose, the mixture became a clean solution that was stirred under reflux for 10 additional minutes. The hot solution was then poured into a 1 L beaker containing ice-water (400 mL) under vigorous stirring until ice melted. CH$_2$Cl$_2$ (120 mL) was added to the stirred solution and the aqueous layer was then removed. The organic layer was washed with ice-cold water (3×400 mL), saturated aqueous NaHCO$_3$ solution (400 mL) and brine (400 mL). The organic solution was then dried over Na$_2$SO$_4$, filtered and finally concentrated under reduced pressure to give a crude yellow oil which $^1$H NMR showed the presence of 4 compounds: α,β-furanose and α,β-pyranose. The yellow oil was solubilized in a minimum amount of Et$_2$O (~25 mL) and the precipitation started by addition of petroleum ether (~50 mL), and finally EtOH (~200 mL). The suspension was kept at 24° C. for 2-3 h and stored at −20° C. for 16 h. The white solid was then filtered and washed with petroleum ether to give a white solid containing ≥95% of the β-pyranose anomer. Pure β-anomer was then obtained from subsequent recrystallization of this solid in a minimum amount of hot EtOH and kept at room temperature for 16 h. The crystals were filtered and washed with cold EtOH and petroleum ether to give penta-O-acetyl-β-D-galactopyranose 20 as white crystals (11.2 g, 28.7 mmol, 47%). R$_f$=0.20, Et$_2$O/petroleum ether 1:1 (α-anomer: R$_f$=0.24, Et$_2$O/Petroleum ether 1:1). mp 142-143° C. (EtOH) [Lit mp 142-144° C.)]. [α]$_D$+23.0 (c 1.0, CHCl$_3$) [Litt. [α]$_D$+23.4 (c 1.0, CHCl$_3$)]. $^1$H NMR (300 MHz, CDCl$_3$) δ 5.69 (d, 1H, $^3J_{1,2}$=8.3 Hz, H$_1$), 5.41 (dd, 1H, $^3J_{3,4}$=3.4 Hz, $^3J_{4,5}$=1.0 Hz, H$_4$), 5.32 (dd, 1H, $^3J_{2,3}$=10.4 Hz, $^3J_{1,2}$=8.3 Hz, H$_2$), 5.07 (dd, 1H, H$_3$), 4.17-4.08 (m, 2H, H$_{6a}$ and H$_{6b}$), 4.06-4.04 (m, 1H, H$_5$), 2.15, 2.11, 2.03, 2.03, 1.98 (5×s, 15H, 5×COCH$_3$). $^{13}$C NMR (151 MHz, CDCl$_3$) δ 170.8, 170.6, 170.4, 169.9, 169.5 (COCH$_3$), 92.6 (C$_1$), 72.2 (C$_5$), 71.3 (C$_3$), 68.4 (C$_2$), 67.4 (C$_4$), 61.6 (C$_6$), 20.8, 20.6, 20.6, 20.5 (5×COCH$_3$). ESI$^+$-HRMS (m/z) for C$_{16}$H$_{22}$O$_{11}$=413.1054 [M+Na]$^+$; found, 413.1052.

2,3,4,6-Tetra-O-acetyl-α-D-galactopyranosyl bromide (21).

The synthesis of this compound was modified according to a literature procedure. A solution of HBr in AcOH (33% w/w, 3.4 mL, 0.058 mol, 11.0 equiv.) was added dropwise over a 10 min period to a solution of penta-O-acetyl-β-D-galactopyranose 20 (2.07 g, 5.31 mmol) in 9 mL of dry CH$_2$Cl$_2$ at 0° C. The resulting mixture was stirred at 0° C. for 30 min, then at room temperature and the progress of the reaction was monitored by TLC (EtOAc/hexanes=2:3) until the complete disappearance of the starting material (~3 h.). The resulting mixture was diluted with 10 mL of CH$_2$Cl$_2$, washed twice with 30 mL saturated aqueous solution of NaHCO$_3$ and once with 20 mL of H$_2$O. The organic phase was then dried over Na$_2$SO$_4$ and concentrated under vacuum to give 2,3,4,6-tetra-O-acetyl-α-D-galactopyranosyl bromide (2.16 g, 5.25 mol, 99%) as a white foam. The product was used in the next step without further purification. R$_f$=0.68, hexanes/AcOEt 1:1. $^1$H NMR (300 MHz, CDCl$_3$) δ 6.67 (d, 1H, $^3J_{1,2}$=3.9 Hz, H$_1$), 5.49 (d, 1H, 1H$_4$), 5.37 (dd, 1H, $^3J_{2,3}$=10.6 Hz, $^3J_{3,4}$=3.3 Hz, H$_3$), 5.01 (dd, 1H, $^3J_{2,3}$=10.6 Hz, $^3J_{1,2}$=4.0 Hz, H$_2$), 4.46 (t, 1H, $^3J_{5,6}$=6.3 Hz, H$_5$), 4.19-4.04 (m, 2H, H$_6$), 2.12, 2.08, 2.03, 1.98 (4×s, 12H, 4×COCH$_3$). $^{13}$C NMR (75 MHz, CDCl$_3$) δ 170.2, 170.0, 169.8, 169.6 (COCH$_3$), 88.0 (C), 71.0 (C$_5$), 67.9 (C$_3$), 66.9 (C$_2$), 66.8 (C$_4$), 60.7 (C$_6$), 20.6, 20.5 (4×COCH$_3$).

2,3,4,6-Tetra-O-acetyl-β-D-galactopyranosyl azide (22).

Compound 22 was prepared according to a literature procedure.$^{xxi}$ To a solution of 2,3,4,6-tetra-O-acetyl-α-D-galactopyranosyl bromide 21 (2.00 g, 4.86 mmol, 1.0 eq.) in dry DMSO (10 mL) was added sodium azide (0.14 g, 5.84 mmol, 1.2 eq.) and the reaction was allowed to stir at room temperature for 30 min. The reaction mixture was then diluted with water (50 mL) and extracted with EtOAc (100 mL). The organic layer was dried over Na$_2$SO$_4$ and evaporated to dryness. The residue was purified by flash chromatography (SiO$_2$, EtOAc/petroleum ether 1:2) to furnish the desired 2,3,4,6-tetra-O-acetyl-γ-D-galactopyranosyl azide 22 as a white solid (1.77 g, 4.76 mmol, 98%). R$_f$=0.50, hexanes/AcOEt 1:1. [α]$_D$−10.3 (c 1.0, CHCl$_3$). mp 92-94° C. (recryst. from EtOH-AcOEt-hexanes). $^1$H NMR (300 MHz, CDCl$_3$) δ 5.38 (d$_{app}$, 1H, H$_4$), 5.13 (dd, 1H, $^3J_{2,3}$=10.4 Hz, $^3J_{1,2}$=8.6 Hz, H$_2$), 5.00 (dd, 1H, $^3J_{2,3}$=10.4 Hz, $^3J_{3,4}$=3.4 Hz, H$_3$), 4.57 (d, 1H, $^3J_{1,2}$=8.6 Hz, H$_1$), 4.14 (m, 2H, H$_{6a,b}$), 3.98 (dd, 1H, $^3J_{5,6}$=7.0 Hz, $^3J_{4,5}$=1.0 Hz, H$_5$), 2.14-1.95 (4×s, 12H, C(O)CH$_3$). $^{13}$C NMR (75 MHz, CDCl$_3$) δ 170.6, 170.3, 170.2, 169.6 (4×COCH$_3$), 88.5 (C$_1$), 73.0 (C$_2$), 70.9 (C$_5$), 68.2 (C$_3$), 67.0 (C$_4$), 61.4 (C$_6$), 20.87, 20.9, 20.8, 20.7 (4×COCH$_3$). ESI$^+$-HRMS (m/z) for C$_{14}$H$_{19}$N$_3$O$_9$=396.1014 [M+Na]$^+$, found 396.1010.

β-D-Galactopyranosyl azide (23).

Compound 23 was synthesized according to a modified literature procedure. To a stirring solution of 2,3,4,6-tetra-O-acetyl-β-D-galactopyranosyl azide 22 (1.00 g, 2.68 mmol, 1.0 eq) in dry MeOH (12 mL) was added a solution of sodium methoxide (1M in MeOH) until pH 9-10 (250 μL). The reaction mixture was stirred at r.t. for 24 h. The solution was then neutralized by addition of ion-exchange resin (Amberlite IR 120 H$^+$) until pH 7, filtered, and the solvent was removed under reduced pressure. The residue was then lyophilized to yield the fully deprotected derivative 23 (547 mg, 2.68 mmol, 99%) as a white solid. The spectroscopic data of sugar 23 are in agreement with those previously reported. $^{Error!\ Bookmark\ not\ defined.xxii}$ $[\alpha]_D$ −5.3 (c 1.0, MeOH). mp 142-144° C. (EtOH/petroleum ether) [Litt.$^{xxiii}$ 140° C.]. $^1$H NMR (300 MHz, D$_2$O) δ 4.51 (d, $^3J_{1,2}$=8.6 Hz, 1H, H$_1$), 3.80 (d$_{app}$, 1H, H$_4$), 3.66-3.58 (m, 4H, H$_5$, H$_{6a}$, H$_{6b}$), 3.53 (dd, 1H, $^3J_{2,3}$=10.0 Hz, $^3J_{3,4}$=3.3 Hz, H$_3$), 3.35 (dd, $^3J_{2,3}$=10.0 Hz, $^3J_{2,3}$=8.6 Hz, 1H, H$_2$). $^{13}$C NMR (75 MHz, D$_2$O) δ 90.2 (C$_1$), 76.8 (C$_5$), 72.2 (C$_3$), 69.9 (C$_2$), 68.1 (C$_4$), 60.6 (C$_6$). ESI$^+$-HRMS (m/z) for C$_6$H$_{11}$N$_3$O$_5$=228.0591 [M+Na]$^+$, found 228.0593.

1,2,3,4,6-Penta-O-acetyl-D-mannopyranose (25).

This compound was synthesized according to a modified literature procedure. D-Mannose 24 (20.0 g, 111 mmol, 1.0 eq.) was slowly added to a solution of Iodine (I$_2$, 1.12 g, 4.41 mmol, 0.04 eq.) in Ac$_2$O (100 mL) at 0° C. and under a nitrogen atmosphere. After stirring 30 min at 0° C. and an additional 16 h at r.t., the reaction mixture was diluted with 125 mL of CH$_2$Cl$_2$ and washed with a cold saturated aqueous solution of Na$_2$SO$_3$ (2×125 mL), then with a saturated aqueous solution of NaHCO$_3$ (4×75 mL). The organic layer was dried over Na$_2$SO$_4$ and evaporated to dryness to afford the desired peracetylated compound 25 (43.0 g, 110 mmol, 99%, mixture of both anomers α/β 10:90) as a clear viscous oil. The spectroscopic data of sugar 25 are in agreement with those previously reported.$^{xxiv}$ $^1$H NMR (300 MHz, CDCl$_3$) Signals for β-anomer: δ 6.07 (d, $^3J_{1,2}$=2.0 Hz, 1H, H$_1$), 5.35-5.33 (m, 2H, H$_3$, H$_2$); 5.29-5.24 (m, 1H, H$_4$), 4.28 (dd, $^2J_{6a,6b}$=12.4 Hz, $^3J_{6b,5}$=4.9 Hz, 1H, H$_{6b}$), 4.11 (dd, $^2J_{6a,6b}$, =12.4 Hz, $^3J_{6a,5}$=2.4 Hz, 1H, H$_{6b}$), 4.07-4.02 (m, 1H, H$_5$), 2.17-2.00 (5×s, 15H, COCH$_3$); Signals for α-anomer: δ 5.85 (d, $^3J_{1,2}$=1.2 Hz, 1H, H$_5$), 5.47 (dd, $^3J_{1,2}$=1.2 Hz, $^3J_{2,3}$=3.0 Hz, 1H, H$_2$); 5.28 (m, 1H, H$_4$), 5.13 (dd, $^3J_{3,4}$=10.0 Hz, $^3J_{2,3}$=3.2 Hz, 1H, H$_3$); 4.29 (dd, $^2J_{6a,6b}$=12.3 Hz, $^3J_{6b,5}$=5.3 Hz, 1H, H$_{6b}$), 4.15 (dd, $^2J_{6a,6b}$=12.3 Hz, $^3J_{6a,5}$=2.5 Hz, 1H, H$_{6b}$), 3.80 (ddd, $^3J_{5,4}$=9.8 Hz, $^3J_{6b,5}$=5.3 Hz, $^3J_{6a,5}$=2.5 Hz, 1H, H$_5$), 2.17-2.00 (5×s, 15H, COCH$_3$). $^{13}$C NMR (75 MHz, CDCl$_3$) Signals for β-anomer: δ 170.5, 169.9, 169.6, 169.4, 168.0 (COCH$_3$), 90.5 (C$_1$), 70.5 (C$_5$), 68.6 (C$_3$), 68.2 (C$_2$), 65.4 (C$_4$), 62.0 (C$_6$), 20.8, 20.7, 20.6, 20.6, 20.6 (COCH$_3$); Signals for α-anomer: δ 171.1, 170.1, 169.6, 169.4, 168.3 (5×COCH$_3$), 90.3 (C$_1$), 73.2 (C$_5$), 70.5 (C$_3$), 68.1 (C$_2$), 65.3 (C$_4$), 62.1 (C$_6$), 20.8, 20.7, 20.6, 20.6, 20.5 (5×COCH$_3$).

2,3,4,6-Tetra-O-acetyl-α-D-mannopyranosyl azide (26).

Compound 26 was synthesized according to a literature procedure. To a solution of 25 (300 mg, 0.77 mmol, 1.0 eq.) in dry CH$_2$Cl$_2$ (3 mL) were added azidotrimethylsilane (TMSiN$_3$, 0.43 mL, 3.07 mmol, 4.00 equiv.) and tin tetrachloride (SnCl$_4$, 1M in CH$_2$Cl$_2$, 0.20 mL, 0.20 mmol, 0.26 equiv.) under nitrogen atmosphere. The mixture was stirred at room temperature. The course of the reaction was monitored by TLC (hexanes/toluene/AcOEt 3:3:4) until complete disappearance of the starting material (6h). CH$_2$Cl$_2$ (15 mL) was added and the solution was washed with a saturated aqueous NaHCO$_3$ (10 mL), water (10 mL) and brine (10 mL). The organic phase was then dried with Na$_2$SO$_4$ and after the evaporation of the solvent, the resulting crude product was purified by flash chromatography (hexanes/AcOEt 3:1) to give 2,3,4,6-tetra-O-acetyl-α-D-mannopyranosyl azide 26 as a colorless oil (276 mg, 0.74 mmol, 96%). The spectroscopic data of sugar 26 are in agreement with those previously reported.$^{xxv}$ R$_f$=0.41, Hexanes/Toluene/AcOEt 3:3:4; R$_f$=0.21, Hexanes/AcOEt 3:1. [α]$_D$+102 (c 0.1, CHCl$_3$) [Litt.$^{xxvi}$ [α]$_D$+105 (c 0.1, CHCl$_3$)]. $^1$H NMR (300 MHz, CDCl$_3$) δ 5.37 (d, $^3J_{1,2}$=1.9 Hz, 1H, H$_1$), 5.25 (dd, $^3J_{3,4}$=$^3J_{4,5}$=9.9 Hz, 1H, H$_4$), 5.21 (dd, $^3J_{2,3}$=2.3 Hz, 1H, H$_3$), 5.12 (m, 1H, H$_2$), 4.25 (dd, $^2J_{6a,6b}$=12.4 Hz, $^3J_{5,6a}$=5.5 Hz, 1H, H$_{6a}$), 4.13 (m, 2H, H$_{6b}$, H$_5$), 2.14, 2.08, 2.02, 1.96 (4×s, 12H, CH$_3$); $^1$H NMR (300 MHz, C$_6$D$_6$) δ 5.55 (dd, $^3J_{3,4}$=$^3J_{4,5}$=10.1 Hz, 1H, H$_4$), 5.41 (dd, $^3J_{2,3}$=3.4 Hz, 1H, H$_3$), 5.25 (dd, $^3J_{2,3}$=3.4 Hz, $^3J_{1,2}$=1.8 Hz, 1H, H$_2$), 4.72 (d, $^3J_{1,2}$=1.8 Hz, 1H, H$_1$), 4.27 (dd, $^2J_{6a,6b}$=12.4 Hz, $^3J_{5,6a}$=5.1 Hz, 1H, H$_{6a}$), 4.03 (dd, $^2J_{6a,6b}$=12.4 Hz, $^3J_{5,6b}$=2.2 Hz, 1H, H$_{6b}$), 3.84 (m, 1H, H$_5$), 1.72, 1.69, 1.66, 1.60 (4×s, 12H, CH$_3$). $^{13}$C NMR (75 MHz, CDCl$_3$) δ 170.5, 169.7, 169.6, 169.5 (COCH$_3$), 87.3 (C$_1$, J$_{C1,H1}$=170.9 Hz (characteristic for α-anomer)), 70.5 (C$_5$), 69.0 (C$_2$), 68.1 (C$_3$), 65.5 (C$_4$), 62.0 (C$_6$), 20.7, 20.6, 20.6, 20.5 ppm (CH$_3$). IR ν$_{max}$ (neat) cm$^{-1}$: 2959 m, 2119 s (N$_3$), 1744 s, 1369 s, 1235 s, 1049 s, 909 s. ESI$^+$-HRMS (m/z) for C$_{14}$H$_{19}$N$_3$O$_9$=396.1014 [M+Na]$^+$; found, 396.1007.

α-D-Mannopyranosyl azide (27).

This compound was synthesized according to a literature procedure.xxii To a stirring solution of 2,3,4,6-tetra-O-acetyl-α-D-mannopyranosyl azide 26 (500 mg, 1.34 mmol, 1.0 eq) in dry MeOH (6 mL) was added a solution of sodium methoxide (1M in MeOH) until pH 9-10 (120 μL). The reaction mixture was stirred at r.t. for 24 h. The solution was then neutralized by addition of ion-exchange resin (Amberlite IR 120 H$^+$) until pH 7, filtered, and the solvent was removed under reduced pressure to afford the fully deprotected derivative 27 (274 mg, 1.34 mmol, 99%) as a colorless syrup. The spectroscopic data of sugar 27 are in agreement with those previously reported. [α]$_D$+194.7 (c 1.0, MeOH). $^1$H NMR (300 MHz, D$_2$O) δ 5.36 (d, $^3J_{1,2}$=1.7 Hz, 1H, H$_1$), 3.83-3.54 (m, 6H, H$_2$, H$_3$, H$_4$, H$_5$, H$_6$). $^{13}$C NMR (75 MHz, D$_2$O) δ 89.3 (C$_1$), 74.2 (C$_5$), 69.4 (C$_3$), 69.3 (C$_2$), 66.0 (C$_4$), 60.4 (C$_6$). ESI$^+$-HRMS (m/z) for C$_6$H$_{11}$N$_3$O$_5$=228.0591 [M+Na]$^+$, found 228.0585.

Octa-O-acetyl-D-lactopyranose (29).

Compound 29 was synthesized according to a modified literature procedure. Error! Bookmark not defined. A suspension of sodium acetate (21.0 g, 256 mmol, 1.1 equiv.) in acetic anhydride (270 mL) was heated at reflux. D-Lactose 28 (84.3 g, 234 mmol, 1.0 equiv.) was then added into the mixture by small portions (1 to 2 g each time). The condenser should be closed immediately after each addition! After complete addition, the mixture became a clean solution that was stirred under reflux for 20 additional min. The hot solution was then poured into a 1 L beaker containing ice-water (600 mL) under vigorous stirring until the ice melted. CH$_2$Cl$_2$ (300 mL) was added to the stirred solution and the aqueous layer was then removed. The organic layer was washed with ice-cold water (3×400 mL), saturated aqueous NaHCO$_3$ solution (3×400 mL) and brine (2×400 mL). The organic solution was then dried over Na$_2$SO$_4$, filtered and finally concentrated under reduced pressure to give a crude yellow oil which was recrystallized from EtOH anh. (~400 mL). The crystals were filtered and washed with cold EtOH and petroleum ether to give octa-O-acetyl-D-lactopyranose (α/β≥5:95) as white crystals (150.6 g, 222 mmol, 95%). R$_f$=0.16, Hexanes/AcOEt 1:1. $^1$H NMR (300

MHz, CDCl$_3$) δ 5.66 (d, 1H, $^3J_{1,2}$=8.3 Hz, H$_{1glc}$), 5.34 (d$_{app}$, 1H, H$_{4gal}$), 5.23 (dd, 1H, $^3J_{2,3}$=9.4 Hz, $^3J_{3,4}$=8.7 Hz, 1H, H$_{3glc}$), 5.13-5.01 (m, 2H, H$_{2gal}$, H$_{2glc}$), 4.93 (dd, 1H, $^3J_{2,3}$=10.4 Hz, $^3J_{3,4}$=8.5 Hz, 1H, H$_{3gal}$), 4.49-4.41 (m, 2H, H$_{1gal}$, H$_{6aglc}$), 4.14-4.07 (m, 3H, H$_{6bglc}$, H$_{6agal}$, H$_{6bgal}$), 3.89-3.81 (m, 2H, H$_{4glc}$, H$_{5gal}$), 3.78-3.76 (m, 1H, H$_5$), 2.15-1.95 (8×s, 24H, 8×COCH$_3$). $^{13}$C NMR (75 MHz, CDC$_3$) δ 170.4, 170.3, 170.2, 170.1, 169.6, 169.6, 169.0, 168.9 (COCH$_3$), 101.0 (C$_{glc}$), 91.5 (C$_{1gal}$), 75.7 (C$_{4glc}$), 73.5 (C$_{3glc}$), 72.6 (C$_{5glc}$), 71.0 (C$_{3gal}$), 70.7 (C$_{5gal}$), 70.5 (C$_{2glc}$), 69.0 (C$_{2gal}$), 66.6 (C$_{4gal}$), 61.7 (C$_{6glc}$), 60.9 (C$_{6gal}$), 20.9, 20.8, 20.8, 20.7, 20.6, 20.6, 20.5, 20.5 (8×COCH$_3$).

2-Azidoethyl 2,3,4,6-tetra-O-acetyl-β-D-galactopyranosyl-(1→4)-2,3,6-tri-O-acetyl-β-D-glucopyranoside (31).

Compound 31 was synthesized according to a literature procedure.[xxvii] To a solution of per-O-acetylated lactose 29 (β anomer, 3.00 g, 4.42 mmol, 1.0 eq) and 2-bromoethanol (1.66 g, 13.3 mmol, 3.0 eq) in dry CH$_2$Cl$_2$ (20 mL) under a nitrogen atmosphere and at 0° C. was added dropwise BF$_3$.Et$_2$O (1.62 mL, 13.3 mmol, 3.0 eq.) over a 15 min period. After stirring overnight (12 h) at r.t. the solution was washed successively with NaHCO$_3$ (20 mL), water (20 mL) and brine (10 mL). The organic phase was then dried over MgSO$_4$ and concentrated under reduced pressure to furnish a yellow oil corresponding to crude 2-bromoethyl 2,3,4,6-tetra-O-acetyl-β-D-galactopyranosyl-(1-4)-2,3,6-tri-O-acetyl-β-D-glucopyranoside (30) that was engaged in the next step without further purification. Obtained crude 30 was dissolved in 40 mL of anhydrous DMF and sodium azide (864 mg, 13.3 mmol, 3.0 eq) was added. The mixture was stirred at 80° C. during 3 h, cooled to ambient temperature, poured into EtOAc (100 mL) and washed with water (4×300 mL) and brine (2×100 mL). The organic layer was dried over Na$_2$SO$_4$, filtered and evaporated to dryness. The residue was purified by chromatography on a silica gel column (toluene-EtOAc, 3:2) to afford the desired 2-azidoethyl 2,3,4,6-tetra-O-acetyl-β-D-galactopyranosyl-(1→4)-2,3,6 tri-O-acetyl-β-D-glucopyranoside 31 (1.87 g, 2.65 mmol, 60% (over 2 steps)) as a colorless solid. The spectroscopic data of sugar 31 are in agreement with those previously reported.[xxvii] [α]$_D$–14.0 (c 1.0, CHCl$_3$) [Litt. [α]$_D$–22.0 (c 1.1, CHCl$_3$)]. m.p. 63-67° C. (uncorrected). $^1$H NMR (300 MHz, CDCl$_3$) δ 5.35 (d$_{app}$, 1H, H$_{4gal}$), 5.20 (dd, $^3J_{4,3}$=9.4 Hz, $^3J_{3,2}$=9.1 Hz, 1H, H$_{3glc}$), 5.10 (dd, $^3J_{2,1}$=10.5 Hz, $^3J_{3,2}$=8.0 Hz, 1H, H$_{2gal}$), 4.95 (dd, $^3J_{2,1}$=10.5 Hz, $^3J_{3,4}$=3.4 Hz, 1H, H$_{3gal}$), 4.90 (dd, $^3J_{2,1}$=9.4 Hz, $^3J_{3,2}$=8.0 Hz, 1H, H$_{2glc}$), 4.52 (d, $^3J_{1,2}$=7.9 Hz, 1H, H$_{1glc}$), 4.48-4.47 (m, 2H, H$_{1gal}$, H$_{6aglc}$), 4.16-3.25 (m, 5H, H$_{6bglc}$, H$_{6agal}$, H$_{6bgal}$, OCH$_2$CH$_2$N$_3$, H$_{4glc}$, H$_{5gla}$, H$_{5glc}$), 2.15-1.96 (7×s, 21H, COCH$_3$). $^{13}$C NMR (75 MHz, CDCl$_3$) δ 170.3, 170.3, 170.1, 170.0, 169.7, 169.6, 169.1, 169.0 (7s, COCH$_3$), 101.0 (C$_{1gal}$), 100.4 (C$_{1glc}$), 76.1 (C$_{4glc}$), 72.8 (C$_{3glc}$), 72.5 (C$_{5glc}$), 71.5 (C$_{2glc}$), 70.9 (C$_{3gal}$), 70.7 (C$_{5gal}$), 69.1 (OCH$_2$), 68.6 (C$_{2gal}$), 66.6 (C$_{4gal}$), 61.8 (C$_{6glc}$), 60.8 (C$_{6gal}$), 50.5 (CH$_2$N$_3$), 20.8, 20.8, 20.7, 20.6, 20.6, 20.6, 20.5 (7s, COCH$_3$). IR ν$_{max}$ (neat) cm$^{-1}$: 2923 m, 2104 m (N$_3$), 1740 s, 1367 s, 1235 s, 1214 s, 1041 s, 907 s. ESI$^+$-HRMS (m/z) for C$_{28}$H$_{39}$N$_3$O$_{18}$=728.2121 [M+Na]$^+$, found 728.2111.

2-Azidoethyl β-D-galactopyranosyl-(1→4)-β-D-glucopyranoside (32).

The synthesis of compound 32 was modified from a literature procedure.xxii To a solution of 2-azidoethyl 2,3,4,6-tetra-O-acetyl-β-D-galactopyranosyl-(1→4)-2,3,6-tri-O-acetyl-β-D-glucopyranoside 31 (600 mg, 0.850 mmol, 1.0 eq) in dry MeOH (6 mL) was added a solution of sodium methoxide (1M in MeOH) until pH 9-10 (100 μL). The reaction mixture was stirred at r.t. for 24 h. The solution was then neutralized by addition of ion-exchange resin (Amberlite IR 120 H$^+$) until pH 7, filtered, and the solvent was removed under reduced pressure. The residue was then lyophilized to yield the fully deprotected derivative 32 (346 mg, 0.847 mmol, 98%) as a white solid. The spectroscopic data are in agreement with those previously reported for sugar 32.xxiv [α]$_D$+0.4 (c 1.0, MeOH). mp 142-145° C. (uncorrected). $^1$H NMR (600 MHz, D$_2$O) δ 4.40 (d, $^3J_{1,2}$=8.0 Hz, 1H, H$_{1glc}$), 4.31 (d, $^3J_{1,2}$=7.8 Hz, 1H, H$_{1gal}$), 3.92 (dt, $^2J_{Ha,Hb}$=10.7 Hz, $^3J$=4.8 Hz, 1H, CH$_a$H$_b$CH$_2$N$_3$), 3.85 (dd, 2J$_{6a,6b}$=12.0 Hz, $^3J_{6b,5}$=1.8 Hz, 1H, H$_{6bglc}$), 3.79 (dd, $^3J_{4,3}$=3.3 Hz, $^3J_{4,5}$=0.7 Hz, 1H, H$_{4gal}$), 3.73-3.39 (m, 12H, CH$_2$ (3H), H$_{3gal}$, H$_{3glc}$, H$_{4glc}$, H$_{5gal}$, H$_{5glc}$, H$_{6aglc}$, H$_{6agal}$, H$_{6bgal}$, H$_{2gal}$), 3.21 (dd, $^3J_{3,2}$=9.2 Hz, $^3J_{2,1}$=8.0 Hz, 1H, H$_{2glc}$). $^{13}$C NMR (151 MHz, D$_2$O) δ 102.5 (C$_{1gal}$), 101.7 (C$_{1glc}$), 77.9 (C$_{4glc}$), 74.9, 74.4, 73.9 (C$_{3glc}$, C$_{5gal}$, C$_{5glc}$), 72.3 (C$_{2glc}$), 72.1 (C$_{3gal}$), 70.5 (C$_{2gal}$), 68.1 (OCH$_2$), 68.1 (C$_{4gal}$), 60.6 (C$_{6glc}$), 59.6 (C$_{6gal}$), 50.1 (CH$_2$N$_3$). ESI$^+$-HRMS (m/z) for C$_{14}$H$_{25}$N$_3$O$_{11}$=434.1381 [M+Na]$^+$, found 434.1391.

Toluene-4-sulfonic acid 2-{2-[2-(2-hydroxy-ethoxy)-ethoxy]-ethoxy}-ethyl ester (34).[xxviii]

To a solution of tetra(ethylene)glycol (300.0 mL, 336.0 g, 1.720 mol, 5.8 eq.) and anhydrous pyridine (120 mL, 1.55 mol, 5.0 eq.) in 600 mL of anhydrous CH$_2$Cl$_2$ was added dropwise a solution of ρ-toluenesulfonyl chloride (57.0 g, 0.299 mol, 1 eq.) in 300 mL of CH$_2$Cl$_2$. The mixture was stirred at room temperature for 20 h. The reaction solution was washed with cold water (2×250 mL) and brine (2×250 mL). The aqueous solution was extracted with CH$_2$Cl$_2$ (2×250 mL) and the combined organic layers were dried over MgSO$_4$. Evaporation of the solvent under reduced pressure provided a colorless oil (containing less than 5% by NMR of the disubstituted product) (84.1 g, 0.242 mol, 81%). The spectroscopic data are in agreement with those previously reported.xxviii R$_f$=0.43, CH$_2$Cl$_2$/MeOH 95:5. $^1$H NMR (300 MHz, CDCl$_3$) δ 7.78 (d, $^3J$=8.3 Hz, 2H, CH=CHCH$_3$), 7.31 (d, $^3J$=8.3 Hz, 2H, CH=CHCH$_3$), 4.14 (m, 2H, CH$_2$CH$_2$OH), 3.55-3.69 (m, 14H, CH$_2$O), 2.55 (br s, 1H, OH), 2.43 (s, 3H, φCH$_3$). $^{13}$C NMR (75 MHz, CDCl$_3$) δ 145.1 (CCH$_3$), 133.3 (CSO$_2$), 130.1 (CH=C—CH$_3$), 128.2 (CHCH=CCH$_3$), 72.7 (CH$_2$CH$_2$OH), 71.0, 70.9, 70.7, 70.6, 69.5, 69.0 (OCH$_2$CH$_2$O), 61.9 (CH$_2$OH), 21.9 (φCH$_3$).

2-(2-(2-[2-(2-Tosyloxy-ethoxy)-ethoxy]-ethoxy)-ethyl) 2,3,4,6-tetra-O-acetyl-β-D-galactopyranosyl-(1→4)-2,3,6 tri-O-acetyl-β-D-glucopyranoside (35).

To a solution of per-O-acetylated lactose 29 (5.00 g, 7.40 mmol, 1.0 eq) and tetra(ethylene)glycol monotosylate 34 (8.10 g, 22.1 mmol, 3.0 eq) in dry CH$_2$Cl$_2$ (60 mL) under a nitrogen atmosphere and at 0° C. was added dropwise BF$_3$.Et$_2$O (2.7 mL, 22.1 mmol, 3.0 eq.) over a 15 min period. After stirring overnight (12 h) at r.t. the solution was washed successively with NaHCO$_3$ (40 mL), water (40 mL) and brine (40 mL). The organic phase was then dried over MgSO$_4$ and concentrated under reduced pressure. Column chromatography on silica (EtOAc/hexanes 5:5 to 8:2) gave the desired compound (2.90 g, 3.00 mmol, 40%) as a colorless oil. Rt=0.23, EtOAc/hexanes 7:3. $^1$H NMR (600 MHz, CDCl$_3$) δ 7.79 (d, $^3J$=8.0 Hz, 2H, CH$_{ar}$), 7.35 (d, $^3J$=8.0 Hz, 2H, CH$_{ar}$), 5.35 (d$_{app}$, 1H, H$_{4gal}$), 5.18 (dd, $^3J_{4,3}$=9.4 Hz, $^3J_{3,2}$=9.1 Hz, 1H, H$_{3glc}$), 5.09 (dd, $^3J_{2,1}$=10.5 Hz, $^3J_{3,2}$=8.0 Hz, 1H, H$_{2glc}$), 4.96 (dd, $^3J_{2,3}$=10.5 Hz, $^3J_{3,4}$=3.4 Hz, 1H, H$_{3gal}$), 4.88 (dd, $^3J_{2,1}$=9.4 Hz, $^3J_{3,2}$=8.0 Hz, 1H, H$_{2gal}$), 4.55 (d, $^3J_{1,2}$=7.9 Hz, 1H, H$^{1glc}$), 4.48-4.47 (m, 2H, H$_{1gal}$, H$_{6glc}$), 4.16-4.05

(m, 5H, $H_{6glc}$, $H_{6gal}$, $H_{6gal}$, CH$_2$OTs), 3.91-3.85 (m, 2H, OCH$_2$), 3.79 (dd, $^3J_{3,4}$=9.9 Hz, $^3J_{4,5}$=9.1 Hz, 1H, $H_{4glc}$), 3.72-3.57 (m, 14H, $H_{5gal}$, $H_{5glc}$, OCH$_2$), 2.44 (s, 3H, CH$_3$), 2.14 (s, 3H, COCH$_3$), 2.11 (s, 3H, COCH$_3$), 2.05 (s, 3H, COCH$_3$), 2.03 (s, 6H, 2×COCH$_3$), 2.02 (s, 3H, COCH$_3$), 1.97 (s, 3H, COCH$_3$). $^{13}$C NMR (151 MHz, CDCl$_3$) δ 170.3, 170.3, 170.1, 170.0, 169.7, 169.6, 169.0 (7s, COCH$_3$), 144.7 (SO$_2$C$_q$), 132.9 (C$_q$CH$_3$), 129.8 (CH$_{ar}$C$_q$CH$_3$), 127.9 (SO$_2$C$_q$CH$_{ar}$), 101.0 (C$_{1gal}$), 100.6 (C$_{1glc}$), 76.2 (C$_{4glc}$), 72.8 (C$_{3glc}$), 72.5 (C$_{5glc}$), 71.6 (C$_{2glc}$), 70.9 (C$_{3gal}$), 70.7 (C$_{5gal}$), 70.6, 70.6, 70.4, 70.1 (OCH$_2$), 69.2 (CH$_2$OTs), 69.0 (C$_{2gal}$), 68.6 (CH$_2$CH$_2$OTs), 66.5 (C$_{4gal}$), 61.9 (C$_{6glc}$), 60.7 (C$_{6gal}$), 21.6 (CH$_3$), 20.8, 20.8, 20.7, 20.6, 20.6, 20.6, 20.5 (7s, COCH$_3$). ESI$^+$-HRMS (m/z) for C$_{41}$H$_{58}$O$_{24}$S=989.2931 [M+Na]$^+$, found 989.2949.

2-(2-{2-[2-(2-Azido-ethoxy)-ethoxy]-ethoxy}-ethyl) 2,3,4,6-tetra-O-acetyl-β-D-galactopyranosyl-(1→4)-2,3,6-tri-O-acetyl-β-D-glucopyrnoside (36).

To a stirring solution of 2-(2-{2-[2-(2-tosyloxy-ethoxy)-ethoxy]-ethoxy}-ethyl) 2,3,4,6-tetra-O-acetyl-β-D-galactopyranosyl-(1→4)-2,3,6-tri-O-acetyl-β-D-glucopyranoside 35 (1.10 g, 1.14 mmol, 1.0 eq) in dry DMF (12 mL) under a nitrogen atmosphere were added sodium azide (148 mg, 2.28 mmol, 2.0 eq.) and sodium iodide (17.1 mg, 0.11 mmol, 0.1 eq.). After stirring overnight (16 h) at 70° C., the solution was washed successively with water (4×100 mL) and brine (3×50 mL). The organic phase was then dried over MgSO$_4$ and concentrated under reduced pressure. Column chromatography on silica (EtOAc/hexanes 6:4 to 8:2) afforded the desired compound 36 (940 mg, 1.13 mmol, 99%) as a colorless oil. R$_f$=0.24, EtOAc/hexanes 7:3. [α]$_D$−10.3 (c 1.0, CHCl$_3$). $^1$H NMR (600 MHz, CDCl$_3$) δ 5.34 (d$_{app}$, 1H, $H_{4gal}$), 5.18 (dd, $^3J_{4,3}$=9.4 Hz, $^3J_{3,2}$=9.1 Hz, 1H, $H_{3glc}$), 5.10 (dd, $^3J_{2,1}$=10.5 Hz, $^3J_{3,2}$=8.0 Hz, 1H, $H_{2gal}$), 4.96 (dd, $^3J_{2,3}$=10.5 Hz, $^3J_{3,4}$=3.4 Hz, 1H, $H_{3gal}$), 4.89 (dd, $^3J_{2,1}$=9.4 Hz, $^3J_{3,2}$=8.0 Hz, 1H, $H_{23}$), 4.57 (d, $^3J_{1,2}$=9.4 Hz, 1H, $H_{1glc}$), 4.48 (dd, $^2J_{6a,6b}$=12.0 Hz, 3J$_{5.6a}$=2.1 Hz, 1H, $H_{6aglc}$), 4.47 (d, $^3J_{1,2}$=7.9 Hz, 1H, $H_{1gal}$), 4.14-4.06 (m, 3H, $H_{6bgal}$, $H_{6bgal}$), 3.92-3.85 (m, 2H, OCH$_2$), 3.78 (dd, $^3J_{3,4}$=9.4 Hz, $^3J_{4,5}$=9.1 Hz, 1H, $H_{4glc}$), 3.73-3.59 (m, 14H, $H_{5gal}$, $H_{5glc}$, OCH$_2$), 3.39 (t, $^3J$=5.1 Hz, 2H, CH$_2$N$_3$), 2.15 (s, 3H, COCH$_3$), 2.12 (s, 3H, COCH$_3$), 2.06 (s, 3H, COCH$_3$), 2.04 (3s, 9H, 3×COCH$_3$), 1.96 (s, 3H, COCH$_3$). $^{13}$C NMR (151 MHz, CDCl$_3$) δ 170.3, 170.1, 170.0, 170.0, 169.7, 169.6, 169.0 (7s, COCH$_3$), 101.1 (C$_{1gal}$), 100.6 (C$_{1glc}$), 76.3 (C$_{4glc}$), 72.6 (C$_{3glc}$), 72.5 (C$_{5glc}$), 71.6 (C$_{2glc}$), 71.0 (C$_{3gal}$), 70.7 (C$_{5gal}$), 70.6, 70.6, 70.3, 70.0 (OCH$_2$), 69.0 (C$_{2gal}$), 69.0 (OCH$_2$), 66.6 (C$_{4gal}$), 62.0 (C$_{6glc}$), 60.7 (C$_{6gal}$), 50.6 (CH$_2$N$_3$), 20.8, 20.8, 20.7, 20.6, 20.6, 20.6, 20.5 (7s, COCH$_3$). IR: ν (cm$^{-1}$): 2871s, 2104m (N$_3$), 1742s, 1367s, 1214s, 1041s. ESI$^+$-HRMS (m/z) for C$_{34}$H$_{51}$N$_3$O$_{21}$=860.2907 [M+Na]$^+$, found 860.2923.

2-(2-{2-[2-(2-Azido-ethoxy)-ethoxy]-ethoxy}-ethyl) β-D-galactopyranosyl-(1→4)-β-D-glucopyranoside (37).

To a stirring solution of 2-(2-{2-[2-(2-azido-ethoxy)-ethoxy]-ethoxy}-ethyl) 2,3,4,6-tetra-O-acetyl-β-D-galactopyranosyl)-(1→4)-2,3,6-tri-O-acetyl-β-D-glucopyranoside 36 (900 mg, 1.07 mmol, 1.0 eq) in dry MeOH (12 mL) was added a solution of sodium methoxide (1M in MeOH) until pH 9-10 (150 μL). The reaction mixture was stirred at r.t. for 24 h. The solution was then neutralized by addition of ion-exchange resin (Amberlite IR 120 H$^+$) until pH 7, filtered, and the solvent was removed under reduced pressure. The residue was then lyophilized to yield the fully deprotected derivative 37 (614 mg, 1.05 mmol, 98%) as a white solid. [α]$_D$−5.6 (c 1.0, MeOH). $^1$H NMR (600 MHz, D$_2$O) δ 4.36 (d, $^3J_{1,2}$=8.0 Hz, 1H, $H_{1glc}$), 4.29 (d, $^3J_{1,2}$=7.8 Hz, 1H, $H_{1gal}$), 3.91 (dt, $^2J_{Ha,Hb}$=10.7 Hz, $^3J$=4.8 Hz, 1H, CH$_a$H$_b$CH$_2$N$_3$), 3.83 (dd, $^2J_{6a,6b}$32 12.0 Hz, $^3J_{6b,5}$=1.8 Hz, 1H, $H_{6bglc}$), 3.77 (dd, $^3J_{4,3}$=3.3 Hz, $^3J_{4,5}$=0.7 Hz, 1H, $H_{4gal}$), 3.71-3.43 (m, 21H, OCH$_2$, 13H, $H_{3gal}$, $H_{3glc}$, $H_{4glc}$, $H_{5gal}$, $H_{5glc}$, $H_{6aglc}$, 2×$H_{6gal}$), 3.39 (dd, $^3J_{2,1}$=9.8 Hz, $^3J_{3,2}$=8.0 Hz, 1H, $H_{2gal}$), 3.36 (t, $^3J$=4.9 Hz, 2H, CH$_2$N$_3$), 3.19 (dd, $^3J_{3,2}$=9.2 Hz, $^3J_{2,1}$=8.0 Hz, 1H, $H_{2glc}$); $^{13}$C NMR (151 MHz, D$_2$O) δ 102.5 (C$_{1gal}$), 101.7 (C$_{1glc}$), 77.9 (C$_{4glc}$), 74.9, 74.3, 73.9 (C$_{3glc}$, C$_{5gal}$, C$_{5glc}$), 72.4 (C$_{2glc}$), 72.1 (C$_{3gal}$), 70.5 (C$_{2gal}$), 69.3, 69.2, 69.2, 69.1, 69.1, 68.8, 68.3, 68.1 (OCH$_2$, C$_{4gal}$), 60.6 (C$_{6glc}$), 59.6 (Ca$_{6gal}$), 49.7 (CH$_2$N$_3$). ESI$^+$-HRMS (m/z) for C$_{20}$H$_{37}$N$_3$O$_{14}$=566.2168 [M+Na]$^+$, found 566.2178.

Supporting Scheme 5. Synthesis of Glycosyl Alkynes 41a, 41d, 43a, 43b, 43c, 43d and 45

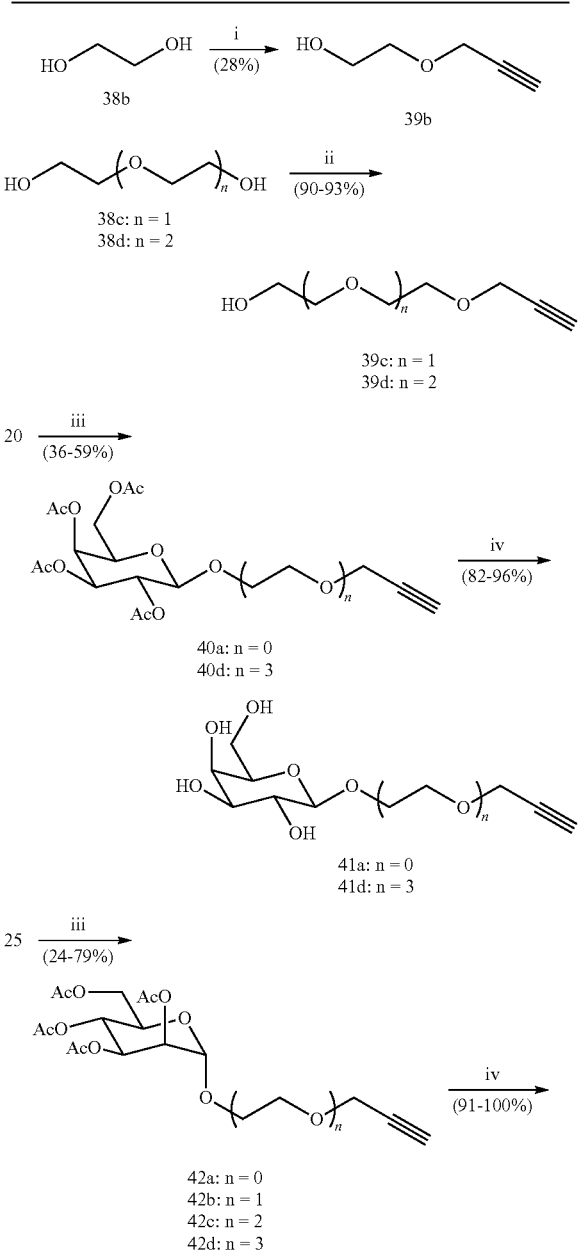

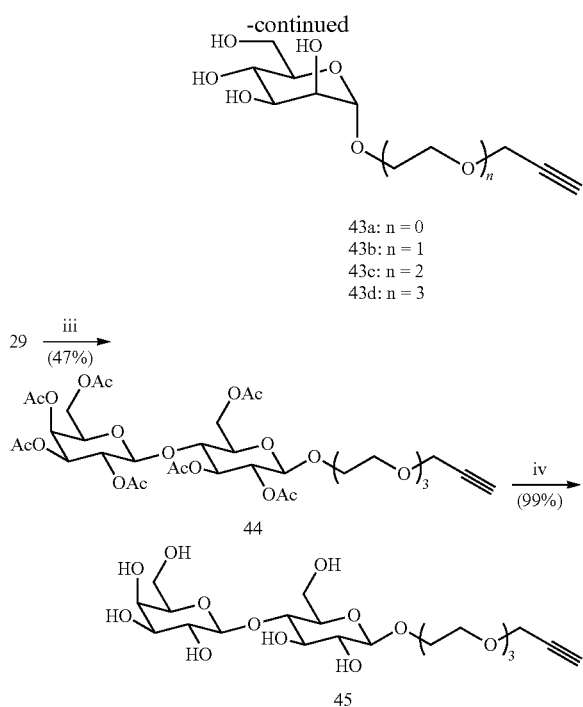

Reagents and conditions: (i) NaH, propargyl bromide, toluene (25° C.); (ii) propargyl bromide, 'BuOK, THF (25° C.); (iii) 39a, 39b, 39c, or propargyl alcohol, BF$_3$·Et$_2$O, CH$_2$Cl$_2$ or CH$_3$CN (0-25° C.); (iv) 1M MeONa in MeOH (25° C.).

2-(Prop-2-yn-1-yloxy)ethanol (39b).

This compound was prepared according to a literature procedure.[xxix] Ethylene glycol (24.83 g, 0.40 mol) was slowly added into the NaH (2.4 g, 0.1 mol) under nitrogen atmosphere. The mixture was stirred until the bubble cease. Propargyl bromide (11.9 g, 0.10 mmol) was added in slowly and the reaction was allowed to stir at 45° C. for 3 h then at room temperature for 12 h. The reaction mixture was extracted with CH$_2$Cl$_2$, washed with water and dried over MgSO$_4$. The crude mixture was filtered, concentrated and purified by reduced pressure distillation to give the product as a colorless liquid (2.81 g, 28%). $^1$H NMR (500 MHz, CDCl$_3$) δ 4.21 (d, J=2.3, 2H, CH$_2$C≡C), 3.82-3.75 (m, 2H, CH$_2$O), 3.69-3.64 (m, 2H, CH$_2$OH), 2.46 (t, J=2.3, 1H, C≡CH), 2.11 (s, 1H, OH). $^{13}$C NMR (126 MHz, CDCl$_3$) δ 79.6 (CH$_2$C≡CH), 74.8 (CH$_2$C≡CH), 71.3 (CH$_2$O), 61.9 (CH$_2$OH), 58.6 (CH$_2$C≡CH). The spectroscopic data of 39b are in agreement with those previously reported.[xxix]

2-(2-(Prop-2-yn-1-yloxy)ethoxy)ethanol (39c).

The preparation of this compound was adapted from a literature procedure.[xxx] Into a suspension of 'BuOK (5.10 g, 45.5 mmol) in dry THF (125 mL) was added die(thylene) glycol (9.55 g, 90.0 mmol) at 0° C. under nitrogen atmosphere. The reaction mixture was allowed to stir at room temperature for 30 min then propargyl bromide (6.69 g, 45.0 mmol) in dry THF (25 mL) was added dropwise. The resulting mixture was allowed to stir at room temperature for 12 h. After completion of the reaction as indicated by NMR, the mixture was diluted with THF and filtered through Celite®. The filtrate was concentrated and the residue was purified by column chromatography (SiO$_2$, EtOAc) to give the product as a pale yellow liquid (4.77 g, 93%). $^1$H NMR (500 MHz, CDCl$_3$) δ 4.22 (d, J=2.4, 2H, CH$_2$C≡C), 3.78-3.69 (m, 6H, CH$_2$), 3.67-3.58 (m, 2H, CH$_2$OH), 2.45 (t, J=2.3, 2H, C≡CH, OH). $^{13}$C NMR (126 MHz, CDCl$_3$) δ 79.6 (CH$_2$C≡CH), 74.8 (CH$_2$C≡CH), 72.6, 70.4, 69.3, 61.9 (CH$_2$OH), 58.6 (CH$_2$C≡CH). The spectroscopic data of 39c are in agreement with those previously reported.

2-(2-(2-(Prop-2-yn-1-yloxy)ethoxy)ethoxy)ethanol (39d).

This compound was prepared according to the literature procedure. Into a suspension of 'BuOK (3.82 g, 33.0 mmol) in dry THF (150 mL) was added tri(ethylene)glycol (9.82 g, 65.4 mmol) at 0° C. under nitrogen atmosphere. The reaction mixture was allowed to stir at room temperature for 30 min then propargyl bromide (3.89 g, 32.7 mmol) in dry THF (25 mL) was added dropwise. The resulting mixture was allowed to stir at room temperature for 14 h. After completion of the reaction as indicated by NMR, the mixture was diluted with THF and filtered through Celite®. The filtrate was concentrated and the residue was purified by column chromatography (SiO2, EtOAc) to give the product as a pale yellow liquid (4.55 g, 90%). $^1$H NMR (500 MHz, CDCl$_3$) δ 4.21 (d, J=2.4, 2H, CH$_2$C≡C), 3.78-3.67 (m, 10H, CH$_2$), 3.65-3.59 (m, 2H, CH$_2$OH), 2.67-2.28 (m, 2H, C≡CH, OH). $^{13}$C NMR (126 MHz, CDCl$_3$) δ 79.7 (CH$_2$C≡CH), 74.7 (CH$_2$C≡CH), 72.6, 70.8, 70.51, 70.48, 69.2, 61.9 (CH$_2$OH), 58.5 (CH$_2$C≡CH). The spectroscopic data of 39d are in agreement with those previously reported.

2-Propynyl-β-D-galactopyranoside (41a).

The preparation of this compound was adapted from a literature procedure.

2-[2-(2-Propargyloxyethoxy)ethoxy]ethanol-β-D-galactopyranoside (41d).

This compound was prepared according to a literature procedure.

2-Propynyl 2,3,4,6-tetra-O-acetyl-α-D-mannopyranoside (42a).

This compound was prepared according to a literature procedure. Into a solution of peracetylated mannose (13.65 g, 35.0 mmol) and propargyl alcohol (9.80 g, 174.8 mmol) in dry CH$_2$Cl$_2$ (100 mL) was added BF$_3$OEt$_2$ (49.63 g, 349.7 mmol) dropwise at 0° C. under nitrogen atmosphere. The resulting mixture was allowed to stir at 0° C. for 15 min and then at room temperature for 24 h. The reaction mixture was diluted with CH$_2$Cl$_2$ and poured into ice-water. The mixture was washed with sat. NaHCO$_3$, water, and dried over MgSO$_4$. The crude mixture was filtered, concentrated and purified by column chromatography (SiO$_2$, 20-30% EtOAc: hexane) to give the product as a white solid (10.63 g, 79%). $^1$H NMR (500 MHz, CDCl$_3$) δ 5.36-5.27 (m, 3H, H-3,4,2), 5.04 (d, J=1.6, 1H, H-1), 4.31-4.26 (m, 3H, H-6b, CH$_2$C≡CH), 4.12 (dd, J=12.2, 2.4, 1H, H-6a), 4.03 (ddd, J=9.4, 5.1, 2.4, 1H, H-5), 2.49 (t, J=2.4, 1H, CH$_2$C≡CH), 2.17 (s, 3H, COCH$_3$), 2.11 (s, 3H, COCH$_3$), 2.04 (s, 3H, COCH$_3$), 1.99 (s, 3H, COCH$_3$). $^{13}$C NMR (126 MHz, CDCl$_3$) δ 170.7 (COCH$_3$), 170.0 (COCH$_3$), 169.9 (COCH$_3$), 169.8 (COCH$_3$), 96.3 (C-1), 78.0 (CH$_2$C≡CH), 75.7 (CH$_2$C≡CH), 69.4 (C-2), 69.1 (C-3), 69.0 (C-5), 66.1 (C-4), 62.4 (C-6), 55.0 (CH$_2$C≡CH), 20.9 (COCH$_3$), 20.80 (COCH$_3$), 20.75 (COCH$_3$), 20.71 (COCH$_3$). The spectroscopic data of 42a are in agreement with those previously reported.

2-Propargyloxyethoxy ethanol-2,3,4,6-tetra-O-acetyl-α-D-mannopyranoside (42b).

Into a solution of peracetylated mannose (4.66 g, 11.9 mmol) and 39b (1.32 g, 13.1 mmol) in dry CH$_3$CN (20 mL) was added BF$_3$OEt$_2$ (3.56 g, 25.1 mmol) dropwise at 0° C. under nitrogen atmosphere. The resulting mixture was allowed to stir at room temperature for 24 h. The reaction mixture was diluted with sat. NaHCO$_3$, extracted with CH$_2$Cl$_2$, washed with water, and dried over MgSO$_4$. The crude mixture was filtered, concentrated and purified by column chromatography (SiO$_2$, 0-2% MeOH:CH$_2$Cl$_2$) to give the product as a pale yellow oil (2.08 g, 40%). $^1$H NMR (500 MHz, CDCl$_3$) δ 5.37 (dd, J=10.0, 3.5, 1H, H-3), 5.31-5.26 (m, 2H-H-4,2), 4.88 (d, J=1.6, 1H, H-1), 4.28 (dd, J=12.2, 5.1, 1H, H-6b), 4.20 (d, J=2.4, 2H, CH$_2$C≡CH), 4.12 (dd, J=12.2, 2.4, 1H, H-6a), 4.08 (ddd, J=10.0, 5.1, 2.4, 1H, H-5), 3.90-3.80 (m, 1H), 3.80-3.64 (m, 3H), 2.46 (t, J=2.4, 1H, CH$_2$C≡CH), 2.16 (s, 3H, COCH$_3$), 2.11 (s, 3H, COCH$_3$), 2.04 (s, 3H, COCH$_3$), 1.99 (s, 3H, COCH$_3$). $^{13}$C NMR (126 MHz, CDCl$_3$) δ 170.8 (COCH$_3$), 170.2 (COCH$_3$), 170.0 (COCH$_3$), 169.9 (COCH$_3$), 97.9 (C-1), 79.6 (CH$_2$C≡CH), 74.9 (CH$_2$C≡CH), 69.7, 69.2, 68.7, 68.6, 67.4, 66.3 (C-4), 62.6 (C-6), 58.6 (CH$_2$C≡CH), 21.0 (COCH$_3$), 20.9 (COCH$_3$), 20.85 (COCH$_3$), 20.83 (COCH$_3$). ESI$^+$-HRMS (m/z) for C$_{19}$H$_{26}$O$_{11}$=453.1373 [M+Na]$^+$; found, 453.1393.

2-(2-Propargyloxyethoxy)ethanol-2,3,4,6-tetra-O-acetyl-α-D-mannopyranoside (42c).

Into a solution of peracetylated mannose (4.65 g, 11.9 mmol) and 39c (1.50 g, 13.1 mmol) in dry CH$_3$CN (20 mL) was added BF$_3$OEt$_2$ (3.55 g, 25.0 mmol) dropwise at 0° C. under nitrogen atmosphere. The resulting mixture was allowed to stir at room temperature for 18 h. The reaction mixture was diluted with sat. NaHCO$_3$, extracted with CH$_2$Cl$_2$, washed with water, and dried over MgSO$_4$. The crude mixture was filtered, concentrated and purified by column chromatography (SiO$_2$, 0-2% MeOH:CH$_2$Cl$_2$) to give the product as a pale yellow oil (1.33 g, 24%). $^1$H NMR (500 MHz, CDCl$_3$) δ 5.37 (dd, J=10.0, 3.5, 1H, H-3), 5.33-5.26 (m, 2H, H-4,2), 4.88 (d, J=1.5, 1H, H-1), 4.30 (dd, J=12.2, 4.9, 1H, H-6b), 4.21 (d, J=2.4, 2H, CH$_2$C≡CH), 4.14-4.07 (m, 2H, H-6a, H-5), 3.88-3.79 (m, 1H), 3.74-3.65 (m, 7H), 2.44 (t, J=2.4, 1H, CH$_2$C≡CH), 2.16 (s, 3H, COCH$_3$), 2.10 (s, 3H, COCH$_3$), 2.04 (s, 3H, COCH$_3$), 1.99 (s, 3H, COCH$_3$). $^{13}$C NMR (126 MHz, CDCl$_3$) δ 170.8 (COCH$_3$), 170.2 (COCH$_3$), 170.0 (COCH$_3$), 169.9 (COCH$_3$), 97.9 (C-1), 79.8 (CH$_2$C CH), 74.7 (CH$_2$C≡CH), 70.7, 70.2, 69.8, 69.3, 69.3, 68.6, 67.5, 66.3 (C-4), 62.6 (C-6), 58.6 (CH$_2$C≡CH), 21.0 (COCH$_3$), 20.9 (COCH$_3$), 20.86 (COCH$_3$), 20.84 (COCH$_3$). ESI$^+$-HRMS (m/z) for C$_{21}$H$_{30}$O$_{12}$=497.1635 [M+Na]$^+$; found, 497.1628.

2-[2-(2-Propargyloxyethoxy)ethoxy]ethanol-2,3,4,6-tetra-O-acetyl-α-D-mannopyranoside (42d).

Into a solution of peracetylated mannose (4.29 g, 11.0 mmol) and 39d (2.28 g, 12.1 mmol) in dry CH$_3$CN (20 mL) was added BF$_3$OEt$_2$ (3.28 g, 23.1 mmol) dropwise at 0° C. under nitrogen atmosphere. The resulting mixture, was extracted with CH$_2$Cl$_2$, washed with water, and dried over MgSO$_4$. The crude mixture was filtered, concentrated and purified by column chromatography (SiO$_2$, 50-100% EtOAc:hexane) to give the product as a colorless oil (2.16 g, 38%). $^1$H NMR (500 MHz, CDCl$_3$) δ 5.36 (dd, J=10.0, 3.5, 1H, H-3), 5.31-5.26 (m, 2H, H-4,2), 4.87 (d, J=1.5, 1H, H-1), 4.30 (dd, J=12.1, 4.8, 1H, H-6b), 4.21 (d, J=2.3, 2H, CH$_2$C≡CH), 4.16-4.03 (m, 2H, H-6a, H-5), 3.85-3.78 (m, 1H), 3.75-3.60 (m, 11H), 2.43 (t, J=2.3, 1H, CH$_2$C≡CH), 2.16 (s, 3H, COCH$_3$), 2.10 (s, 3H, COCH$_3$), 2.04 (s, 3H, COCH$_3$), 1.99 (s, 3H, COCH$_3$). $^{13}$C NMR (126 MHz, CDCl$_3$) δ 170.8 (COCH$_3$), 170.2 (COCH$_3$), 170.0 (COCH$_3$), 169.9 (COCH$_3$), 97.9 (C-1), 79.9 (CH$_2$C≡CH), 74.6 (CH$_2$C≡CH), 70.9, 70.8, 70.6, 70.2, 69.8, 69.3, 69.2, 68.6, 67.5, 66.3 (C-4), 62.6 (C-6), 58.5 (CH$_2$C≡CH), 21.0 (COCH$_3$), 20.9 (COCH$_3$), 20.86 (COCH$_3$), 20.83 (COCH$_3$). The spectroscopic data of 42d are in agreement with those previously reported.

2-Propynyl-α-D-mannopyranoside (43a).

This compound was prepared according to the literature procedure. Into a solution of 42a (6.00 g, 15.5 mmol) in dry MeOH (70 mL) was added 1M NaOMe in MeOH (6.20 mL) at room temperature under nitrogen atmosphere. The resulting mixture was allowed to stir at room temperature for 12 h. The reaction mixture was neutralized by addition of Amberlite IR120 H and filtered off the resin. The filtrate was concentrated and dried under vacuum to give the product as a white solid (3.39 g, 100%). $^1$H NMR (500 MHz, D$_2$O) δ 5.06 (d, J=1.4, 1H, H-1), 4.39 (dd, J=15.9, 2.4, 1H, CH$_a$H$_b$C≡CH), 4.33 (dd, J=16.0, 2.4, 1H, CH$_a$H$_b$C≡CH), 3.98 (dd, J=3.3, 1.7, 1H), 3.96-3.88 (m, 1H), 3.85-3.77 (m, 2H), 3.74-3.66 (m, 2H), 2.96 (t, J=2.4, 1H, CH$_2$C≡CH). $^{13}$C NMR (126 MHz, D$_2$O) δ 99.3 (C-1), 79.4 (CH$_2$C≡CH), 76.7 (CH$_2$C≡CH), 73.7 (C-5), 71.0 (C-3), 70.5 (C-2), 67.2 (C-4), 61.4 (C-6), 55.1 (CH$_2$C≡CH). The spectroscopic data of 43a are in agreement with those previously reported.

2-Propargyloxyethoxy ethanol-α-D-mannopyranoside (43b).

Into a solution of 42b (1.50 g, 3.49 mmol) in dry MeOH (20 mL) was added 1M NaOMe in MeOH (1.40 mL) at 0° C. under nitrogen atmosphere. The resulting mixture was allowed to stir at 0° C. for 1 h. The reaction mixture was neutralized by addition of Amberlite IR120 H and filtered off the resin. The filtrate was concentrated and dried under vacuum to give the product as a pale yellow oil (0.83 g, 91%). $^1$H NMR (500 MHz, D$_2$O) δ 4.92 (br. s, 1H, H-1), 4.29 (d, J=2.1, 2H, CH$_2$C≡CH), 4.01-3.98 (m, 1H), 3.95-3.90 (m, 2H), 3.89-3.71 (m, 5H), 3.71-3.64 (m, 2H), 2.94 (t, J=1.9, 1H, CH$_2$C≡CH). $^{13}$C NMR (126 MHz, D$_2$O) δ 100.5 (C-1), 79.9 (CH$_2$C≡CH), 76.6 (CH$_2$C≡CH), 73.3 (C-5), 71.1 (C-3), 70.5 (C-2), 69.2 (C-4), 67.3, 66.8, 61.5 (C-6), 58.5 (CH$_2$C≡CH). ESI$^+$-HRMS (m/z) for C$_{11}$H$_{18}$O$_7$=285.0950 [M+Na]$^+$; found, 285.0950.

2-(2-Propargyloxyethoxy)ethanol-α-D-mannopyranoside (43c).

Into a solution of 42c (1.25 g, 2.63 mmol) in dry MeOH (20 mL) was added 1M NaOMe in MeOH (1.00 mL) at 0° C. under nitrogen atmosphere. The resulting mixture was allowed to stir at 0° C. for 1 h. The reaction mixture was neutralized by addition of Amberlite IR120 H and filtered off the resin. The filtrate was concentrated and dried under vacuum to give the product as a pale yellow oil (0.80 g, 99%). $^1$H NMR (500 MHz, D$_2$O) δ 4.92 (d, J=1.4, 1H, H-1), 4.29 (d, J=2.3, 2H, CH$_2$C≡CH), 4.00 (dd, J=3.3, 1.6, 1H), 3.94-3.67 (m, 13H), 2.94 (t, J=2.3, 1H, CH$_2$C≡CH). $^{13}$C NMR (126 MHz, D$_2$O) δ 100.5 (C-1), 79.9 (CH$_2$C≡CH), 76.5 (CH$_2$C≡CH), 73.3 (C-5), 71.0 (C-3), 70.5 (C-2), 70.0, 70.0, 69.2, 67.3, 66.9, 61.5 (C-6), 58.4 (CH$_2$C≡CH). ESI$^+$-HRMS (m/z) for C$_{13}$H$_{22}$O$_8$=329.1212 [M+Na]$^+$; found, 329.1216.

2-[2-(2-Propargyloxyethoxy)ethoxy]ethano-α-D-mannopyranoside (43d).

Into a solution of 42d (0.90 g, 1.74 mmol) in dry MeOH (10 mL) was added 1M NaOMe in MeOH (0.70 mL) at 0° C. under nitrogen atmosphere. The resulting mixture was allowed to stir at 0° C. for 1 h. The reaction mixture was neutralized by addition of Amberlite IR120 H and filtered off the resin. The filtrate was concentrated and dried under vacuum to give the product as a pale yellow oil (0.60 g, 99%). $^1$H NMR (500 MHz, D$_2$O) δ 4.92 (br. s, 1H, H-1), 4.28 (d, J=1.0, 2H, CH$_2$C≡CH), 3.99 (s, 1H), 3.92 (d, J=12.7, 2H), 3.85 (s, 1H), 3.83-3.60 (m, 14H), 2.93 (s, 1H, CH$_2$C≡CH). $^{13}$C NMR (126 MHz, D$_2$O) δ 100.6 (C-1), 80.0 (CH$_2$C≡CH), 76.6 (CH$_2$C≡CH), 73.4 (C-5), 71.2 (C-3), 70.6 (C-2), 70.3 (C-4), 70.22, 70.15, 70.10, 69.3, 67.4, 67.0, 61.6 (C-6), 58.6 (CH$_2$C≡CH). ESI$^+$-HRMS (m/z) for C$_{15}$H$_{26}$O$_9$=373.1475 [M+Na]$^+$; found, 373.1479.

2-[2-(2-Propargyloxyethoxy)ethoxy]ethanol-2,3,6-tri-O-acetyl-4-O-(2,3,4,6-tetra-O-acetyl-β-D-galactopyranosyl)-β-D-glucopyranoside (44).

Into a solution of peracetylated lactose (9.83 g, 14.5 mmol) and 39d (3.00 g, 15.9 mmol) in dry $CH_2Cl_2$ (30 mL) was added $BF_3OEt_2$ (3.08 g, 21.7 mmol) in $CH_2Cl_2$ (5 mL) dropwise at 0° C. under nitrogen atmosphere. The resulting mixture was allowed to stir at room temperature for 24 h. The reaction mixture was diluted with sat. $NaHCO_3$, extracted with $CH_2Cl_2$, washed with water, and dried over $MgSO_4$. The crude mixture was filtered, concentrated and purified by column chromatography ($SiO_2$, 50-80% EtOAc:hexane) to give the product as a pale yellow oil (5.48 g, 47%). $^1H$ NMR (500 MHz, $CDCl_3$) δ 5.34 (d, J=3.4, 1H), 5.19 (t, J=9.3, 1H), 5.10 (dd, J=10.3, 7.9, 1H), 4.95 (dd, J=10.4, 3.5, 1H), 4.89 (dd, J=9.4, 8.0, 1H), 4.57 (d, J=7.9, 1H), 4.54-4.46 (m, 2H), 4.20 (d, J=2.4, 2H), 4.19-4.03 (m, 3H), 3.94-3.85 (m, 2H), 3.79 (t, J=9.4, 1H), 3.76-3.58 (m, 12H), 2.44 (t, J=2.4, 1H), 2.15 (s, 3H), 2.12 (s, 3H), 2.06 (s, 3H), 2.05 (s, 3H), 2.04 (s, 3H), 2.04 (s, 3H), 1.96 (s, 3H). $^{13}C$ NMR (126 MHz, $CDCl_3$) δ 170.51, 170.48, 170.3, 170.2, 169.9, 169.8, 169.2, 101.2, 100.8, 79.8, 76.4, 74.7, 73.0, 72.8, 71.8, 71.1, 70.82, 70.77, 70.6, 70.5, 69.3, 69.2, 66.8, 62.2, 60.9, 58.5, 21.01, 20.95, 20.85, 20.77, 20.6. $ESI^+$-HRMS (m/z) for $C_{35}H_{50}O_{21}$=829.2742 $[M+Na]^+$; found, 829.2738. The spectroscopic data of 44 are in agreement with those previously reported.

2-[2-(2-Propargyloxyethoxy)ethoxy]ethanol-(β-D-galactopyranosyl)-β-D-glucopyranoside (45).

Into a solution of 44 (3.50 g, 4.34 mmol) in dry MeOH (25 mL) was added 1M NaOMe in MeOH, 1.70 mL) at 0° C. under nitrogen atmosphere. The resulting mixture was allowed to stir at room temperature for 1 h. The reaction mixture was neutralized by addition of Amberlite IR120 H until pH=6 and filtered off the resin. The filtrate was concentrated and dried under vacuum to give the product as a white solid (2.20 g, 99%). $^1H$ NMR (500 MHz, $D_2O$) δ 4.54 (d, J=8.0, 1H), 4.47 (d, J=7.8, 1H), 4.28 (d, J=2.3, 2H), 4.14-4.05 (m, 1H), 4.01 (dd, J=12.2, 1.9, 1H), 3.95 (d, J=3.2, 1H), 3.91-3.55 (m, 20H), 3.42-3.35 (m, 1H), 2.94 (t, J=2.3, 1H). $^{13}C$ NMR (126 MHz, $D_2O$) δ 103.5, 102.7, 79.9, 79.0, 76.6, 75.9, 75.4, 74.9, 73.4, 73.1, 71.6, 70.3, 70.2, 70.1, 70.0, 69.3, 69.3, 69.1, 61.6, 60.7, 58.5. $ESI^+$-HRMS (m/z) for $C_{21}H_{36}O_{14}$=535.2003 $[M+Na]^+$; found, 535.2001

Modular Synthesis of Amphiphilic Janus Glycodendrimers Via Click Chemistry

Modular Synthesis of Amphiphilic Janus Glycodendrimers (Libraries 1 and 2)

((3,4)12G-PE-TRZ-(galactose)$_2$ (46aa).

Into a solution of 2,2-bis((prop-2-yn-1-yloxy)methyl)propane-1,3-diyl bis(3,4-bis(dodecyloxy)benzoate) (11a) (0.12 g, 0.10 mmol) in THF (1.5 mL) was added 23 (50 mg, 0.24 mmol) in water (0.5 mL), $CuSO_4·5H_2O$ (15.0 mg, 0.061 mmol) in water (0.25 mL), and sodium ascorbate (12.0 mg, 0.061 mmol) in water (0.25 mL) successively under nitrogen atmosphere. The reaction mixture was allowed to stir at room temperature for 36 h. The reaction mixture was diluted with THF, filtered, and washed with THF. The filtrate was concentrated and purified by column chromatography ($SiO_2$, 10-20% MeOH:$CH_2Cl_2$) followed by precipitation from $CH_2Cl_2$ in cold MeOH to give the product as a white solid: 40 mg (25%). Purity (HPLC): 99%+. $^1H$ NMR (500 MHz, THF-$d_8$) δ 8.20 (s, 2H, 2 =CH (triazole)), 7.75 (d, J=8.4 Hz, 2H, 2ArH-6), 7.68 (s, 2H, 2ArH-2), 7.08 (d, J=8.5 Hz, 2H, 2ArH-5), 5.67 (d, J=9.1 Hz, 2H, 2CH (anomeric)), 4.95 (d, J=5.0 Hz, 2H, 2CH$_{gal}$), 4.84-4.68 (m, 6H, 2CH$_2$OCH$_2$-TRZ, 2OH$_{gal}$), 4.57 (s, 4H, 2ArCO$_2$CH$_2$), 4.44-4.33 (m, 4H, 2-CH$_{gal}$, 2OH$_{gal}$), 4.28-4.13 (m, 10H, 4ArOCH$_2$, 2OH$_{gal}$), 4.10 (s, 2H, 2OH$_{gal}$), 3.96-3.75 (m, 12H, 2CH$_2$OCH$_2$-TRZ, 8CH$_{gal}$), 2.01-1.94 (m, 8H, 4ArOCH$_2$CH$_2$), 1.73-1.65 (m, 8H, 4ArOCH$_2$CH$_2$CH$_2$), 1.60-1.39 (m, 64H, 4(CH$_2$)$_8$CH$_3$), 1.07 (t, J=6.6 Hz, 12H, 4CH$_3$). $^{13}C$ NMR (126 MHz, THF-$d_8$) δ 166.4 (C=O), 154.6 (ArC-4), 150.0 (ArC-3), 145.6 (C=CH (triazole)), 124.4 (ArC-1), 123.6 (ArC-6), 122.9 (C=CH (triazole)), 115.2 (ArC-2), 113.1 (ArC-5), 89.8 (CH (anomeric)), 80.0 (C$_{5gal}$), 75.8 (C$_{3gal}$), 71.5 (CH$_2$OCH$_2$-TRZ), 70.4 (C$_{4gal}$), 70.0 (ArOCH$_2$), 69.7 (C$_{2gal}$), 68.1 (ArOCH$_2$), 66.0 (CH$_2$OCH$_2$-TRZ), 64.6 (ArCO$_2$CH$_2$), 62.6 (C$_{6gal}$), 45.3 (C(CH$_2$O)$_4$), 33.1 (CH$_2$CH$_2$CH$_3$), 30.90, 30.87, 30.85, 30.7, 30.63, 30.55, 30.4, 27.33 (ArOCH$_2$CH$_2$CH$_2$), 27.25 (ArOCH$_2$CH$_2$CH$_2$), 23.8 (CH$_2$CH$_3$), 14.7 (CH$_3$). MALDI-TOF (m/z): $[M+Na]^+$ calcd for $C_{85}H_{142}N_6NaO_{20}$, 1590.02; found 1588.24.

(3,4)12G1-PE-TRZ-(mannose)$_2$ (46ab).

Into a solution of 2,2-bis((prop-2-yn-1-yloxy)methyl)propane-1,3-diyl bis(3,4-bis(dodecyloxy)benzoate) (11a) (235 mg, 0.20 mmol) in THF (2.0 mL) was added 27 (100 mg, 0.49 mmol) in water (1.0 mL), $CuSO_4·5H_2O$ (30.4 mg, 0.12 mmol) in water (0.5 mL), and sodium ascorbate (24.1 mg, 0.12 mmol) in water (0.5 mL) successively under nitrogen atmosphere. The reaction mixture was allowed to stir at room temperature for 48 h. The reaction mixture was diluted with THF, filtered, and washed with THF. The filtrate was concentrated and purified by column chromatography ($SiO_2$, 10-20% MeOH:$CH_2Cl_2$) to give the product as a white solid: 40.0 mg (12%). Purity (HPLC): 99%+. $^1H$ NMR (500 MHz, 10% $CD_3OD$ in $CDCl_3$) δ 7.92 (s, 2H, 2 =CH(triazole)), 7.56 (dd, J=8.4 Hz, 1.9, 2H, 2ArH-6), 7.48 (d, J=1.9 Hz, 2H, 2ArH-2), 6.85 (d, J=8.5 Hz, 2H, 2ArH-5), 5.96 (s, 2H, 2CH (anomeric)), 4.70 (s, 2H, 2CH$_{man}$), 4.61 (s, 4H, 2CH$_2$OCH$_2$-TRZ), 4.41 (s, 4H, 2ArCO$_2$CH$_2$), 4.21 (d, J=6.1 Hz, 2H, 2CH$_{man}$), 4.04 (t, J=6.6 Hz, 4H, 2ArOCH$_2$), 4.00 (t, J=6.5 Hz, 4H, 2ArOCH$_2$), 3.92-3.84 (m, 2H, 2CH$_{man}$), 3.81 (s, 4H, 4CH$_{man}$), 3.67 (s, 4H, 2CH$_2$OCH$_2$-TRZ), 3.19 (s, 2H, 2CH$_{man}$), 1.91-1.74 (m, 8H, 4ArOCH$_2$CH$_2$), 1.52-1.42 (m, 8H, 4ArOCH$_2$CH$_2$CH$_2$), 1.40-1.20 (m, 64H, 4(CH$_2$)$_8$CH$_3$), 0.88 (t, J=6.9 Hz, 12H, 4CH$_3$). $^{13}C$ NMR (126 MHz, 10% $CD_3OD$ in $CDCl_3$) δ 166.5 (C=O), 153.6 (ArC-4), 148.7 (ArC-3), 145.2 (C=CH (triazole)), 123.7 (ArC-1), 123.5 (C=CH (triazole)), 122.0 (ArC-6), 114.5 (ArC-2), 112.1 (ArC-5), 90.3 (CH (anomeric)), 87.0 (C$_{5man}$), 74.6 (C$_{3man}$), 71.0 (CH$_2$OCH$_2$-TRZ), 70.7 (C$_{4man}$), 69.5 (ArOCH$_2$), 69.2 (ArOCH$_2$), 68.9 (C$_{2man}$), 66.4 (CH$_2$OCH$_2$-TRZ), 64.7 (ArCO$_2$CH$_2$), 63.6 (C$_{6man}$), 44.3 (C(CH$_2$O)$_4$), 32.0 (CH$_2$CH$_2$CH$_3$), 29.82, 29.79, 29.76, 29.73, 29.57, 29.51, 29.47, 29.3, 29.2, 26.2 (ArOCH$_2$CH$_2$CH$_2$), 26.1 (ArOCH$_2$CH$_2$CH$_2$), 22.8 (CH$_2$CH$_3$), 14.2 (CH$_3$). MALDI-TOF (m/z): $[M+Na]^+$ calcd for $C_{85}H_{142}N_6NaO_{20}$, 1590.02; found 1590.42.

(3,5)12G1-PE-TRZ-(galactose)$_2$ (46ba).

Into a solution of 2,2-bis((prop-2-yn-1-yloxy)methyl)propane-1,3-diyl bis(3,5-bis(dodecyloxy)benzoate) (1 b) (0.12 g, 0.10 mmol) in THF (1.0 mL) was added 23 (50 mg, 0.24 mmol) in water (0.5 mL), $CuSO_4·5H_2O$ (15.0 mg, 0.061 mmol) in water (0.25 mL), and sodium ascorbate (12.0 mg, 0.061 mmol) in water (0.25 mL) successively under nitrogen atmosphere. The reaction mixture was allowed to stir at room temperature for 36 h. The reaction mixture was diluted with THF, filtered, and washed with THF. The filtrate was concentrated and purified by column chromatography ($SiO_2$, 10-20% MeOH:$CH_2Cl_2$) to give the product as a soft solid: 152.4 mg (93%). Purity (HPLC): 99%+. $^1H$ NMR (500 MHz, 2% $CD_3OD$ in $CDCl_3$) δ 8.03 (s, 2H, 2 =CH (triazole)), 7.08 (d, J=2.2 Hz, 4H, 2ArH-2, 6), 6.63 (t, J=2.1

Hz, 2H, 2ArH-4), 5.55 (d, J=9.1 Hz, 2H, 2CH (anomeric)), 4.61 (s, 4H, 2CH$_2$OCH$_2$-TRZ), 4.43 (s, 4H, 2ArCO$_2$CH$_2$), 4.23 (t, J=9.4 Hz, 2H, 2CH$_{gal}$), 4.04 (d, J=2.7 Hz, 2H, 2CH$_{gal}$), 3.94 (t, J=6.5 Hz, 8H, 4ArOCH$_2$), 3.86-3.81 (m, 4H, 4CH$_{gal}$), 3.80-3.72 (m, 4H, 4CH$_{gal}$), 3.67 (s, 4H, 2CH$_2$OCH$_2$-TRZ), 1.82-1.74 (m, 8H, 4ArOCH$_2$CH$_2$), 1.51-1.42 (m, 8H, 4ArOCH$_2$CH$_2$CH$_2$), 1.41-1.18 (m, 64H, 4(CH$_2$)$_8$CH$_3$), 0.88 (t, J=6.9 Hz, 12H, 4CH$_3$). $^{13}$C NMR (126 MHz, 2% CD$_3$OD in CDCl$_3$) δ 166.3 (C=O), 160.1 (ArC-3, 5), 144.5 (C=CH (triazole)), 131.2 (C=CH (triazole)), 122.5 (ArC-1), 107.5 (ArC-2, 6), 106.3 (ArC-4), 88.4 (CH (anomeric)), 78.0 (C$_{5gal}$), 73.8 (C$_{3gal}$), 69.9 (CH$_2$OCH$_2$-TRZ), 68.9 (C$_{4gal}$), 68.4 (C$_{2gal}$), 68.2 (ArOCH$_2$), 64.3 (CH$_2$OCH$_2$-TRZ), 63.7 (ArCO$_2$CH$_2$), 61.1 (C$_{6gal}$), 44.0 (C(CH$_2$O)$_4$), 31.7 (CH$_2$CH$_2$CH$_3$), 29.48, 29.45, 29.44, 29.40, 29.24, 29.17, 29.0, 25.9 (ArOCH$_2$CH$_2$CH$_2$), 22.5 (CH$_2$CH$_3$), 13.8 (CH$_3$). MALDI-TOF (m/z): [M+Na]$^+$ calcd for C$_{85}$H$_{142}$N$_6$NaO$_{20}$, 1590.02; found 1588.68.

(3,5)12G1-PE-TRZ-(mannose)$_2$ (46bb).

Into a solution of 2,2-bis((prop-2-yn-1-yloxy)methyl)propane-1,3-diyl bis(3,5-bis(dodecyloxy)benzoate) (11b) (235 mg, 0.20 mmol) in THF (2.0 mL) was added 27 (100 mg, 0.49 mmol) in water (1.0 mL), CuSO$_4$.5H$_2$O (30.4 mg, 0.12 mmol) in water (0.5 mL), and sodium ascorbate (24.1 mg, 0.12 mmol) in water (0.5 mL) successively under nitrogen atmosphere. The reaction mixture was allowed to stir at room temperature for 48 h. The reaction mixture was diluted with THF, filtered, and washed with THF. The filtrate was concentrated and purified by column chromatography (SiO$_2$, 0-20% MeOH:CH$_2$Cl$_2$) to give the product as a white solid: 0.29 g (90%). Purity (HPLC): 99%+. $^1$H NMR (500 MHz, 10% CD$_3$OD in CDCl$_3$) δ 7.98 (s, 2H, 2 =CH (triazole)), 7.08 (d, J=2.0, 4H, 2ArH-2, 6), 6.63 (s, 2H, 2ArH-4), 6.06 (s, 2H, 2CH (anomeric)), 4.75 (s, 2H, 2CH$_{man}$), 4.66-4.50 (m, 4H, 2CH$_2$OCH$_2$-TRZ), 4.43 (s, 4H, 2ArCO$_2$CH$_2$), 4.30 (s, 2H, 2CH$_{man}$), 3.93 (m, 10H, 4ArOCH$_2$, 2CH$_{man}$), 3.84 (s, 2H, 2CH$_{man}$), 3.77 (d, J=11.4, 2H, 2CH$_{man}$), 3.68 (s, 4H, 2CH$_2$OCH$_2$-TRZ), 3.29 (d, J=8.8, 2H, 2CH$_{man}$), 1.84-1.70 (m, 8H, 4ArOCH$_2$CH$_2$), 1.51-1.40 (m, 8H, 4ArOCH$_2$CH$_2$CH$_2$), 1.26 (m, 64H, 4(CH$_2$)$_8$CH$_3$), 0.88 (t, J=6.8, 12H. 4CH$_3$). $^{13}$C NMR (126 MHz, 10% CD$_3$OD in CDCl$_3$) δ 166.4 (C=O), 160.3 (ArC-3, 5), 145.1 (C=CH (triazole)), 131.5 (C=CH (triazole)), 123.6 (ArC-1), 107.8 (ArC-2, 6), 106.5 (ArC-4), 87.0 (CH (anomeric)), 76.1 (C$_{5man}$), 71.1 (C$_{3man}$), 70.4 (CH$_2$OCH$_2$-TRZ), 69.1 (C$_{4man}$), 68.8 (C$_{2man}$), 68.5 (ArOCH$_2$), 66.5 (CH$_2$OCH$_2$-TRZ), 64.7 (ArCO$_2$CH$_2$), 63.8 (C$_{6man}$), 44.3 (C(CH$_2$O)$_4$), 32.0 (CH$_2$CH$_2$CH$_3$), 29.77, 29.74, 29.73, 29.69, 29.52, 29.45, 29.3, 26.1 (ArOCH$_2$CH$_2$CH$_2$), 22.8 (CH$_2$CH$_3$), 14.2 (CH$_3$). MALDI-TOF (m/z): [M+Na]$^+$ calcd for C$_{85}$H$_{142}$N$_6$NaO$_{20}$, 1590.02; found 1590.14.

(3,4,5)12G1-PE-TRZ-(galactose)$_2$ (46ca).

Into a solution of 2,2-bis((prop-2-yn-1-yloxy)methyl)propane-1,3-diyl bis(3,4,5-tris(dodecyloxy)benzoate) (11c) (0.16 g, 0.10 mmol) in THF (1.5 mL) was added 23 (50 mg, 0.24 mmol) in water (0.5 mL), CuSO$_4$.5H$_2$O (15.0 mg, 0.061 mmol) in water (0.25 mL), and sodium ascorbate (12.0 mg, 0.061 mmol) in water (0.25 mL) successively under nitrogen atmosphere. The reaction mixture was allowed to stir at room temperature for 36 h. The reaction mixture was diluted with THF, filtered, and washed with THF. The filtrate was concentrated and purified by column chromatography (SiO$_2$, 10-20% MeOH:CH$_2$Cl$_2$) followed by precipitation from CH$_2$Cl$_2$ in cold MeOH to give the product as a white solid: 160.0 mg (80%). Purity (HPLC): 99%+. $^1$H NMR (500 MHz, 1% CD$_3$OD in CDCl$_3$) S 7.98 (s, 2H, 2 =CH (triazole)), 7.19 (s, 4H, 2ArH-2, 6), 5.54 (d, J=9.0 Hz, 2H, 2CH (anomeric)), 4.56 (s, 4H, 2CH$_2$OCH$_2$-TRZ), 4.40 (s, 4H, 2ArCO$_2$CH$_2$), 4.28 (t, J=8.7 Hz, 2H, 2CH$_{gal}$), 4.07 (s, 2H, 2CH s), 3.99 (t, J=6.5 Hz, 4H, 2ArOCH$_2$), 3.95 (t, J=6.2 Hz, 8H, 4ArOCH$_2$), 3.89-3.72 (m, 8H, 8CH$_{gal}$), 3.62 (s, 4H, 2CH$_2$OCH$_2$-TRZ), 1.84-1.70 (m, 12H, 6ArOCH$_2$CH$_2$), 1.51-1.43 (m, 12H, 6ArOCH$_2$CH$_2$CH$_2$), 1.39-1.18 (m, 96H, 6(CH$_2$)$_7$CH$_3$), 0.88 (t, J=6.7 Hz, 18H, 6CH$_3$). $^{13}$C NMR (126 MHz, 1% CD$_3$OD in CDCl$_3$) δ 166.4 (C=O), 153.0 (ArC-3, 5), 144.6 (ArC-3, 5), 142.7 (C=CH (triazole)), 124.4 (C=CH (triazole)), 123.2 (ArC-1), 108.1 (ArC-2, 6), 88.5 (CH (anomeric)), 78.0 (C$_{5gal}$), 74.0 (C$_{3gal}$), 73.7 (ArOCH$_2$-4), 70.1 (CH$_2$OCH$_2$-TRZ), 69.3 (ArOCH$_2$-3, 5), 69.1 (C$_{4gal}$), 68.6 (C$_{2gal}$), 64.4 (CH$_2$OCH$_2$-TRZ), 63.6 (ArCO$_2$CH$_2$), 61.3 (C$_{6gal}$), 44.3 (C(CH$_2$O)$_4$), 32.0 (CH$_2$CH$_2$CH$_3$), 30.4, 29.85, 29.82, 29.78, 29.76, 29.69, 29.59, 29.47, 26.3 (ArOCH$_2$CH$_2$CH$_2$), 26.2 (ArOCH$_2$CH$_2$CH$_2$), 22.8 (CH$_2$CH$_3$), 14.2 (CH$_3$). MALDI-TOF (m/z): [M+Na]$^+$ calcd for C$_{109}$H$_{190}$N$_6$NaO$_{22}$, 1958.38; found 1958.76.

(3,4,5)12G1-PE-TRZ-(mannose)$_2$ (46cb).

Into a solution of 2,2-bis((prop-2-yn-1-yloxy)methyl)propane-1,3-diyl bis(3,4,5-tris(dodecyloxy)benzoate) (11c) (0.31 g, 0.20 mmol) in THF (2.0 mL) was added 27 (100 mg, 0.49 mmol) in water (1.0 mL), CuSO$_4$.5H$_2$O (30.4 mg, 0.12 mmol) in water (0.5 mL), and sodium ascorbate (24.1 mg, 0.12 mmol) in water (0.5 mL) successively under nitrogen atmosphere. The reaction mixture was allowed to stir at room temperature for 48 h. The reaction mixture was diluted with THF, filtered, and washed with THF. The filtrate was concentrated and purified by column chromatography (SiO$_2$, 0-15% MeOH:CH$_2$Cl$_2$) followed by precipitation from CH$_2$Cl$_2$ in cold MeOH to give the product as a white solid: 0.28 g (72%). Purity (HPLC): 99%+. $^1$H NMR (500 MHz, THF-d$_8$) δ 8.00 (s, 2H, 2 =CH (triazole)), 7.22 (s, 4H, 2ArH-2, 6), 5.91 (d, J=1.9 Hz, 2H, 2CH (anomeric)), 4.60 (s, 6H, 2ArCO$_2$CH$_2$, 2CH$_{man}$), 4.57 (d, J=3.7 Hz, 2H, 2OH$_{man}$), 4.54 (d, J=5.4 Hz, 2H, 2OH$_{man}$), 4.41 (s, 4H, 2CH$_2$OCH$_2$-TRZ), 4.32 (d, J=4.9 Hz, 2H, 2CH$_{man}$), 4.01-3.93 (m, 14H, 6ArOCH$_2$, 2OH$_{man}$), 3.84 (t, J=6.0 Hz, 2H, 2CH$_{man}$), 3.76-3.60 (m, 10H, 2CH$_2$OCH$_2$-TRZ, 4CH$_{man}$, 2OH$_{man}$), 3.29-3.15 (m, 2H, 2CH$_{man}$), 1.82-1.66 (m, 12H, 6ArOCH$_2$CH$_2$), 1.55-1.48 (m, 12H, 6ArOCH$_2$CH$_2$CH$_2$), 1.42-1.24 (m, 96H, 6(CH$_2$)$_8$CH$_3$), 0.89 (t, J=6.8 Hz, 18H, 6CH$_3$). $^{13}$C NMR (126 MHz, THF-d$_8$) δ 166.4 (C=O), 154.1 3 (ArC-3, 5), 145.9 (ArC-4), 143.8 (C=CH (triazole)), 125.8 (C=CH (triazole)), 124.0 (ArC-1), 108.9 (ArC-2, 6), 88.1 (CH (anomeric)), 78.2 (C$_{5man}$), 73.9 (ArOCH$_2$-4), 72.8 (C$_{3man}$), 70.3 (CH$_2$OCH$_2$-TRZ), 70.1 (C$_{4man}$), 70.0 (ArOCH$_2$-3, 5), 68.9 (C$_{2man}$), 65.9 (CH$_2$OCH$_2$-TRZ), 64.7 (ArCO$_2$CH$_2$), 62.9 (C$_{6man}$), 45.3 (C(CH$_2$O)$_4$), 33.1 (CH$_2$CH$_2$CH$_3$), 31.6, 30.96, 30.93, 30.89, 30.87, 30.85, 30.83, 30.78, 30.67, 30.61, 30.53, 30.52, 27.4, 27.3, 26.0, 23.7 (CH$_2$CH$_3$), 14.6 (CH$_3$). MALDI-TOF (m/z): [M+Na]$^+$ calcd for C$_{109}$H$_{190}$N$_6$NaO$_{22}$, 1958.38; found 1958.39.

(3,4)12G1-PE-TRZ$_i$-Gal$_2$ (47aa).

Into a solution of 14a (0.70 g, 0.62 mmol in THF (6.0 mL) was added 41a (0.32 g, 1.48 mmol) in water (0.5 mL), CuSO$_4$.5H$_2$O (90 mg, 0.37 mmol) in water (0.5 mL), and sodium ascorbate (70 mg, 0.37 mmol) in water (0.5 mL) successively under nitrogen atmosphere. The reaction mixture was allowed to stir at room temperature for 48 h. The reaction mixture was diluted with THF. The filtrate was concentrated and purified by column chromatography: SiO$_2$, CH$_2$Cl$_2$/MeOH (0-20%) followed by precipitation from CH$_2$Cl$_2$ in cold MeOH to give the product as a white solid: 0.19 g (20%). Purity (HPLC):

99%+. $^1$H NMR (360 MHz, 10% CD$_3$OD in CDCl$_3$) δ 7.98 (s, 2H, 2 =CH (triazole)), 7.57 (d, J=8.6, 2H, 2ArH-6), 7.47 (s, 2H, 2ArH-2), 6.84 (d, J=8.6, 2H, 2ArH-5), 4.92 (d, J=12.5, 2H), 4.77 (d, J=12.4, 2H), 4.66 (s, 4H), 4.45 (s, 4H, 2ArCO$_2$CH$_2$), 4.33 (d, J=7.2, 2H), 4.04-4.00 (m, 8H), 3.89-3.75 (m, 6H), 3.61-3.48 (m, 6H), 1.85-1.78 (m, 8H, 4ArOCH$_2$CH$_2$), 1.56-1.11 (m, 72H, 4(CH$_2$)$_9$CH$_3$), 0.88 (t, J=6.7, 12H, 4CH$_3$). $^{13}$C NMR (91 MHz, 10% CD$_3$OD in CDCl$_3$) δ 166.1 (C=O), 154.1 (ArC-4), 149.0 (ArC-3), 144.8 (C=CH(triazole)), 126.5 (C=CH(triazole)), 124.0 (ArC-1), 121.3 (ArC-6), 114.7 (ArC-2), 112.2 (ArC-5), 102.9 (CH(anomeric)), 77.6, 75.1, 73.6, 71.3, 69.7 (ArOCH$_2$), 69.3 (ArOCH$_2$), 63.5 (ArCO$_2$CH$_2$), 62.3, 61.7, 50.5 (CH$_2$N), 44.3 (C(CH$_2$N$_3$)$_2$), 32.1, 29.94, 29.93, 29.89, 29.73, 29.68, 29.58, 29.49, 29.3, 26.31, 26.25, 22.9 (CH$_2$CH$_3$), 14.3 (CH$_3$). MALDI-TOF (m/z): [M+Na]$^+$ calcd for C$_{85}$H$_{142}$N$_6$NaO$_{20}$, 1590.02; found 1590.67.

(3,4)12G1-PE-TRZ$_i$-Man$_2$ (47Ab).

Into a solution of 14a (0.70 g, 0.62 mmol in THF (6.0 mL) was added 43a (0.32 g, 1.48 mmol) in water (0.5 mL), CuSO$_4$.5H$_2$O (90 mg, 0.37 mmol) in water (0.5 mL), and sodium ascorbate (70 mg, 0.37 mmol) in water (0.5 mL) successively under nitrogen atmosphere. The reaction mixture was allowed to stir at room temperature for 48 h. The reaction mixture was diluted with THF, filtered, and washed with THF. The filtrate was concentrated and purified by column chromatography (SiO$_2$, 0-40% MeOH:CH$_2$Cl$_2$) followed by precipitation from CH$_2$Cl$_2$ in cold MeOH to give the product as a white solid: 0.61 g (64%). Purity (HPLC): 99%+. $^1$H NMR (500 MHz, 10% CD$_3$OD in CDCl$_3$) δ 7.98 (s, 2H, 2 =CH (triazole)), 7.56 (d, J=7.7, 2H, 2ArH-6), 7.47 (s, 2H, 2ArH-2), 6.85 (d, J=8.3, 2H, 2ArH-5), 4.86 (s, 2H, CH(anomeric)), 4.70-4.60 (m, 15.4, 8H), 4.42 (s, 4H, 2ArCO$_2$CH$_2$), 4.02 (m, 8H, 4ArOCH$_2$), 3.81 (m, 6H), 3.70 (s, 4H), 3.54 (s, 2H), 1.88-1.74 (m, 8H, 4ArOCH$_2$CH$_2$), 1.47 (d, J=5.2, 8H, 4ArOCH$_2$CH$_2$CH$_2$), 1.40-1.20 (m, 64H, 4(CH$_2$)$_8$CH$_3$), 0.88 (t, J=6.9, 12H, 4CH$_3$). $^{13}$C NMR (126 MHz, 10% CD$_3$OD in CDCl$_3$) δ 166.0 (C=O), 154.2 (ArC-4), 148.9 (ArC-3), 144.3 (C=CH(triazole)), 126.3 (C=CH(triazole)), 124.0 (ArC-1), 121.1 (ArC-6), 114.7 (ArC-2), 112.1 (ArC-5), 99.6 (CH(anomeric)), 77.9, 73.1, 71.3, 70.6, 69.7 (ArOCH$_2$), 69.3 (ArOCH$_2$), 67.1, 63.4 (ArCO$_2$CH$_2$), 61.6, 60.0, 50.4 (CH$_2$N), 44.3 (C(CH$_2$N$_3$)$_2$), 32.1, 29.9, 29.84, 29.79, 29.77, 29.62, 29.57, 29.50, 29.4, 29.22, 26.21, 26.15, 22.8 (CH$_2$CH$_3$), 14.2 (CH$_3$). MALDI-TOF (m/z): [M+Na]$^+$ calcd for C$_{85}$H$_{142}$N$_6$NaO$_{20}$, 1590.02; found 1589.89.

(3,5)12G1-PE-TRZ$_i$-Gal$_2$ (47ba).

Into a solution of 14b (0.70 g, 0.62 mmol) in THF (6.0 mL) was added 41a (0.32 g, 1.48 mmol) in water (0.5 mL), CuSO$_4$.5H$_2$O (90 mg, 0.37 mmol) in water (0.5 mL), and sodium ascorbate (70 mg, 0.37 mmol) in water (0.5 mL) successively under nitrogen atmosphere. The reaction mixture was allowed to stir at room temperature for 48 h. The reaction mixture was diluted with THF, filtered, and washed with THF. The filtrate was concentrated and purified by column chromatography: SiO$_2$, CH$_2$Cl$_2$/MeOH (0-20%) followed by precipitation from CH$_2$Cl$_2$ in cold MeOH to give the product as a white solid: 0.83 g (87%). Purity (HPLC): 99%+. $^1$H NMR (360 MHz, 10% CD$_3$OD in CDCl$_3$) δ 7.98 (s, 2H, 2 =CH (triazole)), 7.06 (d, J=2.1, 4H, 2ArH-2,6), 6.62 (t, J=2.2, 2H, 2ArH-4), 4.92 (d, J=12.6, 2H), 4.76 (d, J=12.4, 2H), 4.65 (s, 4H), 4.47 (s, 4H, 2ArCO$_2$CH$_2$), 4.31 (d, J=7.4, 2H), 3.94-3.88 (m, 10H), 3.73-3.69 (m, 4H), 3.55-3.49 (m, 6H), 1.79-1.71 (m, 8H, 4ArOCH$_2$CH$_2$), 1.43-1.26 (m, 72H, 4(CH$_2$)$_9$CH$_3$), 0.88 (t, J=6.8, 12H, 4CH$_3$). $^{13}$C NMR (91 MHz, 10% CD$_3$OD in CDCl$_3$) δ 166.2 (C=O), 160.6 (ArC-3,5), 144.8 (C=CH(triazole)), 131.0 (ArC-1), 126.6 (C=CH(triazole)), 108.2 (ArC-2,6), 106.9 (ArC-4), 103.0 (CH(anomeric)), 77.7, 75.3, 73.7, 71.4, 69.3, 68.8 (ArOCH$_2$), 64.1, 62.4, 61.8, 50.5 (CH$_2$N), 44.4 (C(CH$_2$N$_3$)$_2$), 32.3, 30.02, 29.99, 29.95, 29.8, 29.7, 29.5, 26.4, 23.0 (CH$_2$CH$_3$), 14.4 (CH$_3$). MALDI-TOF (m/z): [M+Na]$^+$ calcd for C$_{85}$H$_{142}$N$_6$NaO$_{20}$, 1590.02; found 1591.22.

(3,5)12G1-PE-TRZ$_i$-Man$_2$ (47bb).

Into a solution of 14b (0.70 g, 0.62 mmol) in THF (6.0 mL) was added 43a (0.32 g, 1.48 mmol) in water (0.5 mL), CuSO$_4$ 5H$_2$O (90 mg, 0.37 mmol) in water (0.5 mL), and sodium ascorbate (70 mg, 0.37 mmol) in water (0.5 mL) successively under nitrogen atmosphere. The reaction mixture was allowed to stir at room temperature for 48 h. The reaction mixture was diluted with THF, filtered, and washed with THF. The filtrate was concentrated and purified by column chromatography: SiO$_2$, CH$_2$Cl$_2$/MeOH (0-20%) followed by precipitation from CH$_2$Cl$_2$ in cold MeOH to give the product as a white solid: 0.74 g (77%). Purity (HPLC): 99%+. $^1$H NMR (360 MHz, 10% CD$_3$OD in CDCl$_3$) δ 7.95 (s, 2H, 2 =CH (triazole)), 7.06 (d, J=1.9, 4H, 2ArH-2,6), 6.64 (s, 2H, 2ArH-4), 4.87 (s, 2H), 4.76-4.62 (m, 8H), 4.46 (s, 4H, 2ArCO$_2$CH$_2$), 3.93 (t, J=6.4, 8H), 3.85-3.72 (m, 10H), 3.52 (s, 2H), 1.80-1.72 (m, 8H, 4ArOCH$_2$CH$_2$), 1.44-1.26 (m, 72H, 4(CH$_2$)$_9$CH$_3$), 0.88 (t, J=6.8, 12H, 4CH$_3$). $^{13}$C NMR (91 MHz, 10% CD$_3$OD in CDCl$_3$) δ 165.9 (C=O), 160.5 (ArC-3,5), 144.4 (C=CH(triazole)), 130.8 (ArC-1), 126.1 (C=CH(triazole)), 108.0 (ArC-2,6), 106.7 (ArC-4), 99.6 (CH(anomeric)), 77.5, 73.1, 71.3, 70.6, 68.6 (ArOCH$_2$), 67.1, 63.7, 61.5, 60.0, 50.2 (CH$_2$N), 44.3 (C(CH$_2$N$_3$)$_2$), 32.1, 29.81, 29.77, 29.73, 29.6, 29.5, 29.3, 26.2, 22.8 (CH$_2$CH$_3$), 14.2 (CH$_3$). MALDI-TOF (m/z): [M+Na]$^+$ calcd for C$_{85}$H$_{142}$N$_6$NaO$_{20}$, 1590.02; found 1591.42.

(3,4,5)12G1-PE-TRZ$_i$-Gal$_2$ (47ca).

Into a solution of 14c (1.00 g, 0.67 mmol in THF (1.5 mL) was added 41a (0.35 g, 1.60 mmol) in water (0.5 mL), CuSO$_4$.5H$_2$O (100 mg, 0.40 mmol) in water (0.5 mL), and sodium ascorbate (80 mg, 0.40 mmol) in water (0.5 mL) successively under nitrogen atmosphere. The reaction mixture was allowed to stir at room temperature for 24 h. The reaction mixture was diluted with THF, filtered, and washed with THF. The filtrate was concentrated and purified by column chromatography (SiO$_2$, 0-20% MeOH:CH$_2$Cl$_2$) followed by precipitation from CH$_2$Cl$_2$ in cold MeOH to give the product as a white solid: 1.07 g (83%).). Purity (HPLC): 99%+. $^1$H NMR (360 MHz, 10% CD$_3$OD in CDCl$_3$) δ 7.93 (s, 2H, 2 =CH (triazole)), 7.21 (s, 4H, 2ArH-2,6), 4.94 (d, J=12.6, 2H), 4.78 (d, J=12.7, 2H), 4.62 (s, 4H), 4.49 (s, 4H, 2ArCO$_2$CH$_2$), 4.32 (d, J=7.6, 2H), 4.08-3.67 (m, 18H), 3.64-3.55 (m, 2H), 3.55-3.46 (m, 4H), 1.84-1.71 (m, 12H, 6ArOCH$_2$CH$_2$), 1.49-1.44 (m, 12H, 6ArOCH$_2$CH$_2$CH$_2$), 1.30-1.26 (m, 96H, 6(CH$_2$),CH$_3$), 0.88 (t, J=6.7, 18H, 6CH$_3$). $^{13}$C NMR (91 MHz, 10% CD$_3$OD in CDCl$_3$) δ 165.9 (C=O), 153.1 (ArC-3,5), 144.8 (C=CH(triazole)), 143.2 (ArC-1), 126.0 (C=CH(triazole)), 123.6 (ArC-2,6), 108.3 (ArC-4), 102.8 (CH(anomeric)), 77.4, 75.0, 73.8, 73.5, 71.2, 69.5, 69.1, 62.2, 61.7, 50.3 (CH$_2$N), 44.4 (C(CH$_2$N$_3$)$_2$), 32.0, 30.4, 29.82, 29.79, 29.74, 29.67, 29.56, 29.45, 29.44, 26.3, 26.1, 22.7 (CH$_2$CH$_3$), 14.1 (CH$_3$). MALDI-TOF (m/z): [M+Na]$^+$ calcd for C$_{109}$H$_{190}$N$_6$NaO$_{22}$, 1958.38; found 1957.86.

(3,4,5)12G1-PE-TRZ$_i$-Man$_2$ (47cb). Into a solution of 14c (1.00 g, 0.67 mmol) in THF (1.5 mL) was added 43a (0.35 g, 1.60 mmol) in water (0.5 mL), CuSO$_4$. 5H$_2$O (100 mg, 0.40 mmol) in water (0.5 mL), and sodium ascorbate (80 mg, 0.40 mmol) in water (0.5 mL) successively under nitrogen atmosphere. The reaction mixture was allowed to stir at room temperature for 24 h. The reaction mixture was diluted with THF, filtered, and washed with THF. The filtrate was concentrated and purified by column chromatography (SiO$_2$, 0-20% MeOH:CH$_2$Cl$_2$) followed by precipitation from CH$_2$Cl$_2$ in cold MeOH to give the product as a white solid: 1.06 g (82%). Purity (HPLC): 99%+. $^1$H NMR (500 MHz, 10% CD$_3$OD in CDCl$_3$) δ 7.93 (s, 2H, 2 =CH (triazole)), 7.20 (s, 4H, 2ArH-2,6), 4.87 (s, 2H, CH(anomeric)), 4.76 (d, J=12.7, 2H), 4.70-4.56 (m, 6H), 4.46 (s, 4H, 2ArCO$_2$CH$_2$), 4.05-3.95 (m, 12H, 6ArOCH$_2$), 3.84 (br. s, 2H), 3.79 (br. s, 4H, 2NCH$_2$), 3.75-3.66 (m, 4H), 3.61-3.49 (m, 2H), 1.87-1.67 (m, 12H, 6ArOCH$_2$CH$_2$), 1.51-1.43 (m, 12H, 6ArOCH$_2$CH$_2$CH$_2$), 1.39-1.20 (m, 96H, 6(CH$_2$)$_8$CH$_3$), 0.88 (t, J=6.7, 18H, 6CH$_3$). $^{13}$C NMR (126 MHz, 10% CD$_3$OD in CDCl$_3$) δ 165.9 (C=O), 153.1 (ArC-3,5), 145.2 (C=CH (triazole)), 143.3 (ArC-1), 126.1 (C=CH(triazole)), 123.5 (ArC-2,6), 108.4 (ArC-4), 99.6 (CH(anomeric)), 77.9, 73.8, 73.1, 71.3, 70.6, 69.5, 67.2, 63.4, 61.6, 60.1, 50.3 (CH$_2$N), 44.4 (C(CH$_2$N$_3$)$_2$), 32.0, 30.5, 29.87, 29.85, 29.83, 29.78, 29.71, 29.6, 29.50, 29.48, 26.3, 26.2, 22.8 (CH$_2$CH$_3$), 14.2 (CH$_3$). MALDI-TOF (m/z): [M+Na]$^+$ calcd for C$_{109}$H$_{190}$N$_6$NaO$_{22}$, 1958.38; found 1958.54.

3.3.2 Modular Synthesis of Amphiphilic Janus Glycodendrimers (Library 3)

(3,4)2Ethyl8G1-PE-TRZ-(galactose)$_2$ (48aa).

Into a solution of 2,2-bis((prop-2-yn-1-yloxy)methyl)propane-1,3-diyl bis(3,4-bis((2-ethylhexyl)oxy)benzoate)) (11d) (0.10 g, 0.11 mmol) in THF (1.0 mL) was added 23 (53 mg, 0.26 mmol) in water (0.5 mL), CuSO$_4$.5H$_2$O (16.0 mg, 0.064 mmol) in water (0.5 mL), and sodium ascorbate (13.0 mg, 0.064 mmol) in water (0.5 mL) successively under nitrogen atmosphere. The reaction mixture was allowed to stir at room temperature for 18 h. The reaction mixture was diluted with THF, filtered, and washed with THF. The filtrate was concentrated and purified by column chromatography (SiO$_2$, 10-20% MeOH:CH$_2$Cl$_2$) to give the product as a white solid: 0.11 g (79%). Purity (HPLC): 99%+. $^1$H NMR (500 MHz, 10% CD$_3$OD in CDCl$_3$) δ 7.99 (s, 2H, 2 =CH (triazole)), 7.57 (d, J=8.4 Hz, 2H, 2ArH-6), 7.49 (s, 2H, 2ArH-2), 6.85 (d, J=8.5 Hz, 2H, 2ArH-5), 5.55 (d, J=8.2 Hz, 2H, 2CH (anomeric)), 4.58 (s, 4H, 2CH$_2$OCH$_2$-TRZ), 4.39 (s, 4H, 2ArCO$_2$CH$_2$), 4.26 (t, J=7.7 Hz, 2H, 2CH$_{gal}$), 4.07 (s, 2H, 2CH$_{gal}$), 3.90 (dd, J=12.2 Hz, J=4.9 Hz, 8H, 4ArOCH$_2$), 3.86-3.73 (m, 8H, 8CH$_{gal}$), 3.66 (s, 4H, 2CH$_2$OCH$_2$-TRZ), 1.80-1.73 (m, 4H, 4ArOCH$_2$CH), 1.56-1.36 (m, 16H, 2(CH$_2$)$_4$), 1.36-1.29 (m, 16H, 2(CH$_2$)$_4$), 0.95-0.87 (m, 24H, 8CH$_3$). $^{13}$C NMR (126 MHz, 10% CD$_3$OD in CDCl$_3$) δ 166.6 (C=O), 154.0 (ArC-4), 149.1 (ArC-3), 144.9 (C=CH (triazole)), 123.6 (ArC-1), 123.0 (C=CH (triazole)), 121.8 (ArC-6), 114.1 (ArC-2), 111.9 (ArC-5), 88.5 (CH (anomeric)), 78.0 (C$_{5gal}$), 74.0 (C$_{3gal}$), 71.7 (ArOCH$_2$), 71.5 (ArOCH$_2$), 70.1 (CH$_2$OCH$_2$-TRZ), 69.2 (C$_{4gal}$), 68.7 (C$_{2gal}$), 64.5 (CH$_2$OCH$_2$-TRZ), 63.44 (ArCO$_2$CH$_2$), 61.43 (C$_{6gal}$), 44.3 (C(CH$_2$O)$_4$), 39.6 (CHCH$_2$OAr), 39.5 (CHCH$_2$OAr), 30.7 (CH$_2$CH$_2$CH$_3$), 30.6 (CH$_2$CH$_2$CH$_3$), 29.8, 29.19, 29.18, 23.99 (CH$_2$CH$_3$), 23.97 (CH$_2$CH$_3$), 23.95 (CH$_2$CH$_3$), 23.94 (CH$_2$CH$_3$), 23.13 (CH$_2$CH$_3$), 23.12 (CH$_2$CH$_3$), 14.1 (CH$_3$), 11.24 (CH$_3$), 11.19 (CH$_3$). MALDI-TOF (m/z): [M+Na]$^+$ calcd for C$_{69}$H$_{110}$N$_6$NaO$_{20}$, 1365.77; found 1364.55.

(3,4)2Ethyl8G1-PE-TRZ-(mannose)$_2$ (48ab).

Into a solution of 2,2-bis((prop-2-yn-1-yloxy)methyl)propane-1,3-diyl bis(3,4-bis((2-ethylhexyl)oxy)benzoate)) (11d) (0.10 g, 0.11 mmol) in THF (1.0 mL) was added 27 (53 mg, 0.26 mmol) in water (0.5 mL), CuSO$_4$.5H$_2$O (16.0 mg, 0.064 mmol) in water (0.5 mL), and sodium ascorbate (13.0 mg, 0.064 mmol) in water (0.5 mL) successively under nitrogen atmosphere. The reaction mixture was allowed to stir at room temperature for 24 h. The reaction mixture was diluted with THF, filtered, and washed with THF. The filtrate was concentrated and purified by column chromatography (SiO$_2$, 10-20% MeOH:CH$_2$Cl$_2$) to give the product as a white solid: 0.08 g (57%). Purity (HPLC): 99%+. $^1$H NMR (500 MHz, 10% CD$_3$OD in CDCl$_3$) δ 7.96 (s, 2H, 2 =CH(triazole)), 7.58 (dd, J=8.4 Hz, J=1.8 Hz, 2H, 2ArH-6), 7.49 (d, J=1.7 Hz, 2H, 2ArH-2), 6.85 (d, J=8.5 Hz, 2H, 2ArH-5), 6.02 (s, 2H, 2CH (anomeric)), 4.73 (s, 2H, 2CH$_{man}$), 4.61 (s, 4H, 2ArCO$_2$CH$_2$), 4.42 (s, 4H, 2CH$_2$OCH$_2$-TRZ), 4.27 (s, 2H, 2CH$_{man}$), 3.99-3.87 (m, 10H, 4ArOCH$_2$, 2CH$_{man}$), 3.87-3.72 (m, 6H, 6CH$_{man}$), 3.68 (s, 4H, 2CH$_2$OCH$_2$-TRZ), 1.81-1.72 (m, 4H, 4ArOCH$_2$CH), 1.56-1.37 (m, 16H, 2(CH$_2$)$_4$), 1.36-1.29 (m, 16H, 2(CH$_2$)$_4$), 0.95-0.88 (m, 24H, 8CH$_3$). $^{13}$C NMR (126 MHz, 10% CD$_3$OD in CDCl$_3$) δ 166.6 (C=O), 154.0 (ArC-4), 149.2 (ArC-3), 145.3 (C=CH (triazole)), 123.6 (ArC-1), 123.6 C=CH (triazole)), 121.9 (ArC-6), 114.2 (ArC-2), 111.9 (ArC-5), 90.4 (CH (anomeric)), 87.1 (C$_{5man}$), 76.2 (C$_{3man}$), 71.8 (ArOCH$_2$-3), 71.5 (ArOCH$_2$-4), 71.1 (CH$_2$OCH$_2$-TRZ), 69.1 (C$_{4man}$), 69.0 (C$_{2man}$), 66.7 (CH$_2$OCH$_2$-TRZ), 63.5 (ArCO$_2$CH$_2$), 61.1 (C$_{6man}$), 44.4 (C(CH$_2$O)$_4$), 39.7 (CHCH$_2$OAr), 39.5 (CHCH$_2$OAr), 32.0, 30.7, 30.6, 29.8, 29.22, 29.21, 24.0 (CH$_2$CH$_3$), 23.98 (CH$_2$CH$_3$), 23.2 (CH$_2$CH$_3$), 22.8 (CH$_2$CH$_3$), 14.1 (CH$_3$), 11.3 (CH$_3$), 11.2 (CH$_3$). MALDI-TOF (m/z): [M+Na]$^+$ calcd for Ca$_{69}$H$_{110}$N$_6$NaO$_{20}$, 1365.77; found 1363.85.

(3,4)2Et8G1-PE-TRZ$_t$-Man$_2$ (49aa).

Into a solution of 14d (1.00 g, 1.10 mmol) in THF (1.5 mL) was added 43a (0.58 g, 2.70 mmol) in water (0.5 mL), CuSO$_4$.5H$_2$O (0.17 g, 0.68 mmol) in water (0.5 mL), and sodium ascorbate (0.13 g, 0.66 mmol) in water (0.5 mL) successively under nitrogen atmosphere. The reaction mixture was allowed to stir at room temperature for 12 h. The reaction mixture was diluted with THF, filtered, and washed with THF. The filtrate was concentrated and purified by column chromatography (SiO$_2$, 0-40% MeOH:CH$_2$Cl$_2$) followed by recrystalization from CH$_2$Cl$_2$/MeOH mixture to give the product as a white solid: 1.32 g (89%). Purity (HPLC): 99%+. $^1$H NMR (500 MHz, 10% CD$_3$OD in CDCl$_3$) δ 7.93 (s, 2H, 2 =CH (triazole)), 7.58 (dd, J=8.4, 1.7, 2H, 2ArH-6), 7.49 (d, J=1.8, 2H, 2ArH-2), 6.87 (d, J=8.6, 2H, 2ArH-5), 4.87 (s, 2H, CH(anomeric)), 4.75 (d, J=12.6, 2H), 4.69-4.58 (m, 6H), 4.43 (S, 4H), 3.96-3.84 (m, 10H), 3.79 (d, J=2.4, 4H, 2NCH$_2$), 3.76-3.69 (m, 4H), 3.55 (m, 2H), 1.77 (m, 4H, 4ArOCH$_2$CH), 1.59-1.25 (m, 32H, 4CH$_2$CH$_3$, 4(CH$_2$)$_3$CH$_3$), 0.98-0.87 (m, 24H, 8CH$_3$). $^{13}$C NMR (126 MHz, 10% CD$_3$OD in CDCl$_3$) δ 166.0 (C=O), 154.5 (ArC-4), 149.3 (ArC-3), 144.4 (C=CH(triazole)), 126.0 (C=CH(triazole)), 123.7 (ArC-1), 120.9 (ArC-6), 114.2 (ArC-2), 111.9 (ArC-5), 99.5 (CH(anomeric)), 77.9, 73.0, 71.8, 71.5, 71.3, 70.6, 67.2, 63.2, 61.6, 60.0, 50.2 (CH$_2$N), 44.4 (C(CH$_2$N$_3$)$_2$), 39.7, 39.5, 30.7, 30.6, 29.20, 29.18, 23.99, 23.98, 23.95, 23.94, 23.13, 23.12, 14.1 (CH$_3$), 11.3 (CH$_3$), 11.2 (CH$_3$). MALDI-TOF (m/z): [M+Na]+ calcd for C$_{69}$H$_{110}$N$_6$NaO$_{20}$, 1365.77; found 1366.16.

(3,5)2Et8G1-PE-TRZ$_t$-Man$_2$ (49ba).

Into a solution of 14e (1.00 g, 1.10 mmol) in THF (1.5 mL) was added 43a (0.58 g, 2.70 mmol) in water (0.5 mL), CuSO$_4$.5H$_2$O (0.17 g, 0.68 mmol) in water (0.5 mL), and sodium ascorbate (0.13 g, 0.66 mmol) in water (0.5 mL) successively under nitrogen atmosphere. The reaction mixture was allowed to stir at room temperature for 12 h. The reaction mixture was diluted with THF, filtered, and washed with THF. The filtrate was concentrated and purified by column chromatography (SiO$_2$, 0-40% MeOH:CH$_2$Cl$_2$) followed by recrystalization from CH$_2$Cl$_2$/MeOH mixture to give the product as a white solid: 1.25 g (84%). Purity (HPLC): 99%. $^1$H NMR (500 MHz, 10% CD$_3$OD in CDCl$_3$) δ 7.95 (s, 2H, 2 =CH (triazole)), 7.10 (d, J=1.5, 4H, 2ArH-2,6), 6.67 (s, 2H, 2ArH-4), 4.88 (s, 2H, CH(anomeric)), 4.76 (d, J=11.8, 2H), 4.66 (s, 6H), 4.47 (s, 4H), 3.91-3.69 (m, 18H), 3.54 (s, 2H), 1.78-1.65 (m, J=12.0, 4H, 4ArOCH$_2$CH), 1.54-1.24 (m, 32H, 4CH$_2$CH$_3$, 4(CH$_2$)$_3$CH$_3$), 0.96-0.86 (m, 24H, 8CH$_3$). $^{13}$C NMR (126 MHz, 10% CD$_3$OD in CDCl$_3$) δ 166.0 (C=O), 160.7 (ArC-3,5), 144.2 (C=CH(triazole)), 130.7 (ArC-1), 126.2 (C=CH(triazole)), 108.0 (ArC-2,6), 106.7 (ArC-4), 99.5 (CH(anomeric)), 77.8, 73.0, 71.3, 71.2, 71.0, 70.7, 70.6, 67.1, 63.4, 61.5, 60.09, 60.05, 60.03, 59.99, 59.98, 50.2 (CH$_2$N), 44.3 (C(CH$_2$N$_3$)$_2$), 39.5, 30.5, 29.8, 29.2, 23.9 (CH$_2$CH$_3$), 23.1 (CH$_2$CH$_3$), 14.1 (CH$_3$), 11.1 (CH$_3$). MALDI-TOF (m/z): [M+Na]$^+$ calcd for C$_{69}$H$_{110}$N$_6$NaO$_{20}$, 1365.77; found 1365.15.

(3,4,5)2Et8G1-PE-TRZ$_i$-Man$_2$ (49ca).

Into a solution of 14f (1.00 g, 0.86 mmol) in THF (1.5 mL) was added 43a (0.45 g, 2.10 mmol) in water (0.5 mL), CuSO$_4$.5H$_2$O (0.13 g, 0.52 mmol) in water (0.5 mL), and sodium ascorbate (0.10 g, 0.50 mmol) in water (0.5 mL) successively under nitrogen atmosphere. The reaction mixture was allowed to stir at room temperature for 12 h. The reaction mixture was diluted with THF, filtered, and washed with THF. The filtrate was concentrated and purified by column chromatography (SiO$_2$, 0-40% MeOH:CH$_2$Cl$_2$) followed by recrystallization from CH$_2$Cl$_2$/MeOH mixture to give the product as a white solid: 1.19 g (87%). Purity (HPLC): 99%+. $^1$H NMR (500 MHz, 10% CD$_3$OD in CDCl$_3$) δ 7.90 (s, 2H, 2 =CH (triazole)), 7.17 (s, 4H, 2ArH-2,6), 4.83 (s, 2H, CH(anomeric)), 4.69 (s, 2H), 4.56 (br. s, 6H), 4.43 (s, 4H), 4.07-3.56 (m, 22H), 3.48 (s, 2H), 1.72-1.58 (m, 6H, 6ArOCH$_2$CH), 1.57-1.18 (m, 48H, 6CH$_2$CH$_3$, 6(CH$_2$)$_3$CH$_3$), 0.90-0.78 (m, 36H, 12CH$_3$). $^{13}$C NMR (126 MHz, 10% CD$_3$OD in CDCl$_3$) δ 165.9 (C=O), 153.3 (ArC-3,5), 144.8 (C=CH(triazole)), 143.3 (ArC-1), 126.3 (C=CH(triazole)), 123.4 (ArC-2,6), 107.8 (ArC-4), 99.6 (CH(anomeric)), 77.9, 76.3, 73.1, 71.6, 71.3, 70.6, 67.0, 63.1, 61.4, 60.1, 50.3 (CH$_2$N), 44.5 (C(CH$_2$N$_3$)$_2$), 40.7, 39.8, 30.6, 30.5, 29.4, 29.2, 23.9 (CH$_2$CH$_3$), 23.7 (CH$_2$CH$_3$), 23.21 (CH$_2$CH$_3$), 23.15 (CH$_2$CH$_3$), 14.2 (CH$_3$), 14.1 (CH$_3$), 11.2 (CH$_3$). MALDI-TOF (m/z): [M+Na]$^+$ calcd for C$_{85}$H$_{142}$N$_6$NaO$_{22}$, 1622.01; found 1621.04.

(3,4)2Et8G1-PE-TRZ$_i$-3EOGal$_2$ (49ab).

Obtained from 14d and 41d using procedure for the synthesis of analogous compounds with minor modifications. Yield 54%. Purity (HPLC): 99%+. $^1$H NMR (360 MHz, 10% CD$_3$OD in CDCl$_3$) δ 8.01 (s, 2H, 2 =CH (triazole)), 7.55-7.53 (m, 2H, 2ArH-6), 7.47 (d, J=2.0, 2H, 2ArH-2), 6.86 (d, J=8.5, 2H, 2ArH-5), 4.70 (s, 4H, 2ArCO$_2$CH$_2$), 4.63 (s, 4H), 4.37 (s, 4H), 4.24 (d, J=7.1, 2H), 4.04-3.84 (m, 12H), 3.80-3.59 (m, 26H), 3.56-3.46 (m, 6H), 1.81-1.70 (m, 4H, 4ArOCH$_2$CH), 1.58-1.21 (m, 32H, 4CH$_2$CH$_3$, 4(CH$_2$)$_3$CH$_3$), 0.95-0.87 (m, 24H, 8CH$_3$). $^{13}$C NMR (91 MHz, 10% CD$_3$OD in CDCl$_3$) δ 166.1 (C=O), 154.5 (ArC-4), 149.4 (ArC-3), 145.2 (C=CH(triazole)), 125.9 (C=CH(triazole)), 123.8 (ArC-1), 121.1 (ArC-6), 114.3 (ArC-2), 112.0 (ArC-5), 103.7 (CH(anomeric)), 77.6, 75.0, 73.6, 71.9, 71.7, 71.5, 70.53, 70.45, 69.9, 69.1, 68.6, 64.4, 63.4, 61.6, 50.5 (CH$_2$N), 44.4 (C(CH$_2$N$_3$)$_2$), 39.8, 39.6, 30.8, 30.7, 29.31, 29.29, 24.10 (CH$_2$CH$_3$), 24.07 (CH$_2$CH$_3$), 23.23 (CH$_2$CH$_3$), 23.22 (CH$_2$CH$_3$), 14.2 (CH$_3$), 11.4 (CH$_3$), 11.3 (CH$_3$). MALDI-TOF (m/z): [M+Na]$^+$ calcd for C$_{81}$H$_{134}$N$_6$NaO$_{26}$, 1629.94; found 1629.36.

(3,5)2Et8G1-PE-TRZ$_i$-3EOGal$_2$ (49bb).

Obtained from 14e and 41d using procedure for the synthesis of analogous compounds with minor modifications. Yield 47%. Purity (HPLC): 99%+. $^1$H NMR (360 MHz, 10% CD$_3$OD in CDCl$_3$) δ 8.02 (s, 2H, 2 =CH (triazole)), 7.07 (d, J=2.3, 4H, 2ArH-2,6), 6.66 (s, 2H, 2ArH-4), 4.71 (s, 4H), 4.65 (s, 4H, 2ArCO$_2$CH$_2$), 4.40 (s, 4H), 4.26 (d, J=7.3, 2H), 4.02-3.97 (m, 2H), 3.91 (s, 2H), 3.85 (d, J=5.5, 8H), 3.79-3.76 (m, 4H), 3.70-3.63 (m, 22H), 3.55-3.48 (m, 6H), 1.75-1.67 (m, 4H, 4ArOCH$_2$CH), 1.57-1.25 (m, 32H, 4CH$_2$CH$_3$, 4(CH$_2$)$_3$CH$_3$), 0.95-0.88 (m, 24H, 4CH$_3$). $^{13}$C NMR (91 MHz, 10% CD$_3$OD in CDCl$_3$) δ 166.0 (C=O), 160.8 (ArC-3,5), 145.0 (C=CH(triazole)), 130.9 (ArC-1), 126.0 (C=CH(triazole)), 108.1 (ArC-2,6), 106.8 (ArC-4), 103.5 (CH(anomeric)), 77.6, 74.9, 73.5, 71.5, 71.1, 70.4, 70.3, 69.8, 69.1, 68.5, 64.3, 63.6, 61.7, 50.4 (CH$_2$N), 44.3 (C(CH$_2$N$_3$)$_2$), 39.6, 30.7, 29.3, 24.0 (CH$_2$CH$_3$), 23.2 (CH$_2$CH$_3$), 14.2 (CH$_3$), 11.2 (CH$_3$). MALDI-TOF (m/z): [M+Na]$^+$ calcd for C$_{81}$H$_{134}$N$_6$NaO$_{26}$, 1629.94; found 1630.20.

(3,4,5)2Et8G1-PE-TRZ$_i$-3EOGal$_2$ (49cb)

Obtained from 14f and 41d using procedure for the synthesis of analogous compounds with minor modifications. Yield 71%. Purity (HPLC): 99%+. $^1$H NMR (360 MHz, 10% CD$_3$OD in CDCl$_3$) δ 8.01 (s, 2H, 2 =CH (triazole)), 7.21 (s, 4H, 2ArH-2,6), 4.65 (d, J=10.0, 8H), 4.41 (s, 4H, 2ArCO$_2$CH$_2$), 4.24 (d, J=7.2, 2H), 4.05-3.85 (m, 16H), 3.83-3.59 (m, 26H), 3.52-3.48 (m, 6H), 1.79-1.66 (m, 6H, 6ArOCH$_2$CH), 1.60-1.31 (m, 48H, 6CH$_2$CH$_3$, 6(CH$_2$)$_3$CH$_3$), 0.95-0.87 (m, 36H, 12CH$_3$). $^{13}$C NMR (91 MHz, 10% CD$_3$OD in CDCl$_3$) δ 165.8 (C=O), 153.2 (ArC-3,5), 144.9 (C=CH(triazole)), 143.1 (ArC-1), 125.7 (C=CH(triazole)), 123.4 (ArC-2,6), 107.7 (ArC-4), 103.5 (CH(anomeric)), 77.4, 76.2, 74.7, 73.4, 71.5, 71.3, 70.28, 70.25, 69.8, 68.9, 68.4, 64.2, 63.1, 61.6, 50.2 (CH$_2$N), 44.3 (C(CH$_2$N$_3$)$_2$), 40.6, 39.6, 30.5, 30.4, 29.3, 29.1, 23.8 (CH$_2$CH$_3$), 23.6 (CH$_2$CH$_3$), 23.1 (CH$_2$CH$_3$), 23.0 (CH$_2$CH$_3$), 14.03 (CH$_3$), 13.99 (CH$_3$), 11.1 (CH$_3$). MALDI-TOF (m/z): [M+Na]$^+$ calcd for C$_{97}$H$_{166}$N$_6$NaO$_{28}$, 1886.18; found 1884.60.

(3,4)2Et8G1-PE-TRZ$_1$-Gal$_2$ (49Ac).

Into a solution of 14d (1.00 g, 1.10 mmol in THF (1.5 mL) was added 41a (0.58 g, 2.70 mmol) in water (0.5 mL), CuSO$_4$.5H$_2$O (0.17 g, 0.68 mmol) in water (0.5 mL), and sodium ascorbate (0.13 g, 0.66 mmol) in water (0.5 mL) successively under nitrogen atmosphere. The reaction mixture was allowed to stir at room temperature for 12 h. The reaction mixture was diluted with THF, filtered, and washed with THF. The filtrate was concentrated and purified by column chromatography (SiO$_2$, 0-40% MeOH:CH$_2$Cl$_2$) followed by recrystallization from CH$_2$Cl$_2$/MeOH mixture to give the product as a white solid: 0.67 g (45%). $^1$H NMR (360 MHz, 10% CD$_3$OD in CDCl$_3$) δ 7.98 (s, 2H, 2 =CH (triazole)), 7.58 (dd, J=8.4, 1.7, 2H, 2ArH-6), 7.48 (d, J=1.8, 2H, 2ArH-2), 6.85 (d, J=8.6, 2H, 2ArH-5), 4.94 (d, J=12.6, 2H), 4.76 (d, J=12.6, 2H), 4.65 (s, 4H), 4.46 (s, 4H, 2ArCO$_2$CH$_2$), 4.32 (d, J=7.6, 2H), 4.04-3.67 (m, 14H), 3.65-3.55 (m, 2H), 3.53-3.48 (m, 4H), 1.87-1.64 (m, 4H, 4ArOCH$_2$CH), 1.55-1.31 (m, 32H, 4CH$_2$CH$_3$, 4(CH$_2$)$_3$CH$_3$), 0.95-0.89 (m, 24H, 8CH$_3$). $^{13}$C NMR (91 Mhz, 10% CD$_3$OD in CDCl$_3$) δ 166.0 (C=O), 154.4 (ArC-4), 149.3 (ArC-3), 144.6 (C=CH(triazole)), 126.3 (C=CH(triazole)), 123.7 (ArC-1), 121.1 (ArC-6), 114.2 (ArC-2), 111.9 (ArC-5), 102.8 (CH(anomeric)), 77.5, 75.0, 73.5, 71.8, 71.6, 71.2, 69.1, 63.4, 62.2, 61.6, 50.3 (CH$_2$N), 44.3 (C(CH$_2$ N$_3$)$_2$), 39.7, 39.5, 30.7, 30.6, 29.2, 23.98 (CH$_2$CH$_3$), 23.96 (CH$_2$CH$_3$), 23.1 (CH$_2$CH$_3$), 14.1 (CH$_3$), 11.3 (CH$_3$), 11.2 (CH$_3$). MALDI-TOF (m/z): [M+Na]$^+$ calcd for C$_{69}$H$_{110}$N$_6$NaO$_{20}$, 1365.77; found 1365.82.

(3,5)2Et8G1-PE-TRZ$_t$-Gal$_2$ (49bc). Into a solution of 14e (1.00 g, 1.10 mmol) in THF (1.5 mL) was added 41a (0.58 g, 2.70 mmol) in water (0.5 mL), CuSO$_4$.5H$_2$O (0.17 g, 0.68 mmol) in water (0.5 mL), and sodium ascorbate (0.13 g, 0.66 mmol) in water (0.5 mL) successively under nitrogen atmosphere. The reaction mixture was allowed to stir at room temperature for 12 h. The reaction mixture was diluted with THF, filtered, and washed with THF. The filtrate was concentrated and purified by column chromatography (SiO$_2$, 0-40% MeOH:CH$_2$Cl$_2$) followed by recrystallization from CH$_2$Cl$_2$/MeOH mixture to give the product as a white solid: 0.51 g (34%). $^1$H NMR (360 MHz, 10% CD$_3$OD in CDCl$_3$) δ 7.93 (s, 2H, 2 =CH (triazole)), 7.11 (d, J=2.2, 4H, 2ArH-2,6), 6.67 (t, J=2.1, 2H, 2ArH-4), 4.94 (d, J=12.7, 2H), 4.78 (d, J=12.7, 2H), 4.65 (s, 4H), 4.48 (s, 4H, 2ArCO$_2$CH$_2$), 4.32 (d, J=7.6, 2H), 3.94-3.69 (m, 14H), 3.65-3.55 (m, 2H), 3.55-3.44 (m, 4H), 1.79-1.64 (m, 4H, 4ArOCH$_2$CH), 1.59-1.21 (m, 32H, 4CH$_2$CH$_3$, 4(CH$_2$)$_3$CH$_3$), 0.95-0.88 (m, 24H, 8CH$_3$). $^{13}$C NMR (91 MHz, 10% CD$_3$OD in CDCl$_3$) δ 166.0 (C=O), 160.7 (ArC-3,5), 144.7 (C=CH(triazole)), 130.8 (ArC-1), 126.2 (C=CH(triazole)), 108.0 (ArC-2,6), 106.6 (ArC-4), 102.8 (CH(anomeric)), 77.5, 75.0, 73.6, 71.2, 71.0, 69.1, 63.6 62.2, 61.7, 50.2 (CH$_2$N), 44.3 (C(CH$_2$N$_3$)$_2$), 39.5, 30.6, 29.3, 23.9 (CH$_2$CH$_3$), 23.1 (CH$_2$CH$_3$), 14.1 (CH$_3$), 11.1 (CH$_3$). MALDI-TOF (m/z): [M+Na]$^+$ calcd for C$_{69}$H$_{110}$N$_6$NaO$_{20}$, 1365.77; found 1366.32.

(3,4,5)2Et8G1-PE-TRZ$_t$-Gal$_2$ (49cc).

Into a solution of 14f (1.00 g, 0.86 mmol) in THF (1.5 mL) was added 41l (0.45 g, 2.10 mmol) in water (0.5 mL), CuSO$_4$.5H$_2$O (0.13 g, 0.52 mmol) in water (0.5 mL), and sodium ascorbate (0.10 g, 0.50 mmol) in water (0.5 mL) successively under nitrogen atmosphere. The reaction mixture was allowed to stir at room temperature for 12 h. The reaction mixture was diluted with THF, filtered, and washed with THF. The filtrate was concentrated and purified by column chromatography (SiO$_2$, 0-40% MeOH:CH$_2$Cl$_2$) followed by recrystalization from CH$_2$Cl$_2$/MeOH mixture to give the product as a white solid: 0.67 g (49%). $^1$H NMR (360 MHz, 10% CD$_3$OD in CDCl$_3$) δ 7.92 (s, 2H, 2 =CH (triazole)), 7.25 (s, 4H, 2ArH-2,6), 4.94 (d, J=12.5, 2H), 4.79 (d, J=12.5, 2H), 4.62 (s, 4H), 4.51 (s, 4H, 2ArCO$_2$CH$_2$), 4.33 (d, J=7.6, 2H), 4.00-3.68 (m, 18H), 3.61 (t, J=8.5, 2H), 3.53-3.49 (m, 4H), 1.78-1.66 (m, 6H, 6ArOCH$_2$CH), 1.63-1.29 (m, 48H, 6CH$_2$CH$_3$, 6(CH$_2$)$_3$CH$_3$), 0.95-0.87 (m, 36H, 12CH$_3$). $^{13}$C NMR (91 MHz, 10% CD$_3$OD in CDCl$_3$) δ 166.0 (C=O), 153.3 (ArC-3,5), 144.8 (C=CH(triazole)), 143.3 (ArC-1), 126.1 (C=CH(triazole)), 123.5 (ArC-2,6), 107.9 (ArC-4), 102.8 (CH(anomeric)), 77.5, 76.3, 75.0, 73.6, 71.6, 71.3, 69.2, 63.3, 62.3, 61.7, 50.3 (CH$_2$N), 44.6 (C(CH$_2$N$_3$)$_2$), 40.8, 39.8, 30.7, 30.5, 29.4, 29.2, 23.9 (CH$_2$CH$_3$), 23.7 (CH$_2$CH$_3$), 23.22 (CH$_2$CH$_3$), 23.16 (CH$_2$CH$_3$), 14.2 (CH$_3$), 14.1 (CH$_3$), 11.2 (CH$_3$). MALDI-TOF (m/z): [M+Na]$^+$ calcd for C$_{85}$H$_{142}$N$_6$NaO$_{22}$, 1622.01; found 1622.51.

Modular Synthesis of Amphiphilic Janus Glycodendrimers (Library 4)

(3,4)12G1-PE-spacer-TRZ-(galactose)$_2$ (50aa). Into a mixture of O,O'-(2,2-bis(((3,4-bis(dodecyloxy) benzoyl)oxy)methyl)propane-1,3-diyl) di(prop-2-yn-1-yl) disuccinate (18a) (0.70 g, 0.52 mmol) and 23 (0.26 g, 1.2 mmol) in THF (4 ml) and water (2 ml) were added CuSO$_4$.5H$_2$O (76.6 mg, 0.31 mmol) and sodium ascorbate (61.9 mg, 0.31 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 2-15% MeOH:CH$_2$Cl$_2$). The pure product was obtained as an oil which eventually becomes white solid: 556.6 mg (61%). Purity (HPLC): 99%+. $^1$H NMR (500 MHz, 10% CD$_3$OD in CDCl$_3$) δ 8.07 (s, 2H, 2 =CH (triazole))), 7.57 (d, J=8.4 Hz, 2H, 2ArH-6), 7.49 (s, 2H, 2ArH-2), 6.85 (d, J=8.5 Hz, 2H, 2ArH-5), 5.52 (d, J=9.1 Hz, 2H, CH (anomeric)), 5.20 (s, 4H, 2OCH$_2$-TRZ), 4.45 (s, 4H, 2ArCO$_2$CH$_2$), 4.32 (s, 4H, 2CH$_2$O$_2$CCH$_2$CH$_2$), 4.18 (t, J=9.3 Hz, 2H, 2CH$_{gal}$), 4.09-3.98 (m, 10H, 4ArOCH$_2$, 2CH$_{gal}$), 3.87-3.73 (m, 6H, 6CH$_{gal}$), 3.71 (d, J=9.5 Hz, 2H, 2CH$_{gal}$), 2.65 (s, 8H, 2CH$_2$O$_2$CCH$_2$CH$_2$), 1.87-1.78 (m, 8H, 4ArOCH$_2$CH$_2$), 1.52-1.44 (m, 8H, 4ArOCH$_2$CH$_2$CH$_2$), 1.31 (m, 64H, 4(CH$_2$)$_8$CH$_3$), 0.88 (t, J=6.8 Hz, 12H, 4CH$_3$). $^{13}$C NMR (126 MHz, 10% CD$_3$OD in CDCl$_3$) δ 172.4 (C=O)-succ., 172.3 (C=O)-succ., 166.3 (ArCO$_2$), 153.9 (ArC-4), 148.8 (ArC-3), 142.8 (C=CH (triazole)), 124.0 (ArC-1), 123.8 (C=CH (triazole)), 121.6 (ArC-6), 114.6 (ArC-2), 112.2 (ArC-5), 88.7 (CH (anomeric)), 78.2 (C$_{5gal}$), 77.9 (C$_{3gal}$), 74.0 (C$_{4gal}$), 70.2 (C$_{2gal}$), 69.6 (ArOCH$_2$-4), 69.3 (ArOCH$_2$-3), 69.1 (CH$_2$O$_2$CCH$_2$CH$_2$), 63.0 (ArCO$_2$CH$_2$), 61.5 (C$_{6gal}$), 57.8 (OCH$_2$-TRZ), 42.8 (C(CH$_2$O)$_4$), 32.1 (CH$_2$CH$_2$CH$_3$), 29.86, 29.84, 29.81, 29.80, 29.76, 29.60, 29.55, 29.51, 29.50, 29.4, 29.2, 29.01, 28.97, 26.2 (ArOCH$_2$CH$_2$CH$_2$), 26.1 (ArOCH$_2$CH$_2$CH$_2$), 22.8 (CH$_2$CH$_3$), 14.2 (CH$_3$). MALDI-TOF (m/z): [M+Na]$^+$ calcd for C$_{93}$H$_{150}$N$_6$NaO$_{26}$, 1790.05; found 1787.97.

(3,4)12G1-PE-spacer-TRZ-(mannose)$_2$ (50ab).

Into a mixture of O,O'-(2,2-bis(((3,4-bis(dodecyloxy) benzoyl)oxy)methyl)propane-1,3-diyl) di(prop-2-yn-1-yl) disuccinate (18a) (0.41 g, 0.30 mmol) and 27 (149.6 mg, 0.72 mmol) in THF (4 ml) and water (2 ml) were added CuSO$_4$.5H$_2$O (44.9 mg, 0.18 mmol) and sodium ascorbate (36.3 mg, 0.18 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 2-10% MeOH: CH$_2$Cl$_2$). The pure product was obtained as an oil which eventually becomes white solid: 123.0 mg (23%). Purity (HPLC): 99%+. $^1$H NMR (500 MHz, 10% CD$_3$OD in CDCl$_3$) δ 8.02 (s, 2H, 2 =CH (triazole))), 7.57 (dd, J=8.4 Hz, J=1.9 Hz, 2H, 2ArH-6), 7.48 (d, J=1.9 Hz, 2H, 2ArH-2), 6.84 (d, J=8.6 Hz, 2H, 2ArH-5), 6.05 (s, 2H, CH (anomeric)), 5.21 (s, 4H, 2OCH$_2$-TRZ), 4.74 (s, 2H, 2CH$_{man}$), 4.44 (s, 4H, 2ArCO$_2$CH$_2$), 4.31 (s, 4H, 2CH$_2$O$_2$CCH$_2$CH$_2$), 4.23 (d, J=7.7 Hz, 2H, 2CH$_{man}$), 4.05-3.99 (m, 8H, 4ArOCH$_2$), 3.98-3.91 (m, 2H, 2CH$_{man}$), 3.80 (m, 4H, 4CH$_{man}$), 3.29 (d, J=9.0 Hz, 2H, 2CH$_{man}$), 2.65 (s, 8H, 2CH$_2$O$_2$CCH$_2$CH$_2$), 1.86-1.78 (m, 8H, 4ArOCH$_2$CH$_2$), 1.50-1.44 (m, 8H, 4ArOCH$_2$CH$_2$CH$_2$), 1.39-1.20 (m, 64H, 4(CH$_2$)$_8$CH$_3$), 0.88 (t, J=6.8 Hz, 12H, 4CH$_3$). $^{13}$C NMR (126 MHz, 10% CD$_3$OD in CDCl$_3$) δ 172.3 (C=O)-succ., 172.1 (C=O)-succ., 166.2 (ArCO$_2$), 153.8 (ArC-4), 148.8 (ArC-3), 143.0 (C=CH (triazole)), 124.7 (ArC-1), 123.8 (C=CH (triazole)), 121.6 (ArC-6), 114.5 (ArC-2), 112.1 (ArC-5), 87.1 (CH (anomeric)), 77.8 (C$_{5man}$), 76.1 (C$_{3man}$), 71.0 (C$_{4man}$), 69.5 (ArOCH$_2$-4), 69.2 (ArOCH$_2$-3), 67.0 C$_{2man}$), 66.6 (CH$_2$O$_2$CCH$_2$CH$_2$), 62.9 (ArCO$_2$CH$_2$), 61.1 (C$_{6man}$), 57.7 (OCH$_2$-TRZ), 42.8 (C(CH$_2$O)$_4$), 32.0 (CH$_2$CH$_2$CH$_3$), 29.80, 29.78, 29.75, 29.74, 29.71, 29.6, 29.50, 29.45, 29.3, 29.2, 28.94, 28.93, 26.14

(ArOCH$_2$CH$_2$CH$_2$), 26.08 (ArOCH$_2$CH$_2$CH$_2$), 22.8 (CH$_2$CH$_3$), 14.1 (CH$_3$). MALDI-TOF (m/z): [M+Na]$^+$ calcd for C$_{93}$H$_{150}$N$_6$NaO$_{26}$, 1790.05; found 1788.99.

(3,5)12G1-PE-spacer-TRZ-(galactose)$_2$ (50ba).

Into a mixture of O,O'-(2,2-bis(((3,5-bis(dodecyloxy)benzoyl)oxy)methyl)propane-1,3-diyl) di(prop-2-yn-1-yl) disuccinate (18b) (428 mg, 0.32 mmol) and 23 (156.2 mg, 0.75 mmol) in THF (6 ml) and water (2 ml) were added CuSO$_4$.5H$_2$O (46.9 mg, 0.19 mmol) and sodium ascorbate (37.9 mg, 0.19 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 2-15% MeOH: CH$_2$Cl$_2$). The pure product was obtained as an oil which eventually becomes white solid: 379.4 mg (68%). Purity (HPLC): 99%+. $^1$H NMR (500 MHz, 10% CD$_3$OD in CDCl$_3$) δ 8.08 (s, 2H, 2 =CH (triazole)), 7.08 (d, J=2.3 Hz, 4H, 2ArH-2, 6), 6.64 (d, J=2.2 Hz, 2H, 2ArH-4), 5.51 (d, J=9.1 Hz, 2H, CH (anomeric)), 5.21 (s, 4H, 2OCH$_2$-TRZ), 4.47 (s, 4H, 2ArCO$_2$CH$_2$), 4.32 (s, 4H, 2CH$_2$O$_2$CCH$_2$CH$_2$), 4.18 (t, J=9.3 Hz, 2H, 2CH$_{gal}$), 4.04 (d, J=3.2 Hz, 2H, 2CH$_{gal}$), 3.94 (t, J=6.5 Hz, 8H, 4ArOCH$_2$), 3.83-3.74 (m, 6H, 6CH$_{gal}$), 3.70 (dd, J=9.5 Hz, J=3.2 Hz, 2H, 2CH$_{gal}$), 2.66 (s, 8H, 2CH$_2$O$_2$CCH$_2$CH$_2$), 1.83-1.70 (m, 8H, 4ArOCH$_2$CH$_2$), 1.49-1.41 (m, 8H, 4ArOCH$_2$CH$_2$CH$_2$), 1.38-1.20 (m, 64H, 4(CH$_2$)$_8$CH$_3$), 0.88 (t, J=6.9 Hz, 12H, 4CH$_3$). $^{13}$C NMR (126 MHz, 10% CD$_3$OD in CDCl$_3$) δ 172.4 (C=O)-succ., 172.3 (C=O)-succ., 166.3 (ArCO$_2$), 160.4 (ArC-3, 5), 142.8 (C=CH (triazole)), 131.2 (C=CH (triazole)), 123.8 (ArC-1), 108.0 (ArC-2, 6), 106.8 (ArC-4), 88.8 (CH (anomeric)), 78.2 (C$_{5gal}$), 74.1 (C$_{3gal}$), 70.2 (C$_{4gal}$), 69.1 (C$_{2gal}$), 68.6 (ArOCH$_2$), 63.3 (CH$_2$O$_2$CCH$_2$CH$_2$), 62.9 (ArCO$_2$CH$_2$), 61.5 (C$_{6gal}$), 57.8 (OCH$_2$-TRZ), 42.9 (C(CH$_2$O)$_4$), 32.1 (CH$_2$CH$_2$CH$_3$), 29.82, 29.79, 29.77, 29.74, 29.6, 29.5, 29.3, 29.1, 29.0, 28.98, 28.94, 26.2 (ArOCH$_2$CH$_2$CH$_2$), 22.8 (CH$_2$CH$_3$), 14.2 (CH$_3$). MALDI-TOF (m/z): [M+Na]$^+$ calcd for C$_{93}$H$_{150}$N$_6$NaO$_{26}$, 1790.05; found 1789.85.

(3,5)12G1-PE-spacer-TRZ-(mannose)$_2$ (50bb).

Into a mixture of O,O'-(2,2-bis(((3,5-bis(dodecyloxy)benzoyl)oxy)methyl)propane-1,3-diyl) di(prop-2-yn-1-yl) disuccinate (18b) (254.8 mg, 0.19 mmol) and 27 (93.0 mg, 0.45 mmol) in THF (4 ml) and water (2 ml) were added CuSO$_4$.5H$_2$O (27.9 mg, 0.11 mmol) and sodium ascorbate (22.5 mg, 0.11 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 2-15% MeOH: CH$_2$Cl$_2$). The pure product was obtained as an oil which eventually becomes white sticky solid: 172.7 mg (52%). Purity (HPLC): 99%+. $^1$H NMR (500 MHz, 10% CD$_3$OD in CDCl$_3$) δ 8.06 (s, 2H, 2 =CH (triazole)), 7.07 (d, J=1.9 Hz, 4H, 2ArH-2, 6), 6.62 (s, 2H, 2ArH-4), 6.08 (s, 2H, CH (anomeric)), 5.20 (s, 4H, 2OCH$_2$-TRZ), 4.74 (s, 2H, 2CH$_{man}$), 4.47 (s, 4H, 2ArCO$_2$CH$_2$), 4.39-4.16 (m, 6H, 2CH$_2$O$_2$CCH$_2$CH$_2$, 2CH$_{man}$), 4.07-3.96 (m, 2H, 2CH$_{man}$), 3.93 (t, J=6.4 Hz, 8H, 4ArOCH$_2$), 3.79 (m, 4H, 4CH$_{man}$), 3.27 (d, J=8.6 Hz, 2H, 2CH$_{man}$), 2.66 (s, 8H, 2CH$_2$O$_2$CCH$_2$CH$_2$), 1.80-1.71 (m, 8H, 4ArOCH$_2$CH$_2$), 1.48-1.40 (m, 8H, 4ArOCH$_2$CH$_2$CH$_2$), 1.40-1.12 (m, 64H, 4(CH$_2$)$_8$CH$_3$), 0.87 (t, J=6.8 Hz, 12H, 4CH$_3$). $^{13}$C NMR (126 MHz, 10% CD$_3$OD in CDCl$_3$) δ 172.1 (C=O)-succ., 171.9 (C=O)-succ., 165.9 (ArCO$_2$), 160.1 (ArC-3, 5), 142.7 (C=CH (triazole)), 130.9 (ArC-1), 124.6 (C=CH (triazole)), 107.6 (ArC-6), 106.4 (ArC-4), 86.9 (CH (anomeric)), 75.8 (C$_{5man}$), 70.7 (C$_{3man}$), 68.8 (C$_{4man}$), 68.2 (ArOCH$_{2man}$), 66.0 (C$_{2man}$), 62.9 (CH$_2$O$_2$CCH$_2$CH$_2$), 62.4 (ArOCH$_2$), 60.6 (C$_{6man}$), 57.4 (OCH$_2$-TRZ), 42.5 (C(CH$_2$O)$_4$), 31.8 (CH$_2$CH$_2$CH$_3$), 29.52, 29.48, 29.47, 29.43, 29.3, 29.2, 29.0, 28.7, 25.9 (ArOCH$_2$CH$_2$CH$_2$), 22.5 (CH$_2$CH$_3$), 13.9 (CH$_3$). MALDI-TOF (m/z): [M+Na]$^+$ calcd for C$_{93}$H$_{150}$N$_6$NaO$_{26}$, 1790.05; found 1788.68.

(3,4,5)12G1-PE-spacer-TRZ-(galactose)$_2$ (50ca).

Into a mixture of O,O'-(2,2-bis(((3,4,5-tris(dodecyloxy)benzoyl)oxy)methyl)propane-1,3-diyl) di(prop-2-yn-1-yl) disuccinate (18c) (500.0 mg, 0.29 mmol) and 23 (143.5 mg, 0.63 mmol) in THF (14 ml) and water (4.8 ml) were added CuSO$_4$.5H$_2$O (43.0 mg, 0.17 mmol) and sodium ascorbate (34.8 mg, 0.17 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 2-15% MeOH: CH$_2$Cl$_2$). The pure product was obtained as an oil which eventually becomes white solid: 380.0 mg (61%). Purity (HPLC): 99%+. $^1$H NMR (500 MHz, 10% CD$_3$OD in CDCl$_3$) δ 8.07 (s, 2H, 2 =CH(triazole)), 7.19 (s, 4H, 2ArH-2, 6), 5.53 (d, J=8.2 Hz, 2H, CH (anomeric)), 5.18 (s, 4H, 2OCH$_2$-TRZ), 4.45 (s, 4H, 2ArCO$_2$CH$_2$), 4.29 (s, 4H, 2CH$_2$O$_2$CCH$_2$CH$_2$), 4.25-4.16 (m, 2H, 2CH$_{gal}$), 4.07 (s, 2H, 2CH$_{gal}$), 4.00 (t, J=6.6 Hz, 4H, 2ArOCH$_2$), 3.96 (t, J=6.2 Hz, 8H, 4ArOCH$_2$), 3.86-3.69 (m, 8H, 8CH$_{gal}$), 2.65 (s, 8H, 2CH$_2$O$_2$CCH$_2$CH$_2$), 1.86-1.69 (m, 12H, 6ArOCH$_2$CH$_2$), 1.50-1.44 (m, 12H, 6ArOCH$_2$CH$_2$CH$_2$), 1.39-1.17 (m, 96H, 6(CH$_2$)$_8$CH$_3$), 0.88 (t, J=6.7 Hz, 18H, 6CH$_3$). $^{13}$C NMR (126 MHz, 10% CD$_3$OD in CDCl$_3$) δ 172.4 (C=O)-succ., 172.1 (C=O)-succ., 166.1 (ArCO$_2$), 153.0 (ArC-3, 5), 142.9 (ArC-4), 142.7 (C=CH (triazole)), 124.1 (C=CH (triazole)), 124.0 (ArC-1), 108.2 (ArC-2, 6), 88.5 (CH (anomeric)), 77.9 (C$_{5gal}$), 73.81 (C$_{3gal}$), 73.75 (ArOCH$_2$-4), 70.1 (C$_{4gal}$), 69.4 (ArOCH$_2$-3, 5), 69.0 (C$_{2gal}$), 62.9 (CH$_2$O$_2$CCH$_2$CH$_2$), 62.7 (ArCO$_2$CH$_2$), 61.3, 57.7 (C$_{6gal}$), 42.9 (OCH$_2$-TRZ), 32.0 (CH$_2$CH$_2$CH$_3$), 30.4, 29.9, 29.84, 29.82, 29.79, 29.77, 29.70, 29.6, 29.48, 29.47, 28.9, 26.3 (ArOCH$_2$CH$_2$), 26.2 (ArOCH$_2$CH$_2$CH$_2$), 22.8 (CH$_2$CH$_3$), 14.2 (CH$_3$). MALDI-TOF (m/z): [M+Na]$^+$ calcd for C$_{117}$H$_{19}$N$_6$NaO$_{28}$, 2158.42; found 2158.44.

(3,4,5)12G1-PE-spacer-TRZ-(mannose)$_2$ (50cb).

Into a mixture of O,O'-(2,2-bis(((3,4,5-tris(dodecyloxy)benzoyl)oxy)methyl)propane-1,3-diyl) di(prop-2-yn-1-yl) disuccinate (18c) (300.0 mg, 0.17 mmol) and 27 (86.1 mg, 0.42 mmol) in THF (8.4 ml) and water (3 ml) were added CuSO$_4$.5H$_2$O (25.8 mg, 0.10 mmol) and sodium ascorbate (20.9 mg, 0.10 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 2-10% MeOH: CH$_2$Cl$_2$). The pure product was obtained as an oil which eventually becomes white solid: 119.0 mg (56%). Purity (HPLC): 99%+. $^1$H NMR (500 MHz, 10% CD$_3$OD in CDCl$_3$) δ 8.01 (s, 2H, 2 =CH(triazole)), 7.19 (s, 4H, 2ArH-2, 6), 6.02 (s, 2H, CH(anomeric)), 5.21 (s, 4H, 2OCH$_2$-TRZ), 4.72 (s, 2H, 2CH$_{man}$), 4.45 (s, 4H, 2ArCO$_2$CH$_2$), 4.31 (s, 4H, 2CH$_2$O$_2$CCH$_2$CH$_2$), 4.19 (d, J=6.4 Hz, 2H, 2CH$_{man}$), 4.01 (t, J=6.6 Hz, 4H, 2ArOCH$_2$), 3.97 (t, J=6.4 Hz, 8H, 4ArOCH$_2$), 3.91 (t, J=9.0 Hz, 2H, 2CH$_{man}$), 3.83-3.75 (m, 4H, 4CH$_{man}$), 3.29 (d, J=9.1 Hz, 2H, 2CH$_{man}$), 2.66 (s, 8H, 2CH$_2$O$_2$CCH$_2$CH$_2$), 1.83-1.77 (m, 8H, 4ArOCH$_2$CH$_2$), 1.76-1.71 (m, 4H, 2ArOCH$_2$CH$_2$), 1.50-1.43 (m, 12H, 6ArOCH$_2$CH$_2$CH$_2$), 1.39-1.20 (m, 96H, 6(CH$_2$)$_8$CH$_3$), 0.88 (t, J=6.5 Hz, 18H, 6CH$_3$). $^{13}$C NMR (126 MHz, 10% CD$_3$OD in CDCl$_3$) δ 172.1 (C=O)-succ., 171.9 (C=O)-succ., 166.0 (ArCO$_2$), 152.9 (ArC-3, 5), 142.9 (C=CH (triazole)), 142.8 (ArC-4), 124.5 (C=CH (triazole)), 123.9 (ArC-1), 108.1 (ArC-2, 6), 87.0 (CH (anomeric)), 76.0 (C$_{5man}$), 73.7 (ArOCH$_2$-4), 71.0 (C$_{3man}$), 69.3 (ArOCH$_2$-3, 5), 68.9 (C$_{4man}$), 66.7 (C$_{2man}$), 62.8 (CH$_2$O$_2$CCH$_2$CH$_2$), 62.6 (ArCO$_2$CH$_2$), 61.2 (OCH$_2$-TRZ), 57.6 (C$_{6man}$), 42.9 (C(CH$_2$O)$_4$), 31.9 (CH$_2$CH$_2$CH$_3$), 30.3, 29.75, 29.74, 29.72, 29.69, 29.67, 29.60, 29.5, 29.39, 29.37, 28.9, 28.8, 26.2 (ArOCH$_2$CH$_2$CH$_2$), 26.1 (ArOCH$_2$CH$_2$CH$_2$), 22.7 (CH$_2$CH$_3$), 14.0 (CH$_3$). MALDI-TOF (m/z): [M+Na]$^+$ calcd for C$_{117}$H$_{198}$N$_6$NaO$_{28}$, 2158.42; found 2158.37.

Modular Synthesis of Amphiphilic Janus Glycodendrimers (Library 5)

(3,4)12G1-PE-TRZ$_i$-3EOGal$_2$ (51aa).

Into a solution of 14a (0.44 g, 0.39 mmol) and 41d (0.30 g, 0.86 mmol) in THF (7.0 mL) was added CuSO$_4$.5H$_2$O (58 mg, 0.23 mmol) in water (1.0 mL), and sodium ascorbate (46 mg, 0.23 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-20% MeOH:CH$_2$Cl$_2$) followed by recrystalization from CH$_2$Cl$_2$ and MeOH mixture to give the product as a white solid: 0.38 g (54%). Purity (HPLC): 99%+. $^1$H NMR (360 MHz, 10% CD$_3$OD in CDCl$_3$) δ 8.03 (s, 2H, 2 =CH(triazole)), 7.55 (d, J=8.4, 2H, 2ArH-6), 7.48 (s, 2H, 2ArH-2), 6.87 (d, J=8.6, 2H, 2ArH-5), 4.72 (s, 4H), 4.64 (s, 4H, 2ArCO$_2$CH$_2$), 4.39 (s, 4H), 4.25 (d, J=7.2, 2H), 4.08-3.98 (m, 10H), 3.91 (d, J=2.5, 2H), 3.86-3.40 (m, 32H), 1.89-1.79 (m, 8H, 4ArOCH$_2$CH$_2$), 1.51-1.28 (m, 72H, 4(CH$_2$),CH$_3$), 0.89 (t, J=6.7, 12H, 4CH$_3$). $^{13}$C NMR (91 MHz, 10% CD$_3$OD in CDCl$_3$) δ 166.1 (C=O), 154.2 (ArC-4), 149.1 (ArC-3), 145.2 (C=CH(triazole)), 126.0 (C=CH(triazole)), 124.1 (ArC-1), 121.4 (ArC-6), 114.9 (ArC-2), 112.4 (ArC-5), 103.8 (CH(anomeric)), 77.7, 75.1, 73.7, 71.6, 70.64, 70.60, 70.1, 69.8, 69.5 69.2, 68.7, 64.5, 63.7, 61.9, 50.6 (CH$_2$N), 44.4 (C(CH$_2$N$_3$)$_2$), 32.2, 30.01, 29.99, 29.95, 29.92, 29.76, 29.71, 29.66, 29.5, 29.4, 26.4, 26.3, 23.0 (CH$_2$CH$_3$), 14.3 (CH$_3$). MALDI-TOF (m/z): [M+Na]$^+$ calcd for C$_{97}$H$_{166}$N$_6$NaO$_{26}$, 1854.17; found 1854.0.

(3,5)12G1-PE-TRZ$_i$-3EOGal$_2$ (51ba).

Into a solution of 14b (0.44 g, 0.39 mmol) and 41d (0.30 g, 0.86 mmol) in THF (7.0 mL) was added CuSO$_4$.5H$_2$O (58 mg, 0.23 mmol) in water (1.0 mL), and sodium ascorbate (46 mg, 0.23 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-20% MeOH:CH$_2$Cl$_2$) followed by recrystallization from CH$_2$Cl$_2$ and MeOH mixture to give the product as a white solid: 0.25 g (36%). $^1$H NMR (360 MHz, 10% CD$_3$OD in CDCl$_3$) δ 8.03 (s, 2H, 2 =CH (triazole)), 7.05 (d, J=2.2, 4H, 2ArH-2,6), 6.64 (t, J=2.2, 2H, 2ArH-4), 4.72 (s, 4H), 4.65 (s, 4H, 2ArCO$_2$CH$_2$), 4.40 (s, 4H), 4.24 (d, J=7.1, 2H), 4.07-3.86 (m, 12H), 3.85-3.45 (m, 32H), 1.88-1.67 (m, 8H, 4ArOCH$_2$CH$_2$), 1.56-1.16 (m, 72H, 4(CH$_2$),CH$_3$), 0.88 (t, J=6.8, 12H, 4CH$_3$). $^{13}$C NMR (91 MHz, 10% CD$_3$OD in CDCl$_3$) δ 165.9 (C=O), 160.4 (ArC-3,5), 145.0 (C=CH(triazole)), 130.8 (ArC-1), 125.9 (C=CH(triazole)), 108.0 (ArC-2,6), 106.6 (ArC-4), 103.6 (CH(anomeric)), 77.5, 74.8, 73.5, 71.4, 70.42, 70.36, 69.8, 69.0, 68.6, 68.5, 64.3, 61.7, 50.3 (CH$_2$N), 44.2 (C(CH$_2$N$_3$)$_2$), 32.0, 29.8, 29.73, 29.69, 29.5, 29.4, 29.3, 26.1, 22.8 (CH$_2$CH$_3$), 14.2 (CH$_3$). MALDI-TOF (m/z): [M+Na]$^+$ calcd for C$_{97}$H$_{166}$N$_6$NaO$_{26}$, 1854.17; found 1853.92.

(3,4,5)12G1-PE-TRZ$_i$-3EOGal$_2$ (51ca).

Into a solution of 14c (0.55 g, 0.37 mmol) and 41d (0.39 g, 1.10 mmol) in THF (5.0 mL) and CH$_2$Cl$_2$ (2.0 mL) was added CuSO$_4$.5H$_2$O (55 mg, 0.22 mmol) in water (0.5 mL), and sodium ascorbate (44 mg, 0.22 mmol) in water (0.5 mL) successively under nitrogen atmosphere. The reaction mixture was allowed to stir at room temperature for 72 h. The reaction mixture was diluted with THF, filtered, and washed with THF. The filtrate was concentrated and purified by column chromatography (SiO$_2$, 5-15% MeOH:CH$_2$Cl$_2$) followed by precipitation from CH$_2$Cl$_2$ in cold MeOH to give the product as a white solid: 0.28 g (35%). Purity (HPLC): 99%+. $^1$H NMR (360 MHz, 10% CD$_3$OD in CDCl$_3$) δ 8.04 (s, 2H, 2 =CH (triazole)), 7.17 (s, 4H, 2ArH-2,6), 4.66 (d, J=13.5, 8H), 4.41 (s, 4H, 2ArCO$_2$CH$_2$), 4.24 (d, J=7.2, 2H), 4.01-3.97 (m, 14H), 3.89 (d, J=2.7, 2H), 3.80-3.63 (m, 26H), 3.52-3.40 (m, 6H), 1.84-1.71 (m, 12H, 6ArOCH$_2$CH$_2$), 1.49-1.44 (m, 12H, 6ArOCH$_2$CH$_2$CH$_2$), 1.30-1.26 (m, 96H, 6(CH$_2$)$_8$CH$_3$), 0.88 (t, J=6.7, 18H, 6CH$_3$). $^{13}$C NMR (91 MHz, 10% CD$_3$OD in CDCl$_3$) δ 166.1 (C=O), 153.3 (ArC-3,5), 145.2 (C=CH(triazole)), 143.2 (ArC-1), 126.0 (C=CH(triazole)), 123.8 (ArC-2,6), 108.6 (ArC-4), 103.9 (CH(anomeric)), 87.2, 77.7, 75.1, 74.1, 73.7, 71.7, 70.72, 70.70, 70.66, 70.2, 69.8, 69.3, 68.8, 64.6, 63.8, 62.0, 50.7 (CH$_2$N), 44.6 (C(CH$_2$N$_3$)$_2$), 32.3, 30.7, 30.11, 30.08, 30.03, 29.96, 29.86, 29.75, 29.73, 26.6, 26.4, 23.0 (CH$_2$CH$_3$), 14.4 (CH$_3$). MALDI-TOF (m/z): [M+Na]$^+$ calcd for C$_{121}$H$_{214}$N$_6$NaO$_{28}$, 2222.54; found 2222.21.

(3,4)12G1-PE-TRZ$_i$-3EOMan$_2$ (51ab).

Into a solution of 14a (0.44 g, 0.39 mmol) and 43d (0.30 g, 0.86 mmol) in THF (7.0 mL) was added CuSO$_4$.5H$_2$O (58 mg, 0.23 mmol) in water (1.0 mL), and sodium ascorbate (46 mg, 0.23 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-20% MeOH:CH$_2$Cl$_2$) followed by recrystallization from CH$_2$Cl$_2$ and MeOH mixture to give the product as a white solid: 0.42 g (59%). Purity (HPLC): 99%+. $^1$H NMR (500 MHz, 10% CD$_3$OD in CDCl$_3$) δ 7.98 (s, 2H, 2 =CH(triazole)), 7.56 (dd, J=8.4, 2.0, 2H, 2ArH-6), 7.48 (d, J=2.0, 2H, 2ArH-2), 6.87 (d, J=8.6, 2H, 2ArH-5), 4.83 (d, J=1.4, 2H, CH(anomeric)), 4.68 (s, 4H, 2ArCO$_2$CH$_2$), 4.64 (s, 4H, 2OCH$_2$-TRZ), 4.36 (s, 4H, 2NCH$_2$), 4.04 (m, 8H, 4ArOCH$_2$), 3.89-3.86 (m, 2H), 3.84-3.71 (m, 1 OH), 3.69-3.54 (m, 24H), 1.88-1.77 (m, 8H, 4ArOCH$_2$CH$_2$), 1.51-1.45 (m, 8H, 4ArOCH$_2$CH$_2$CH$_2$), 1.41-1.21 (m, 64H, 4(CH$_2$)$_8$CH$_3$), 0.88 (t, J=6.9, 12H, 4CH$_3$). $^{13}$C NMR (126 MHz, 10% CD$_3$OD in CDCl$_3$) δ 165.8 (C=O), 154.0 (ArC-4), 148.9 (ArC-3), 145.1 (C=CH(triazole)), 125.7 (C=CH(triazole)), 123.9 (ArC-1), 121.1 (ArC-6), 114.6 (ArC-2), 112.1 (ArC-5), 100.3 (CH(anomeric)), 77.9, 72.5, 71.4, 70.72, 70.66, 70.57, 70.52, 70.3, 69.9, 69.6, 69.2, 67.0, 66.7, 64.2, 63.3, 61.6, 50.2 (CH$_2$N), 44.3 (C(CH$_2$N$_3$)$_2$), 32.0, 29.80, 29.78, 29.74, 29.71, 29.6, 29.50, 29.45, 29.3, 29.2, 26.2, 26.1, 22.8 (CH$_2$CH$_3$), 14.1 (CH$_3$). MALDI-TOF (m/z): [M+Na]+ calcd for C97H166N6NaO26, 1854.17; found 1853.44.

(3,5)12G1-PE-TRZ$_i$-3EOMan$_2$ (51bb).

Into a solution of 14b (0.44 g, 0.39 mmol) and 43d (0.30 g, 0.86 mmol) in THF (5.0 mL) was added CuSO$_4$.5H$_2$O (58 mg, 0.23 mmol) in water (1.0 mL), and sodium ascorbate (46 mg, 0.23 mmol) in water (1.0 mL) successively under nitrogen atmosphere. The reaction mixture was allowed to stir at room temperature for 16 h. The reaction mixture was concentrated under reduced pressure and purified by column chromatography ($SiO_2$, 0-20% $MeOH:CH_2Cl_2$) followed by recrystalization from $CH_2Cl_2$/MeOH mixture to give the product as a white sticky solid: 0.48 g (68%). Purity (HPLC): 99%+. $^1$H NMR (500 MHz, 10% $CD_3OD$ in $CDCl_3$) δ 7.98 (s, 2H, 2 =CH(triazole)), 7.06 (d, J=2.3, 4H, 2ArH-2,6), 6.66 (t, J=2.2, 2H, 2ArH-4), 4.83 (d, J=0.9, 2H, CH(anomeric)), 4.68 (s, 4H, $2ArCO_2CH_2$), 4.66 (s, 4H, $2OCH_2$-TRZ), 4.37 (s, 4H, $2NCH_2$), 3.96 (t, J=6.5, 8H, $4ArOCH_2$), 3.88 (s, 2H), 3.84-3.72 (m, 10H), 3.69-3.55 (m, 24H), 1.82-1.75 (m, 8H, $4ArOCH_2CH_2$), 1.51-1.40 (m, 8H, $4ArOCH_2CH_2CH_2$), 1.40-1.19 (m, 64H, $4(CH_2)_8CH_3$), 0.88 (t, J=6.9, 12H, $4CH_3$). $^{13}$C NMR (126 MHz, 10% $CD_3OD$ in $CDCl_3$) δ 165.8 (C=O), 160.4 (ArC-3,5), 145.1 (C=CH (triazole)), 130.7 (ArC-1), 125.7 (C=CH(triazole)), 108.0 (ArC-2,6), 106.7 (ArC-4), 100.3 (CH(anomeric)), 77.9, 72.5, 71.4, 70.70, 70.68, 70.59, 70.53, 70.3, 69.9, 68.6, 67.1, 66.7, 64.2, 63.5, 61.6, 50.1 ($CH_2N$), 44.3 ($C(CH_2N_3)_2$), 32.0, 29.76, 29.73, 29.72, 29.68, 29.5, 29.4, 29.3, 26.1, 22.8 ($CH_2CH_3$), 14.1 ($CH_3$). MALDI-TOF (m/z): $[M+Na]^+$ calcd for $C_{97}H_{166}N_6NaO_{26}$, 1854.17; found 1853.16.

(3,4,5)12G1-PE-TRZ$_i$-3EOMan$_2$ (51cb). Into a solution of 14c (0.55 g, 0.37 mmol) and 43d (0.39 g, 1.10 mmol) in THF (5.0 mL) and $CH_2Cl_2$ (2.0 mL) was added $CuSO_4.5H_2O$ (55 mg, 0.22 mmol) in water (0.5 mL), and sodium ascorbate (44 mg, 0.22 mmol) in water (0.5 mL) successively under nitrogen atmosphere. The reaction mixture was allowed to stir at room temperature for 72 h. The reaction mixture was diluted with THF, filtered, and washed with THF. The filtrate was concentrated and purified by column chromatography ($SiO_2$, 5-15% $MeOH:CH_2Cl_2$) followed by precipitation from $CH_2Cl_2$ in cold MeOH to give the product as a white solid: 0.62 g (77%). Purity (HPLC): 99%+. $^1$H NMR (500 MHz, 10% $CD_3OD$ in $CDCl_3$) δ 8.00 (s, 2H, 2 =CH (triazole)), 7.19 (s, 4H, 2ArH-2,6), 4.83 (s, 2H, CH(anomeric)), 4.65 (s, 8H, $2ArCO_2CH_2$, $2OCH_2$-TRZ), 4.39 (s, 4H, $2NCH_2$), 4.00 (m, 12H, $6ArOCH_2$), 3.87 (s, 2H), 3.83-3.71 (m, 10H), 3.70-3.55 (m, 24H), 1.88-1.68 (m, 12H, $6ArOCH_2CH_2$), 1.52-1.44 (m, 12H, $6ArOCH_2CH_2CH_2$), 1.39-1.20 (m, 96H, $6(CH_2)_8CH_3$), 0.88 (t, J=6.8, 18H, $6CH_3$). $^{13}$C NMR (126 MHz, 10% $CD_3OD$ in $CDCl_3$) δ 165.8 (C=O), 153.1 (ArC-3,5), 145.1 (C=CH (triazole)), 143.2 (ArC-1), 125.8 (C=CH(triazole)), 123.6 (ArC-2,6), 108.3 (ArC-4), 100.3 (CH(anomeric)), 77.9, 73.8, 72.5, 71.4, 70.71, 70.68, 70.59, 70.53, 70.3, 70.0, 69.5, 67.2, 66.7, 64.3, 63.3, 61.6, 50.2 ($CH_2N$), 44.4 ($C(CH_2N_3)_2$), 32.0, 30.4, 29.86, 29.84, 29.83, 29.80, 29.77, 29.70, 29.6, 29.49, 29.48, 26.3, 26.2, 22.8 ($CH_2CH_3$), 14.2 ($CH_3$). MALDI-TOF (m/z): $[M+Na]^+$ calcd for $C_{121}H_{214}N_6NaO_{28}$, 2222.54; found 2221.43.

(3,4)12G1-PE-TRZ$_i$-2EOMan$_2$ (51ac).

Into a solution of 14a (0.47 g, 0.42 mmol) and 43c (0.28 g, 0.91 mmol) in THF (7.0 mL) was added $CuSO_4.5H_2O$ (62 mg, 0.25 mmol) in water (1.0 mL), and sodium ascorbate (49 mg, 0.25 mmol) in water (1.0 mL) successively under nitrogen atmosphere. The reaction mixture was allowed to stir at room temperature for 24 h. The reaction mixture was concentrated under reduced pressure and purified by column chromatography ($SiO_2$, 0-20% $MeOH:CH_2Cl_2$) followed by recrystalization from MeOH to give the product as a white solid: 0.52 g (72%). Purity (HPLC): 99%+. $^1$H NMR (500 MHz, 10% $CD_3OD$ in $CDCl_3$) δ 7.99 (s, 2H, 2 =CH (triazole)), 7.55 (dd, J=8.4, 2.0, 2H, 2ArH-6), 7.48 (d, J=1.9, 2H, 2ArH-2), 6.87 (d, J=8.6, 2H, 2ArH-5), 4.84 (d, J=1.4, 2H, CH(anomeric)), 4.68 (s, 4H, $2ArCO_2CH_2$), 4.64 (s, 4H, $2OCH_2$-TRZ), 4.37 (s, 4H, $2NCH_2$), 4.04 (m, 8H, $4ArOCH_2$), 3.89-3.85 (m, 2H), 3.81-3.71 (m, 10H), 3.63 (m, 16H), 1.89-1.77 (m, 8H, $4ArOCH_2CH_2$), 1.52-1.44 (m, 8H, $4ArOCH_2CH_2CH_2$), 1.40-1.21 (m, 64H, $4(CH_2)_8CH_3$), 0.88 (t, J=6.9, 12H, $4CH_3$). $^{13}$C NMR (126 MHz, 10% $CD_3OD$ in $CDCl_3$) δ 165.9 (C=O), 154.0 (ArC-4), 148.8 (ArC-3), 145.1 (C=CH(triazole)), 125.7 (C=CH(triazole)), 123.9 (ArC-1), 121.1 (ArC-6), 114.6 (ArC-2), 112.1 (ArC-5), 100.3 (CH(anomeric)), 77.9, 72.6, 71.4, 70.7, 70.6, 70.4, 69.9, 69.6, 69.2, 66.9, 66.7, 64.3, 63.3, 61.5, 50.2 ($CH_2N$), 44.3 ($C(CH_2N_3)_2$), 32.0, 29.81, 29.79, 29.75, 29.72, 29.56, 29.51, 29.46, 29.3, 29.2, 26.2, 26.1, 22.8 ($CH_2CH_3$), 14.2 ($CH_3$). MALDI-TOF (m/z): $[M+Na]^+$ calcd for $C_{93}H_{158}N_6NaO_{24}$, 1766.12; found 1765.80.

(3,5)12G1-PE-TRZ$_i$-2EOMan$_2$ (51bc).

Into a solution of 14b (0.47 g, 0.42 mmol) and 43c (0.28 g, 0.91 mmol) in THF (5.0 mL) was added $CuSO_4.5H_2O$ (62 mg, 0.25 mmol) in water (1.0 mL), and sodium ascorbate (49 mg, 0.25 mmol) in water (1.0 mL) successively under nitrogen atmosphere. The reaction mixture was allowed to stir at room temperature for 18 h. The reaction mixture was concentrated under reduced pressure and purified by column chromatography ($SiO_2$, 0-30% $MeOH:CH_2Cl_2$) followed by recrystalization from MeOH to give the product as a white solid: 0.42 g (58%). Purity (HPLC): 99%+. $^1$H NMR (500 MHz, 10% $CD_3OD$ in $CDCl_3$) δ 7.98 (s, 2H, 2 =CH (triazole)), 7.06 (d, J=2.3, 4H, 2ArH-2,6), 6.66 (t, J=2.2, 2H, 2ArH-4), 4.84 (d, J=1.1, 2H, CH(anomeric)), 4.68 (s, 4H, $2ArCO_2CH_2$), 4.66 (s, 4H, $2OCH_2$-TRZ), 4.37 (s, 4H), 3.95 (t, J=6.5, 8H, $4ArOCH_2$), 3.87 (s, 2H), 3.80-3.71 (m, 11H), 3.69-3.57 (m, 17H), 1.81-1.75 (m, 8H, $4ArOCH_2CH_2$), 1.48-1.42 (m, 8H, $4ArOCH_2CH_2CH_2$), 1.38-1.20 (m, 64H, $4(CH_2)_8CH_3$), 0.88 (t, J=6.9, 12H, $4CH_3$). $^{13}$C NMR (126 MHz, 10% $CD_3OD$ in $CDCl_3$) δ 165.9 (C=O), 160.4 (ArC-3,5), 145.1 (C=CH(triazole)), 130.7 (ArC-1), 125.8 (C=CH(triazole)), 108.0 (ArC-2,6), 106.7 (ArC-4), 100.2 (CH(anomeric)), 77.8, 72.5, 71.4, 70.7, 70.6, 70.4, 69.9, 68.6, 67.1, 66.7, 64.3, 63.5, 61.6, 50.1 ($CH_2N$), 44.3 ($C(CH_2N_3)_2$), 32.0, 29.76, 29.73, 29.72, 29.68, 29.5, 29.4, 29.3, 26.1, 22.8 ($CH_2CH_3$), 14.1 ($CH_3$). MALDI-TOF (m/z): $[M+Na]+$ calcd for $C_{93}H_{158}N_6NaO_{24}$, 1766.12; found 1766.10.

(3,4,5)12G1-PE-TRZ$_i$-2EOMan$_2$ (51cc).

Into a solution of 14c (0.63 g, 0.42 mmol) and 43c (0.28 g, 0.91 mmol) in THF (5.0 mL) was added $CuSO_4.5H_2O$ (62 mg, 0.25 mmol) in water (1.0 mL), and sodium ascorbate (49 mg, 0.25 mmol) in water (1.0 mL) successively under nitrogen atmosphere. The reaction mixture was allowed to stir at room temperature for 18 h. The reaction mixture was concentrated under reduced pressure and purified by column chromatography ($SiO_2$, 0-20% $MeOH:CH_2Cl_2$) followed by recrystalization from $CH_2Cl_2$/MeOH mixture to give the product as a white solid: 0.65 g (73%). Purity (HPLC): 99%+. $^1$H NMR (500 MHz, 10% $CD_3OD$ in $CDCl_3$) δ 8.00 (s, 2H, 2 =CH(triazole)), 7.19 (s, 4H, 2ArH-2,6), 4.84 (s, 2H, CH(anomeric)), 4.65 (s, 4H, $2ArCO_2CH_2$), 4.64 (s, 4H, $2OCH_2$-TRZ), 4.39 (s, 4H, $2NCH_2$), 4.00 (m, 12H, $6ArOCH_2$), 3.87 (s, 2H), 3.82-3.72 (m, 11H), 3.63 (qd, J=12.6, 7.1, 16H), 1.84-1.71 (m, 12H, $6ArOCH_2CH_2$), 1.51-1.44 (m, 12H, $6ArOCH_2CH_2CH_2$), 1.39-1.21 (m, 96H, $6(CH_2)_8CH_3$), 0.88 (t, J=6.9, 18H, $6CH_3$). $^{13}$C NMR (126 MHz, 10% $CD_3OD$ in $CDCl_3$) δ 165.8 (C=O), 153.1 (ArC-3,5), 145.4 (C=CH(triazole)), 143.1 (ArC-1), 126.3 (C=CH(triazole)), 123.6 (ArC-2,6), 108.3 (ArC-4), 100.3 (CH(anomeric)), 77.9, 73.8, 72.6, 71.4, 70.8, 70.6, 70.4, 69.9, 69.4, 66.8, 66.7, 64.4, 63.4, 61.4, 50.3 ($CH_2N$), 44.3

(C(CH$_2$N$_3$)$_2$), 32.0, 30.4, 29.86, 29.84, 29.82, 29.77, 29.70, 29.6, 29.49, 29.47, 26.3, 26.2, 22.8 (CH$_2$CH$_3$), 14.2 (CH$_3$). MALDI-TOF (m/z): [M+Na]+ calcd for C$_{117}$H$_{206}$N$_6$NaO$_{26}$, 2134.49; found 2134.85.

(3,4)12G1-PE-TRZ-1EOMan$_2$ (51ad).

Into a solution of 14a (0.40 g, 0.35 mmol) and 43b (0.20 g, 0.78 mmol) in THF (9.0 mL) was added CuSO$_4$.5H$_2$O (53 mg, 0.21 mmol) in water (1.0 mL), and sodium ascorbate (42 mg, 0.21 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-30% MeOH:CH$_2$Cl$_2$) followed by recrystallization from MeOH to give the product as a white solid: 0.26 g (43%). Purity (HPLC): 99%+. $^1$H NMR (500 MHz, 10% CD$_3$OD in CDCl$_3$) δ 8.02 (s, 2H, 2 =CH (triazole)), 7.55 (d, J=8.3, 2H, 2ArH-6), 7.48 (s, 2H, 2ArH-2), 6.86 (d, J=8.5, 2H, 2ArH-5), 4.83 (s, 2H, CH(anomeric)), 4.66 (s, 4H, 2ArCO$_2$CH$_2$), 4.63 (s, 4H, 2OCH$_2$-TRZ), 4.37 (s, 4H, 2NCH$_2$), 4.03 (m, 8H, 4ArOCH$_2$), 3.89 (s, 2H), 3.77 (m, 10H), 3.69 (m, 4H), 3.60 (m, 4H), 1.83 (m, 7.2, 8H, 4ArOCH$_2$CH$_2$), 1.48 (m, 8H, 4ArOCH$_2$CH$_2$CH$_2$), 1.31 (m, 64H, 4(CH$_2$)$_8$CH$_3$), 0.88 (t, J=6.8, 12H, 4CH$_3$). $^{13}$C NMR (126 MHz, 10% CD$_3$OD in CDCl$_3$) δ 165.9 (C=O), 154.1 (ArC-4), 148.9 (ArC-3), 145.2 (C=CH(triazole)), 125.6 (C=CH(triazole)), 123.9 (ArC-1), 121.1 (ArC-6), 114.6 (ArC-2), 112.1 (ArC-5), 100.2 (CH(anomeric)), 77.8, 72.6, 71.4, 70.7, 69.7, 69.6, 69.2, 66.9, 66.6, 64.3, 63.2, 61.5, 50.0 (CH$_2$N), 44.4 (C(CH$_2$N$_3$)$_2$), 32.0, 29.81, 29.79, 29.75, 29.72, 29.6, 29.51, 29.46, 29.3, 29.2, 26.2, 26.1, 22.8 (CH$_2$CH$_3$), 14.2 (CH$_3$). MALDI-TOF (m/z): [M+Na]$^+$ calcd for C$_{89}$H$_{150}$N$_6$NaO$_{22}$, 1678.07; found 1677.99.

(3,5)12G1-PE-TRZ$_t$-1EOMan$_2$ (51bd).

Into a solution of 14b (0.40 g, 0.35 mmol) and 43b (0.20 g, 0.78 mmol) in THF (7.0 mL) was added CuSO$_4$.5H$_2$O (53 mg, 0.21 mmol) in water (1.0 mL), and sodium ascorbate (42 mg, 0.21 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-20% MeOH:CH$_2$Cl$_2$) followed by recrystallization from MeOH to give the product as a white solid: 0.50 g (83%). Purity (HPLC): 99%+. $^1$H NMR (500 MHz, 10% CD$_3$OD in CDCl$_3$) δ 8.00 (s, 2H, 2 =CH (triazole)), 7.06 (d, J=2.3, 4H, 2ArH-2,6), 6.65 (t, J=2.3, 2H, 2ArH-4), 4.83 (d, J=1.2, 2H, CH(anomeric)), 4.65 (s, 8H, 2ArCO$_2$CH$_2$, 2OCH$_2$-TRZ), 4.38 (s, 4H, 2NCH$_2$), 3.95 (t, J=6.5, 8H, 4ArOCH$_2$), 3.89 (s, 2H), 3.85-3.72 (m, 10H), 3.69 (t, J=4.1, 4H), 3.63 (m, 2H), 3.57 (m, 2H), 1.83-1.73 (m, 8H, 4ArOCH$_2$CH$_2$), 1.49-1.42 (m, 8H, 4ArOCH$_2$CH$_2$CH$_2$), 1.39-1.21 (m, 64H, 4(CH$_2$)$_8$CH$_3$), 0.88 (t, J=7.0, 12H). $^{13}$C NMR (126 MHz, 10% CD$_3$OD in CDCl$_3$) δ 165.9 (C=O), 160.4 (ArC-3,5), 145.2 (C=CH (triazole)), 130.7 (ArC-1), 125.7 (C=CH(triazole)), 108.0 (ArC-2,6), 106.7 (ArC-4), 100.2 (CH(anomeric)), 77.8, 72.6, 71.3, 70.7, 69.8, 68.6, 67.0, 66.6, 64.3, 63.4, 61.5, 49.9 (CH$_2$N), 44.3 (C(CH$_2$N$_3$)$_2$), 32.0, 29.8, 29.73, 29.71, 29.68, 29.5, 29.4, 29.3, 26.1, 22.8 (CH$_2$CH$_3$), 14.1 (CH$_3$). MALDI-TOF (m/z): [M+Na]$^+$ calcd for C$_{89}$H$_{150}$N$_6$NaO$_{22}$, 1678.07; found 1677.66.

(3,4,5)12G1-PE-TRZ$_t$-1EOMan$_2$ (51cd). Into a solution of 14c (0.53 g, 0.35 mmol) and 43b (0.20 g, 0.78 mmol) in THF (7.0 mL) was added CuSO$_4$.5H$_2$O (53 mg, 0.21 mmol) in water (1.0 mL), and sodium ascorbate (42 mg, 0.21 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-20% MeOH:CH$_2$Cl$_2$) followed by recrystallization from MeOH to give the product as a white solid: 0.54 g (75%). Purity (HPLC): 99%+. $^1$H NMR (500 MHz, 10% CD$_3$OD in CDCl$_3$) δ 8.01 (s, 2H, 2 =CH(triazole)), 7.19 (s, 4H, 2ArH-2,6), 4.83 (s, 2H, CH(anomeric)), 4.65 (s, 4H, 2ArCO$_2$CH$_2$), 4.62 (s, 4H, 2OCH$_2$-TRZ), 4.39 (s, 4H, 2NCH$_2$), 4.01 (m, 12H, 6ArOCH$_2$), 3.89 (s, 2H), 3.85-3.73 (m, 10H), 3.69 (m, 4H), 3.63 (m, 2H), 3.56 (m, 2H), 1.86-1.70 (m, 12H, 6ArOCH$_2$CH$_2$), 1.47 (m, 12H, 6ArOCH$_2$CH$_2$CH$_2$), 1.30 (m, 96H, 6(CH$_2$)$_8$CH$_3$), 0.88 (t, J=6.7, 18H, 6CH$_3$). $^{13}$C NMR (126 MHz, 10% CD$_3$OD in CDCl$_3$) δ 165.8 (C=O), 153.1 (ArC-3,5), 145.3 (C=CH (triazole)), 143.2 (ArC-1), 125.6 (C=CH(triazole)), 123.6 (ArC-2,6), 108.4 (ArC-4), 100.2 (CH(anomeric)), 77.8, 73.8, 72.6, 71.3, 70.7, 69.8, 69.5, 67.0, 66.6, 64.4, 63.2, 61.6, 50.0 (CH$_2$N), 44.5 (C(CH$_2$N$_3$)$_2$), 32.0, 30.4, 29.85, 29.84, 29.82, 29.77, 29.70, 29.6, 29.49, 29.47, 26.3, 26.2, 22.8 (CH$_2$CH$_3$), 14.1 (CH$_3$). MALDI-TOF (m/z): [M+Na]$^+$ calcd for C$_{113}$H$_{198}$N$_6$NaO$_{24}$, 2046.44; found 2044.45.

Modular Synthesis of Amphiphilic Janus Glycodendrimers (Library 6)

(3,4)12G1-PE-TRZ-4EOLac$_2$ (52ad).

Into a solution of 11a (0.48 g, 0.41 mmol) and 37 (0.50 g, 0.91 mmol) in THF (5.0 mL) was added CuSO$_4$.5H$_2$O (62 mg, 0.25 mmol) in water (1.0 mL), and sodium ascorbate (49 mg, 0.25 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.59 g (63%). Purity (HPLC): 99%+. $^1$H NMR (500 MHz, 10% CD$_3$OD in CDCl$_3$) δ 7.76 (s, 2H, 2 =CH (triazole)), 7.50 (dd, J=8.5, 1.4, 2H, 2ArH-6), 7.44 (d, J=1.7, 2H, 2ArH-2), 6.83 (d, J=8.5, 2H, 2ArH-5), 4.61 (s, 4H, 2CH$_2$OCH$_2$-TRZ), 4.44 (t, J=5.1, 4H), 4.38 (m, 6H), 4.33 (d, J=7.8, 2H), 4.04 (t, J=6.6, 4H, 2ArOCH$_2$), 3.99 (m, 6H), 3.90-3.81 (m, 12H), 3.78-3.56 (m, 38H), 3.53 (dd, J=9.6, 3.1, 2H), 3.25 (m, 2H), 1.81 (m, 8H, 4ArOCH$_2$CH$_2$), 1.45 (m, 8H, 4ArOCH$_2$CH$_2$CH$_2$), 1.39-1.21 (m, 64H, 4(CH$_2$)$_8$CH$_3$), 0.88 (t, J=6.9, 12H, 4CH$_3$). $^{13}$C NMR (126 MHz, 10% CD$_3$OD in CDCl$_3$) δ 166.4 (C=O), 153.6 (ArC-4), 148.7 (ArC-3), 144.8 (C=CH(triazole)), 124.2 (C=CH(triazole)), 123.7 (ArC-1), 122.1 (ArC-6), 114.5 (ArC-2), 112.1 (ArC-5), 103.8 (CH(anomeric)), 103.0 (CH(anomeric)), 79.9, 77.9, 75.5, 75.0, 74.8, 73.5, 73.3, 71.1, 70.43, 70.40, 70.35, 69.5, 69.4, 69.2, 69.1, 69.0, 68.7, 64.9, 63.7, 61.6, 61.3, 50.3 (OCH$_2$-TRZ), 44.2 (C(CH$_2$O)$_2$), 32.0, 29.81, 29.79, 29.75, 29.72, 29.57, 29.52, 29.46, 29.3, 29.2, 26.2, 26.1, 22.8 (CH$_2$CH$_3$), 14.1 (CH). MALDI-TOF (m/z): [M+Na]$^+$ calcd for C$_{113}$H$_{194}$N$_6$NaO$_{38}$, 2266.33; found 2265.75.

(3,5)12G1-PE-TRZ-4EOLac$_2$ (52bd).

Into a solution of 11b (0.48 g, 0.41 mmol) and 37 (0.50 g, 0.91 mmol) in THF (5.0 mL) was added CuSO$_4$.5H$_2$O (62 mg, 0.25 mmol) in water (1.0 mL), and sodium ascorbate (49 mg, 0.25 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.49 g (53%). Purity (HPLC): 99%+. $^1$H NMR (500 MHz, 10% CD$_3$OD in CDCl$_3$) δ 7.76 (s, 2H, 2 =CH (triazole)), 7.04 (d, J=2.2, 4H, 2ArH-2,6), 6.62 (t, J=2.2, 2H, 2ArH-4), 4.60 (s, 4H, 2CH$_2$OCH$_2$-TRZ), 4.48 (t, J=4.9, 4H), 4.42 (m, 6H), 4.34 (d, J=7.5, 2H), 3.98 (s, 2H), 3.92 (t, J=6.5, 10H), 3.88-3.81 (m, 10H), 3.78-3.53 (m, 38H), 3.50 (s, 2H), 3.37 (m, 2H), 1.76 (dd, J=14.6, 6.8, 8H, 4ArOCH$_2$CH$_2$), 1.47-1.41 (m, 8H, 4ArOCH$_2$CH$_2$CH$_2$), 1.38-1.21 (m, 64H, 4(CH$_2$)$_8$CH$_3$), 0.88 (t, J=6.9, 12H, 4CH$_3$). $^{13}$C NMR (126 MHz, 10% CD$_3$OD in CDCl$_3$) δ 166.3 (C=O), 160.3 (ArC-3,5), 144.7 (C=CH(triazole)), 131.6 (ArC-1), 124.2 (C=CH(triazole)), 107.8 (ArC-2,6), 106.5 (ArC-4), 103.7 (CH(anomeric)), 103.0 (CH(anomeric)), 79.8, 77.9, 75.5, 75.0, 74.7, 73.5, 73.2, 71.1, 70.43, 70.39, 69.4, 69.1, 69.0, 68.7, 68.5, 64.9, 64.0, 61.5, 61.2, 50.3 (OCH$_2$-TRZ), 44.2 (C(CH$_2$O)$_2$), 32.0, 29.8, 29.73, 29.72, 29.68, 29.5, 29.4, 29.3, 26.1, 22.8 (CH$_2$CH$_3$), 14.2 (CH$_3$). MALDI-TOF (m/z): [M+Na]$^+$ calcd for C$_{113}$H$_{194}$N$_6$NaO$_{38}$, 2266.33; found 2265.42.

(3,4,5)12G1-PE-TRZ-4EOLac$_2$ (52cd).

Into a solution of 11c (0.63 g, 0.41 mmol) and 37 (0.50 g, 0.91 mmol) in THF (5.0 mL) was added CuSO$_4$.5H$_2$O (62 mg, 0.25 mmol) in water (1.0 mL), and sodium ascorbate (49 mg, 0.25 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from CH$_2$Cl$_2$/MeOH mixture to give the product as a white solid: 0.70 g (65%). Purity (HPLC): 99%+. $^1$H NMR (500 MHz, 10% CD$_3$OD in CDCl$_3$) δ 7.74 (s, 2H, 2 =CH(triazole)), 7.14 (s, 4H, 2ArH-2,6), 4.60 (s, 4H, 2CH$_2$OCH$_2$-TRZ), 4.45 (t, J=5.0, 4H), 4.42-4.37 (m, 6H), 4.33 (d, J=7.8, 2H), 3.99 (t, J=6.6, 6H), 3.94 (t, J=6.3, 8H, 4ArOCH$_2$), 3.90-3.82 (m, 12H), 3.77-3.58 (m, 38H), 3.54 (dd, J=9.6, 2.9, 2H), 3.37 (m, 2H), 1.84-1.71 (m, 12H, 6ArOCH$_2$CH$_2$), 1.46 (m, 12H, 6ArOCH$_2$CH$_2$CH$_2$), 1.39-1.21 (m, 96H, 6(CH$_2$)$_8$CH$_3$), 0.88 (T, J=6.9, 18H, 6CH$_3$). $^{13}$C NMR (126 MHz, 10% CD$_3$OD in CDCl$_3$) δ 166.3 (C=O), 153.0 (ArC-3,5), 144.7 (C=CH(triazole)), 142.6 (ArC-1), 124.5 (ArC-2,6), 124.2 (C=CH(triazole)), 108.0 (ArC-4 103.7 (CH(anomeric)), 103.0 (CH(anomeric)), 79.7, 77.9, 75.5, 75.0, 74.8, 73.8, 73.5, 73.3, 71.1, 70.4, 69.4, 69.3, 69.2, 69.1, 68.7, 64.9, 63.9, 61.6, 61.2, 50.3 (OCH$_2$-TRZ), 44.3 (C(CH$_2$O)$_2$), 32.0, 30.4, 29.87, 29.85, 29.84, 29.78, 29.72, 29.6, 29.49, 29.48, 26.3, 26.2, 22.8 (CH$_2$CH$_3$), 14.2 (CH$_3$). MALDI-TOF (m/z): [M+Na]$^+$ calcd for C$_{137}$H$_{242}$N$_6$NaO$_{40}$, 2634.70; found 2634.90.

(3,4,5)12G1-PE-spacer-TRZ-(1EO-lactose)$_2$ (52dc).

Into a mixture of O,O'-2,2-bis(((3,4,5-tris(dodecyloxy)benzoyl)oxy)methyl)propane-1,3-diyl) di(prop-2-yn-1-yl) disuccinate (18c) (112.0 mg, 0.065 mmol) and 32 (64.1 mg, 0.16 mmol) in THF (2 ml) and water (1 ml) were added CuSO$_4$.5H$_2$O (9.7 mg, 0.039 mmol) and sodium ascorbate (7.8 mg, 0.039 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 10-30% MeOH: CH$_2$Cl$_2$) followed by precipitation from CH$_2$Cl$_2$ in cold MeOH to give the product as a white solid: 125.0 mg (76%). Purity (HPLC): 99%+. $^1$H NMR (500 MHz, 10% CD$_3$OD in CDCl$_3$) δ 7.95 (s, 2H, 2 =CH (triazole)), 7.18 (s, 4H, 2ArH-2, 6), 5.18 (s, 4H, 2OCH$_2$-TRZ), 4.59 (s, 4H, 4CH (anomeric)), 4.45 (s, 4H, 2ArCO$_2$CH$_2$), 4.37 (d, J=7.0 Hz, 2H, 2CH$_{lac}$), 4.35-4.25 (m, 6H, 2CH$_2$O$_2$CCH$_2$CH$_2$, 2CH$_{lac}$), 4.22 (s, 2H, 2CH$_{lac}$), 4.00 (t, J=6.6 Hz, 4H, 2ArOCH$_2$), 3.96 (t, J=6.3 Hz, 8H, 4ArOCH$_2$), 3.85 (m, 8H, 8CH$_{lac}$), 3.73 (s, 2H, 2CH$_{lac}$), 3.68-3.49 (m, 10H, 2OCH$_2$CH$_2$N, 2CH$_{lac}$), 3.41 (s, 2H, 2CH$_{lac}$), 3.33 (t, J=7.8 Hz, 2H, 2CH$_{lac}$), 3.17 (s, 2H, 2CH$_{lac}$), 2.66 (s, 8H, 2CH$_2$O$_2$CCH$_2$CH$_2$), 1.83-1.70 (m, 12H, 6ArOCH$_2$CH$_2$), 1.51-1.42 (m, 12H, 6ArOCH$_2$CH$_2$CH$_2$), 1.38-1.20 (m, 96H, 6(CH$_2$)$_8$CH$_3$), 0.88 (t, J=6.9 Hz, 18H, 6CH$_3$). $^{13}$C NMR (126 MHz, 10% CD$_3$OD in CDCl$_3$) δ 172.4 (C=O)-succ., 172.1 (C=O)-succ., 166.1 (ArCO$_2$), 153.0 (ArC-3, 5), 142.9 (ArC-4), 142.5 (C=CH (triazole)), 125.7 (C=CH (triazole)), 124.0 (ArC-1), 108.2 (ArC-2, 6), 103.6 (CH (anomeric)), 102.9 (CH (anomeric)), 79.4 (C$_{4glc}$), 75.5 (C$_{5gal}$), 75.0 (C$_{5glc}$), 74.8 (C$_{3gal}$), 73.7 (ArOCH$_2$), 73.4 (C$_{3glc}$), 73.1 (C$_{2gal}$), 71.0 (C$_{2glc}$), 69.4 (ArOCH$_2$), 69.2 (C$_{4gal}$), 68.0, (OCH$_2$CH$_2$N) 62.9 (C$_{6gal}$), 62.7 (C$_{6glc}$), 61.7 (CH$_2$O$_2$CCH$_2$CH$_2$), 61.1 (ArCO$_2$CH$_2$), 57.8 (OCH$_2$-TRZ), 50.4 (OCH$_2$CH$_2$N), 42.9 (C(CH$_2$O)$_4$), 32.0 (CH$_2$CH$_2$CH$_3$), 30.4, 29.85, 29.83, 29.82, 29.79, 29.76, 29.7, 29.58, 29.48, 29.46, 28.9, 26.3 (ArOCH$_2$CH$_2$CH$_2$), 26.2 (ArOCH$_2$CH$_2$CH$_2$), 22.8 (CH$_2$CH$_3$), 14.1 (CH$_3$). MALDI-TOF (m/z): [M+Na]$^+$ calcd for C$_{133}$H$_{226}$N$_6$NaO$_{40}$, 2570.57; found 2568.76.

(3,4,5)12G1-PE-spacer-TRZ-(4EO-lactose)$_2$ (52dd).

Into a mixture of O,O'-2,2-bis(((3,4,5-tris(dodecyloxy)benzoyl)oxy)methyl)propane-1,3-diyl) di(prop-2-yn-1-yl) disuccinate (18c) (200.0 mg, 0.12 mmol) and 37 (151.3 mg, 0.28 mmol) in THF (2 ml) and water (1 ml) were added CuSO$_4$.5H$_2$O (17.4 mg, 0.070 mmol) and sodium ascorbate (13.9 mg, 0.070 mmol) under nitrogen atmosphere. The reaction was stirred at room temperature in nitrogen atmosphere until the TLC indicated full conversion (about 48 h). The reaction mixture was diluted with THF and filtered. The solvent was then evaporated and the crude product was purified by column chromatography (SiO$_2$, 10-30% MeOH: CH$_2$Cl$_2$) followed by precipitation from CH$_2$Cl$_2$ in cold MeOH to give the product as a white solid: 223.0 mg (68%). Purity (HPLC): 99%+. $^1$H NMR (500 MHz, 10% CD$_3$OD in CDCl$_3$) δ 7.85 (s, 2H, 2 =CH (triazole)), 7.19 (s, 4H, 2ArH-2, 6), 5.19 (s, 4H, 2OCH$_2$-TRZ), 4.55 (t, J=5.1 Hz, 4H, 4CH (anomeric)), 4.45 (s, 4H, 2ArCO$_2$CH$_2$), 4.38 (d, J=7.8 Hz, 2H, 2CH$_{lac}$), 4.33 (m, 6H, 2CH$_2$O$_2$CCH$_2$CH$_2$, 2CH$_{lac}$), 4.02-3.96 (m, 14H, 6ArOCH$_2$, 2CH$_{lac}$), 3.91-3.82 (m, 12H, 2OCH$_2$CH$_2$N, 4CH$_{lac}$), 3.77-3.74 (m, 2H, 2CH$_{lac}$), 3.69-3.55 (m, 30H, 6OCH$_2$CH$_2$O, 6CH$_{lac}$), 3.51 (dd, J=9.6 Hz, J=3.2 Hz, 2H, 2CH$_{lac}$), 3.42-3.38 (m, 2H, 2CH$_{lac}$), 3.36-3.31 (m, 2H, 2CH$_{lac}$), 2.66 (s, 8H, 2CH$_2$O$_2$CCH$_2$CH$_2$), 1.84-1.77 (m, 8H, 4ArOCH$_2$CH$_2$), 1.76-1.71 (m, 4H, 2ArOCH$_2$CH$_2$), 1.51-1.44 (m, 12H, 6ArOCH$_2$CH$_2$CH$_2$), 1.40-1.20 (m, 96H, 6(CH$_2$)$_8$CH$_3$), 0.88 (t, J=6.9 Hz, 18H, 6CH$_3$). $^{13}$C NMR (126 MHz, 10% CD$_3$OD in CDCl$_3$) δ 172.3 (C=O)-succ., 172.0 (C=O)-succ., 166.1 (ArCO$_2$), 153.1 (ArC-3, 5), 142.8 (C=CH (triazole)), 142.4 (ArC-4), 125.4 (ArC-1), 124.1 (C=CH (triazole)), 108.2 (ArC-2, 6), 103.8 (CH (anomeric)), 103.1 (CH (anomeric)), 80.0 (C$_{2glc}$), 75.6 (C$_{5gal}$), 75.0 (C$_{5glc}$), 74.9 (C$_{3gal}$), 73.8 (ArOCH$_2$-4), 73.7 (C$_{3glc}$), 73.4 (C$_{2gal}$), 71.2 (C$_{2glc}$), 70.55 (OCH$_2$CH$_2$O), 70.53 (OCH$_2$CH$_2$O), 70.50 (OCH$_2$CH$_2$O), 70.48 (OCH$_2$CH$_2$O), 70.43 (OCH$_2$CH$_2$O), 69.4 (ArOCH$_2$-3, 5), 69.3 (C$_{4gal}$), 68.8 (OCH$_2$CH$_2$N), 62.9 (C$_{6gal}$), 62.8 (C$_{6glc}$), 61.8 (CH$_2$O$_2$CCH$_2$CH$_2$), 61.5 (ArCO$_2$CH$_2$), 57.9 (OCH$_2$-TRZ), 50.5 (OCH$_2$CH$_2$N), 43.0 (C(CH$_2$O)$_4$), 32.1 (CH$_2$CH$_2$CH$_3$), 30.5, 29.90, 29.88, 29.87, 29.84, 29.82, 29.7, 29.6, 29.53, 29.51, 29.0, 26.3 (ArOCH$_2$CH$_2$CH$_2$), 26.2 (ArOCH$_2$CH$_2$CH$_2$), 22.8 (CH$_2$CH$_3$), 14.2 (CH$_3$). MALDI-TOF (m/z): [M+Na]$^+$ calcd for C$_{145}$H$_{250}$N$_6$NaO$_{46}$, 2834.73; found 2832.29.

Molecular Synthesis of Amphiphilic Janis Glycodendrimers (Library 7)

(3,4)12G1-PE-TRZ$_i$-3EOLac$_2$ (53aa).

Into a solution of 14a (0.10 g, 0.088 mmol) and 45 (0.10 g, 0.19 mmol) in THF (1.6 mL) was added CuSO$_4$.5H$_2$O (13 mg, 0.053 mmol) in water (0.2 mL), and sodium ascorbate (11 mg, 0.053 mmol) in water (0.2 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.12 g (63%). Purity (HPLC): 99%+. $^1$H NMR (500 MHz, 10% CD$_3$OD in CDCl$_3$) δ 8.01 (s, 2H, 2 =CH (triazole)), 7.53 (dd, J=8.4, 1.8, 2H, 2ArH-6), 7.46 (d, J=1.8, 2H, 2ArH-2), 6.86 (d, J=8.6, 2H, 2ArH-5), 4.71 (s, 4H, 2ArCO$_2$CH$_2$), 4.63 (s, 4H), 4.38 (m, 6H), 4.33 (d, J=7.8, 2H), 4.08-3.96 (m, 10H), 3.91-3.82 (m, 8H), 3.77-3.58 (m, 34H), 3.52 (dd, J=9.7, 3.1, 2H), 3.34 (dd, J=10.1, 6.5, 2H), 1.87-1.79 (m, 8H, 4ArOCH$_2$CH$_2$), 1.53-1.44 (m, 8H, 4ArOCH$_2$CH$_2$CH$_2$), 1.43-1.21 (m, 64H, 4(CH$_2$)$_8$CH$_3$), 0.88 (t, J=6.9, 12H, 4CH$_3$). $^{13}$C NMR (126 MHz, 10% CD$_3$OD in CDCl$_3$) δ 165.9 (C=O), 154.0 (ArC-4), 148.8 (ArC-3), 145.1 (C=CH(triazole)), 125.8 (C=CH(triazole)), 123.9 (ArC-1), 121.2 (ArC-6), 114.6 (ArC-2), 112.1 (ArC-5), 103.7 (CH(anomeric)), 103.1 (CH(anomeric)), 79.8, 77.9, 75.5, 75.0, 74.8, 73.6, 73.3, 71.1, 70.5, 70.44, 70.42, 69.8, 69.6, 69.4, 69.3, 68.7, 64.3, 63.5, 61.8, 61.5, 50.4 (CH$_2$N), 44.2 (C(CH$_2$N$_3$)$_2$), 32.0, 29.82, 29.80, 29.76, 29.74, 29.58, 29.53, 29.47, 29.3, 29.2, 26.2, 26.1, 22.8 (CH$_2$CH$_3$), 14.2 (CH$_3$). MALDI-TOF (m/z): [M+Na]$^+$ calcd for C$_{109}$H$_{186}$N$_6$NaO$_{36}$, 2178.28; found 2176.59.

(3,5)12G1-PE-TRZ$_i$-3EOLac$_2$ (53ba).

Into a solution of 14b (0.25 g, 0.22 mmol) and 45 (0.25 g, 0.49 mmol) in THF (3.5 mL) was added CuSO$_4$.5H$_2$O (33 mg, 0.13 mmol) in water (0.5 mL), and sodium ascorbate (26 mg, 0.13 mmol) in water (0.5 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.33 g (69%). Purity (HPLC): 99%+. $^1$H NMR (500 MHz, 10% CD$_3$OD in CDCl$_3$) δ 8.00 (s, 2H, 2 =CH (triazole)), 7.04 (d, J=2.2, 4H, 2ArH-2,6), 6.64 (t, J=2.1, 2H, 2ArH-4), 4.70 (s, 4H, 2ArCO$_2$CH$_2$), 4.65 (s, 4H, 2OCH$_2$-TRZ), 4.38 (m, 6H), 4.33 (d, J=7.8, 2H), 4.01-3.93 (m, 10H), 3.91-3.82 (m, 8H), 3.78-3.57 (m, 34H), 3.53 (dd, J=9.6, 3.2, 2H), 3.36-3.31 (m, 2H), 1.83-1.74 (m, 8H, 4ArOCH$_2$CH$_2$), 1.49-1.42 (m, 8H, 4ArOCH$_2$CH$_2$CH$_2$), 1.39-1.22 (s, 64H, 4(CH$_2$)$_8$CH$_3$), 0.88 (t, J=6.9, 12H, 4CH$_3$). $^{13}$C NMR (126 MHz, 10% CD$_3$OD in CDCl$_3$) δ 165.9 (C=O), 160.4 (ArC-3,5), 145.1 (C=CH(triazole)), 130.8 (ArC-1), 125.8 (C=CH(triazole)), 108.0 (ArC-2,6), 106.7 (ArC-4), 103.7 (CH(anomeric)), 103.1 (CH(anomeric)), 79.8, 77.9, 75.5, 75.0, 74.8, 73.6, 73.3, 71.1, 70.5, 69.8, 69.3, 68.7, 68.6, 64.3, 63.7, 61.80, 61.5, 50.3 (CH$_2$N), 44.2 (C(CH$_2$N$_3$)$_2$), 32.0, 29.8, 29.74, 29.69, 29.53, 29.45, 29.3, 26.1, 22.8 (CH$_2$CH$_3$), 14.2 (CH$_3$). MALDI-TOF (m/z): [M+Na]$^+$ calcd for C$_{133}$H$_{234}$N$_6$NaO$_{36}$, 2546.65; found 2546.58. MALDI-TOF (m/z): [M+Na]$^+$ calcd for C$_{109}$H$_{186}$N$_6$NaO$_{36}$, 2178.28; found 2176.73.

(3,4,5)12G1-PE-TRZ$_i$-3EOLac$_2$ (53ca).

Into a solution of 14c (0.67 g, 0.44 mmol) and 45 (0.50 g, 0.98 mmol) in THF (7.0 mL) was added CuSO$_4$.5H$_2$O (66 mg, 0.27 mmol) in water (1.0 mL), and sodium ascorbate (53 mg, 0.27 mmol) in water (1.0 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from CH$_2$Cl$_2$/MeOH mixture to give the product as a white solid: 0.89 g (79%). Purity (HPLC): 99%+. $^1$H NMR (500 MHz, 10% CD$_3$OD in CDCl$_3$) δ 8.02 (s, 2H, 2 =CH (triazole)), 7.16 (s, 4H, 2ArH-2,6), 4.67 (s, 4H, 2ArCO$_2$CH$_2$), 4.63 (s, 4H, 2OCH$_2$-TRZ), 4.45-4.36 (m, 6H), 4.32 (d, J=7.8, 2H), 3.99 (m, 14H), 3.91-3.81 (m, 8H), 3.80-3.55 (m, 32H), 3.52 (dd, J=9.7, 3.2, 2H), 3.37-3.31 (m, 2H), 1.85-1.71 (m, 12H, 6ArOCH$_2$CH$_2$), 1.53-1.44 (m, 12H, 6ArOCH$_2$CH$_2$CH$_2$), 1.40-1.21 (m, 96H, 6(CH$_2$)$_8$CH$_3$), 0.88 (t, J=6.9, 18H, 6CH$_3$). $^{13}$C NMR (126 MHz, 10% CD$_3$OD in CDCl$_3$) δ 165.9 (C=O), 153.1 (ArC-3,5), 145.1 (C=CH (triazole)), 143.1 (ArC-1), 125.8 (C=CH(triazole)), 123.7 (ArC-2,6), 108.3 (ArC-4), 103.7 (CH(anomeric)), 103.1 (CH(anomeric)), 79.8, 77.9, 75.5, 75.0, 74.8, 73.8, 73.6, 73.3, 71.1, 70.5, 70.4, 69.9, 69.5, 69.4, 68.7, 64.3, 63.5, 61.8, 61.5, 50.4 (CH$_2$N), 44.3 (C(CH$_2$N$_3$)$_2$), 32.0, 30.5, 29.87, 29.85, 29.83, 29.78, 29.71, 29.6, 29.50, 29.48, 26.3, 26.2, 22.8 (CH$_2$CH$_3$), 14.2 (CH$_3$). MALDI-TOF (m/z): [M+Na]$^+$ calcd for C$_{133}$H$_{234}$N$_6$NaO$_{38}$, 2546.65; found 2546.58.

(3,4)2Et8G1-PE-TRZ$_i$-3EOLac$_2$ (53da). Into a solution of 14d (0.20 g, 0.22 mmol) and 45 (0.25 g, 0.49 mmol) in THF (3.5 mL) was added CuSO$_4$.5H$_2$O (33 mg, 0.13 mmol) in water (0.5 mL), and sodium ascorbate (26 mg, 0.13 mmol) in water (0.5 mL) successively under nitrogen atmosphere. The reaction mixture was allowed to stir at room temperature for 12 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.32 g (74%). Purity (HPLC): 99%+. $^1$H NMR (500 MHz, 10% CD$_3$OD in CDCl$_3$) δ 8.00 (s, 2H, 2 =CH (triazole)), 7.54 (dd, J=8.4, 1.7, 2H, 2ArH-6), 7.46 (d, J=1.7, 2H, 2ArH-2), 6.87 (d, J=8.5, 2H, 2ArH-5), 4.71 (s, 4H, 2ArCO$_2$CH$_2$), 4.63 (s, 4H), 4.38 (m, 6H), 4.33 (d, J=7.7, 2H), 3.98 (dd, J=9.9, 4.6, 2H), 3.95-3.83 (m, 16H), 3.77-3.58 (m, 34H), 3.53 (dd, J=9.8, 2.2, 2H), 3.36-3.33 (m, 2H), 1.77 (m, 4H, 4ArOCH$_2$CH), 1.57-1.24 (m, 32H, 4CH$_2$CH$_3$, 4(CH$_2$)$_3$CH$_3$), 0.98-0.86 (m, 24H, 8CH$_3$). $^{13}$C NMR (126 MHz, 10% CD$_3$OD in CDCl$_3$) δ 165.9 (C=O), 154.3 (ArC-4), 149.2 (ArC-3), 145.0 (C=CH(triazole)), 125.7 (C=CH(triazole)), 123.7 (ArC-1), 121.0 (ArC-6), 114.1 (ArC-2), 111.9 (ArC-5), 103.8 (CH(anomeric)), 103.0 (CH(anomeric)), 80.0, 77.9, 75.5, 74.9, 74.7, 73.5, 73.3, 71.7, 71.5, 71.1, 70.4, 69.8, 69.1, 68.7, 64.3, 63.3, 61.5, 61.3, 50.3 (CH$_2$N), 44.3 (C(CH$_2$N$_3$)$_2$), 39.6, 39.5, 30.7, 30.6, 29.19, 29.17, 23.98, 23.97, 23.94, 23.93, 23.12, 23.11, 14.1 (CH$_3$), 11.3 (CH$_3$), 11.2 (CH$_3$). MALDI-TOF (m/z): [M+Na]$^+$ calcd for C$_{93}$H$_{154}$N$_6$NaO$_{36}$, 1954.03; found 1953.25.

(3,5)2Et8G1-PE-TRZ$_i$-3EOLac$_2$ (53ea).

Into a solution of 14e (0.20 g, 0.22 mmol) and 45 (0.25 g, 0.49 mmol) in THF (3.5 mL) was added CuSO$_4$.5H$_2$O (33 mg, 0.13 mmol) in water (0.5 mL), and sodium ascorbate (26 mg, 0.13 mmol) in water (0.5 mL) successively under nitrogen atmosphere. The reaction mixture was allowed to stir at room temperature for 12 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.34 g (79%). Purity (HPLC): 99%+. $^1$H NMR (500 MHz, 10% CD$_3$OD in CDCl$_3$) δ 7.98 (s, 2H, 2 =CH (triazole)), 7.07 (d, J=2.1, 4H, 2ArH-2,6), 6.67 (t, J=1.9, 2H, 2ArH-4), 4.69 (s, 4H, 2ArCO$_2$CH$_2$), 4.65 (s, 4H, 2OCH$_2$-TRZ), 4.38 (m, 6H), 4.33 (d, J=7.7, 2H), 4.01-3.95 (m, 2H), 3.86 (m, 16H), 3.80-3.55 (m, 34H), 3.54 (dd, J=9.8, 2.5, 2H), 3.35 (m, 2H), 1.72 (m, 4H, 4ArOCH$_2$CH), 1.56-1.25 (m, 32H, 4CH$_2$CH$_3$, 4(CH$_2$)$_3$CH$_3$), 0.92 (m, 8CH$_3$). $^{13}$C NMR (126 MHz, 10% CD$_3$OD in CDCl$_3$) δ 165.9 (C=O), 160.7 (ArC-3,5), 145.1 (C=CH(triazole)), 130.7 (ArC-1), 125.7 (C=CH(triazole)), 107.9 (ArC-2,6), 106.7 (ArC-4), 103.7 (CH(anomeric)), 103.0 (CH(anomeric)), 79.8, 77.8, 75.5, 74.9, 74.8, 73.6, 73.3, 71.0, 70.4, 69.8, 69.3, 68.7, 64.3, 63.5, 61.8, 61.5, 50.2 (CH$_2$N), 44.3 (C(CH$_2$N$_3$)$_2$), 39.5, 30.6, 29.2, 23.9 (CH$_2$CH$_3$), 23.1 (CH$_2$CH$_3$), 14.1 (CH$_3$), 11.2 (CH$_3$). MALDI-TOF (m/z): [M+Na]$^+$ calcd for C$_{93}$H$_{154}$N$_6$NaO$_{36}$, 1954.03; found 1954.48.

(3,4,5)2Et8G1-PE-TRZ$_t$-3EOLac$_2$ (53fa).

Into a solution of 14f (0.26 g, 0.22 mmol) and 45 (0.25 g, 0.49 mmol) in THF (3.5 mL) was added CuSO$_4$.5H$_2$O (33 mg, 0.13 mmol) in water (0.5 mL), and sodium ascorbate (26 mg, 0.13 mmol) in water (0.5 mL) successively under nitrogen atmosphere. The reaction mixture was allowed to stir at room temperature for 24 h. The reaction mixture was concentrated under reduced pressure and purified by column chromatography (SiO$_2$, 0-50% MeOH:CH$_2$Cl$_2$) followed by recrystallization from MeOH to give the product as a white solid: 0.36 g (73%). Purity (HPLC): 99%+. $^1$H NMR (500 MHz, 10% CD$_3$OD in CDCl$_3$) δ 7.99 (s, 2H, 2 =CH (triazole)), 7.19 (s, 4H, 2ArH-2,6), 4.65 (s, 4H, 2ArCO$_2$CH$_2$), 4.63 (s, 4H, 2OCH$_2$-TRZ), 4.46-4.37 (m, 6H), 4.33 (d, J=7.8, 2H), 3.98 (dd, J=8.8, 4.2, 2H), 3.94-3.82 (m, 20H), 3.77-3.58 (m, 34H), 3.55 (d, J=9.3, 2H), 3.35 (t, J=7.8, 2H), 1.79-1.66 (m, 6H, 6ArOCH$_2$CH), 1.62-1.24 (m, 48H, 6CH$_2$CH$_3$, 6(CH$_2$)$_3$CH$_3$), 1.01-0.86 (m, 36H, 12CH$_3$). $^{13}$C NMR (126 MHz, 10% CD$_3$OD in CDCl$_3$) δ 165.9 (C=O), 153.2 (ArC-3,5), 145.1 (C=CH(triazole)), 143.1 (ArC-1), 125.7 (C=CH(triazole)), 123.5 (ArC-2,6), 107.8 (ArC-4), 103.7 (CH(anomeric)), 103.0 (CH(anomeric)), 79.7, 77.8, 76.2, 75.4, 74.9, 74.7, 73.5, 73.2, 71.5, 71.0, 70.4, 69.8, 69.3, 68.7, 64.3, 63.2, 61.8, 61.4, 50.3 (CH$_2$N), 44.4 (C(CH$_2$N$_3$)$_2$), 40.7, 39.7, 30.6, 30.5, 29.4, 29.2, 23.9 (CH$_2$CH$_3$), 23.7 (CH$_2$CH$_3$), 23.2 (CH$_2$CH$_3$23.1 (CH$_2$CH$_3$), 14.2 (CH$_3$), 14.1 (CH$_3$), 11.2 (CH$_3$). MALDI-TOF (m/z): [M+Na]$^+$ calcd for C$_{109}$H$_{186}$N$_6$NaO$_{38}$, 2210.27; found 2211.24.

Self-Assembly of Dendrimersomes
Small Unilamellar Glycodendrimersomes

Small unilamellar glycodendrimersomes were prepared by solvent injection method$^{Error!\ Bookmark\ not\ defined.}$ by injection of 100 μL of THF solution containing 10 mg of glycodendrimer dissolved in 1 mL of THF into 2 mL ultrapure water followed by vortex mixing to give the final glycodendrimer concentration of 0.5 mg/mL with respect to water. Any exceptions to this protocol are noted in the figure captions of the experiment in question.

Giant Unilamellar Glycodendrimersomes

Giant unilamellar dendrimersomes were prepared by film hydration and were used for visualization by differential interfering contrast microscopy (DIC) and bright field microscopy. An aliquot of 200 μL of a 5 mg/mL glycodendrimer solution in CH$_2$Cl$_2$ was uniformly deposited on the surface of a flat bottom of the 20 mL scintillation glass vial, followed by evaporation of the solvent for 12 h. Addition of ultrapure water (2.0 mL), and subsequent hydration at 60° C. for 24 h, led to the formation of giant dendrimersomes. The sample was then mixed using a vortex mixer for 5 s. Dendrimersomes encapsulating hydrophilic dyes visualized by fluorescence microscopy were obtained by the same method of film hydration with the hydrophobic Nile red dye (1 mg/mL in CH$_2$Cl$_2$) 5 μL was dissolved into the CH$_2$Cl$_2$ glycodendrimer solution. For micropipette aspiration, giant unilamellar dendrimersomes were prepared by film hydration with 290 mM sucrose solution (2.0 mL).

What is claimed:
1. A compound of the formula:

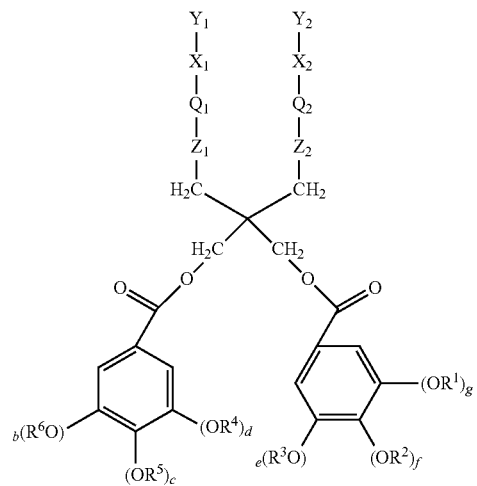

wherein:
Y$^1$ and Y$^2$ are independently a monosaccharide or disaccharide;
X$^1$ and X$^2$ are independently —(R$^9$—O)$_m$—, —(R$^{10}$)$_p$—, —O—(R$^{11}$—O)$_q$—, —R$^{16}$—O—R$^{17}$—O— or a covalent bond;
Q$^1$ and Q$^2$ are independently a nitrogen-containing heterocycle moiety;
Z$^1$ and Z$^2$ are independently —(O—R$^7$)—, —(O—C (=O)—R$^8$)$_a$—, —O—C(=O)—R$^{12}$—C(=O)—R$^{13}$—, —O—C(=O)—R$^{14}$—C(=O)—R$^{15}$ or a covalent bond;
R$_7$-R$^{17}$ are each independently C$_1$-C$_6$ alkyl;
R$^1$-R$^6$ are each independently a linear or branched alkyl group;
b, c, d, e, f, and g are 0 or 1, provided b+c+d equals at least 2 and e+f+g equals at least 2; and
a, m, p, and q are each an integer from 1-6.

2. The compound of claim 1, wherein R$^1$-R$^6$ are each independently C$_4$-C$_{20}$ linear or branched alkyl group.

3. The compound of claim 1, wherein Y$^1$ and Y$^2$ are independently D-Mannose, D-Galactose or D-Lactose.

4. The compound of claim 1, wherein Y$^1$ and Y$^2$ are the same.

5. The compound of claim 1, wherein Q$^1$ and Q$^2$ are

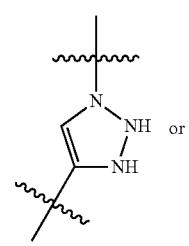

III

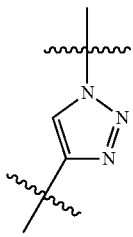

where ⌇⌇⌇ indicates a bond position.

6. The compound of claim 1, wherein a, m, p, and q are each independently an integer from 1-4.

7. The compound of claim 1, wherein $X^1$, $X^2$, $Z^1$ and $Z^2$ are covalent bonds.

8. The compound of claim 1, wherein $X^1$ and $X^2$ are covalent bonds.

9. The compound of claim 1, wherein $Z^1$ and $Z^2$ are covalent bonds.

10. A method for producing a compound of formula I

I

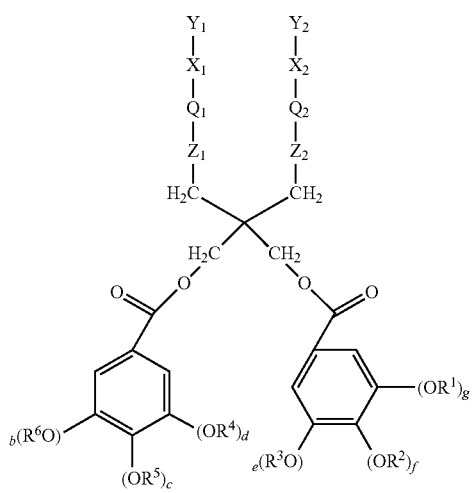

wherein:
- $Y^1$ and $Y^2$ are independently a monosaccharide or disaccharide;
- $X^1$ and $X^2$ are independently —$(R^9$—$O)_m$—, —$(R^{10})_p$—, —$O$—$(R^{11}$—$O)_q$—, —$R^{16}$—$O$—$R^{17}$—$O$— or a covalent bond;
- $Q^1$ and $Q^2$ are independently a nitrogen-containing heterocycle moiety;
- $Z^1$ and $Z^2$ are independently —$(O$—$R^7)$—, —$(O$—$C(=O)$—$R^8)_a$—, —$O$—$C(=O)$—$R^{12}$—$C(=O)$—$R^{13}$—, —$O$—$C(=O)$—$R^{14}$—$C(=O)$—$R^{15}$ or a covalent bond;
- $R^7$-$R^{17}$ are each independently $C_1$-$C_6$ alkyl;
- $R^1$-$R^6$ are each independently a linear or branched alkyl group;
- b, c, d, e, f, and g are 0 or 1, provided b+c+d equals at least 2 and e+f+g equals at least 2; and
- a, m, p, and q are each an integer from 1-6;
- said method comprising contacting compounds of formula $Y^1$—$X^1$-E and $Y^2$—$X^2$-E with a compounds of formula IV

IV

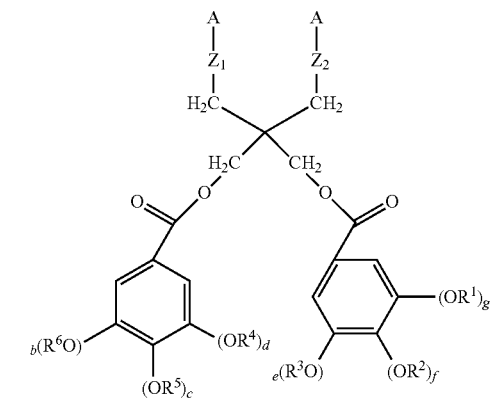

wherein A and E are selected from —C≡CH or —$N_3$ provided that A and E are not the same.

11. The method of claim 10, wherein $X^1$ and $X^2$ are covalent bonds.

12. The method of claim 10, wherein $Z^1$ and $Z^2$ are covalent bonds.

13. The method of claim 10, wherein $X^1$, $X^2$, $Z^1$ and $Z^2$ are covalent bonds.

14. The method of claim 10, wherein $R^1$-$R^6$ are each independently $C_4$-$C_{20}$ linear or branched alkyl group.

15. The method of claim 10, wherein $Y^1$ and $Y^2$ are independently D-Mannose, D-Galactose or D-Lactose.

16. The method of claim 10, wherein $Y^1$ and $Y^2$ are the same.

17. The method of claim 10, wherein $Q^1$ and $Q^2$ are

II

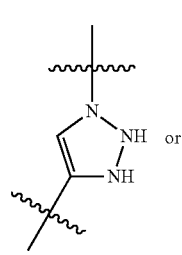

or

III

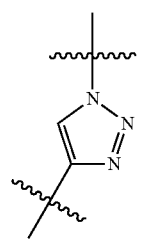

where ⌇⌇⌇ indicates a bond position.

18. The method of claim 10, wherein $R^1$-$R^6$ are the same.

19. A method of producing self-assembled amphiphilic Janus glycodendrimers comprising introducing a compound of claim 1 into an aqueous media.

* * * * *

UNITED STATES PATENT AND TRADEMARK OFFICE
CERTIFICATE OF CORRECTION

PATENT NO. : 9,777,034 B2  
APPLICATION NO. : 14/892044  
DATED : October 3, 2017  
INVENTOR(S) : Virgil Percec Page 1 of 1

It is certified that error appears in the above-identified patent and that said Letters Patent is hereby corrected as shown below:

In the Claims

Claim 1, Column 88, at Line 42, delete "$R_7$-$R^{17}$ are each independently $C_1$-$C_6$ alkyl;" and insert -- $R^7$-$R^{17}$ are each independently $C_1$-$C_6$ alkyl; --.

Signed and Sealed this  
Fourth Day of December, 2018

Andrei Iancu  
*Director of the United States Patent and Trademark Office*